United States Patent [19]

Wilson et al.

[11] Patent Number: 5,091,423

[45] Date of Patent: Feb. 25, 1992

[54] USE OF KETONES, KETOESTERS AND ALCOHOL IN REPELLING INSECTS; USE OF ALIPHATIC ESTER IN ATTRACTING INSECTS AND PROCESS AND APPARATUS FOR DETERMINATION OF INSECT REPELLENCY AND ATTRACTANCY

[75] Inventors: Richard A. Wilson, Westfield; Braja D. Mookherjee, Holmdel, both of N.J.; Jerry F. Butler, Gainesville, Fla.

[73] Assignees: International Flavors and Fragrances Inc., New York, N.Y.; The University of Florida, Gainesville, Fla.

[21] Appl. No.: 691,638

[22] Filed: Apr. 25, 1991

Related U.S. Application Data

[62] Division of Ser. No. 589,016, Sep. 27, 1990.

[51] Int. Cl.$^5$ ............................................. A01N 35/02
[52] U.S. Cl. ................................. 514/690; 514/919; 514/675
[58] Field of Search .................. 514/919, 690, 675

[56] References Cited

U.S. PATENT DOCUMENTS 4,759,228  7/1988  Butler et al. ...................... 514/919

Primary Examiner—Allen J. Robinson
Assistant Examiner—John D. Pak
Attorney, Agent, or Firm—Arthur L. Liberman

[57] ABSTRACT

A method of repelling *Musca domestica* L. (Diptera Muscidae) or *Aedes aegyptae* for a finite period of time from a three-dimensional space inhabitable by *Musca domestica* L. (Diptera Muscidae) or *Aedes aegyptae* is disclosed. The method consists essentially of the step of exposing a three-dimensional space to an effective *Musca domestica* L. (Diptera Muscidae) or *Aedes aegyptae*—repelling concentration and quantity of a compound selected from the group consisting of a compound defined according to the structure:

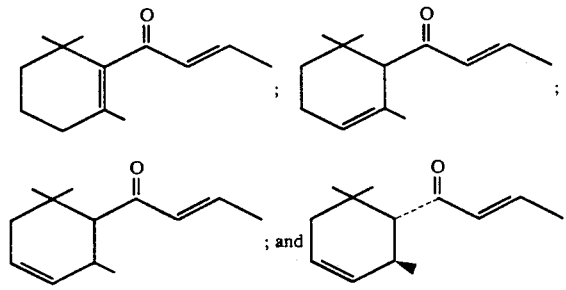

4 Claims, 85 Drawing Sheets

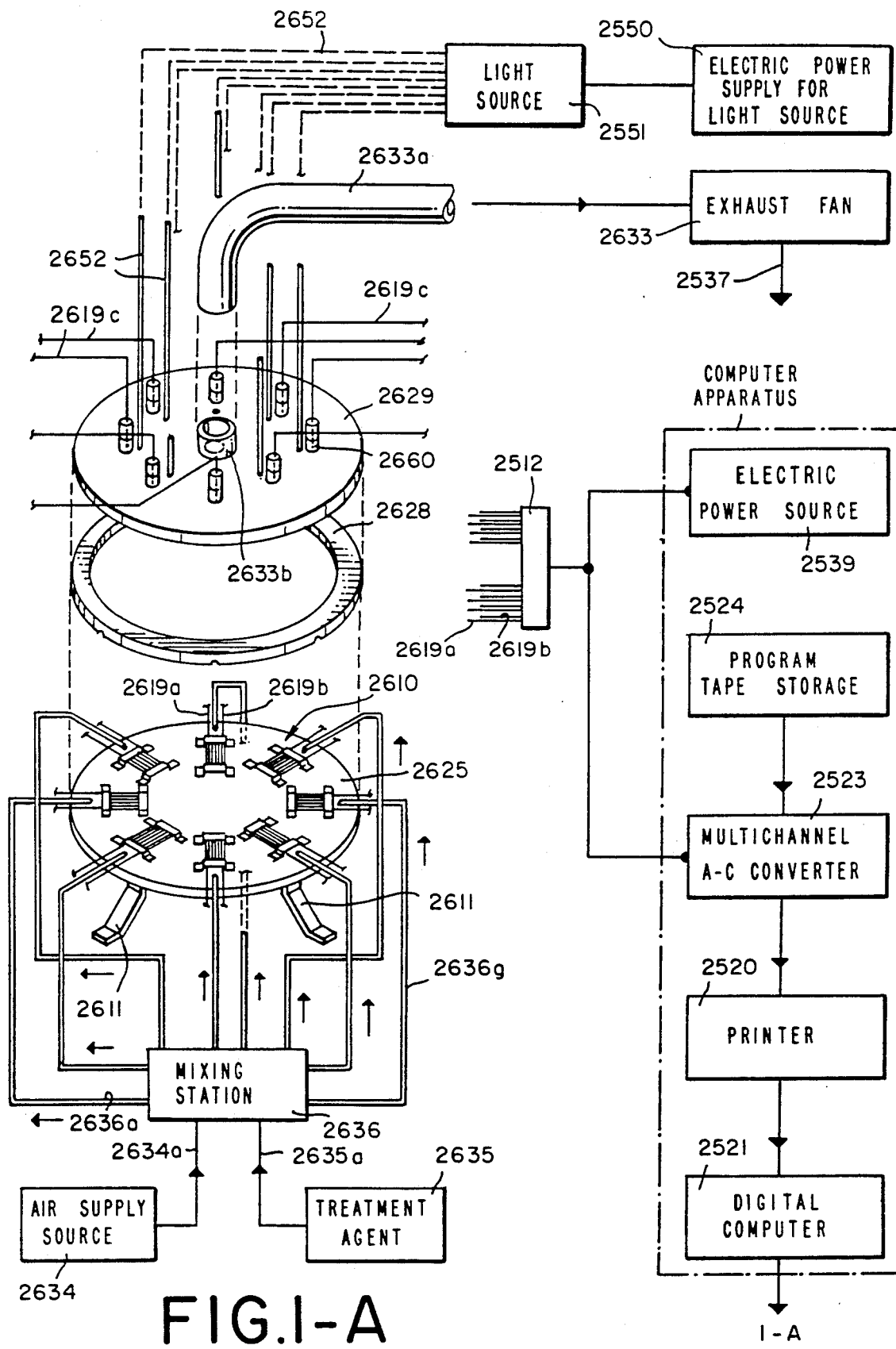
FIG.I-A

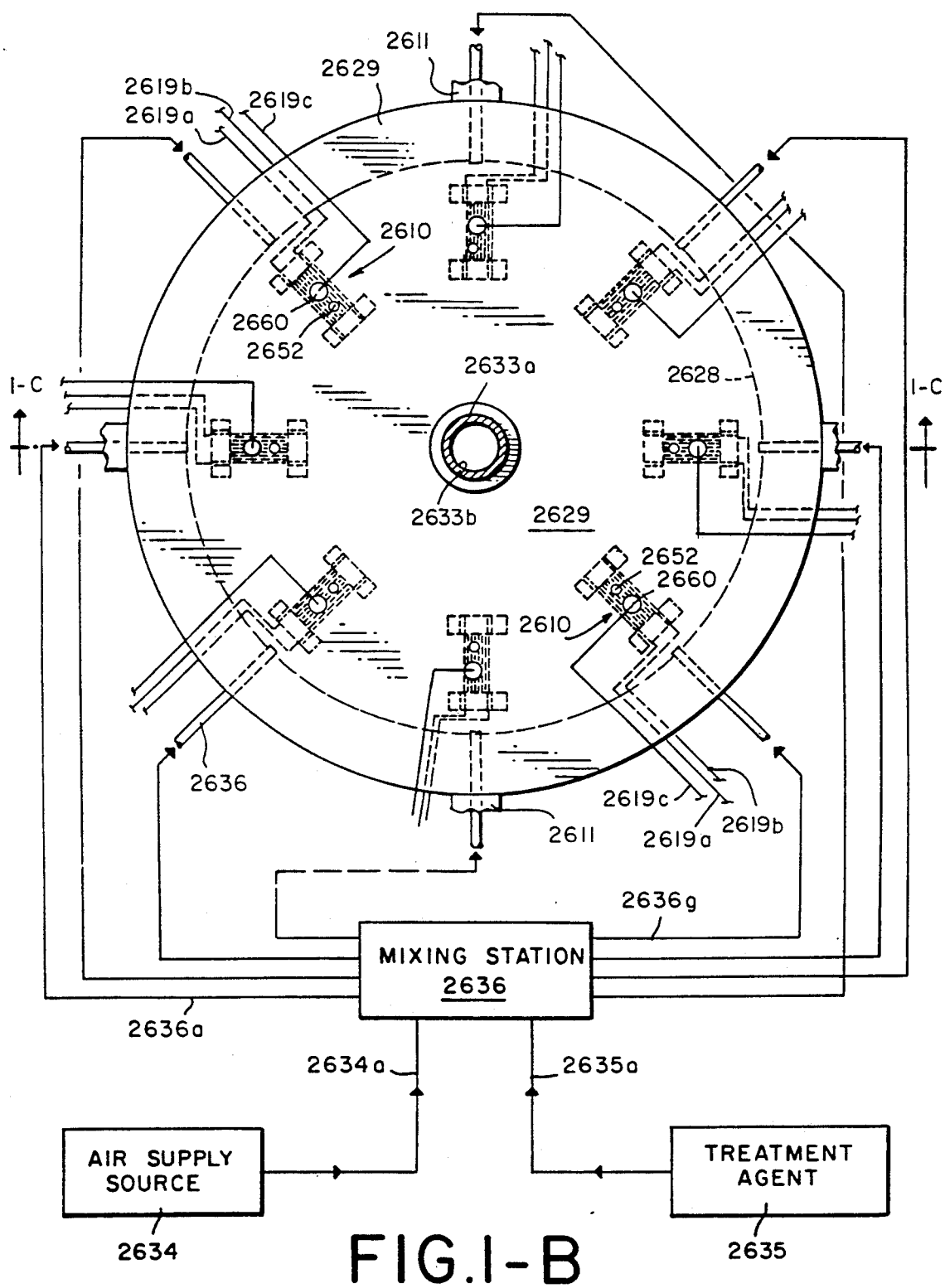
FIG.I-B

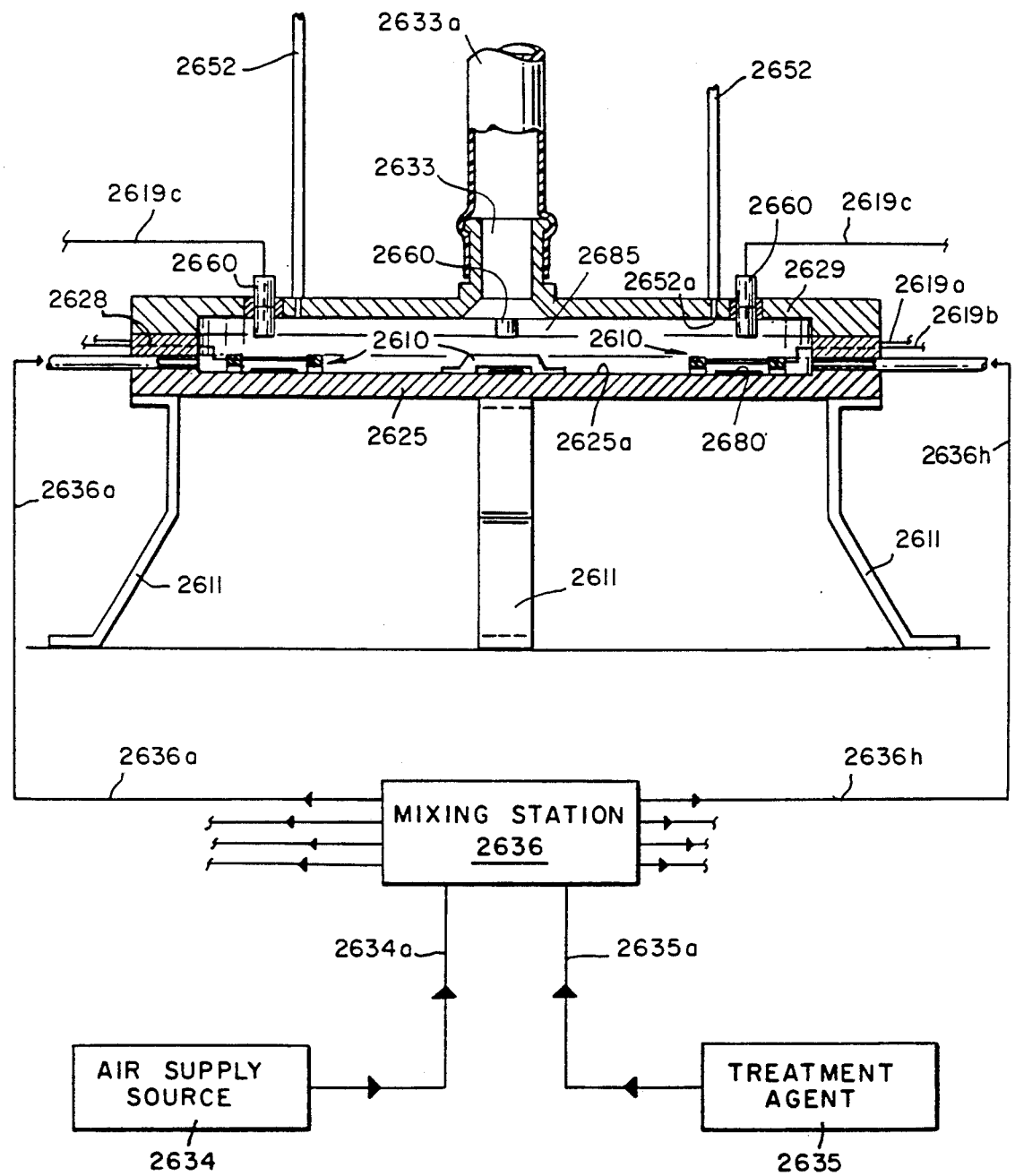
FIG.I-C

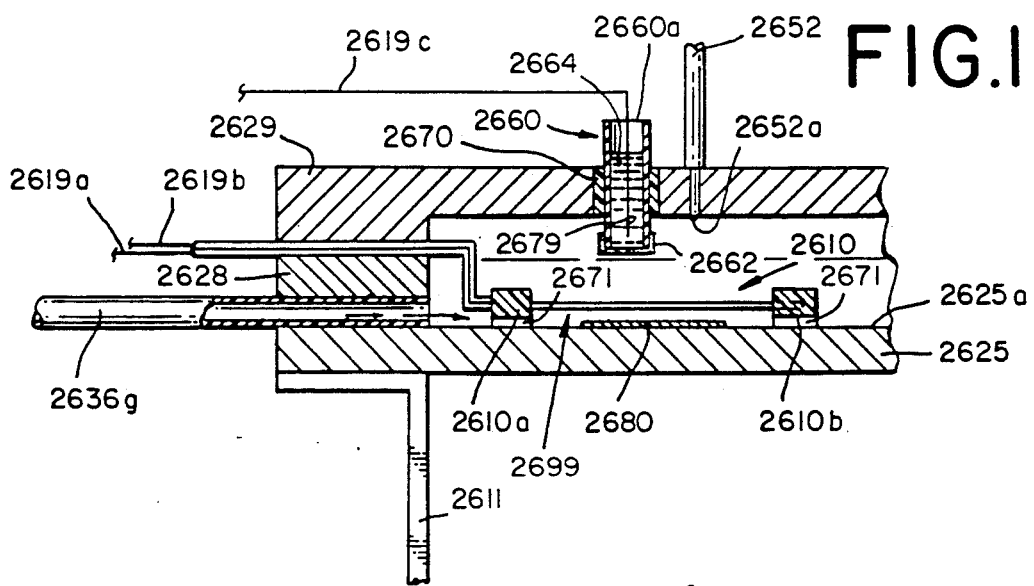
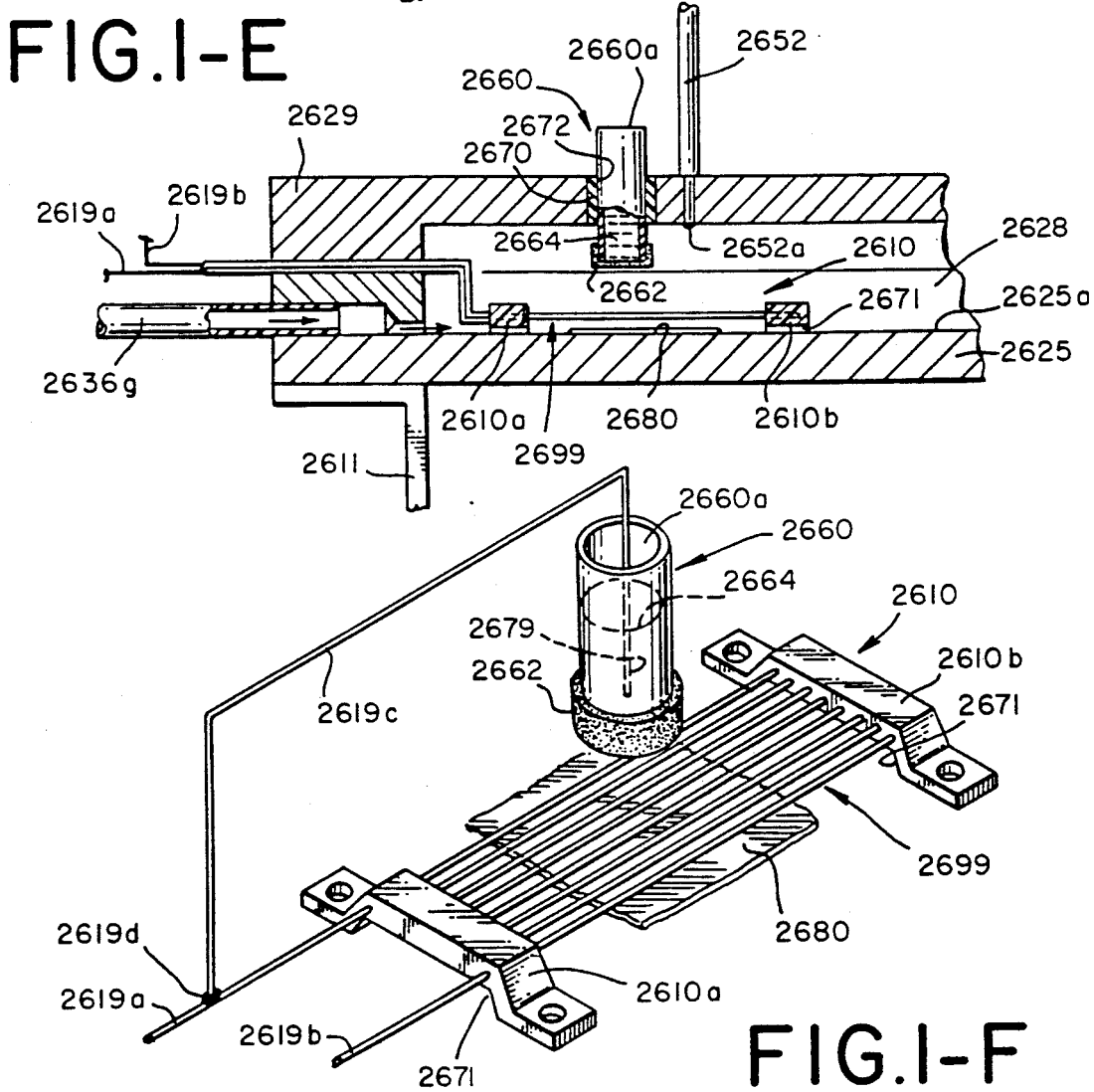

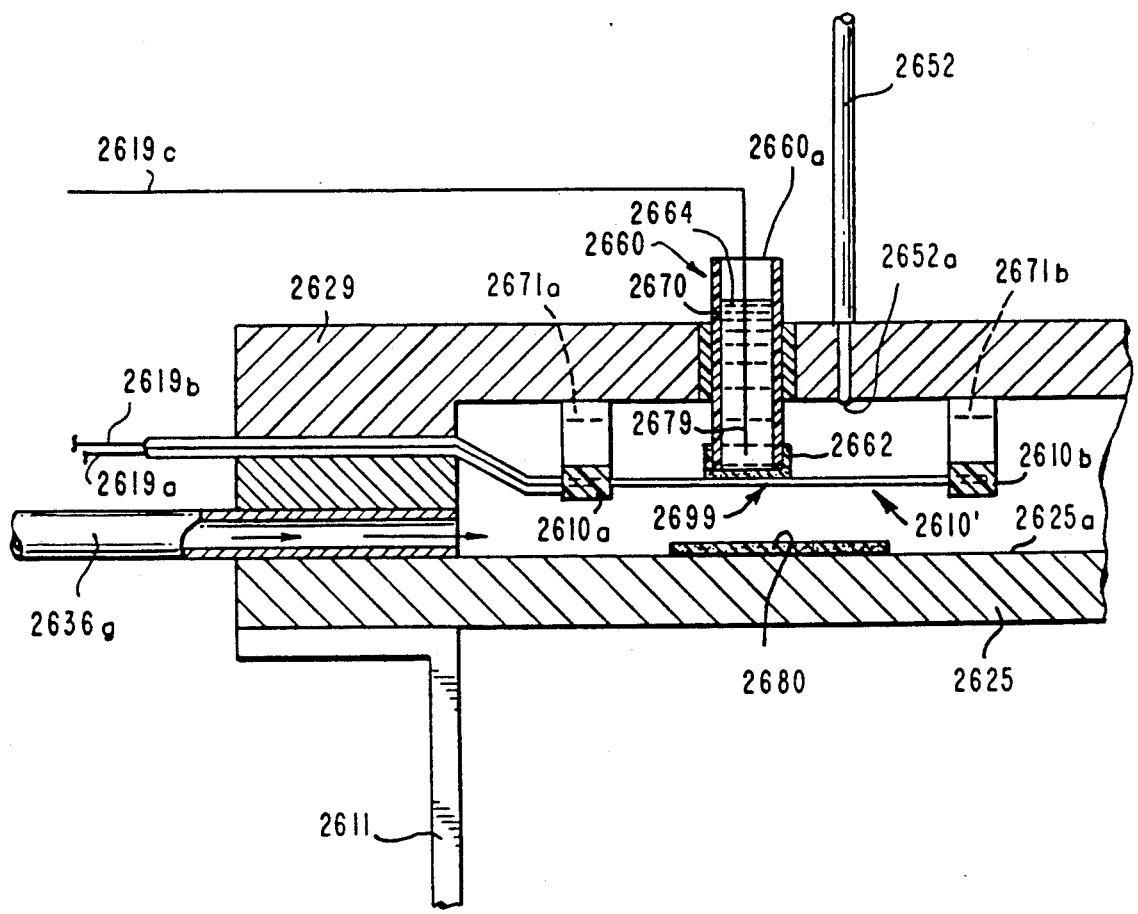
FIG.I-Da

FIG.1-G
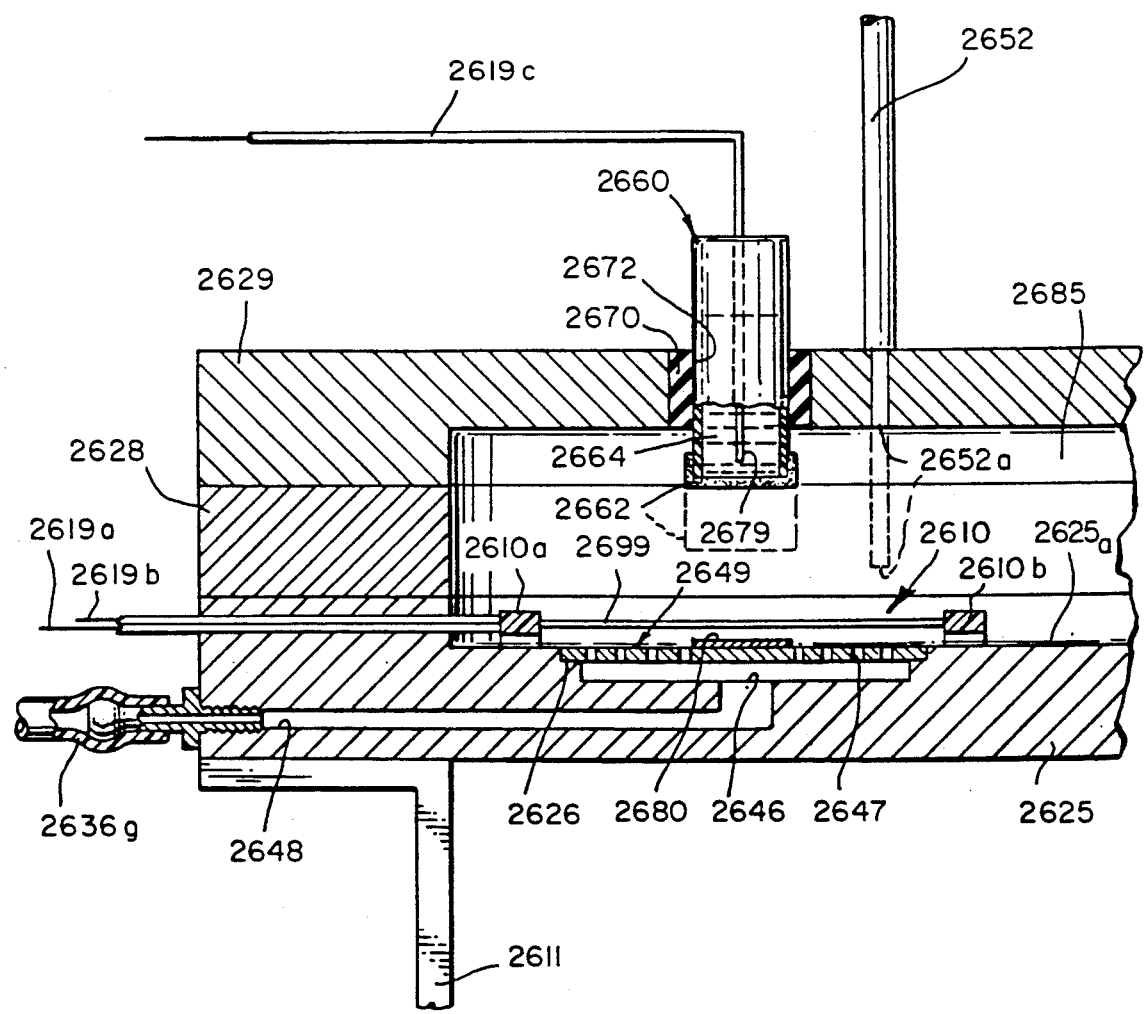

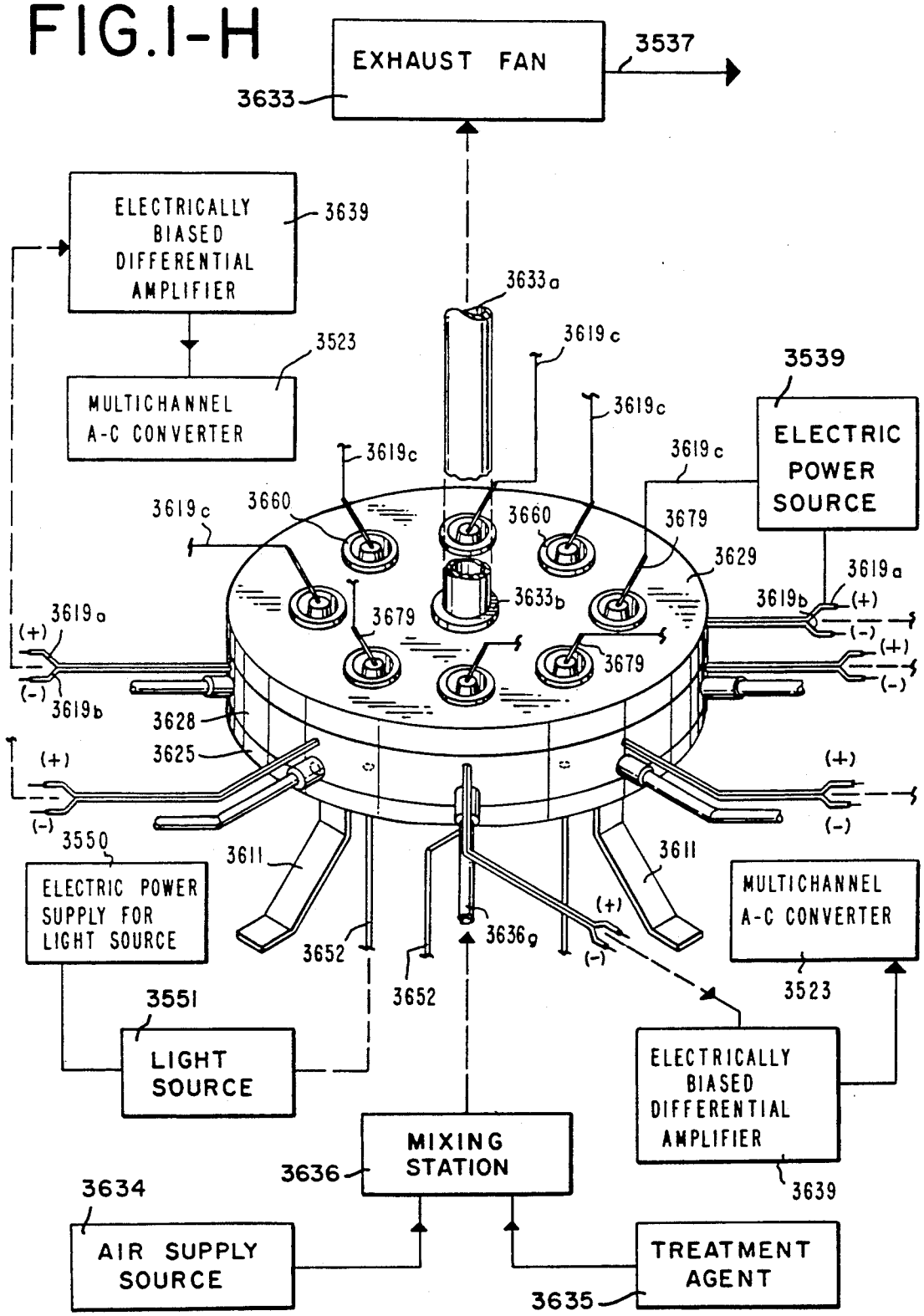

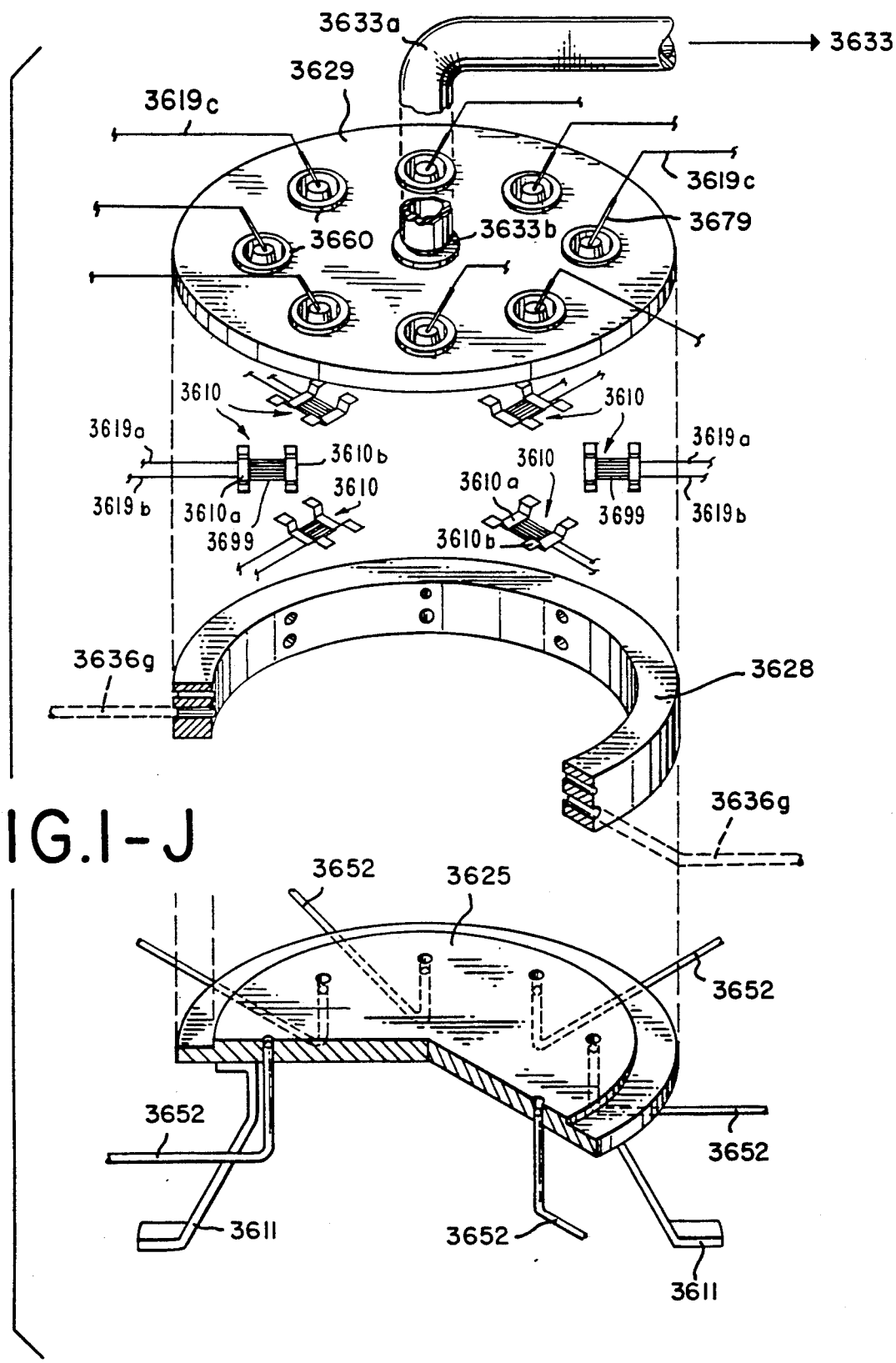
FIG.I-J

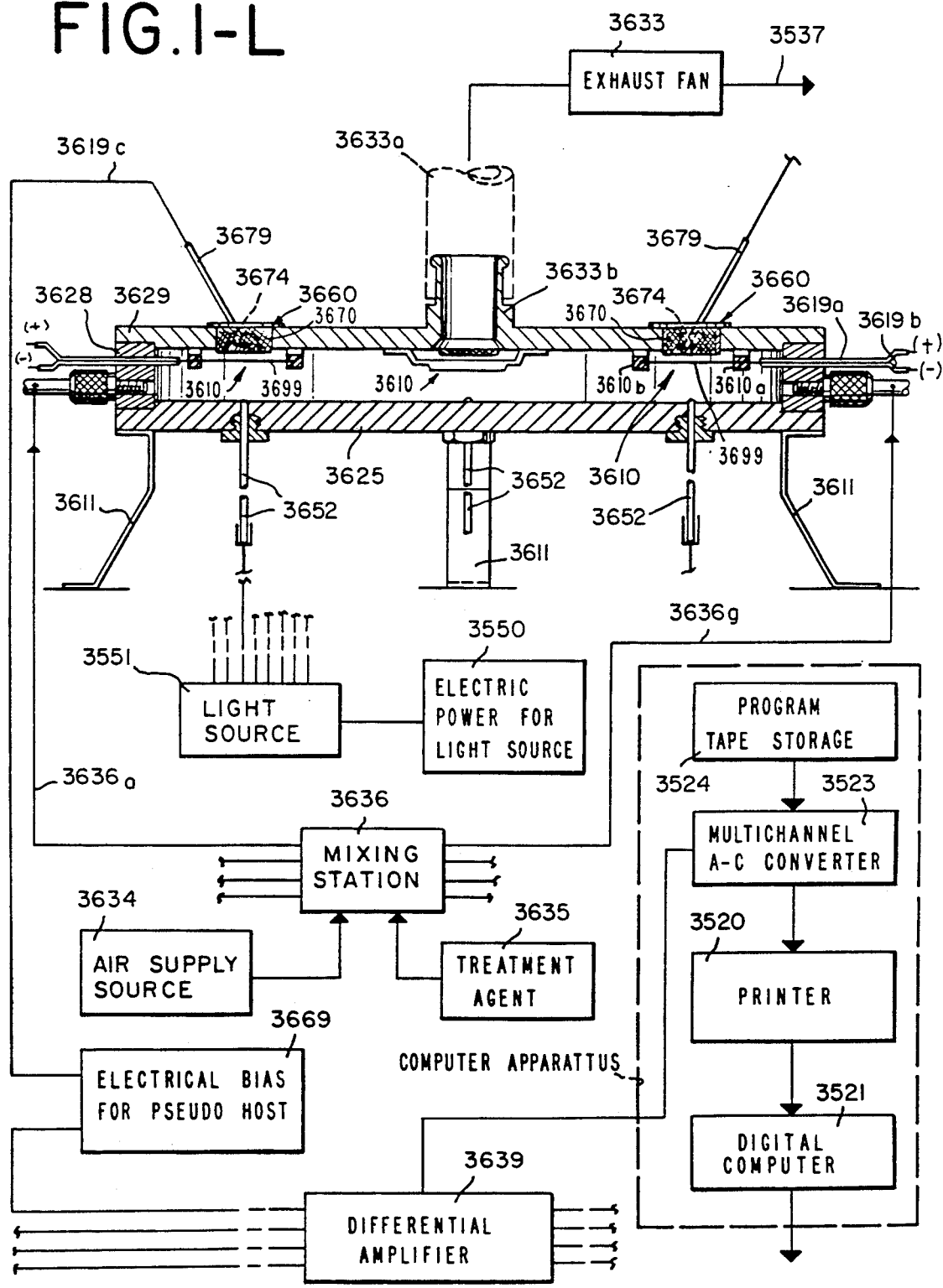
FIG.1-L

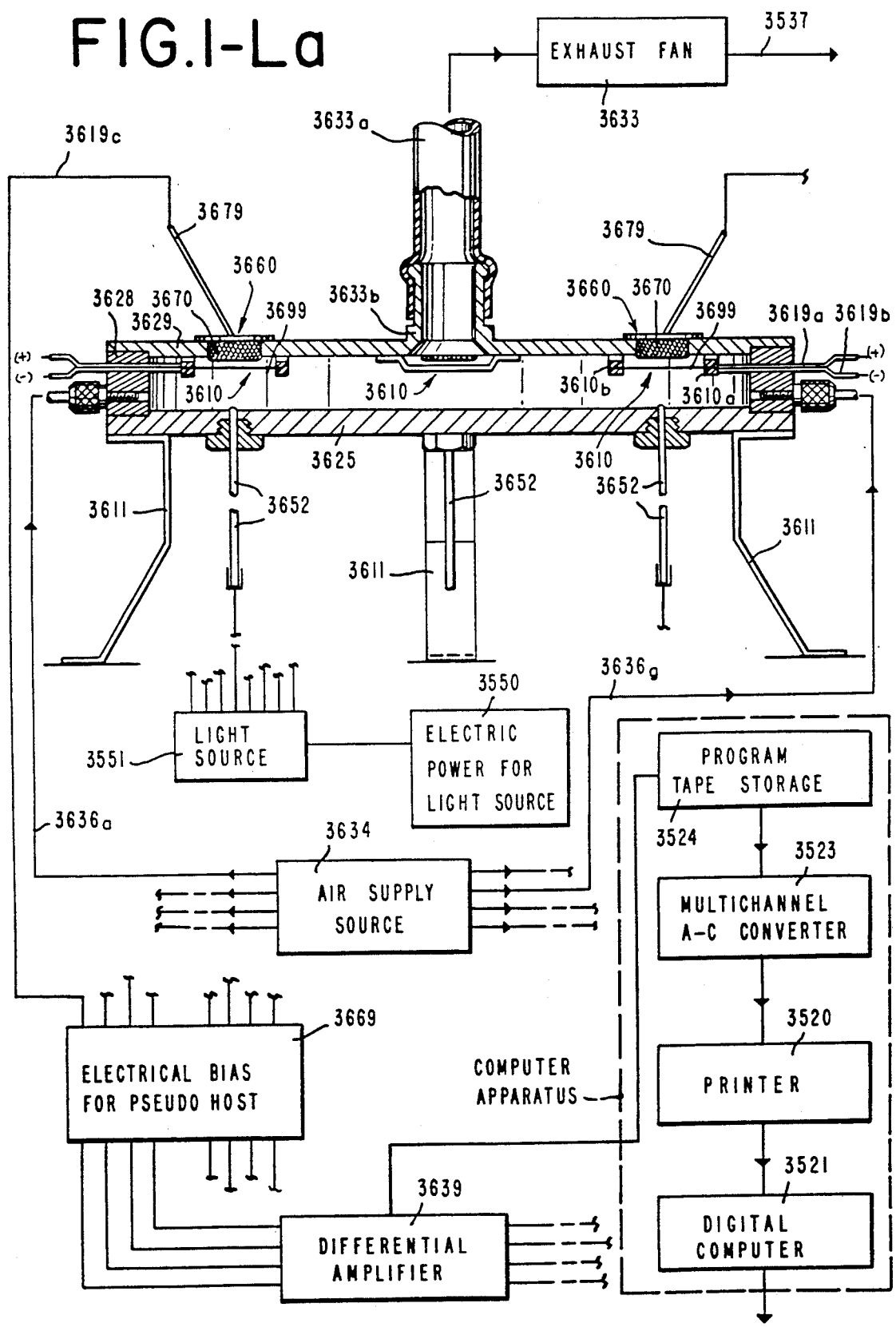
FIG.I-La

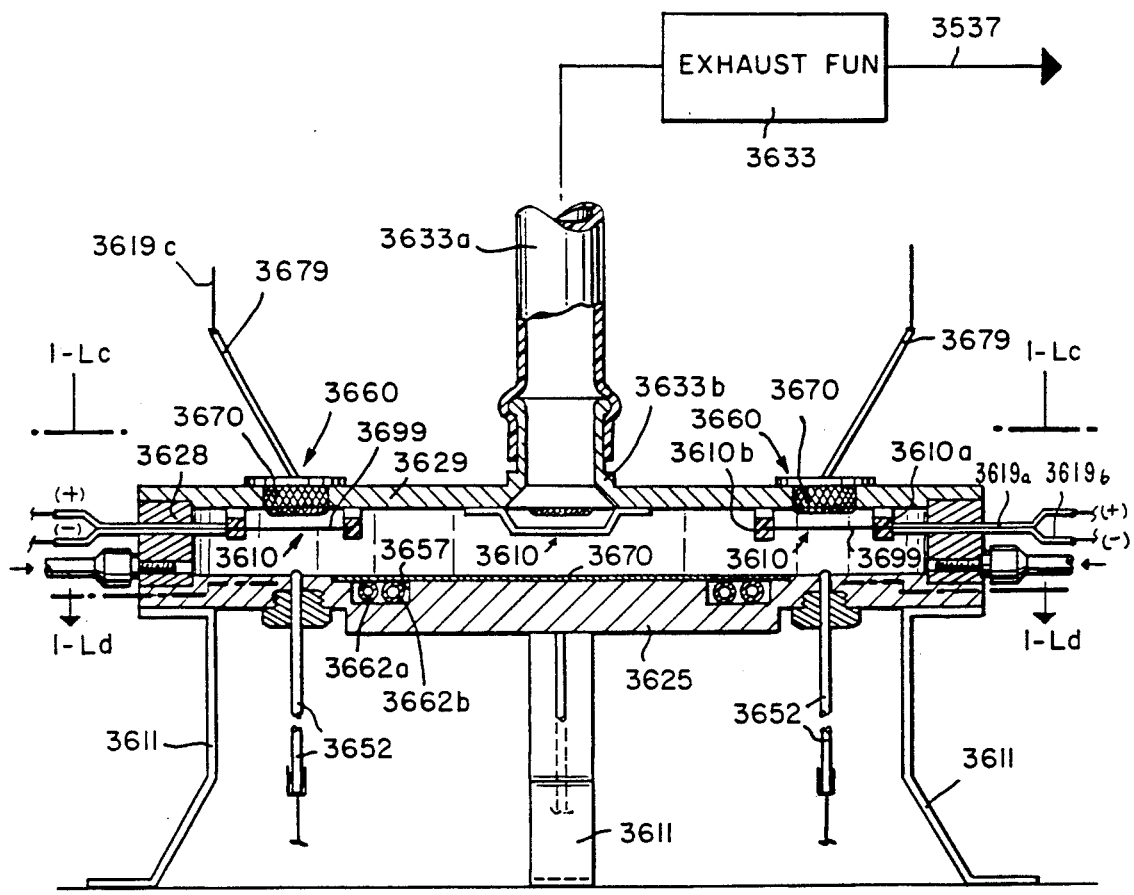
FIG.I-Lb

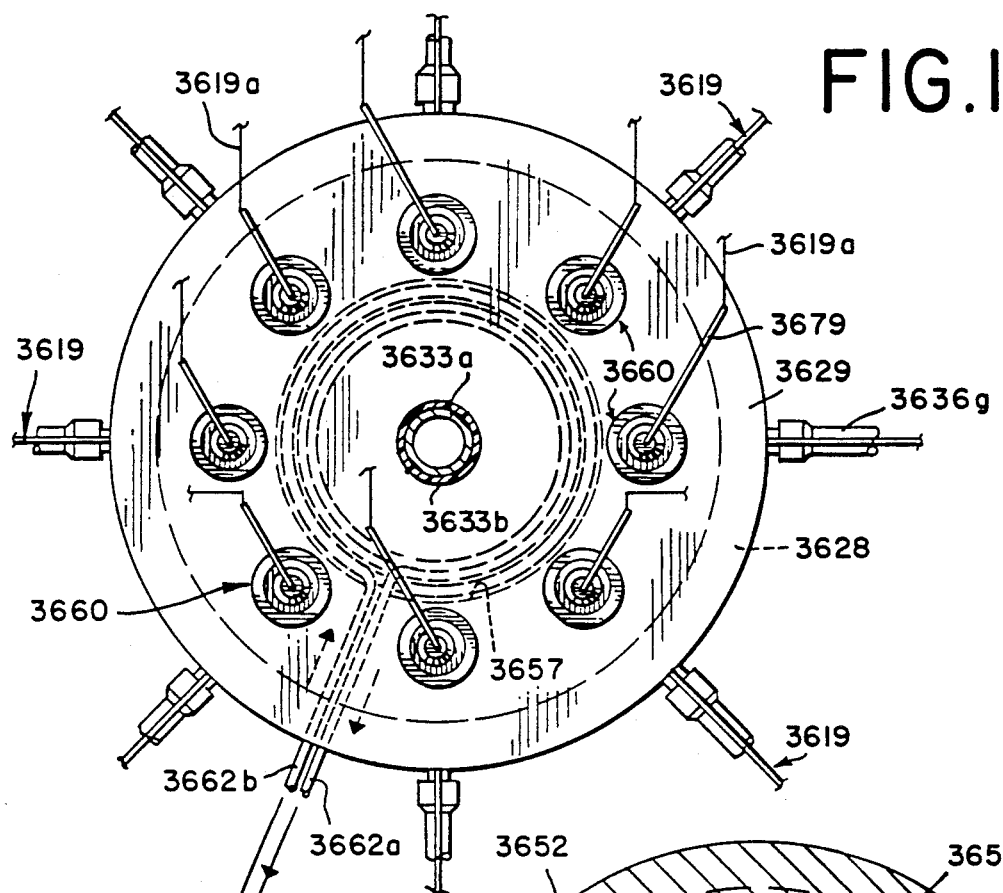
FIG.I-Lc
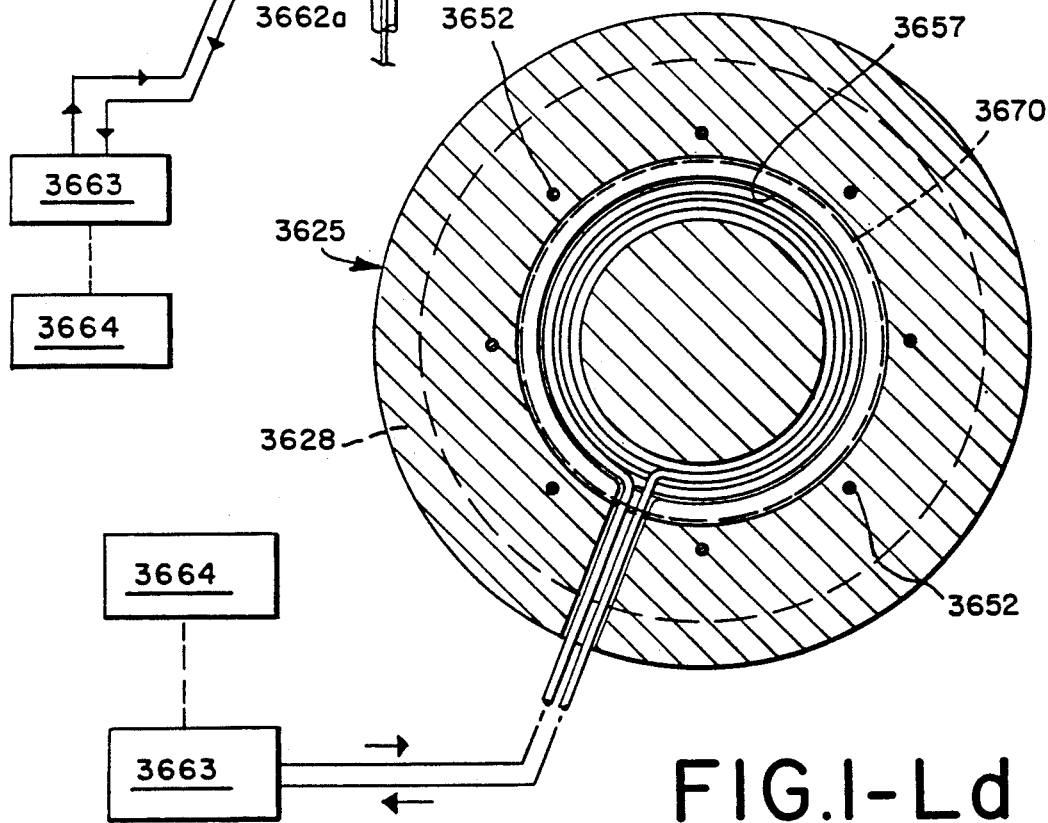
FIG.I-Ld

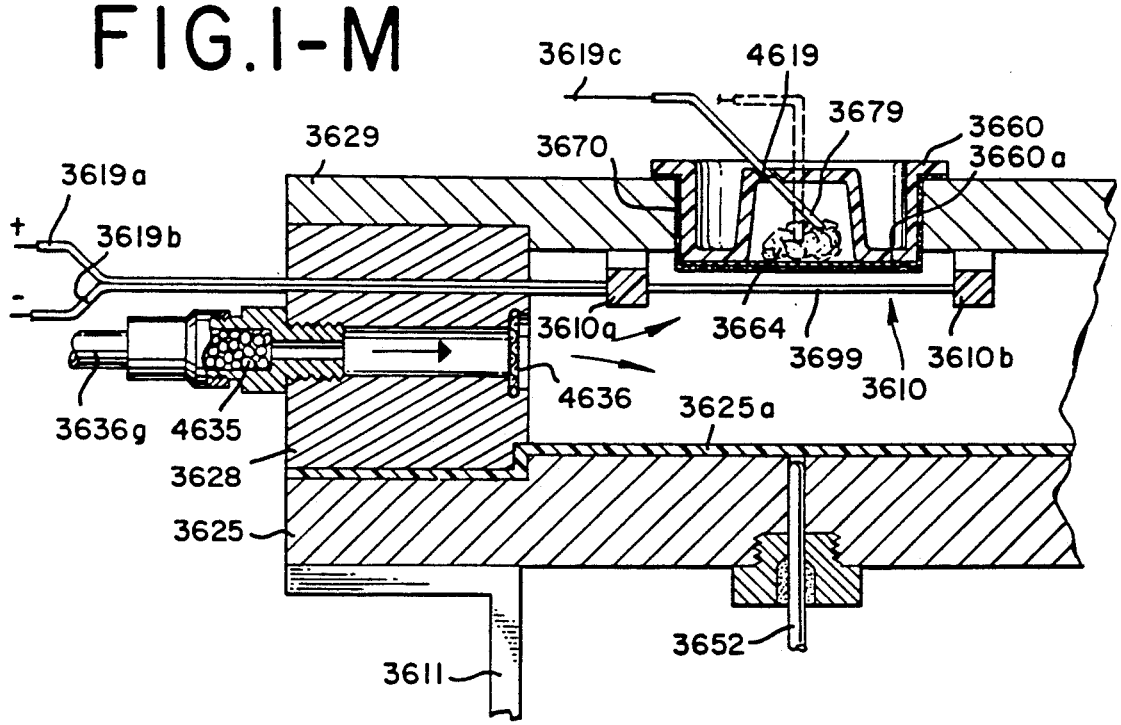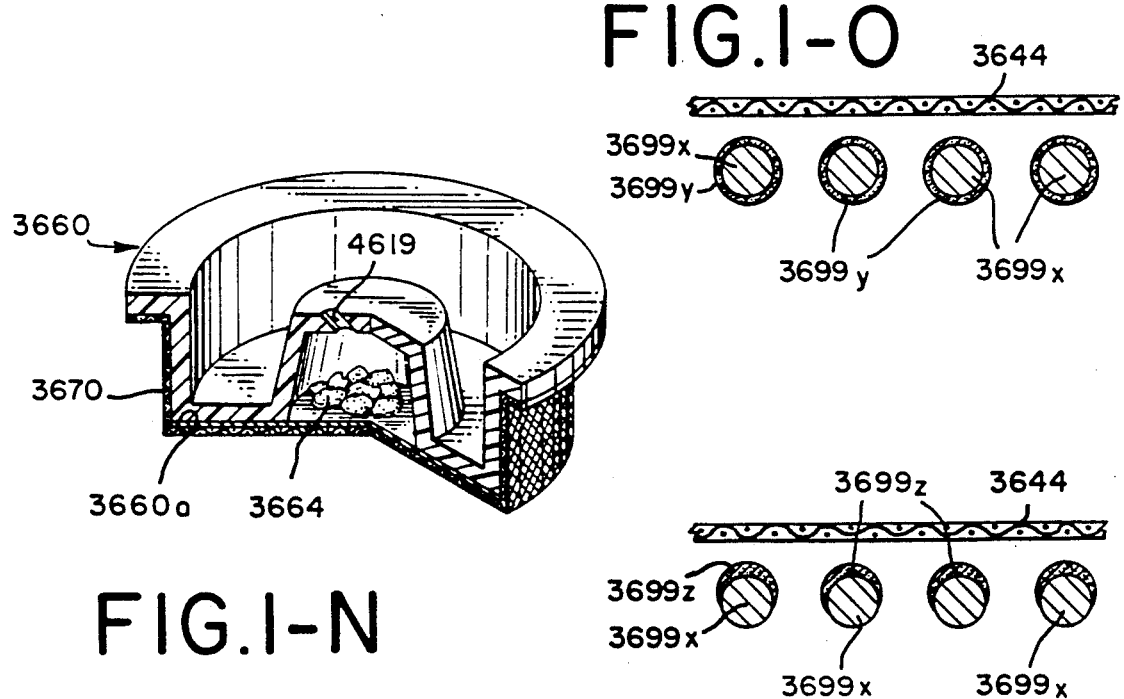

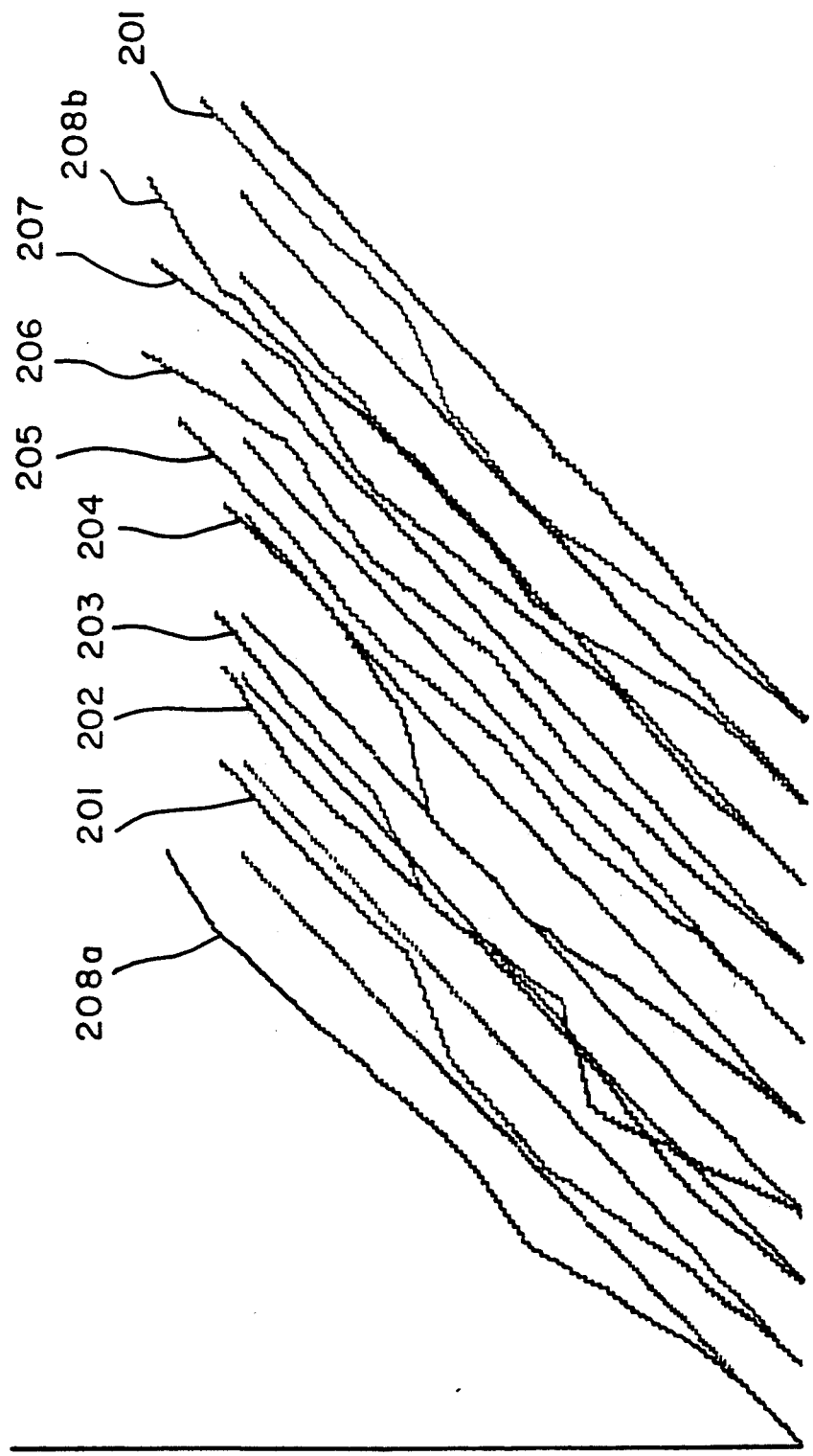
FIG.2-A

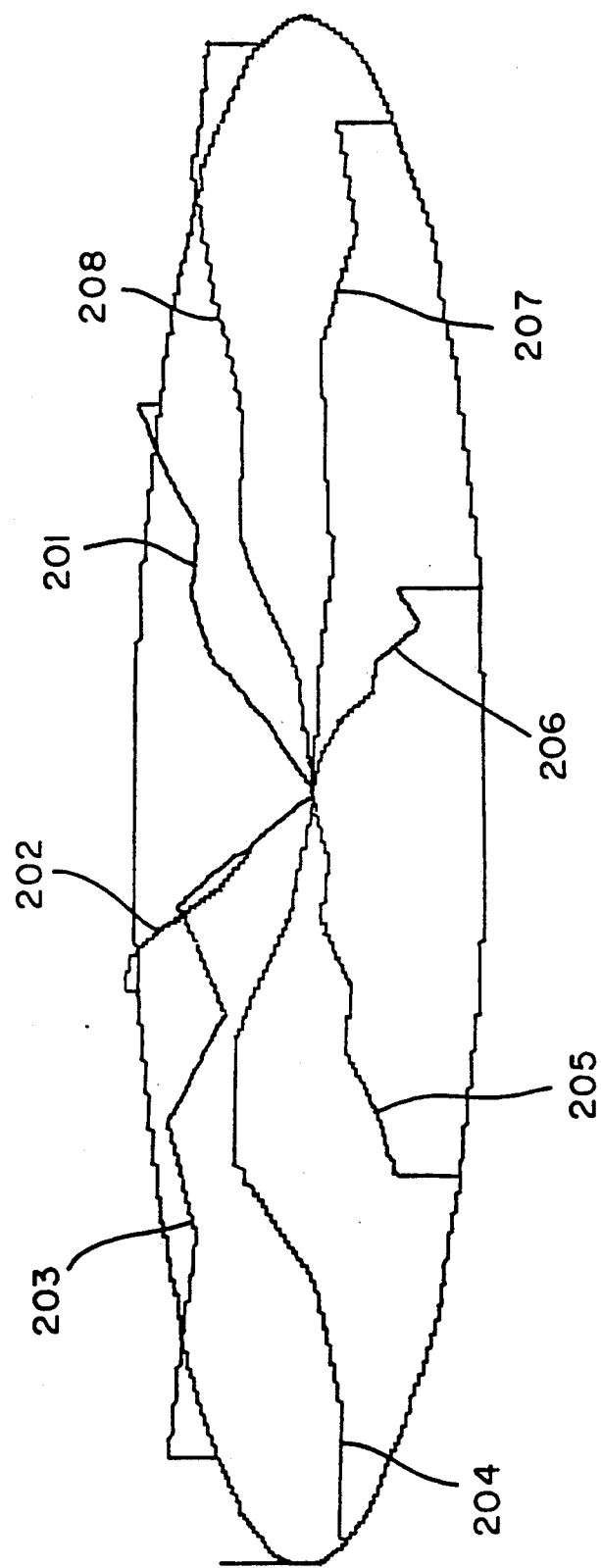
FIG.2-B

FIG.2-C
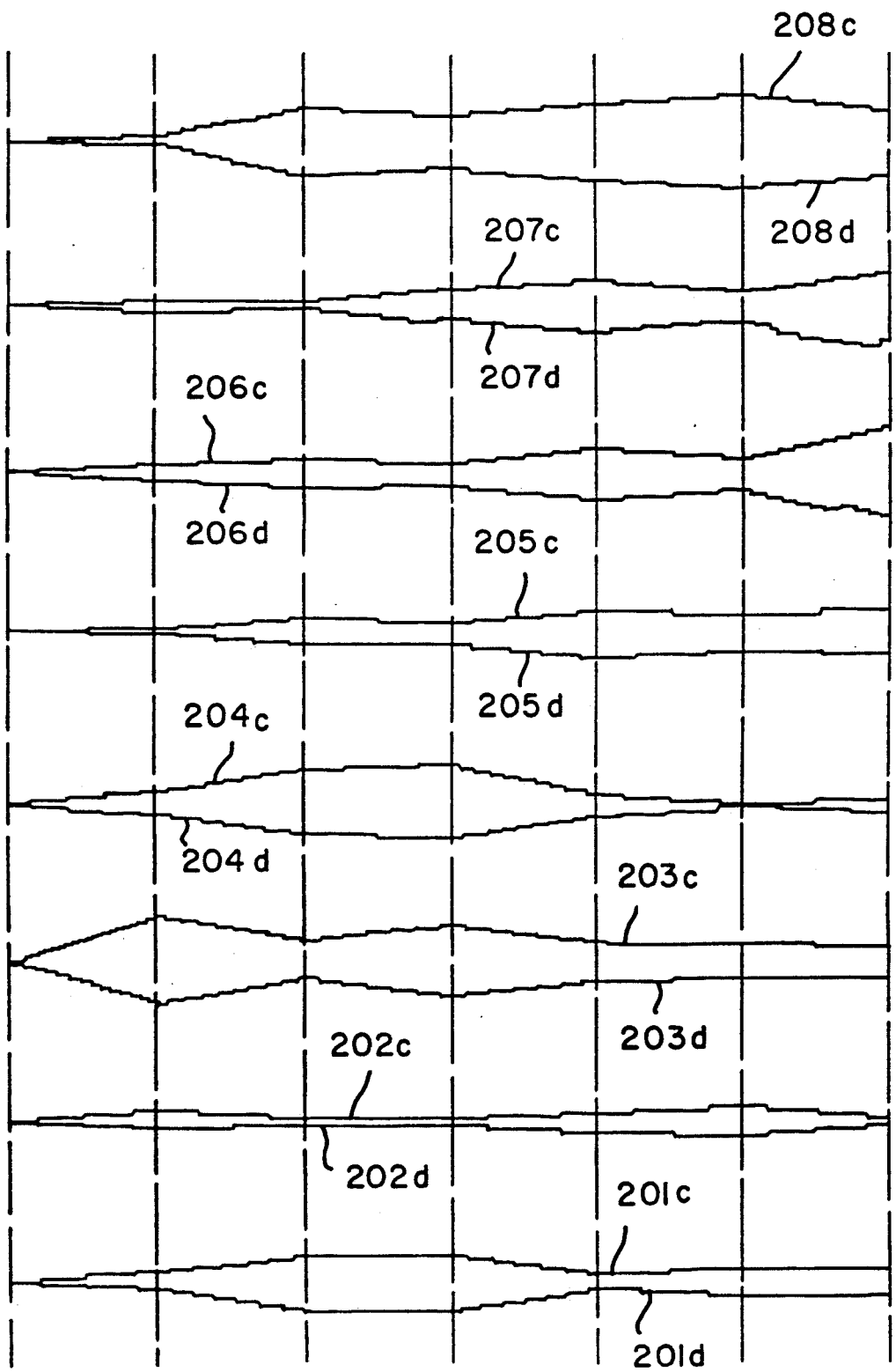

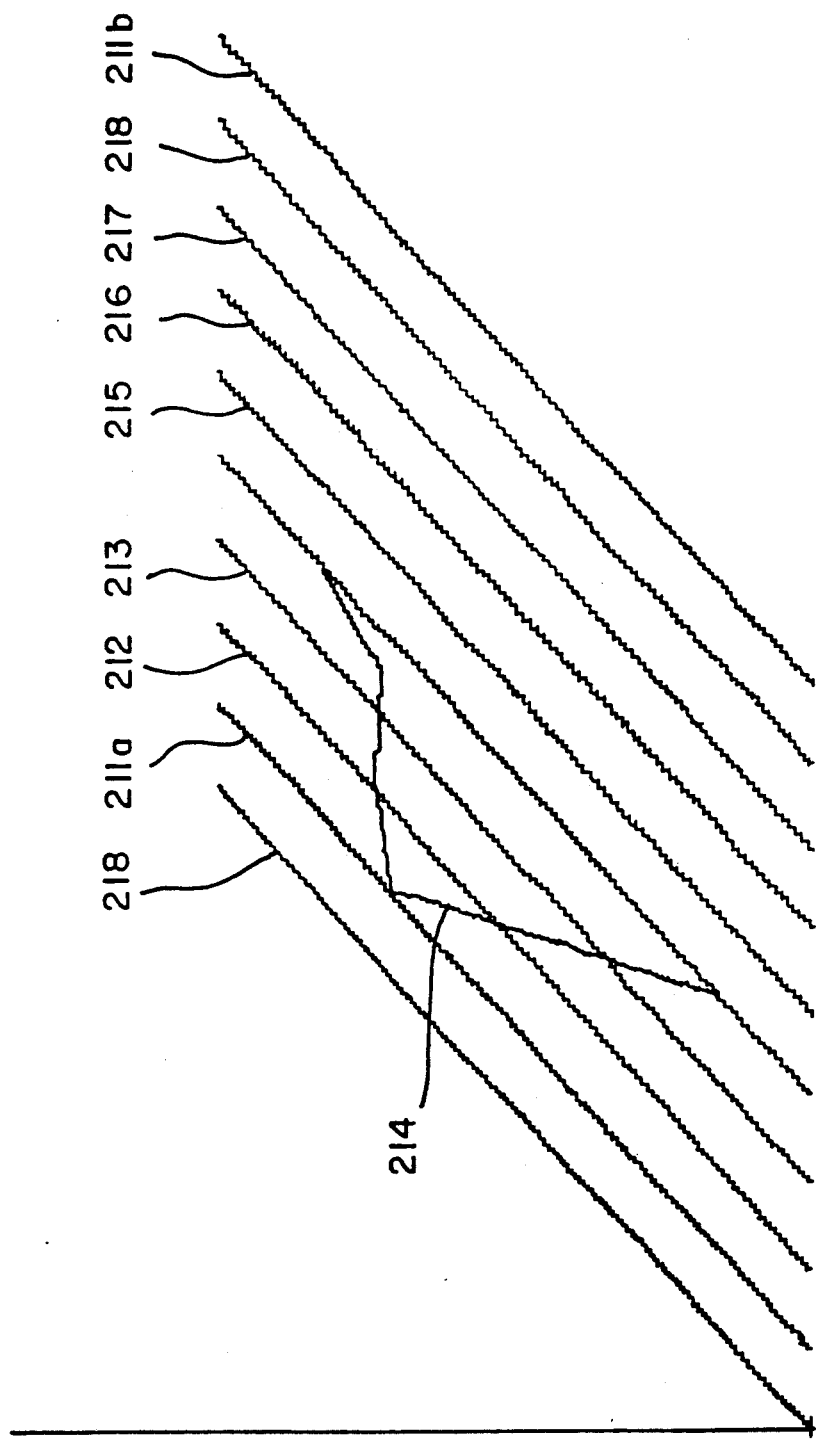

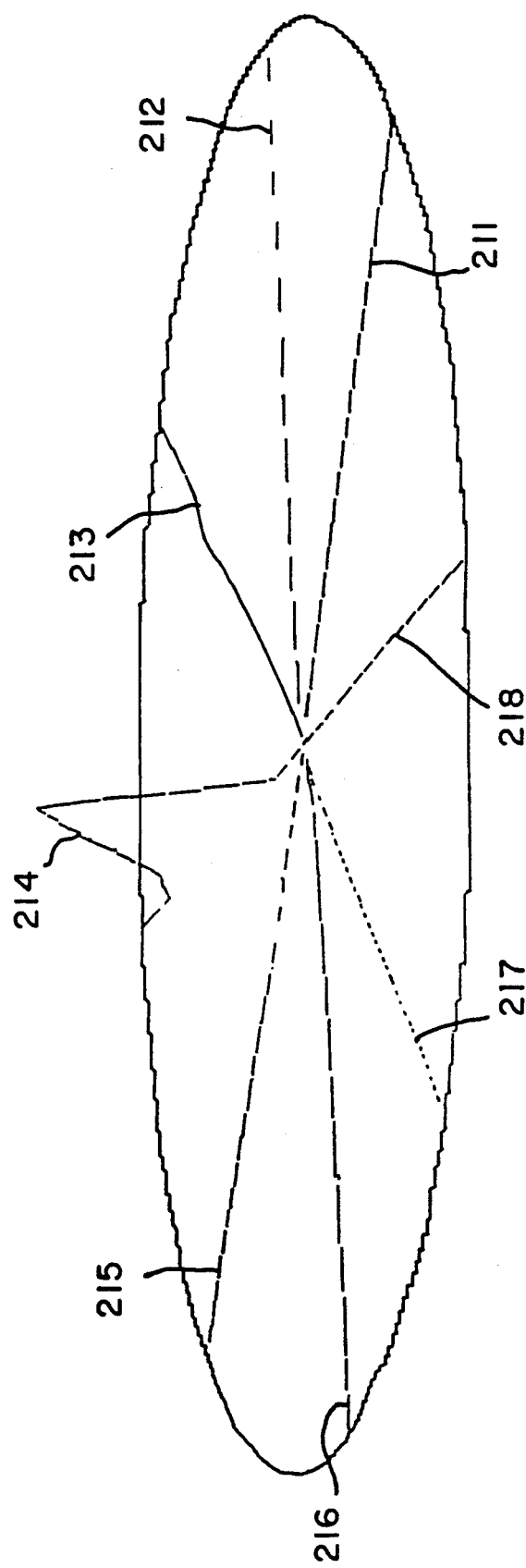
FIG.3-B

FIG.3-C
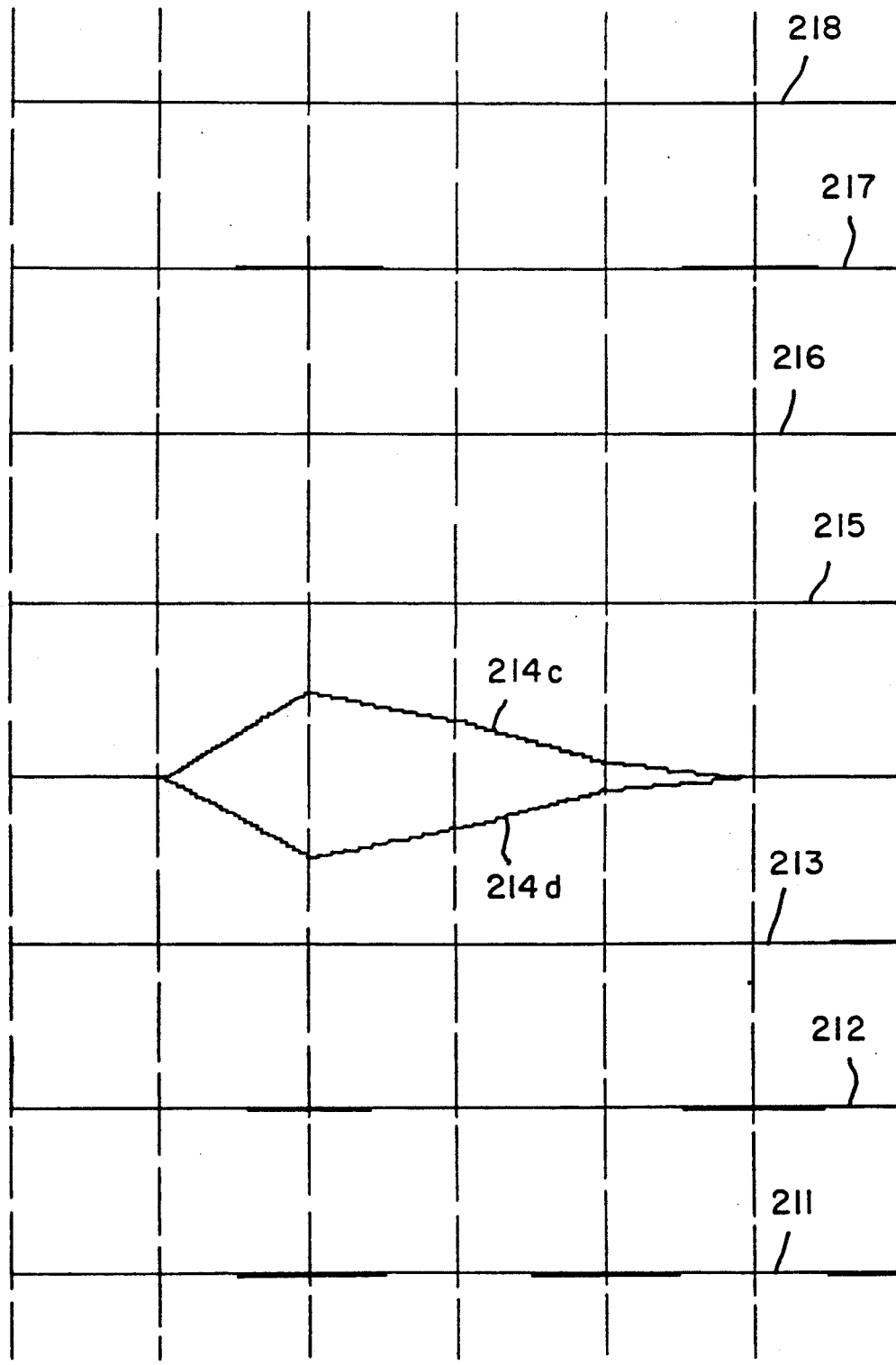

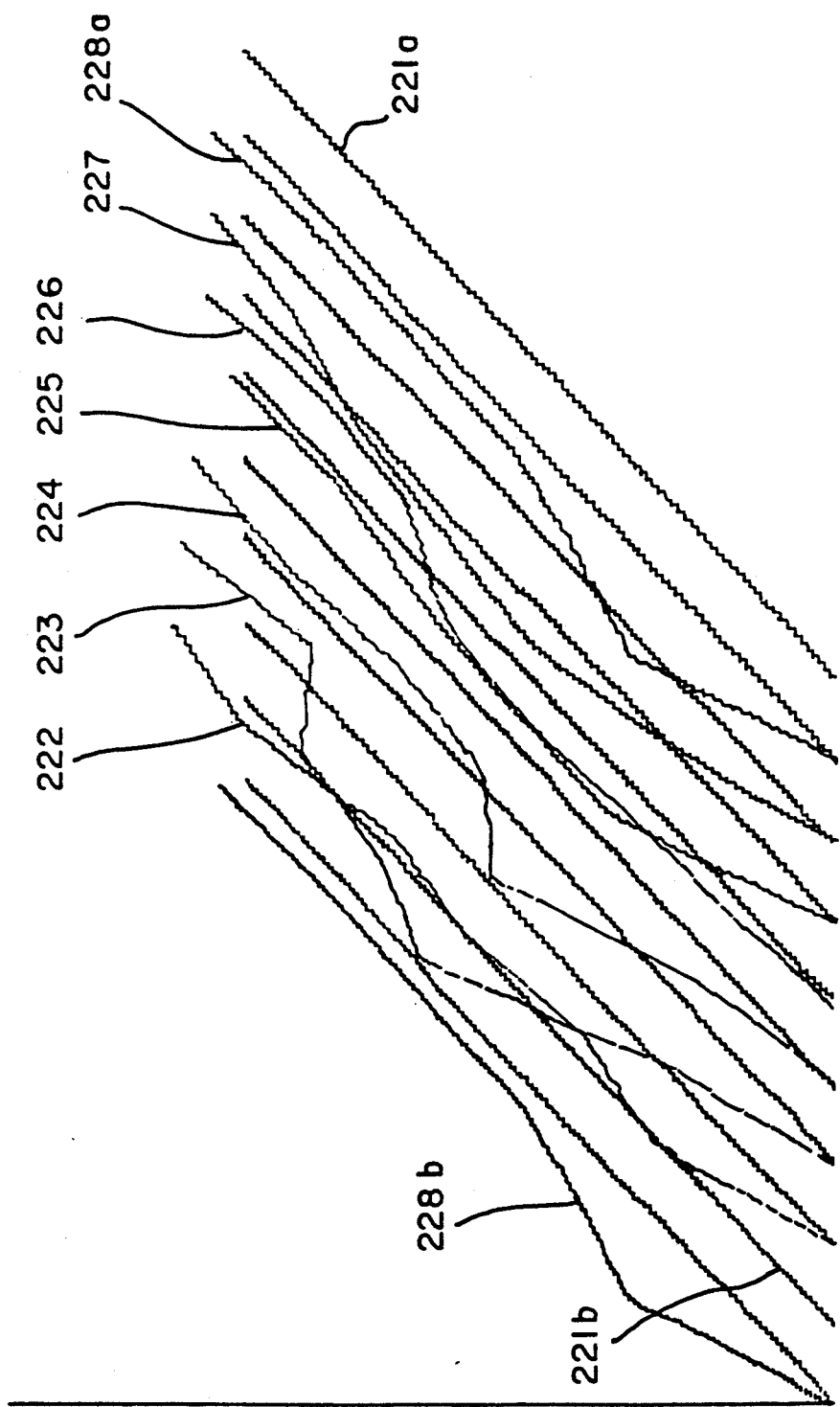
FIG.4-A

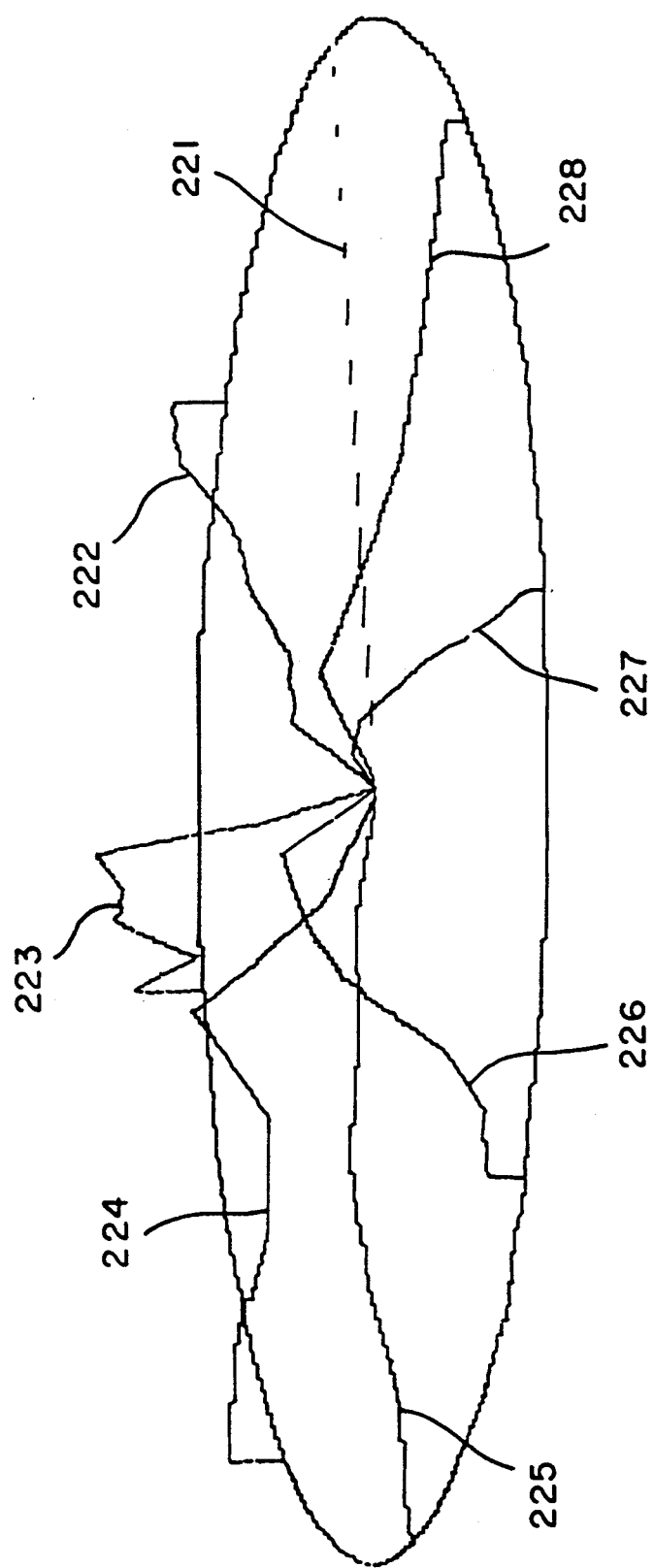
FIG. 4-B

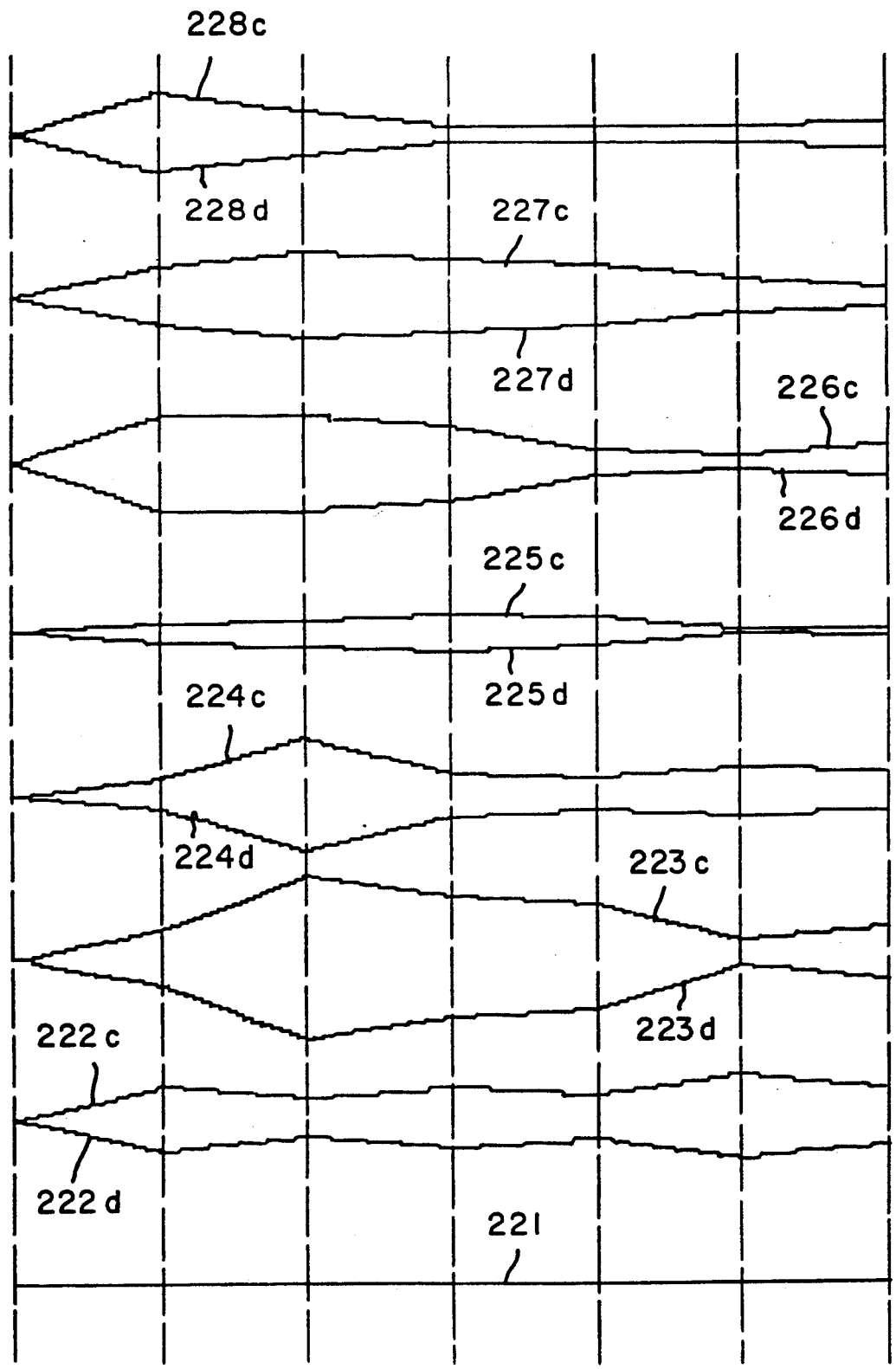
FIG. 4-C

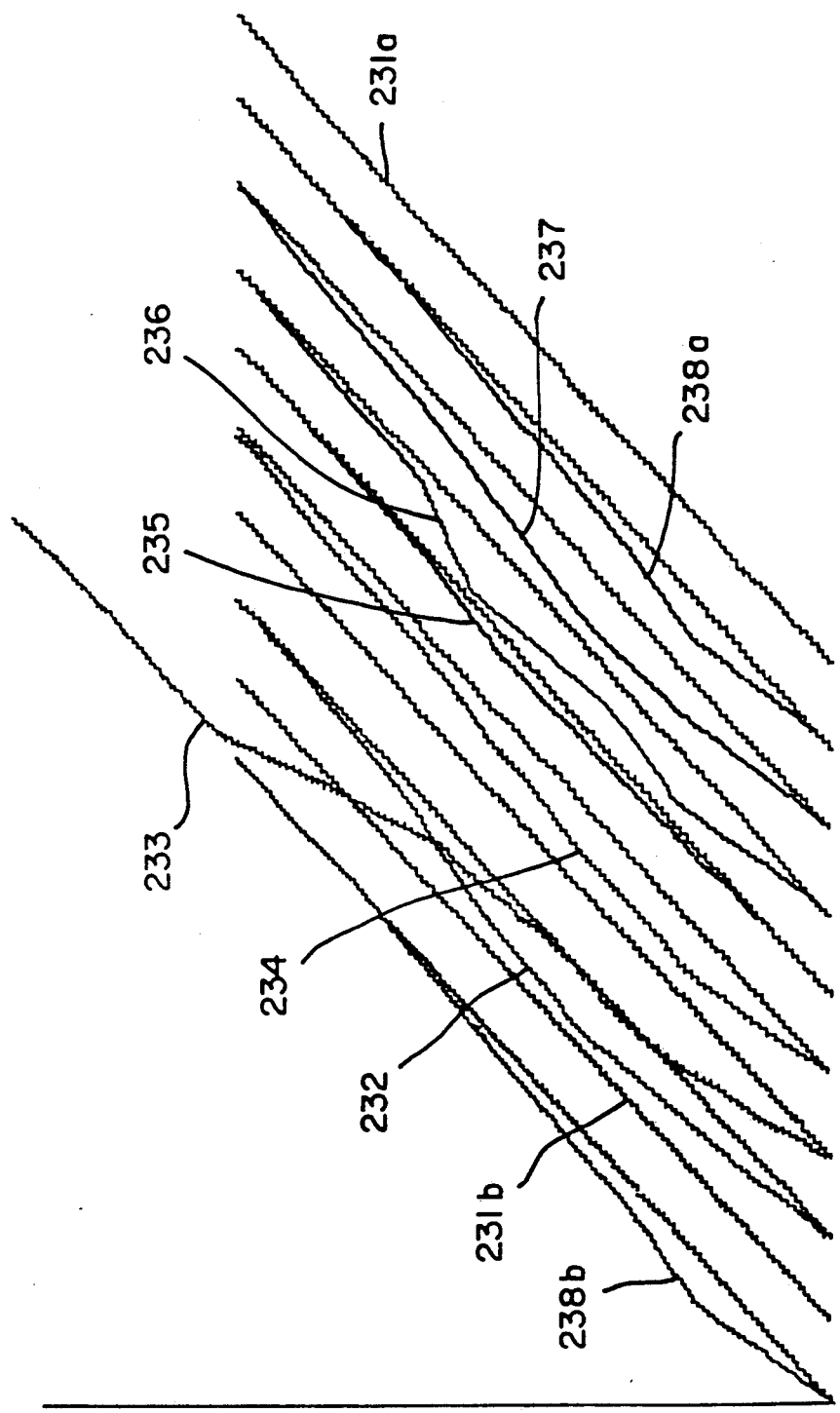

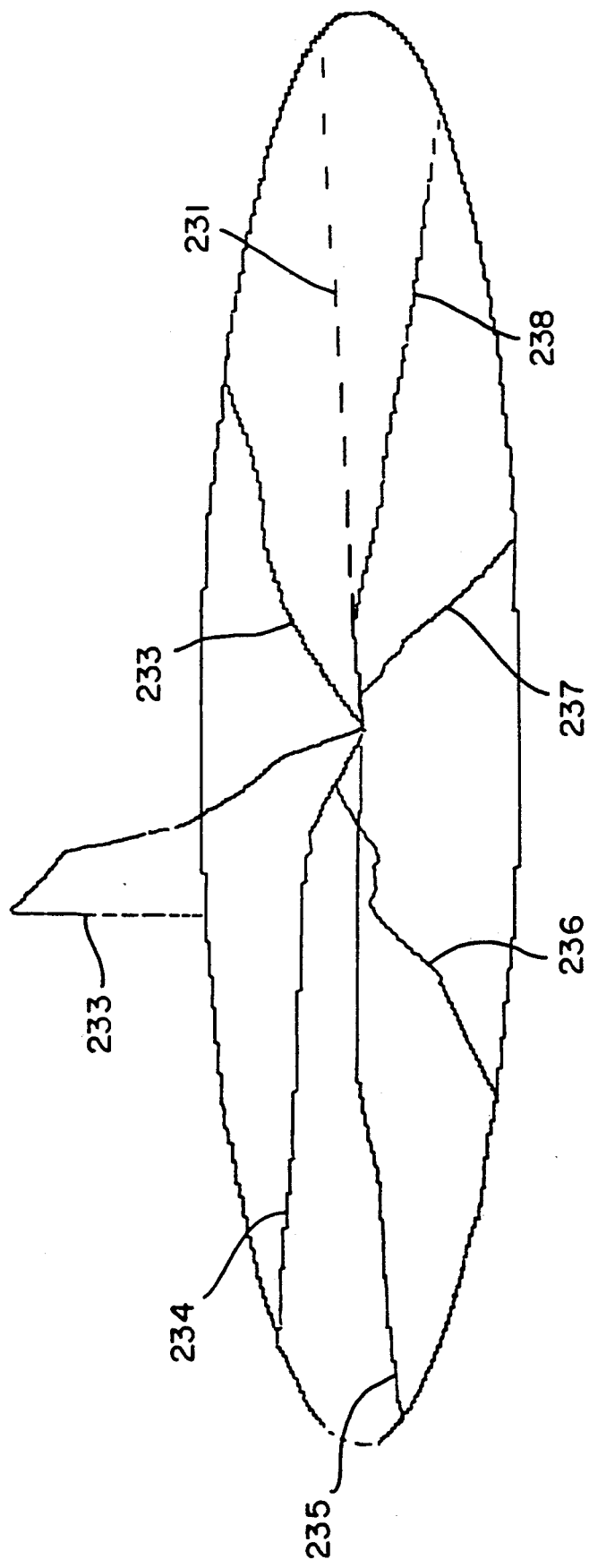

FIG.5-C
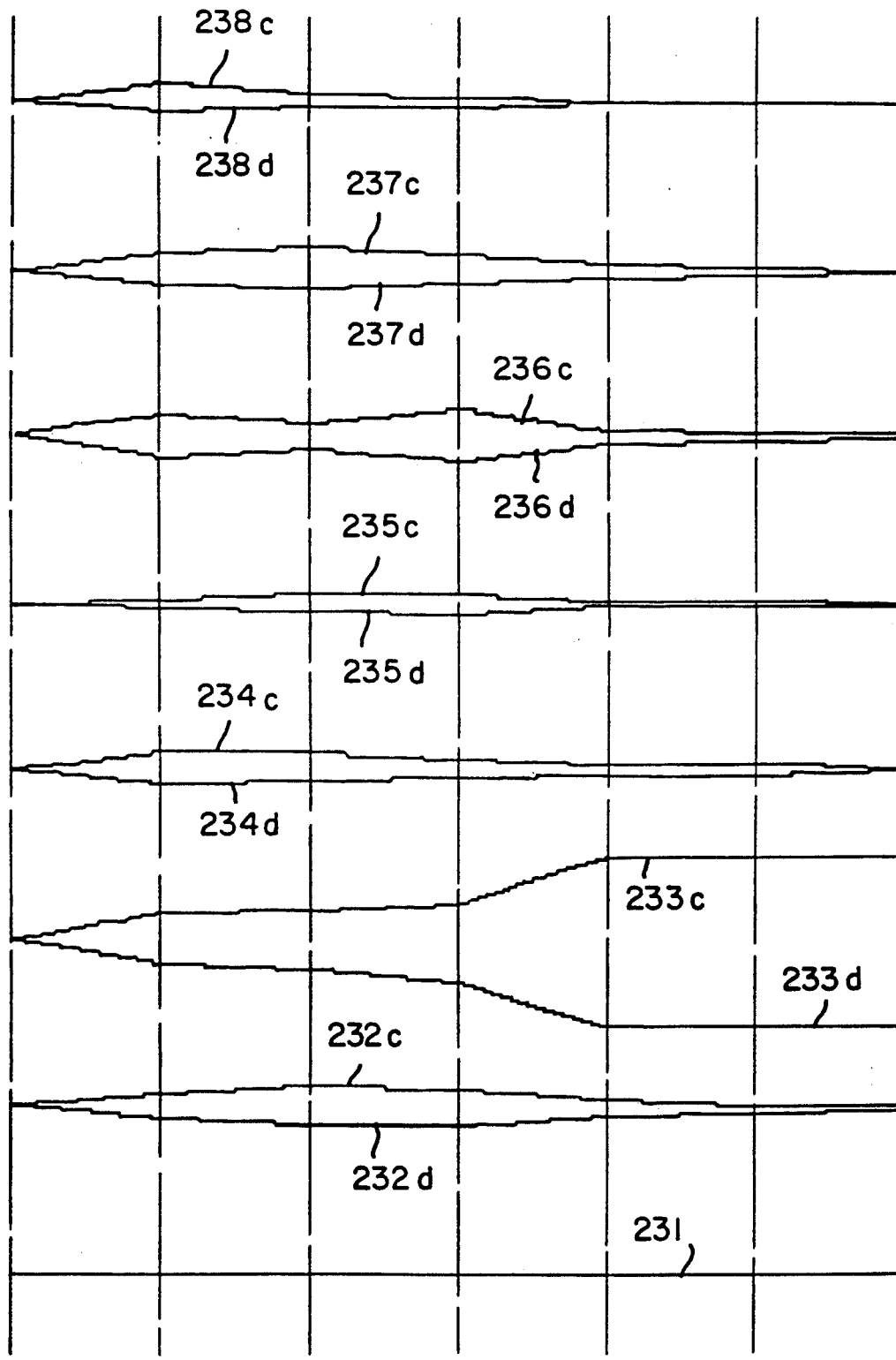

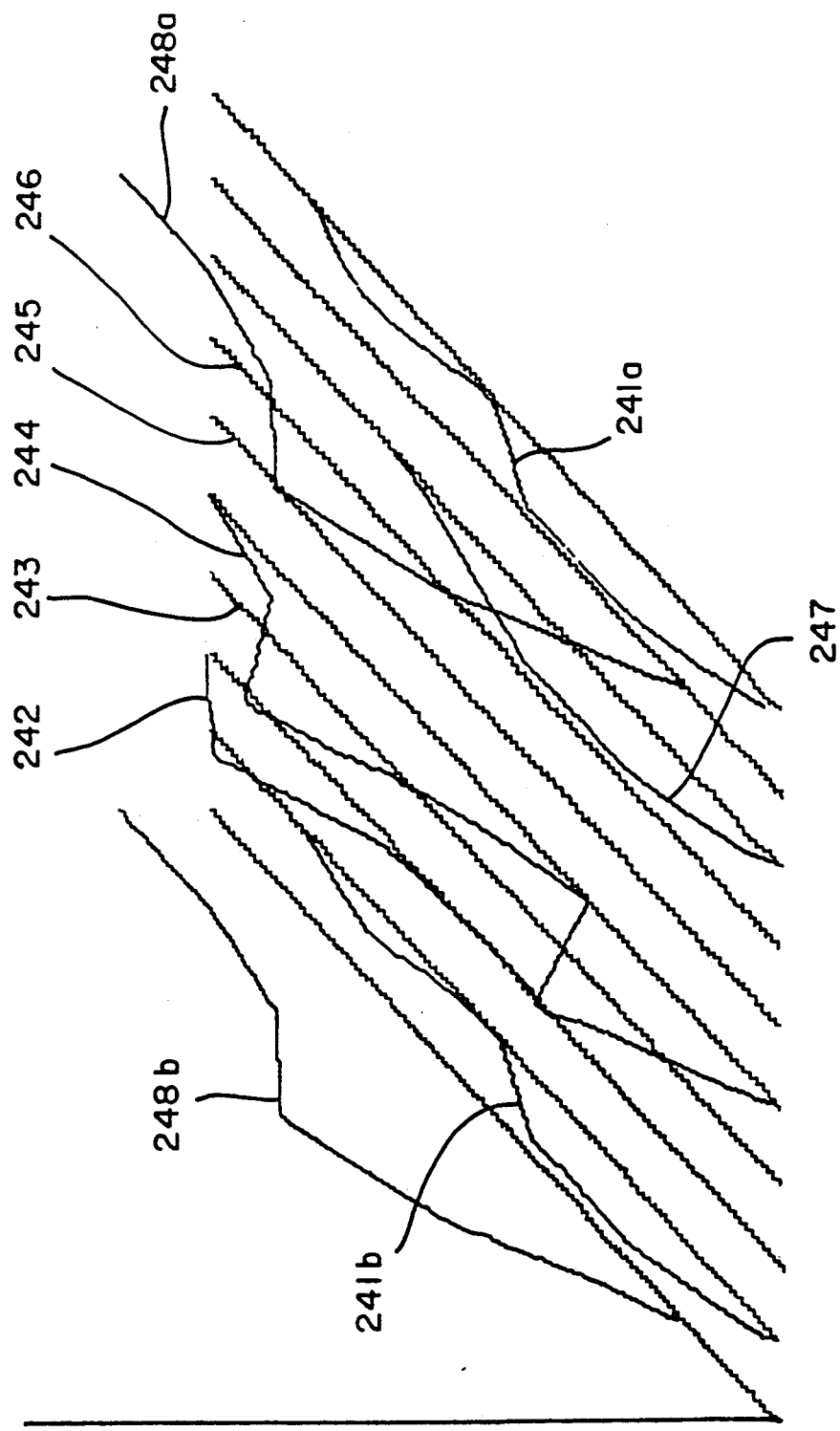
FIG.6-A

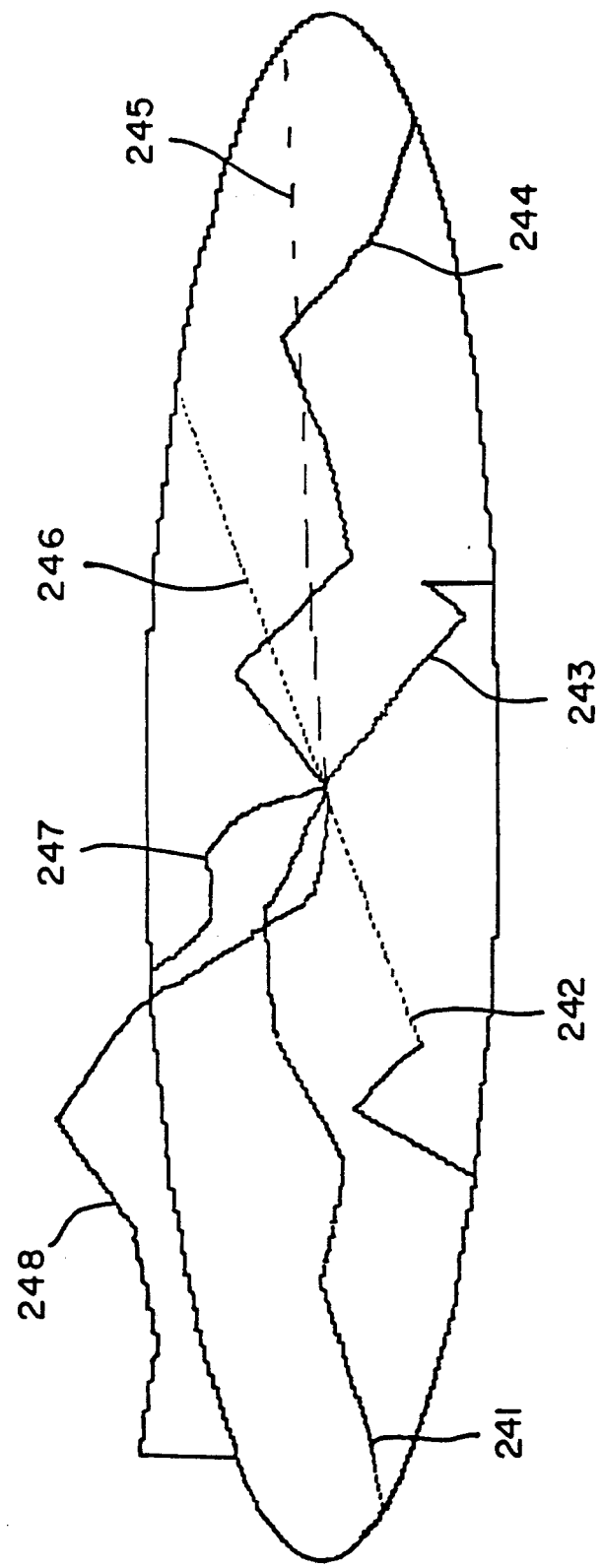
FIG.6-B

FIG.6-C
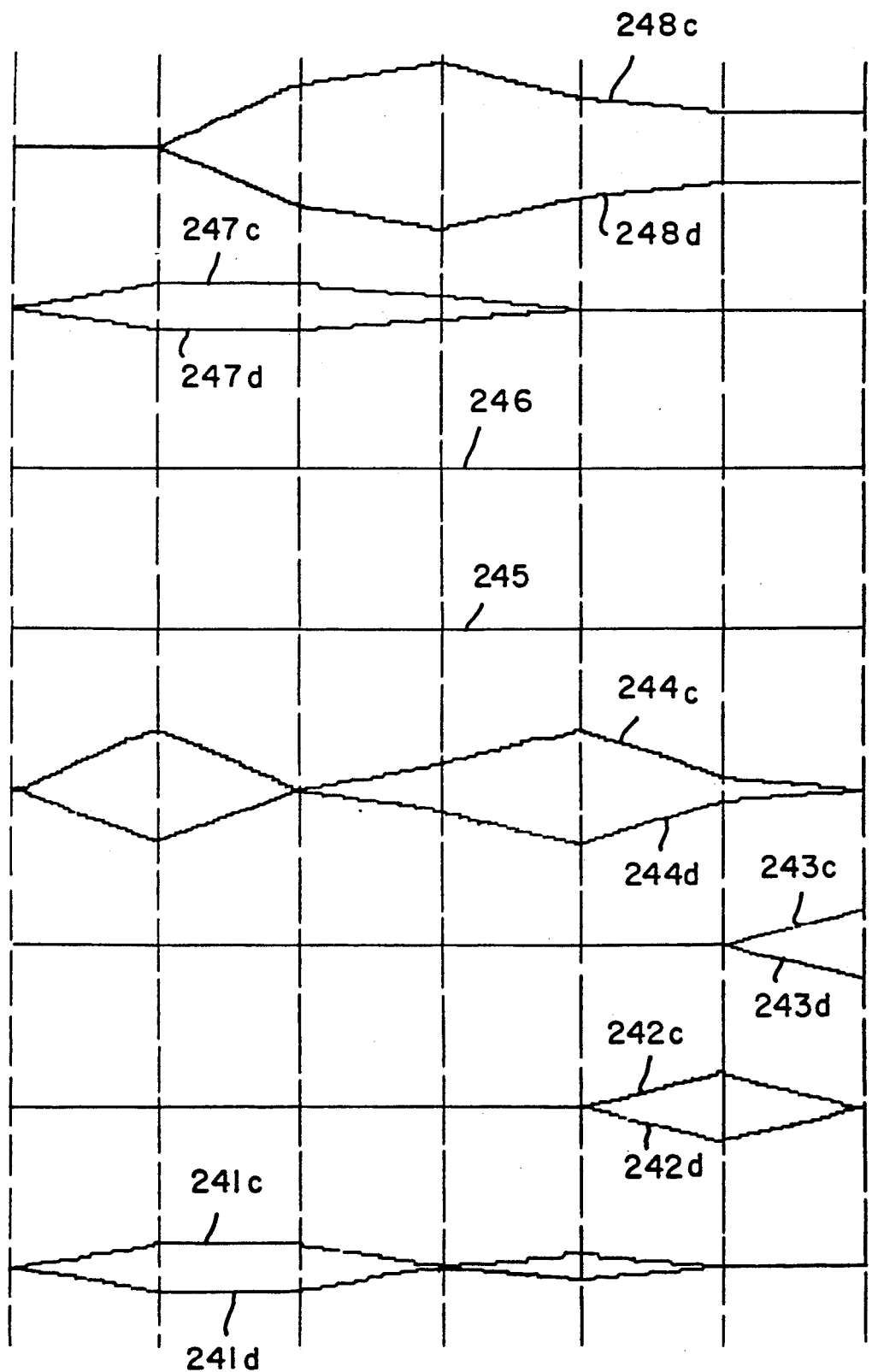

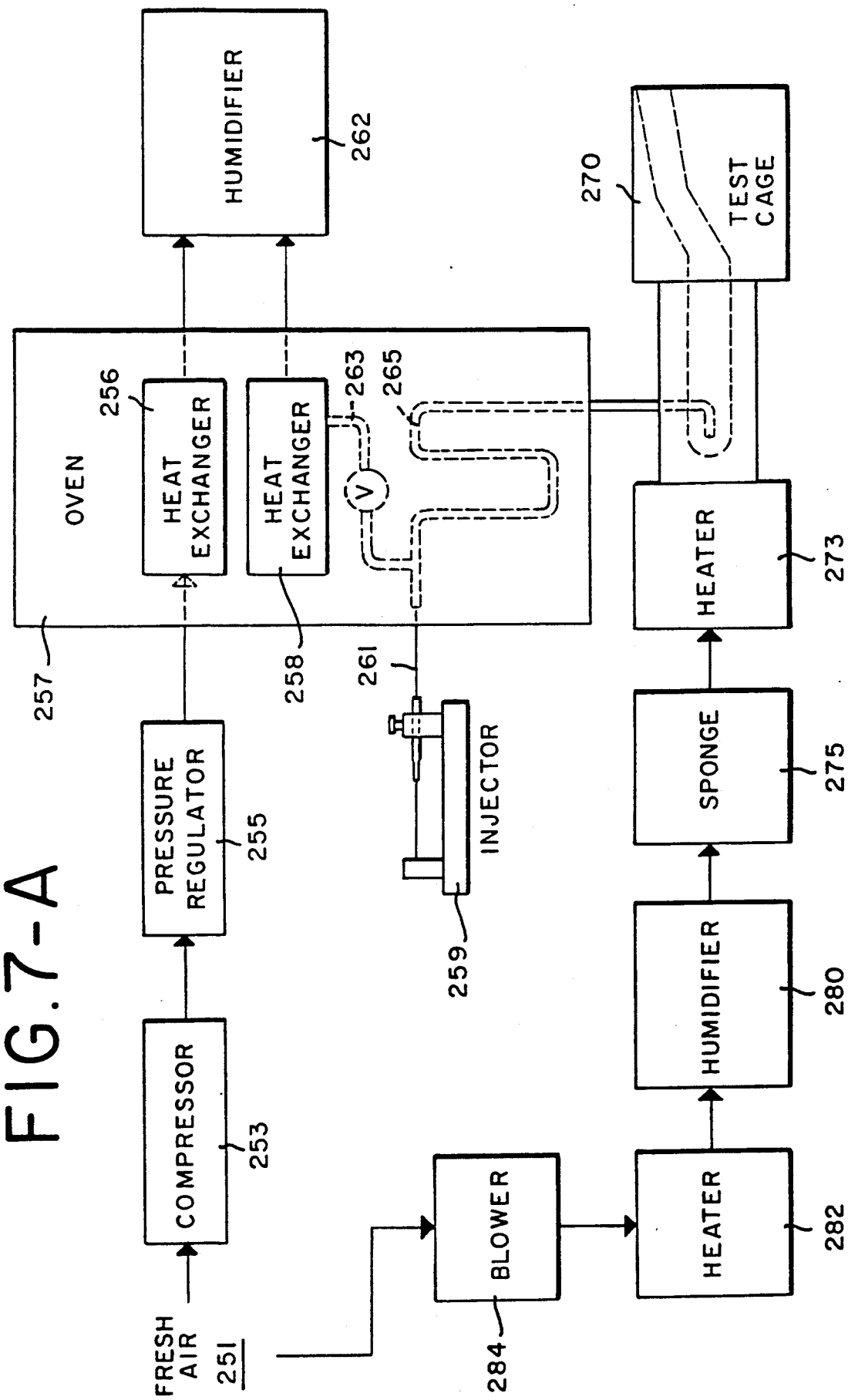

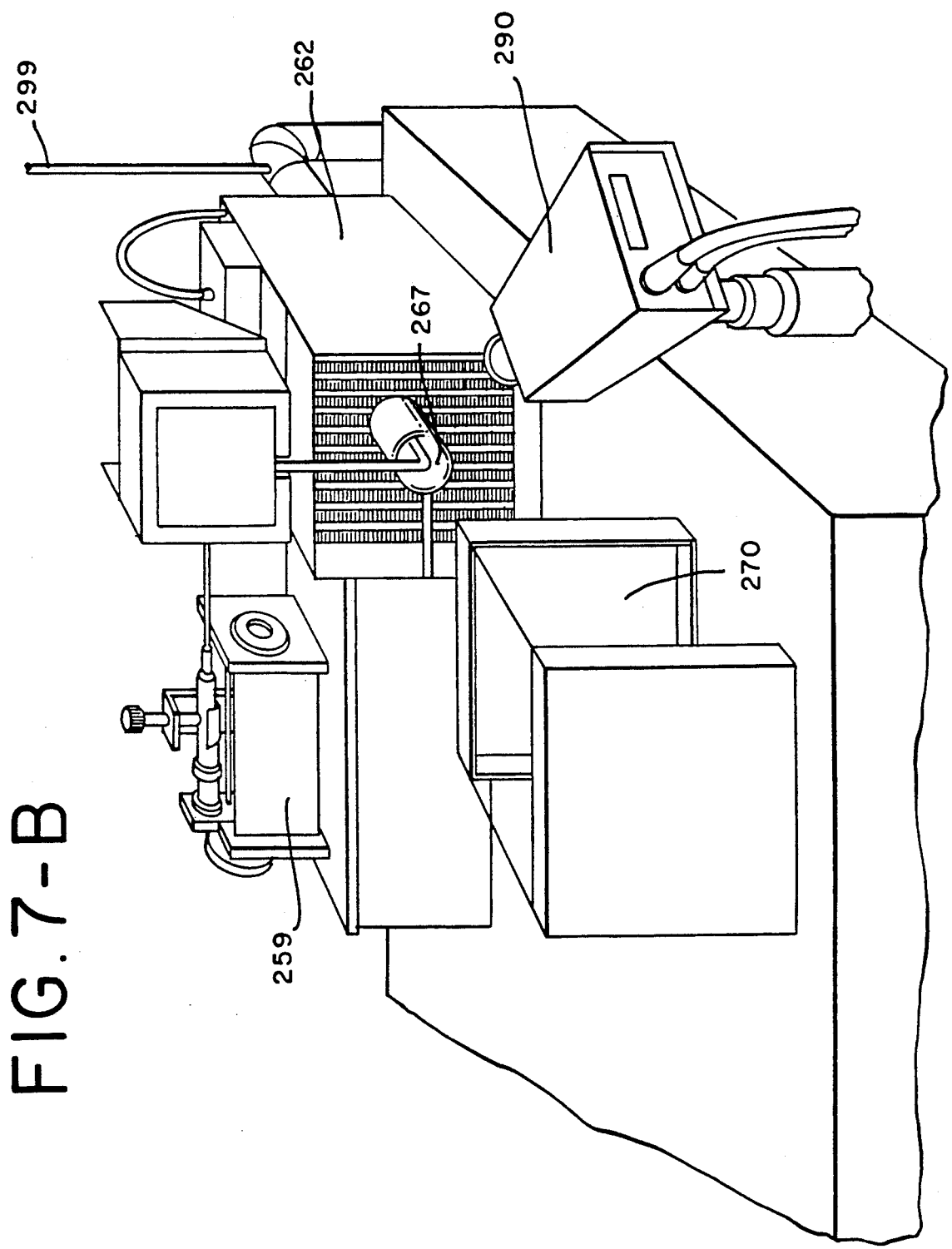
FIG. 7-B

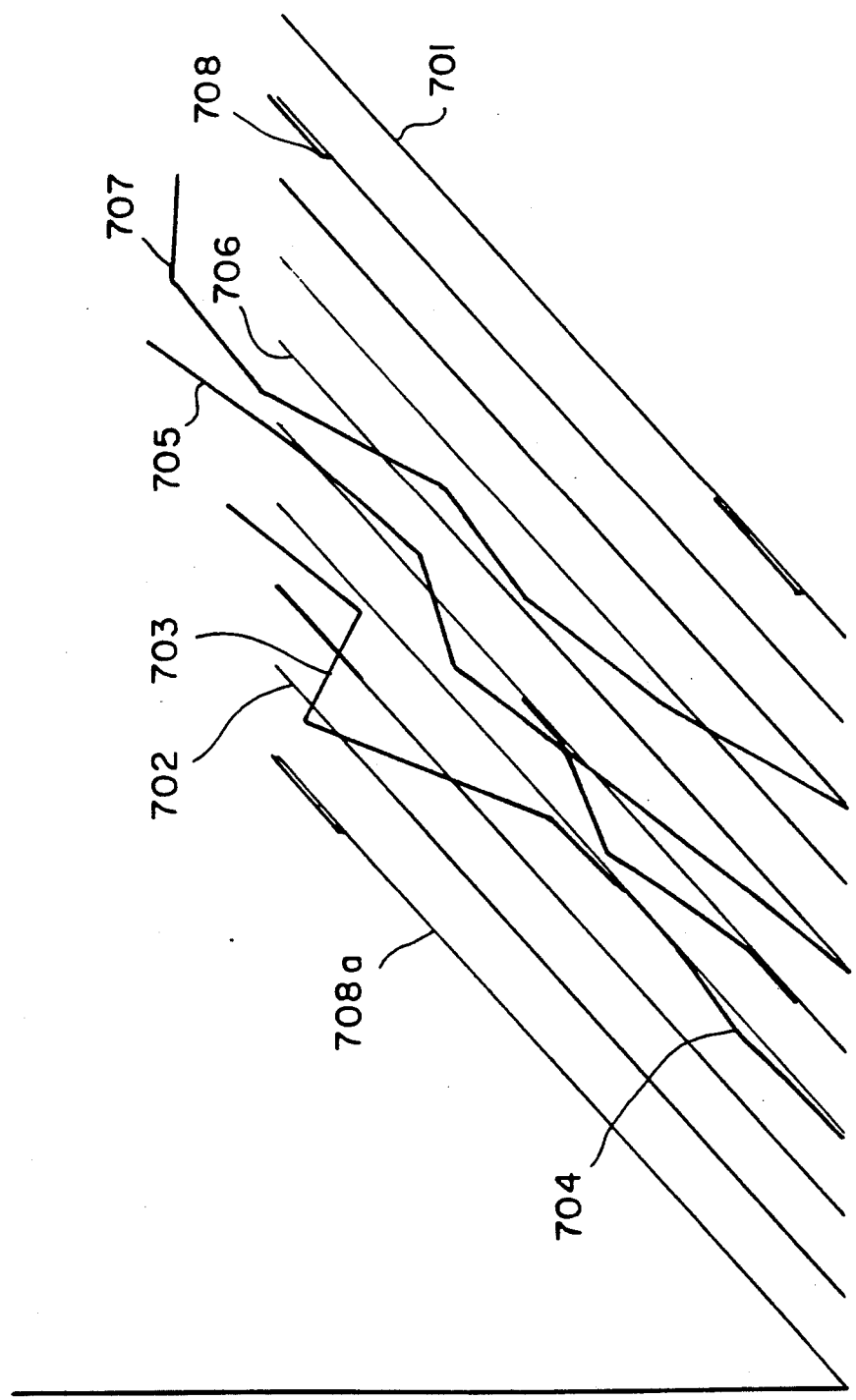
FIG.38-A

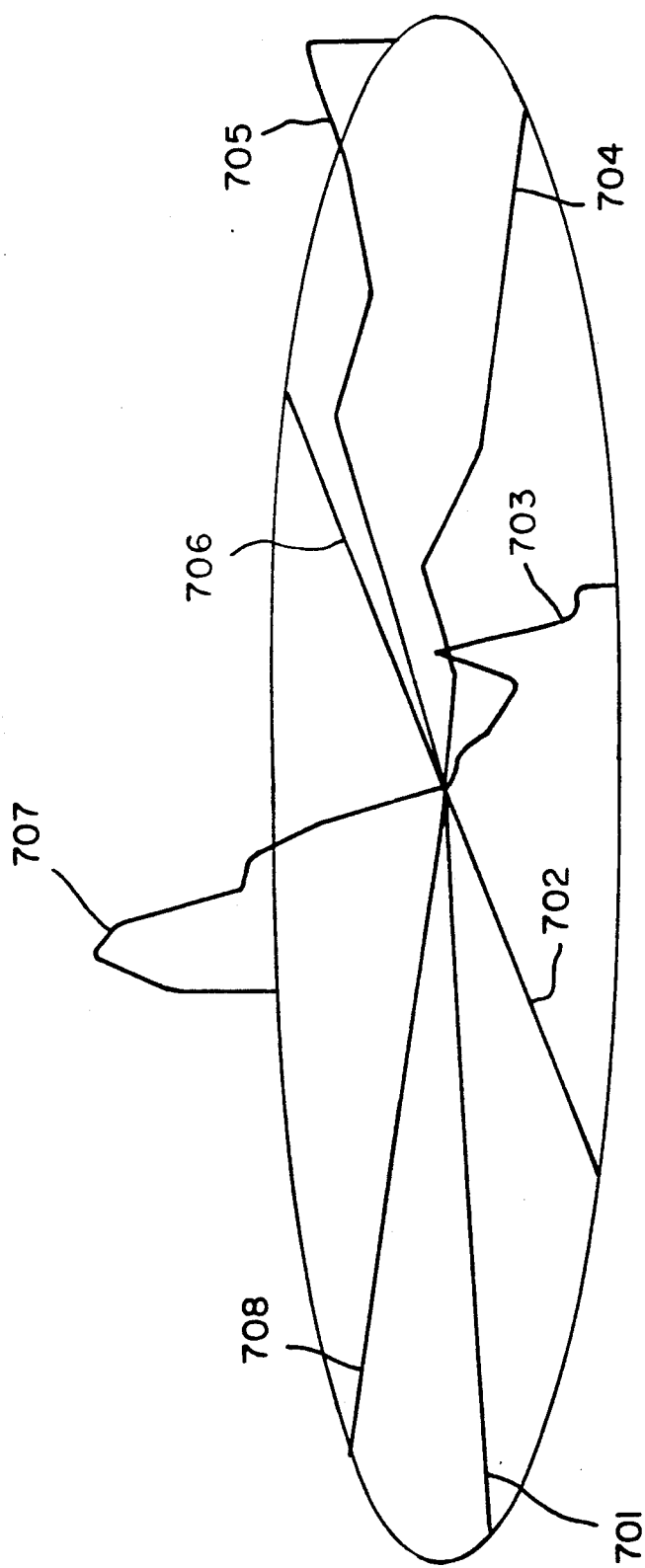
FIG.38-B

FIG.38-C
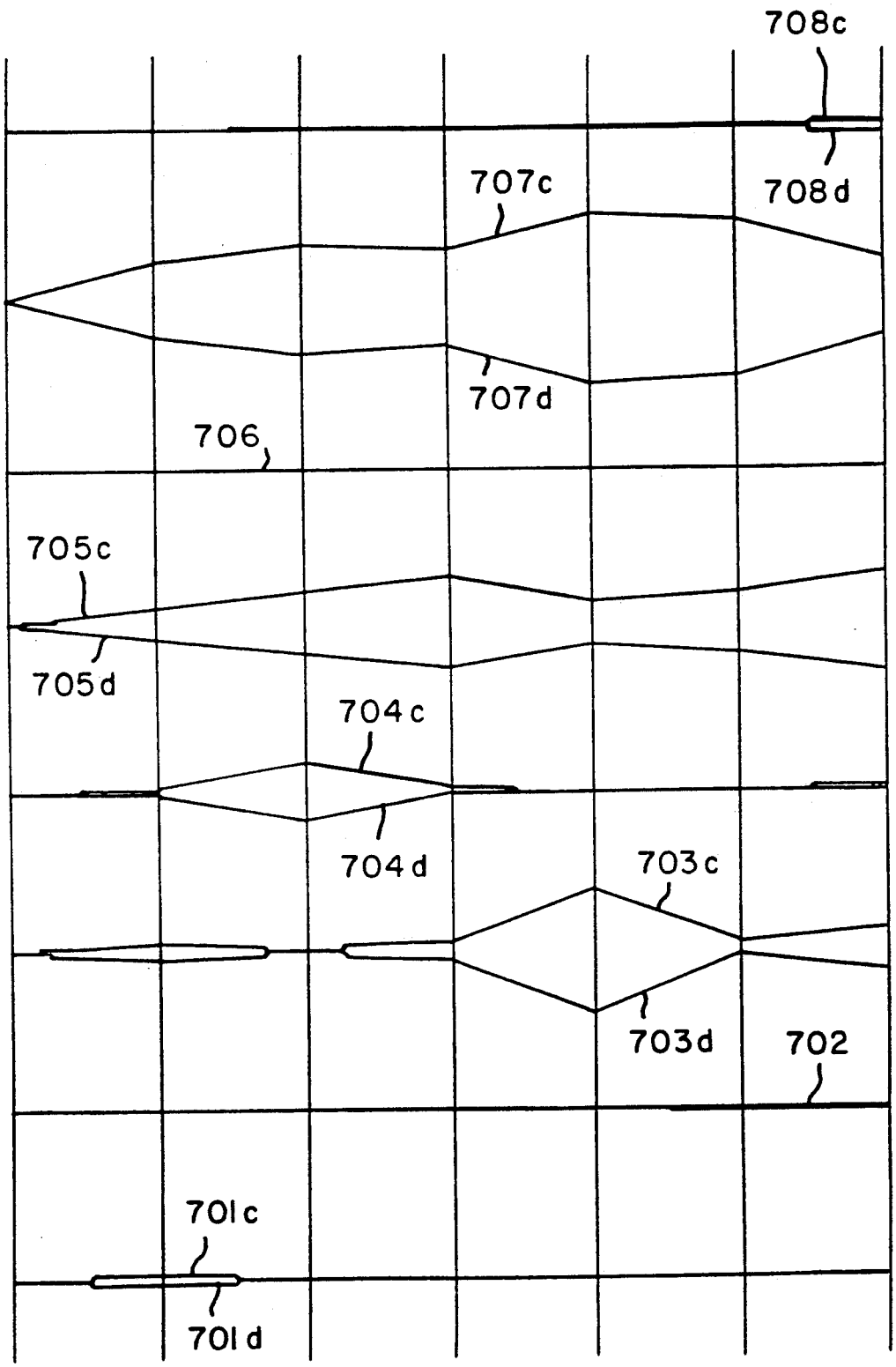

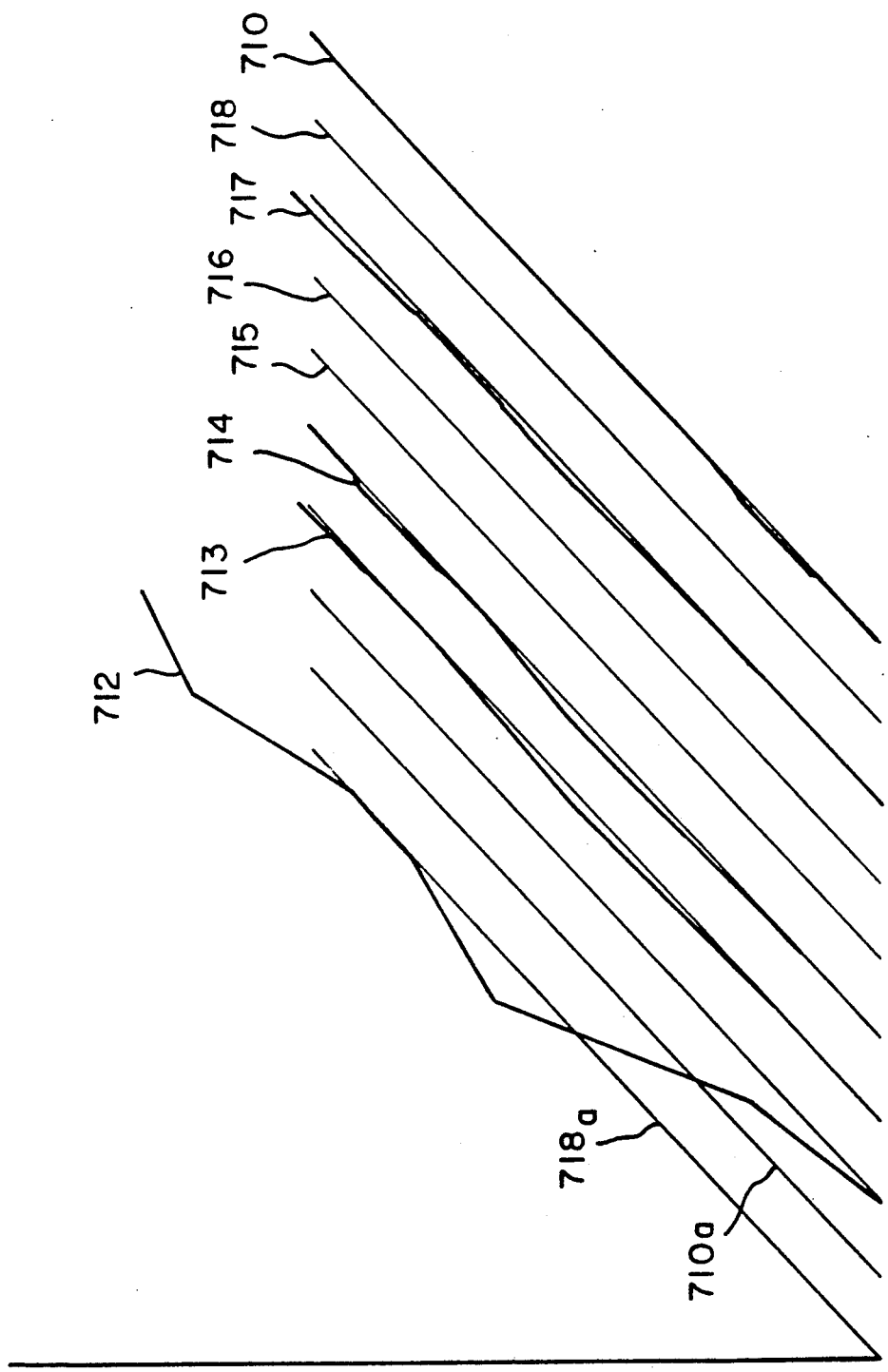
FIG.39-A

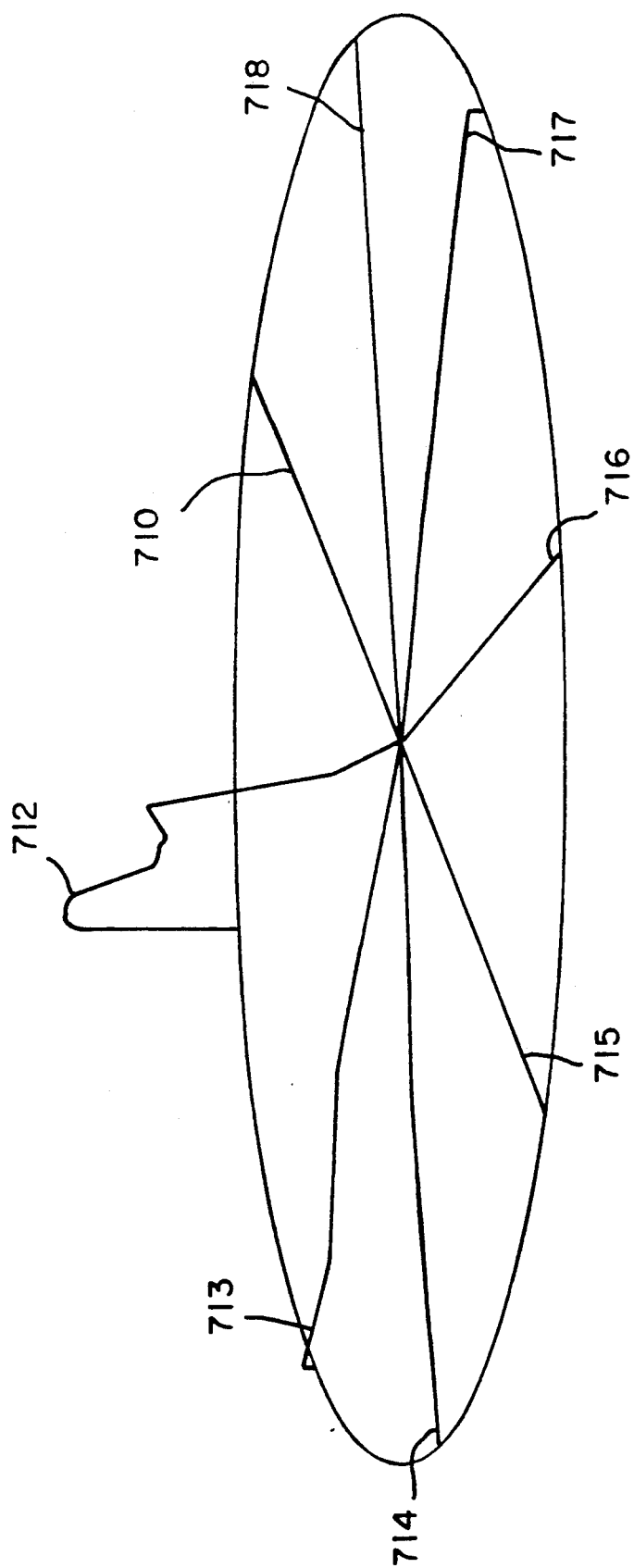
FIG.39-B

FIG. 39-C
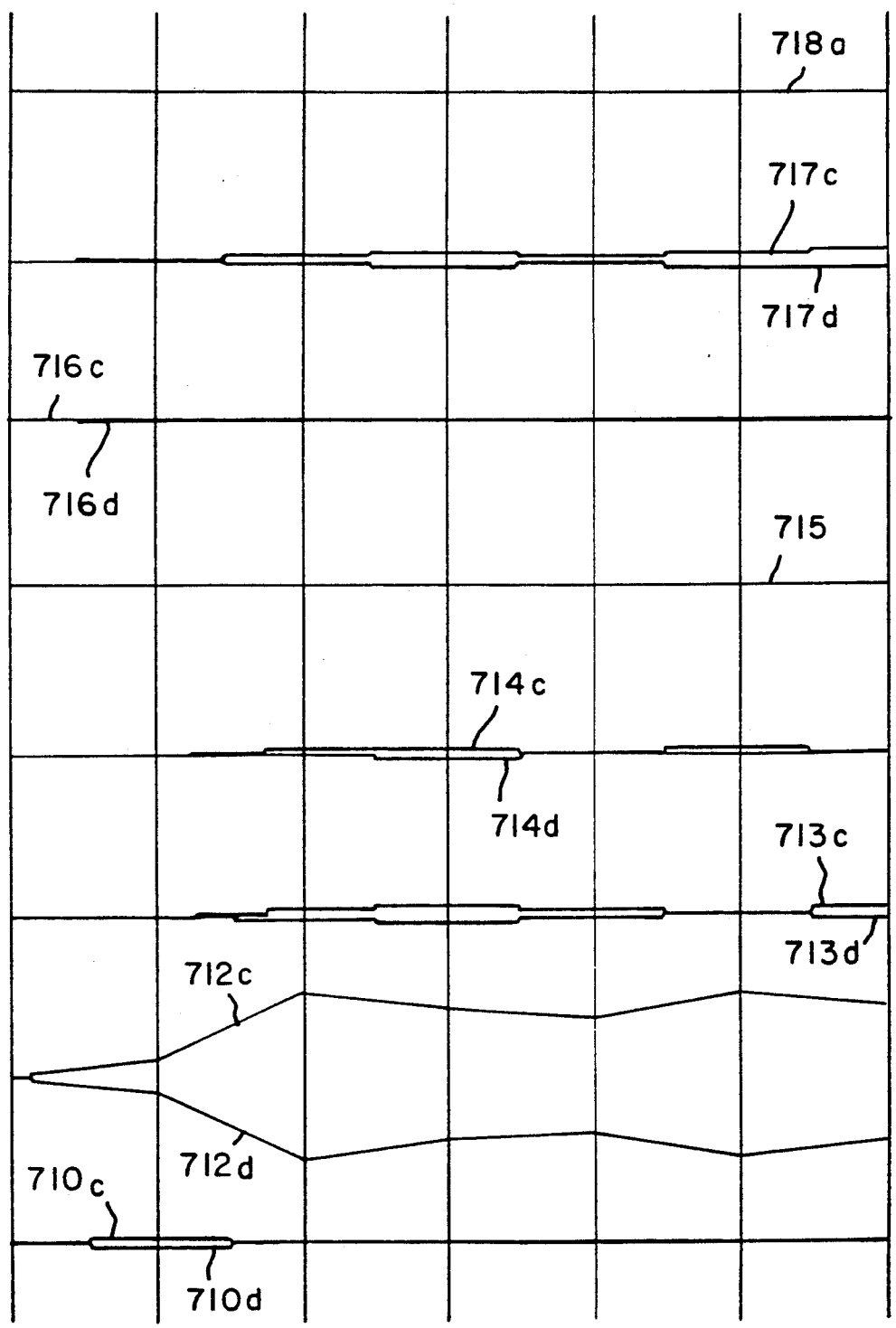

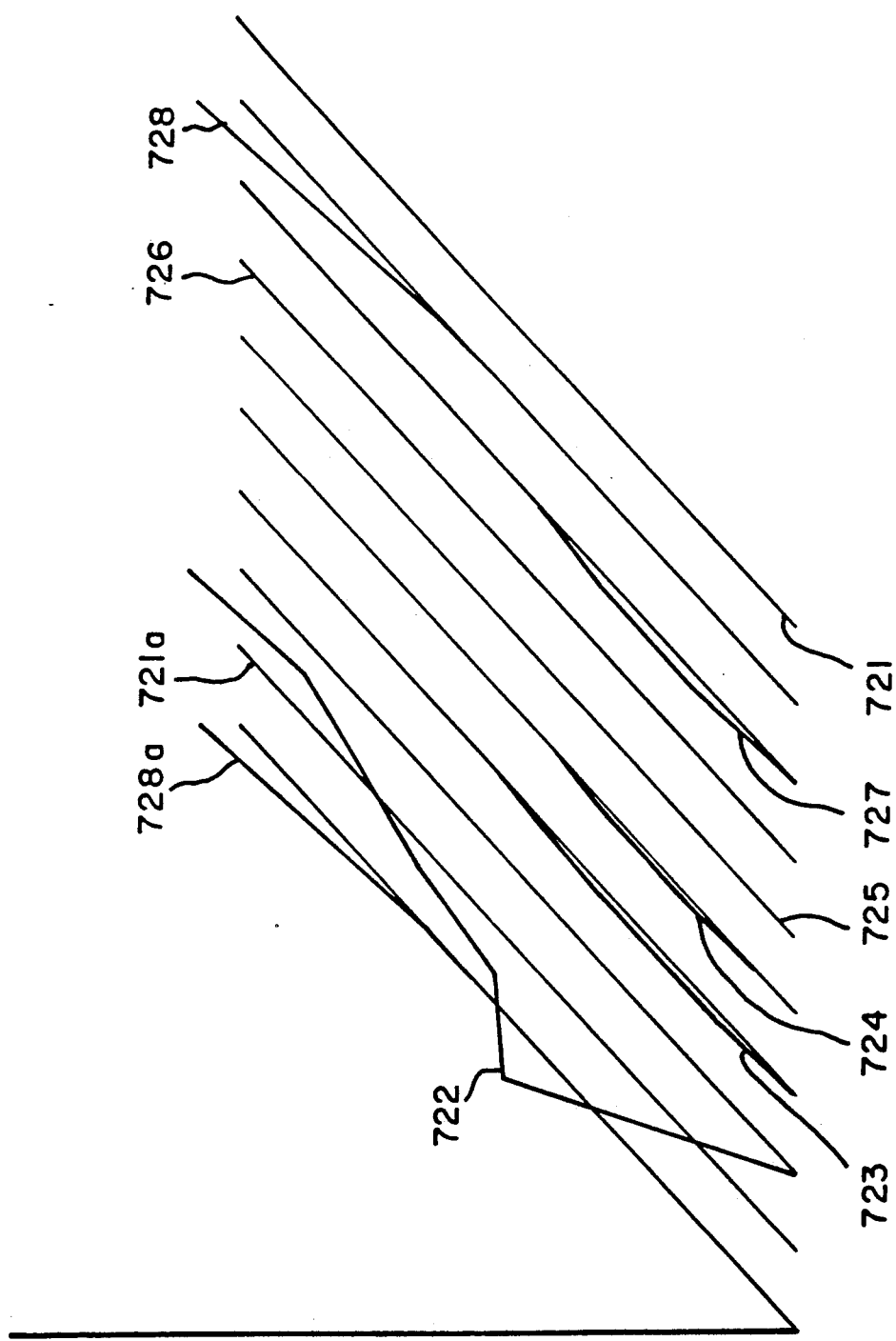
FIG.40-A

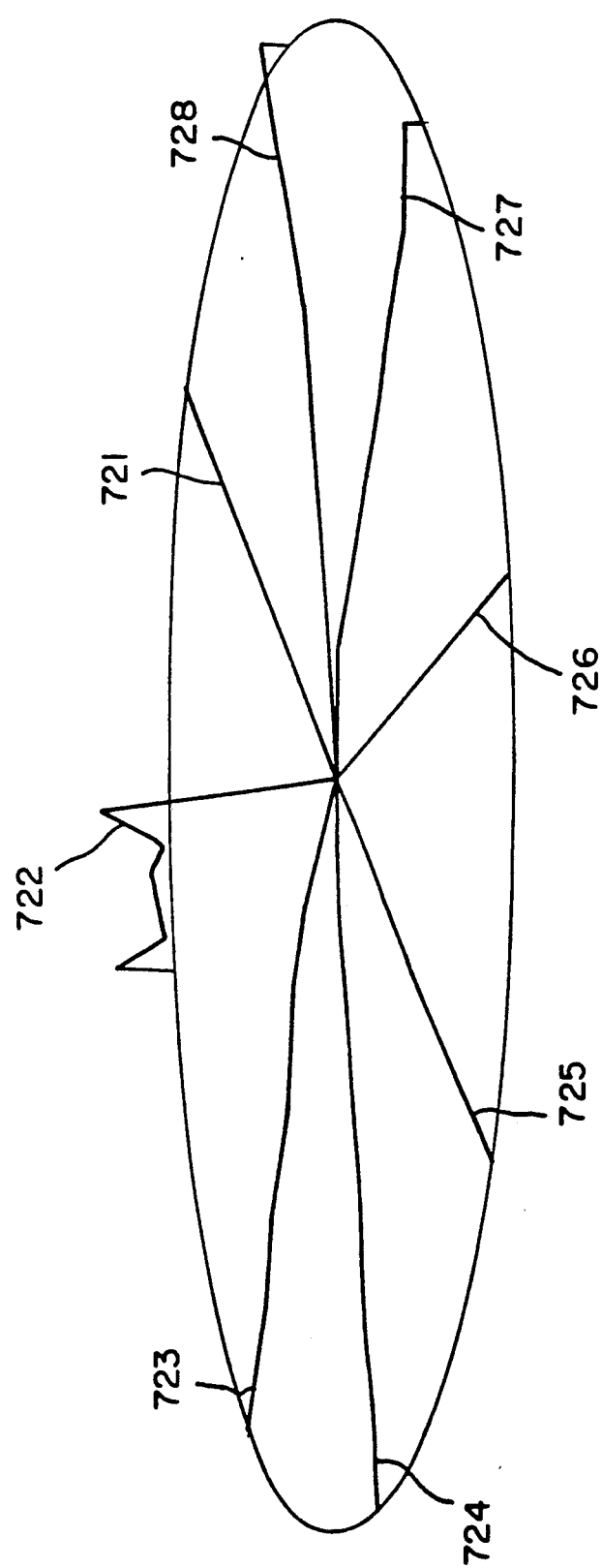
FIG.40-B

FIG. 40-C
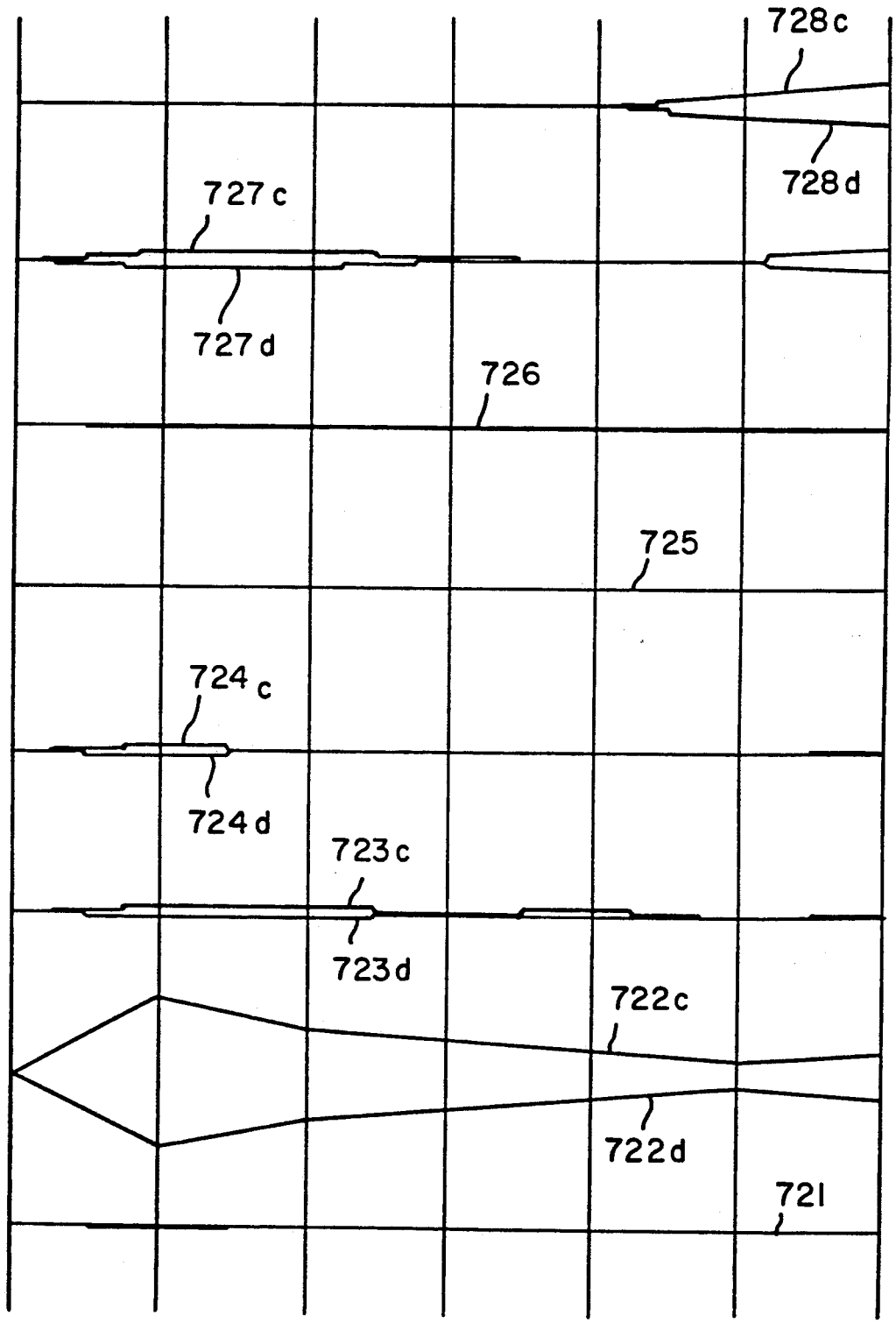

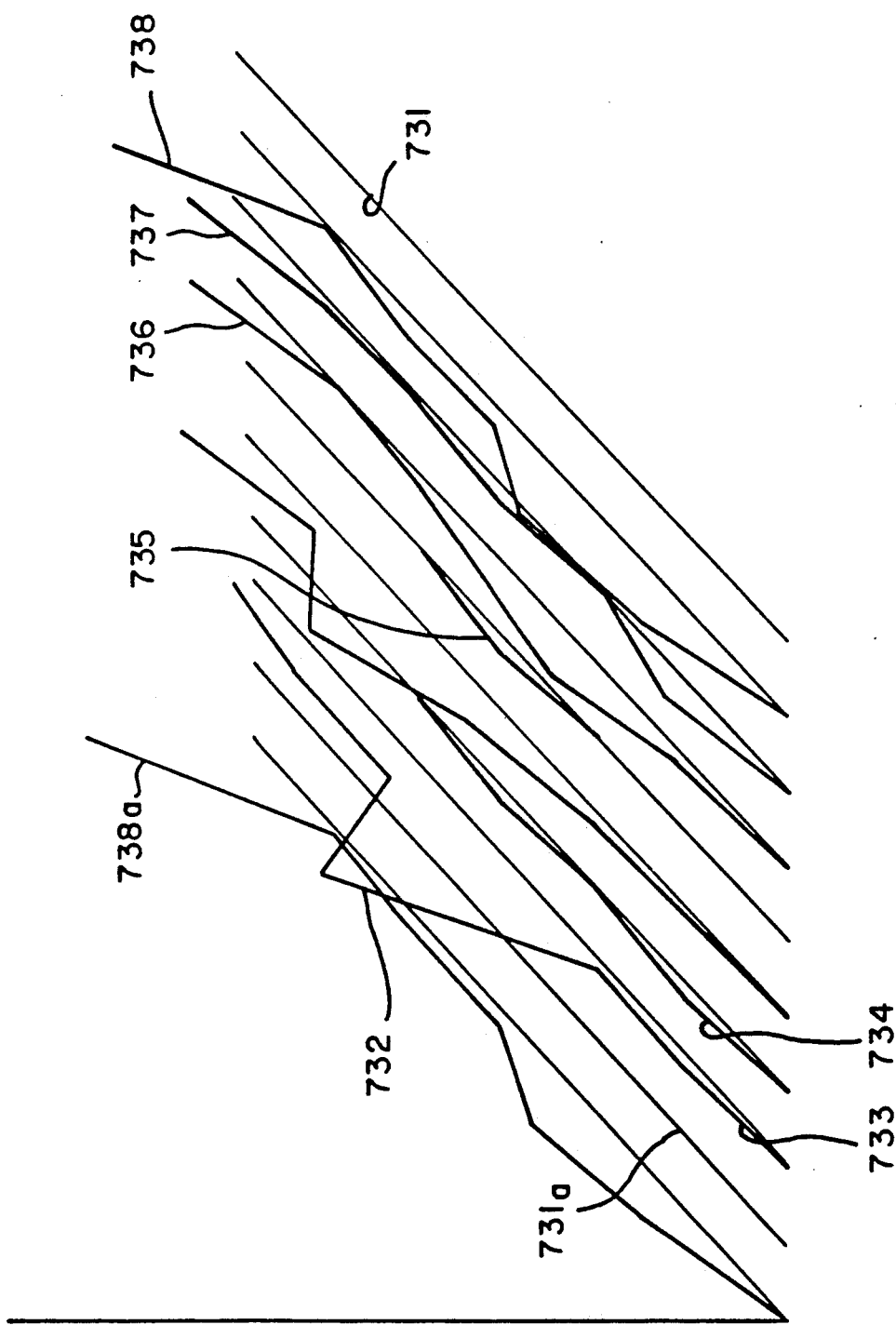
FIG. 41-A

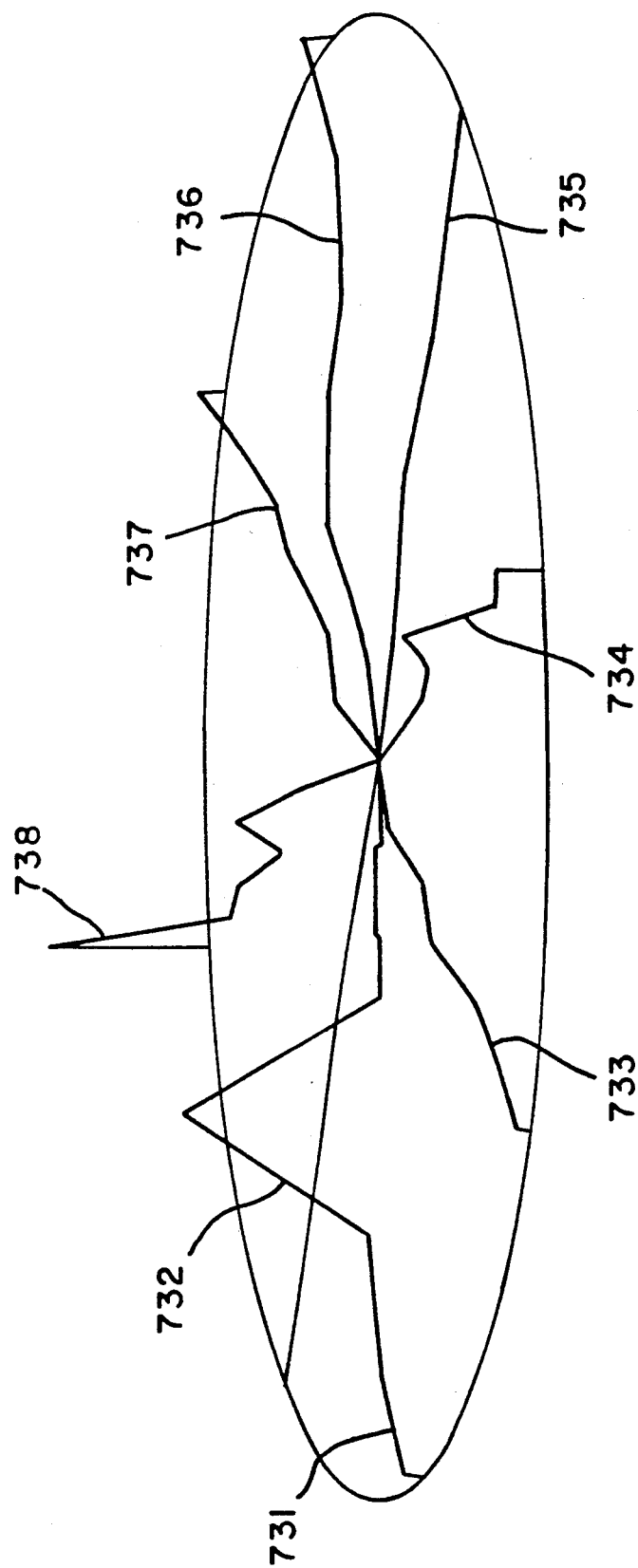
FIG. 41-B

FIG. 41-C
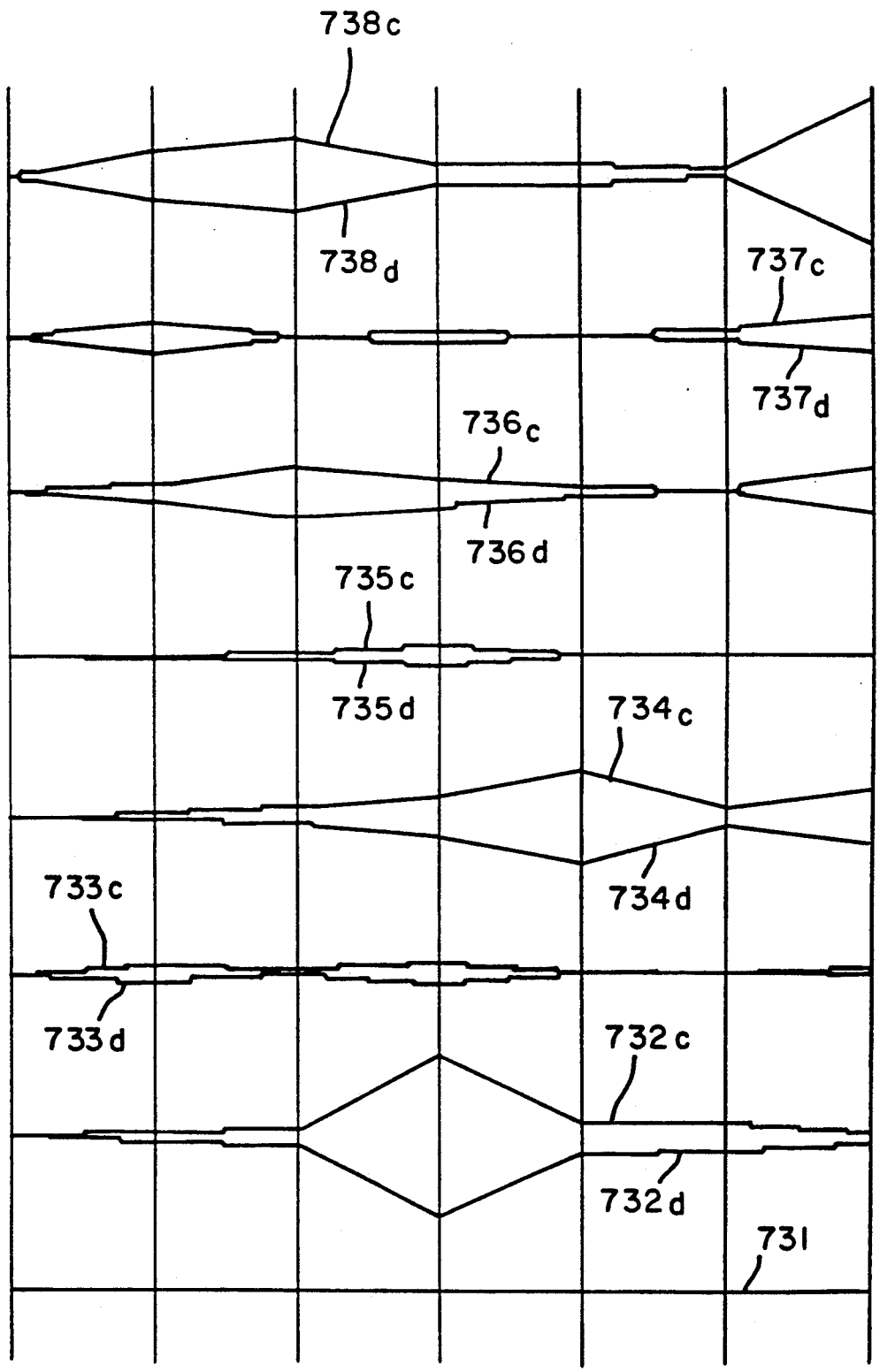

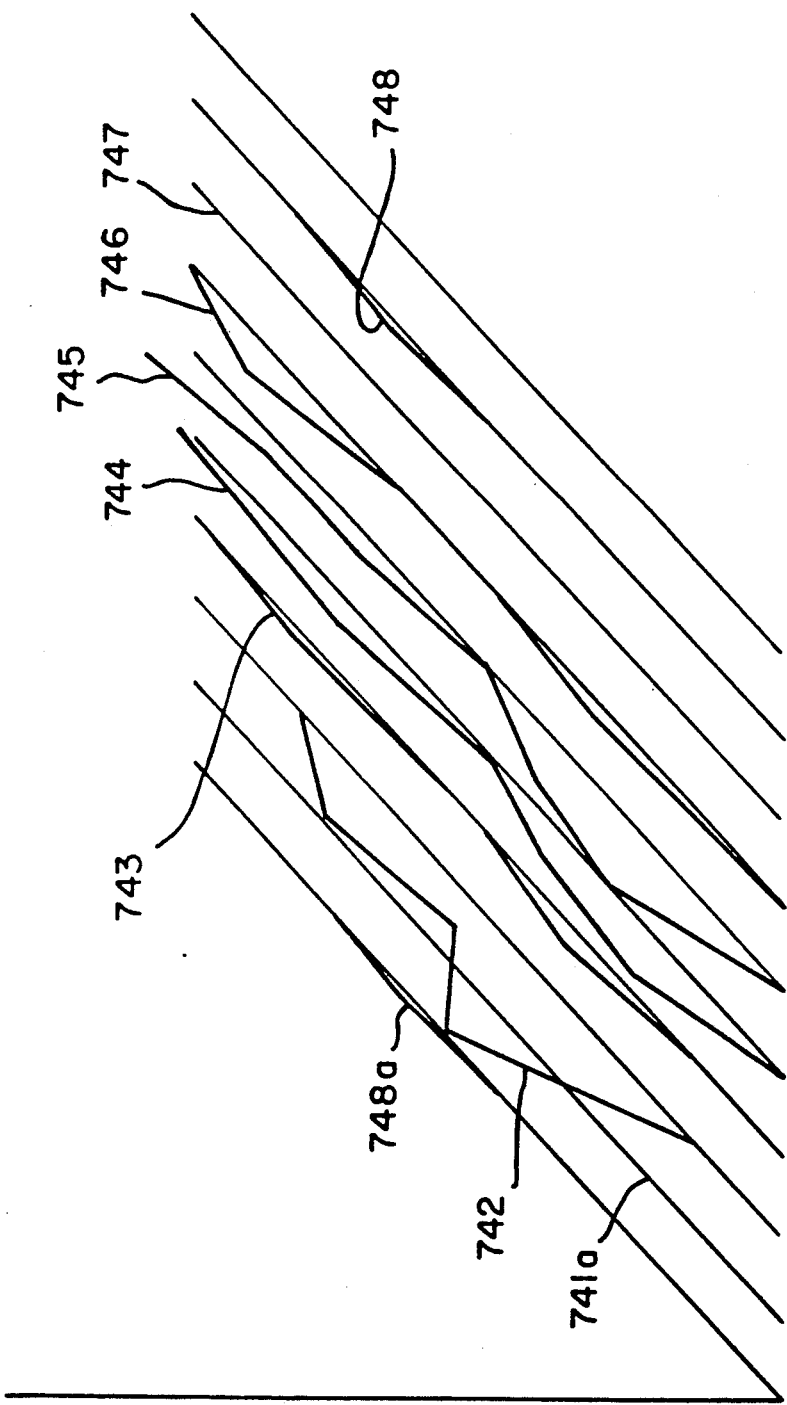
FIG. 42-A

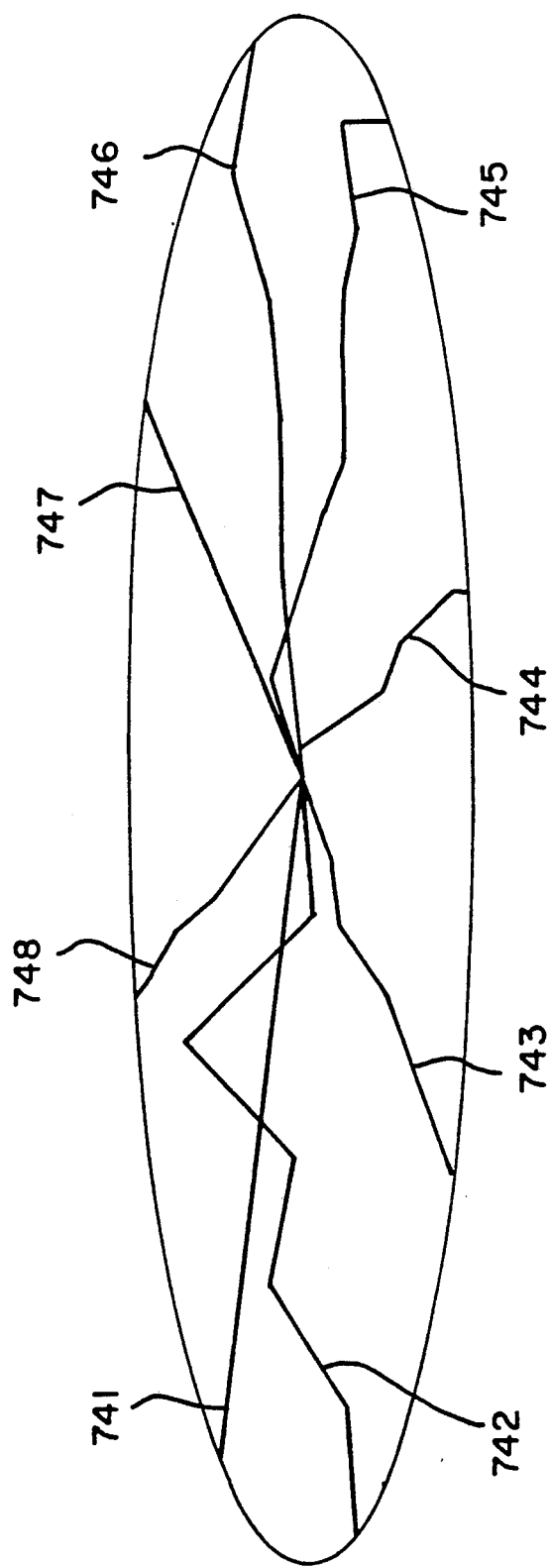
FIG. 42-B

FIG.42-C
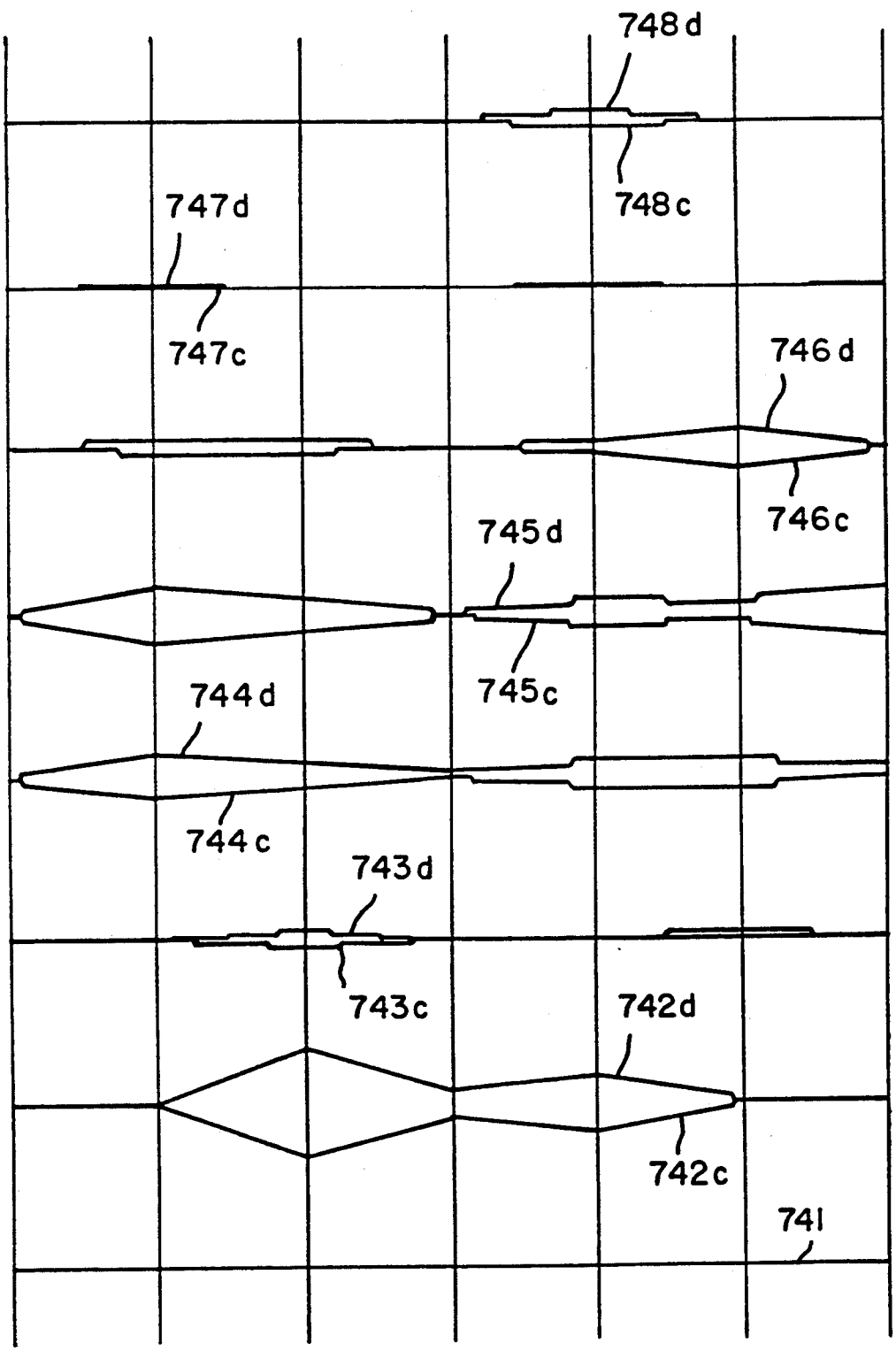

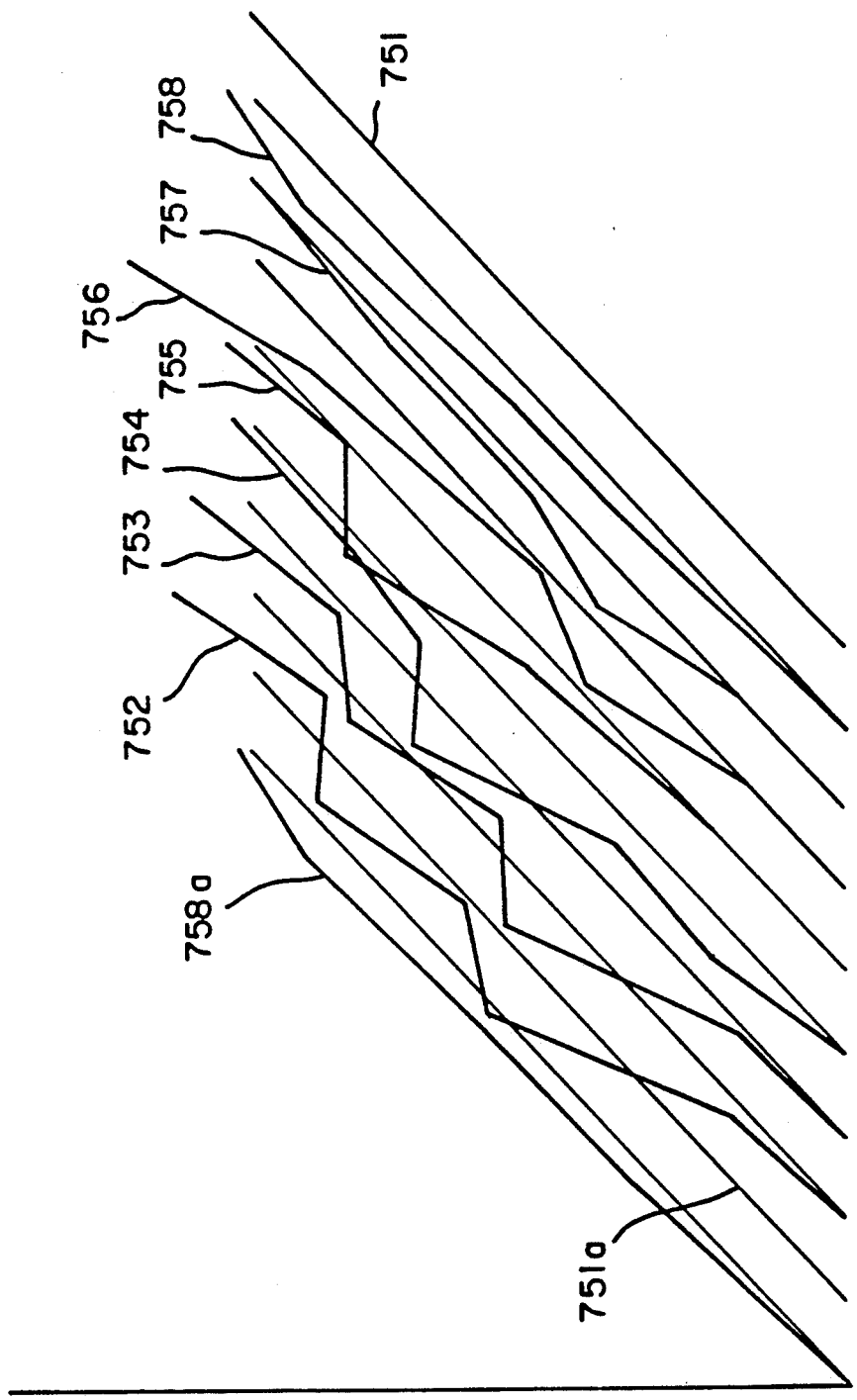

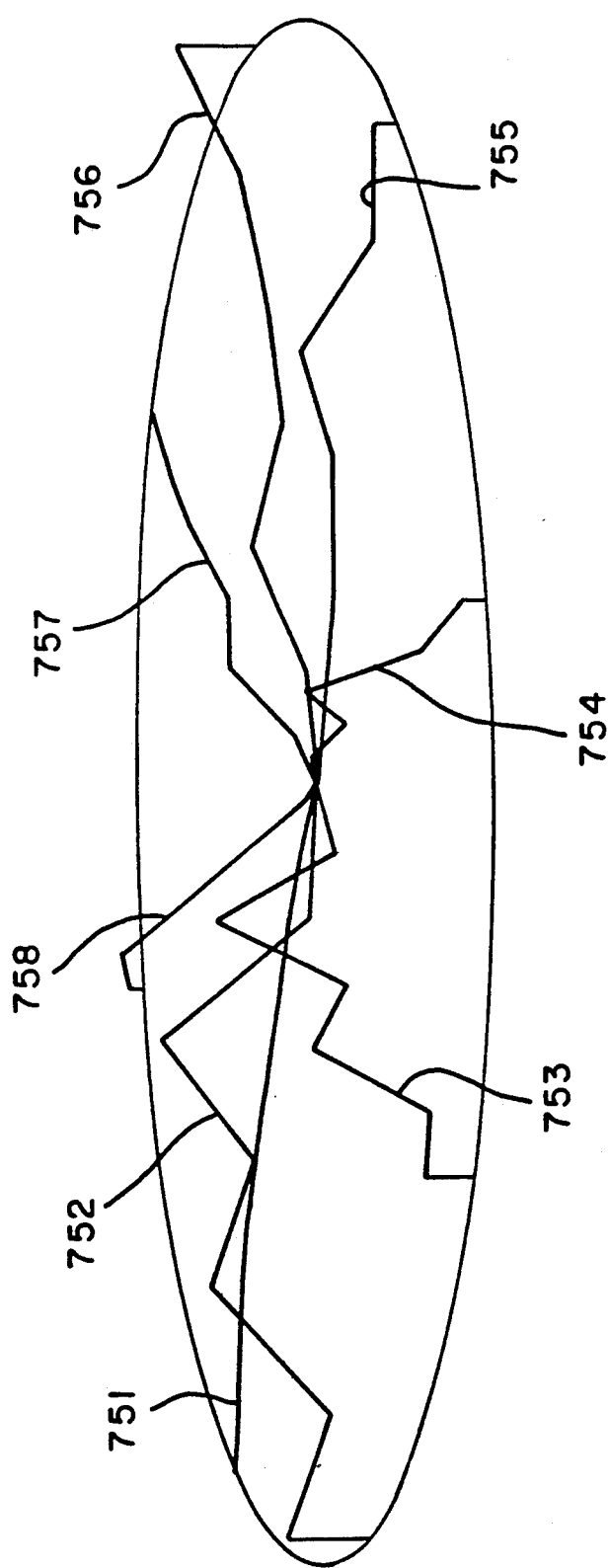
FIG. 43-B

FIG.43-C
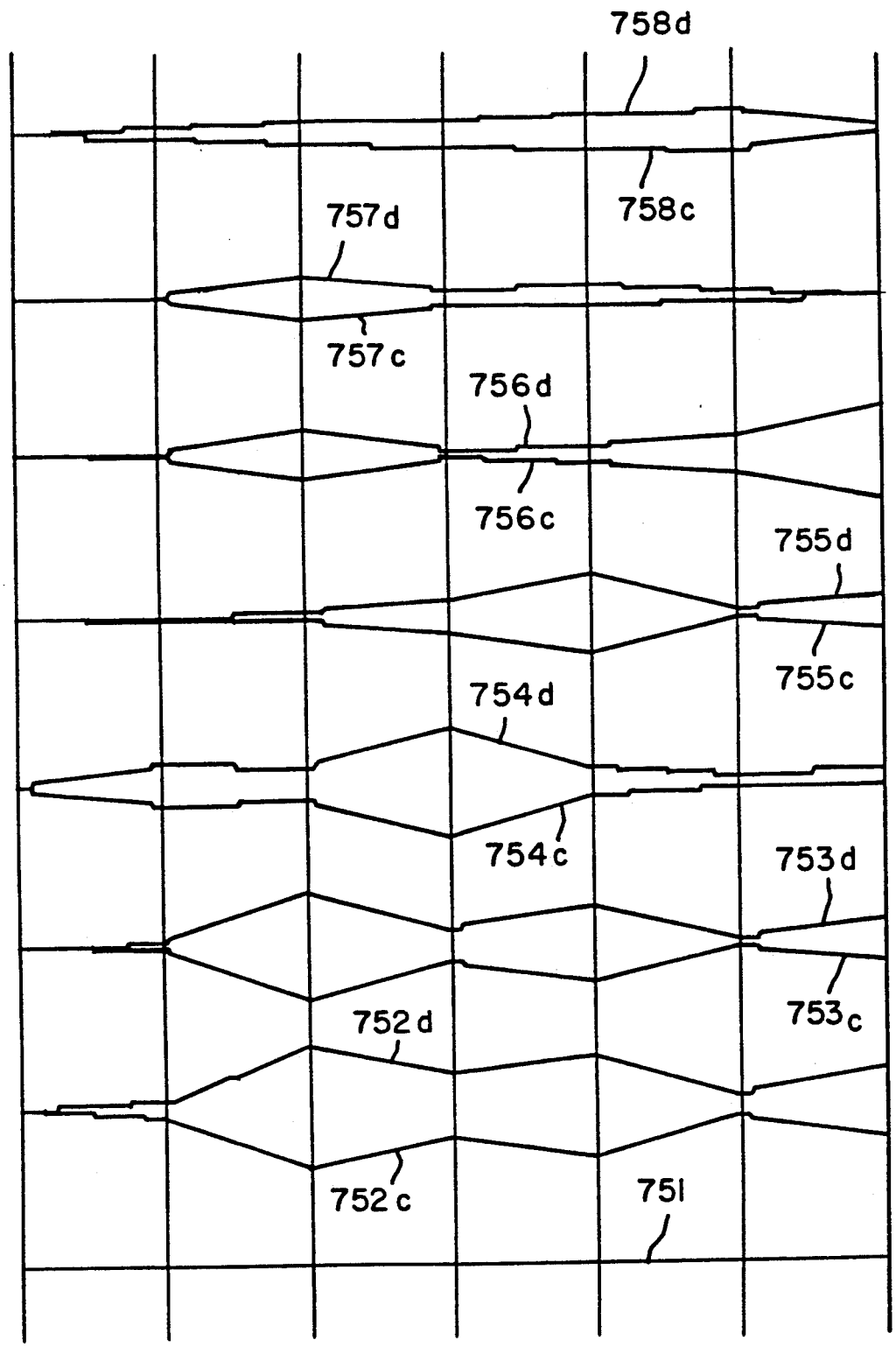

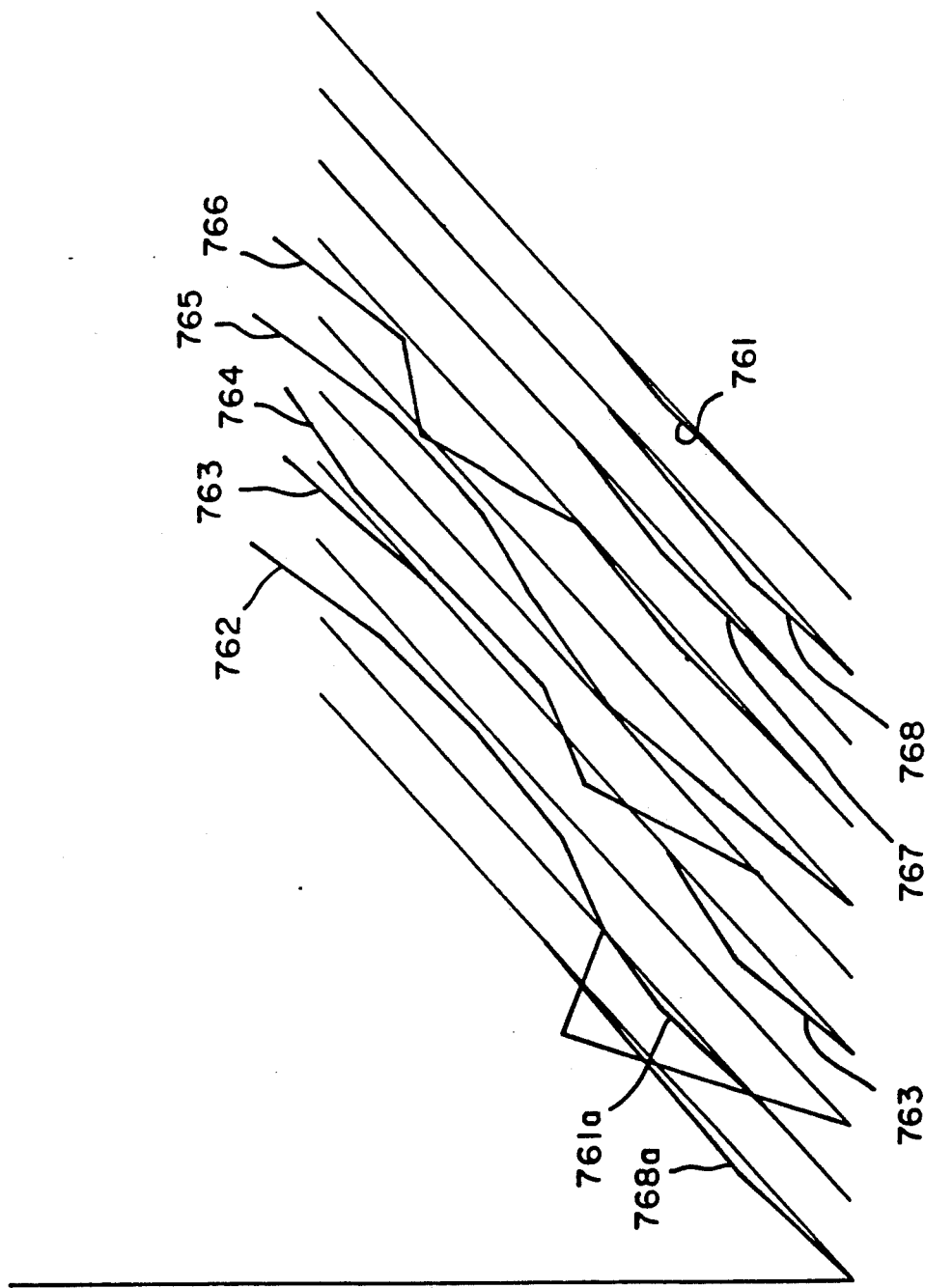
FIG.44-A

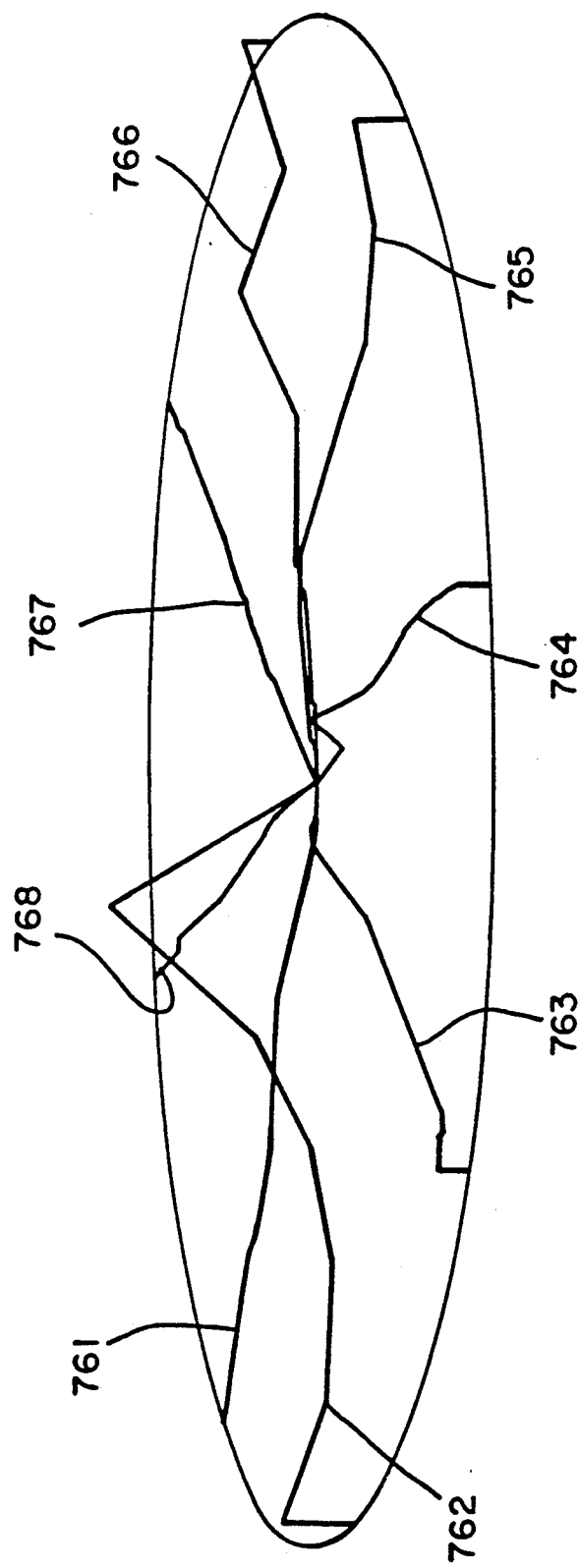
FIG. 44-B

FIG.44-C
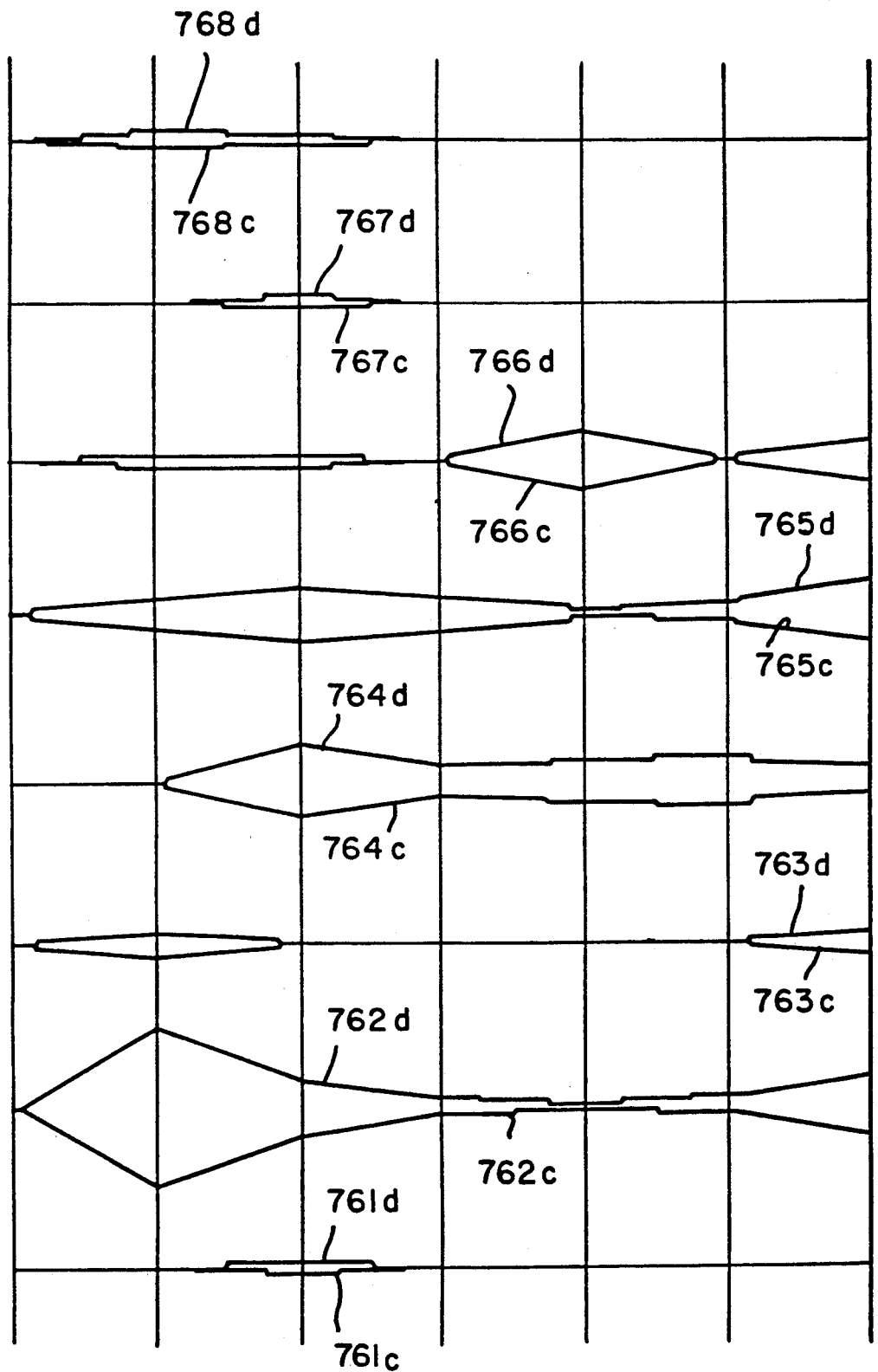

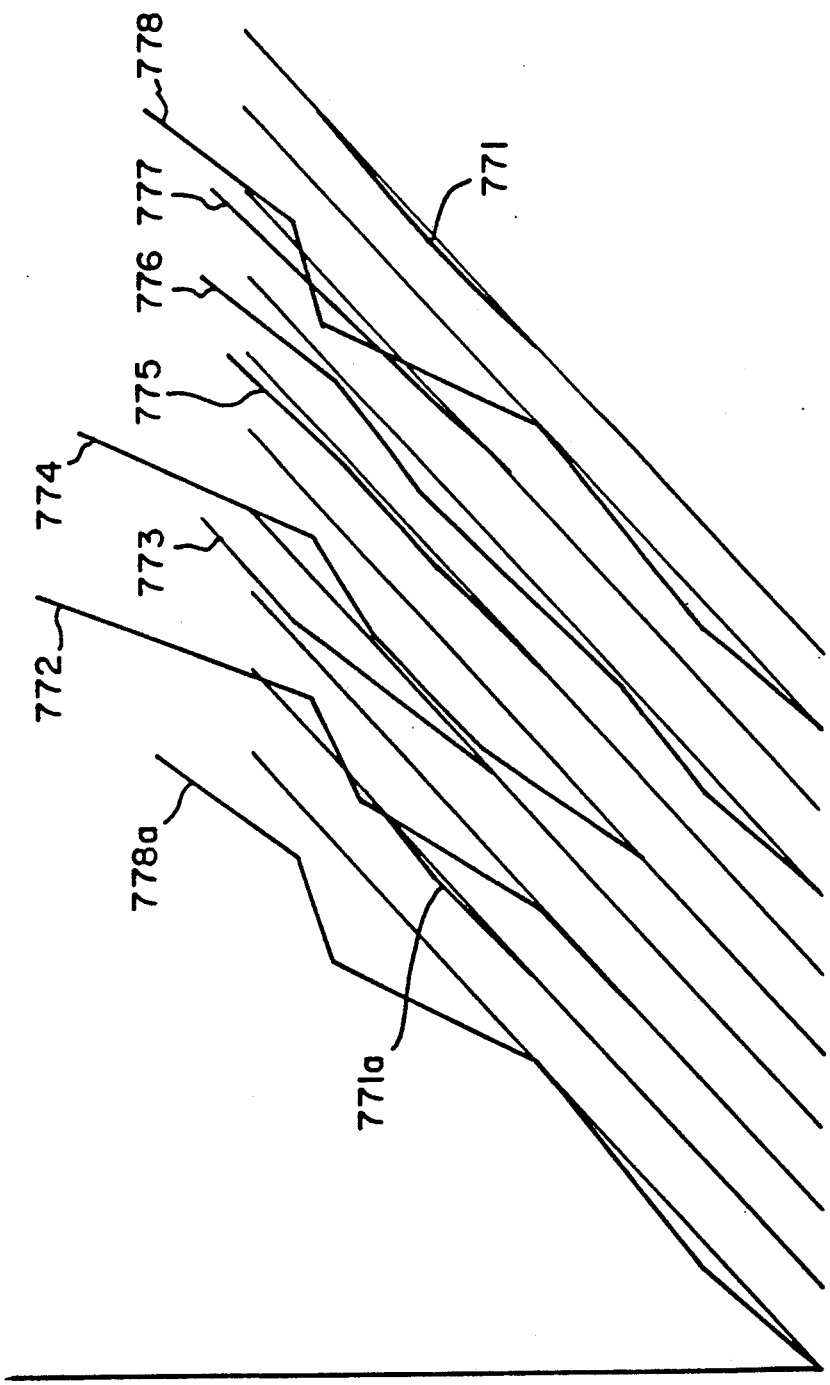
FIG. 45-A

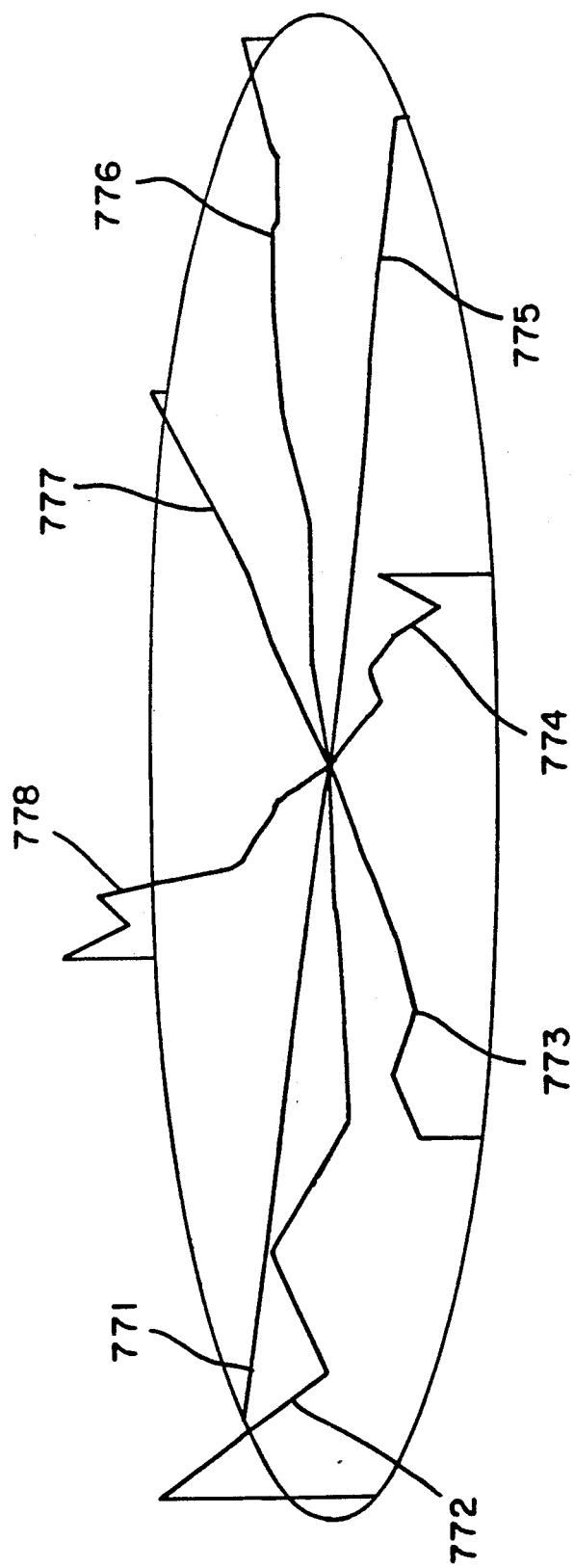
FIG. 45-B

FIG.45-C
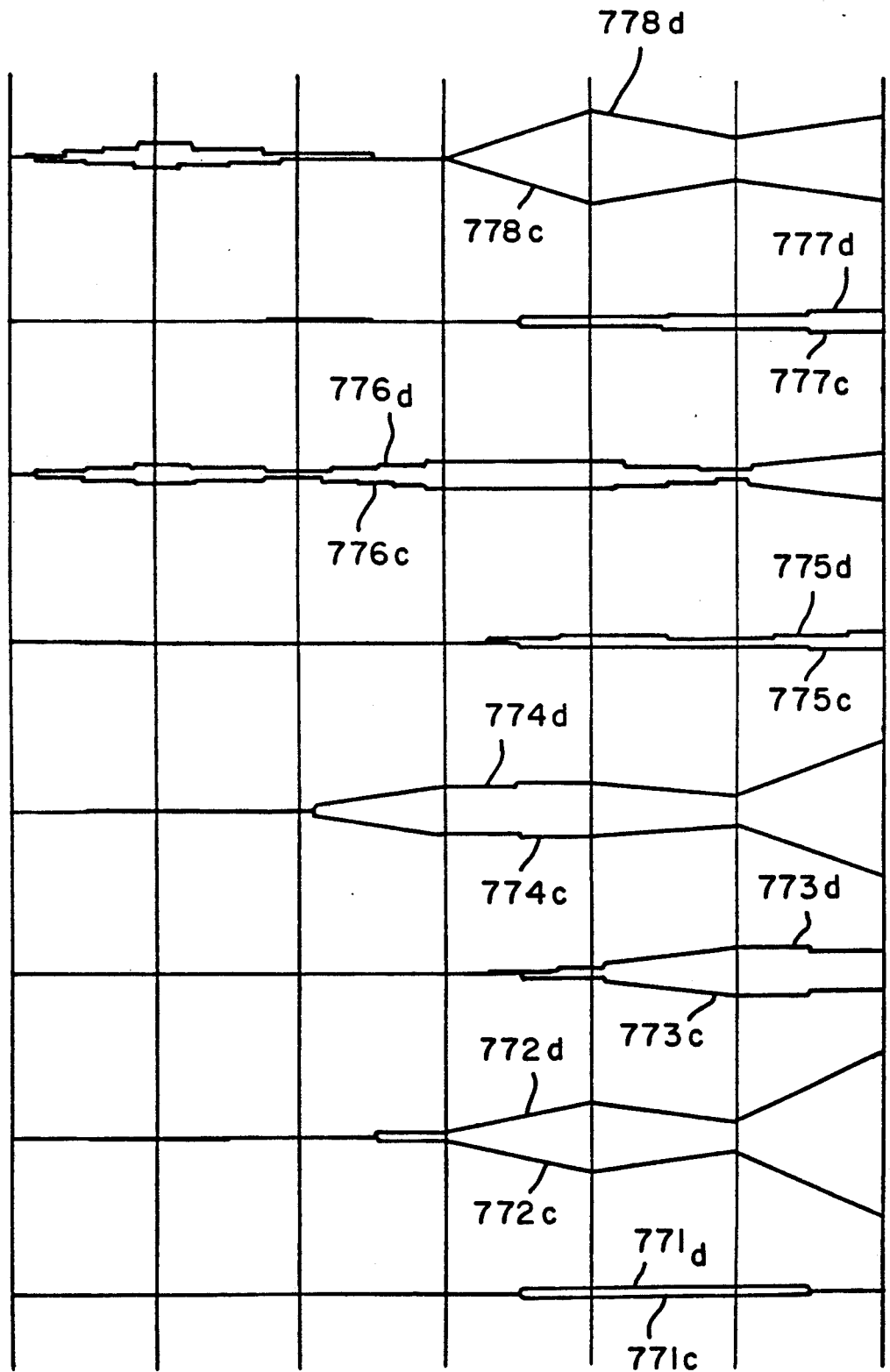

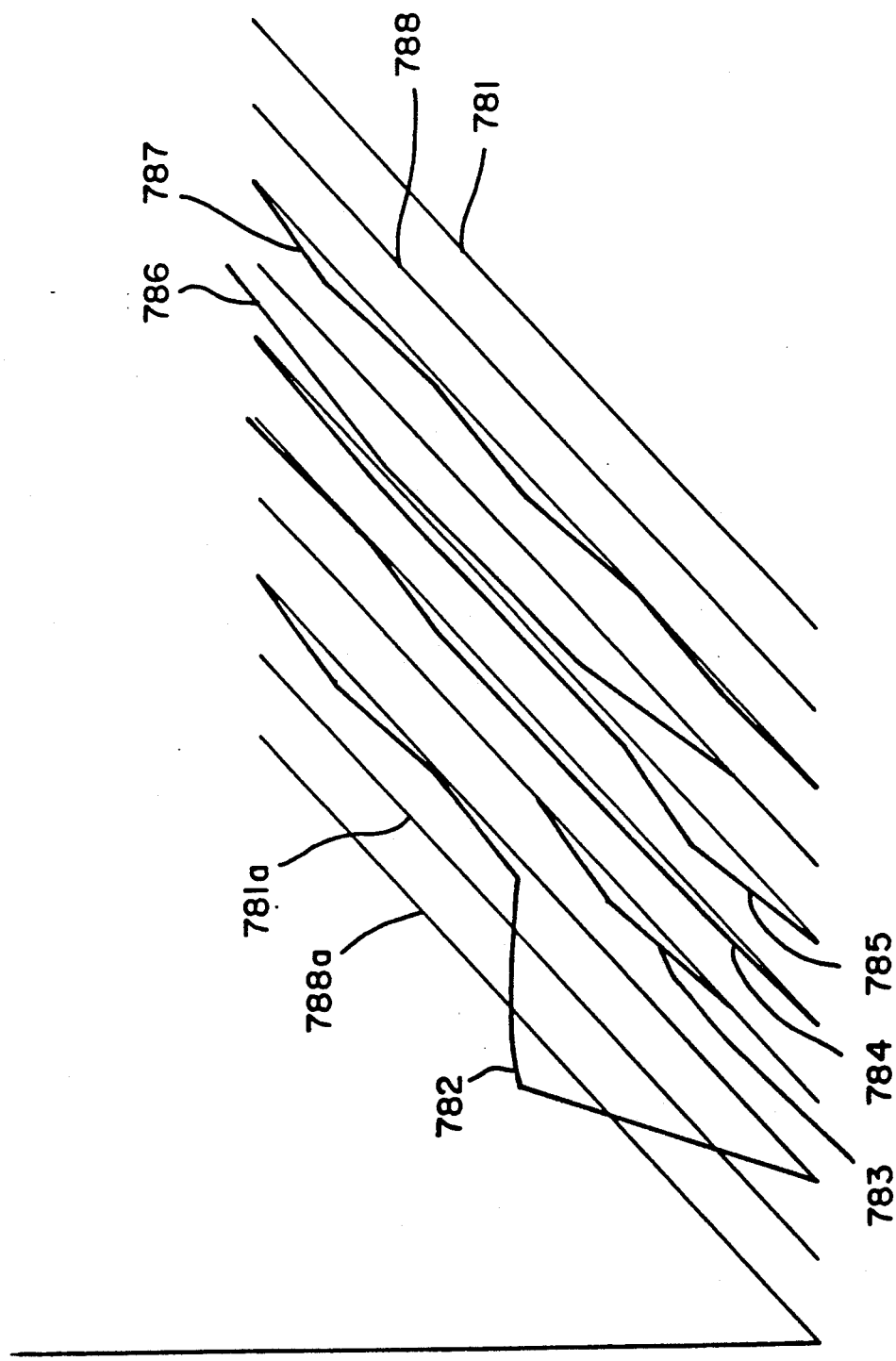
FIG.46-A

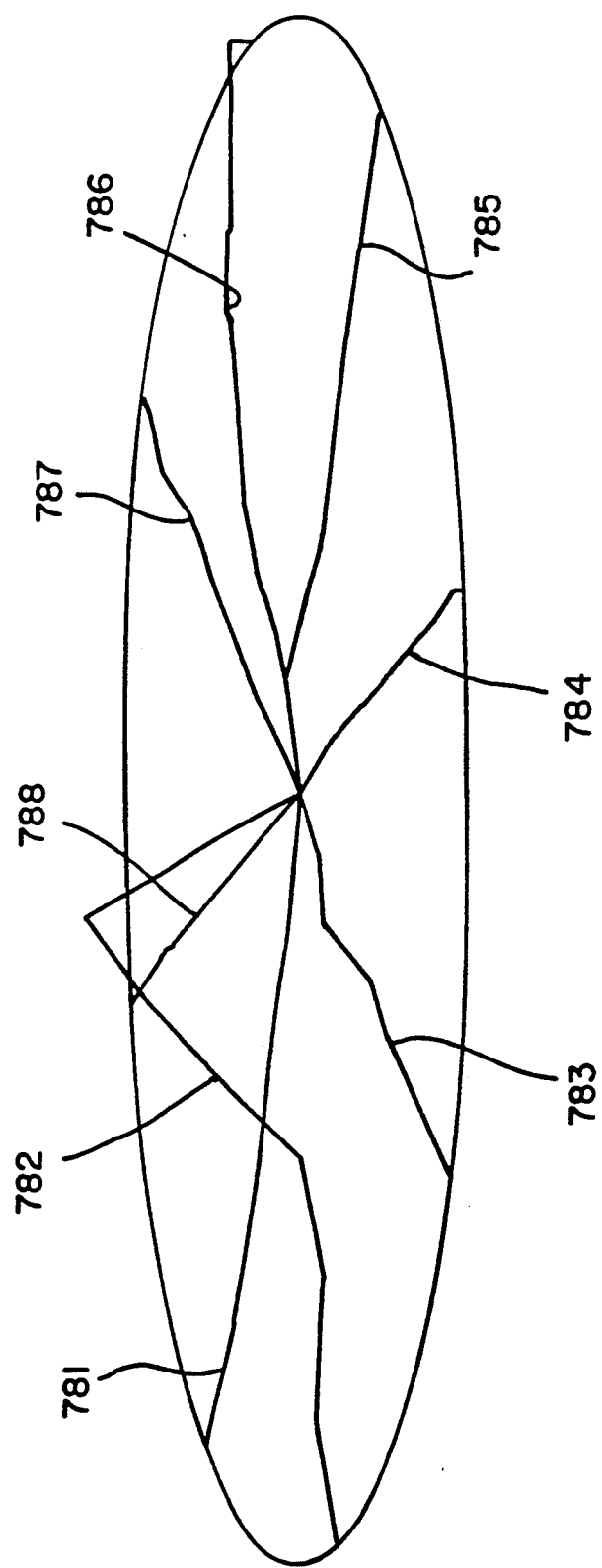
FIG.46-B

FIG.46-C
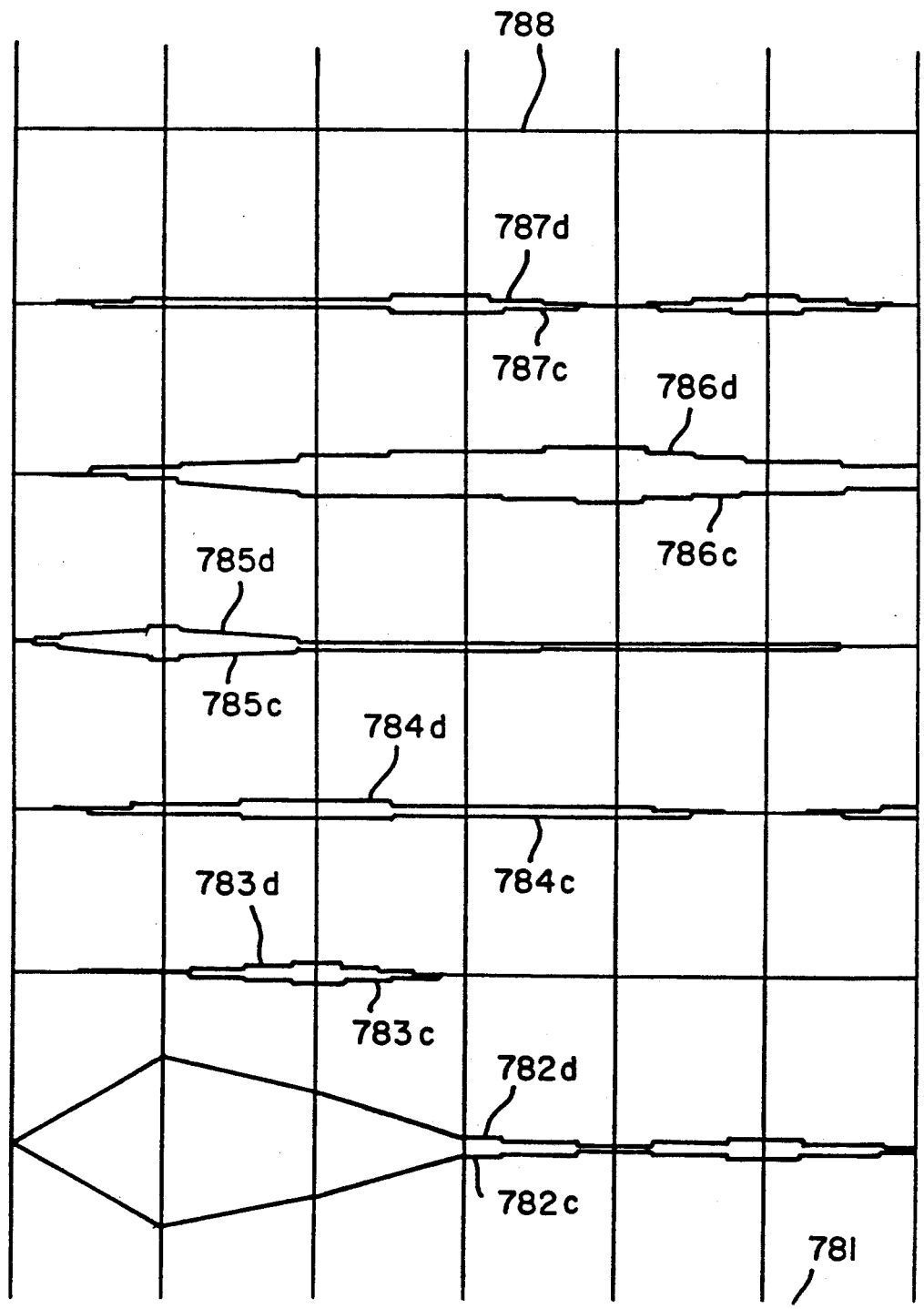

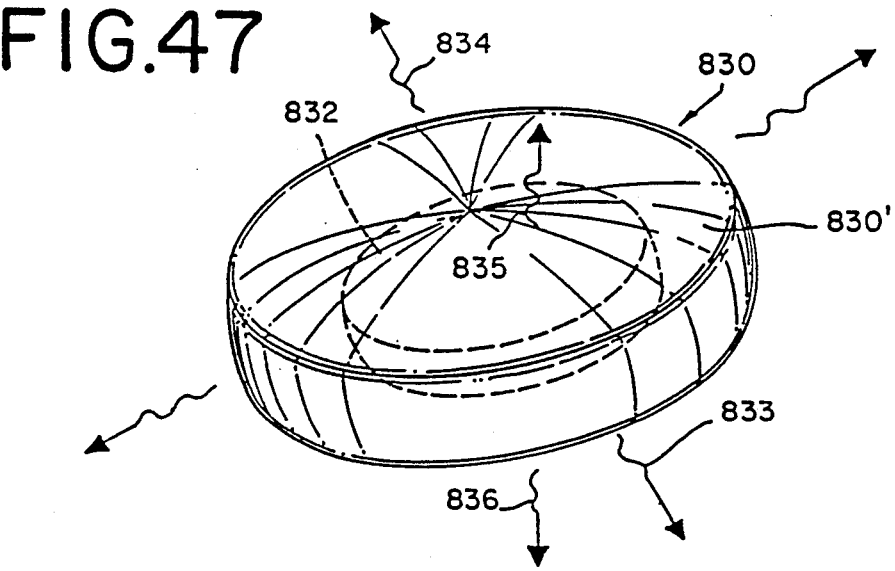
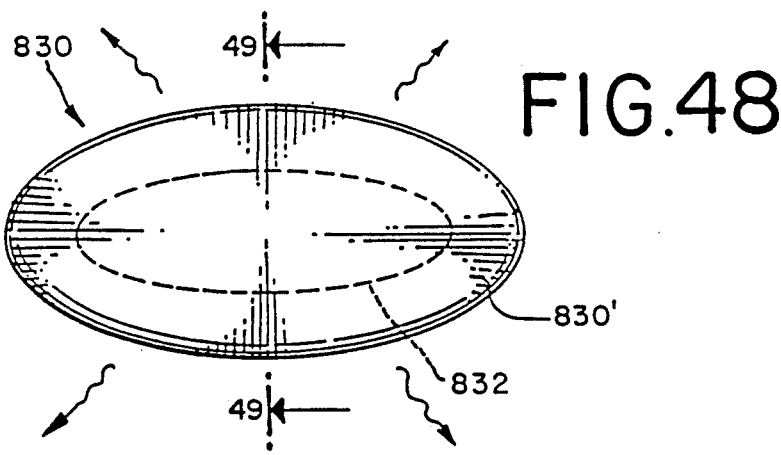
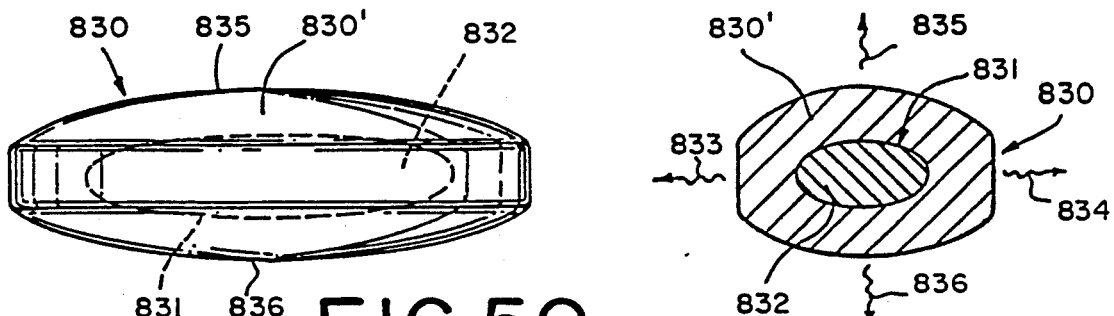

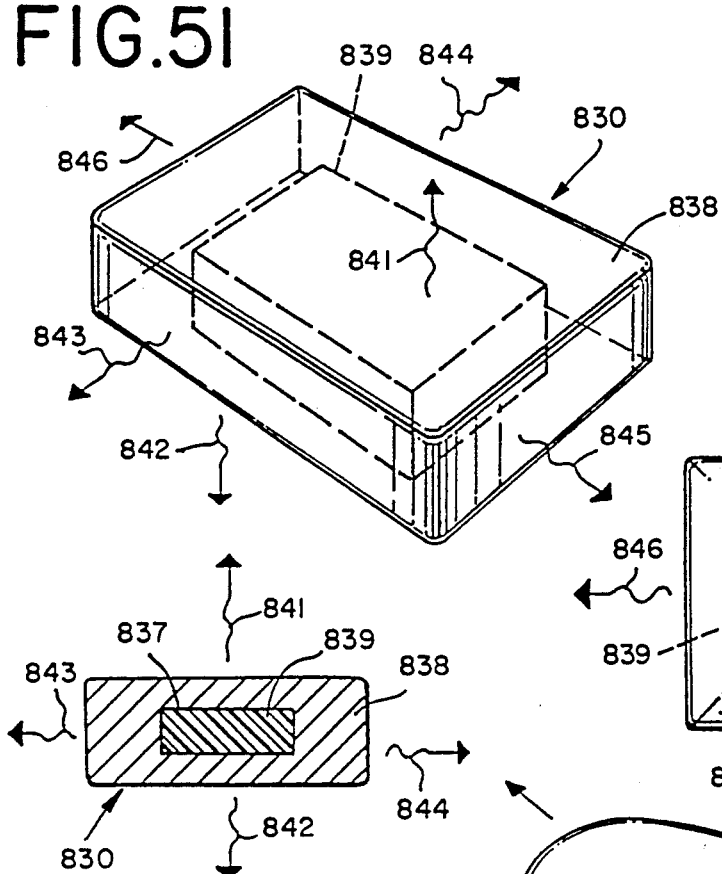
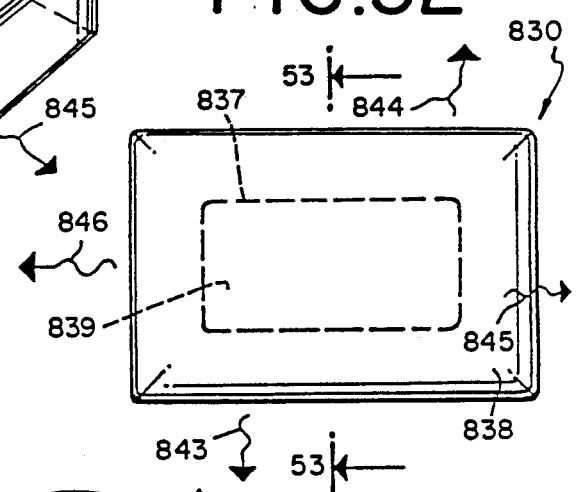
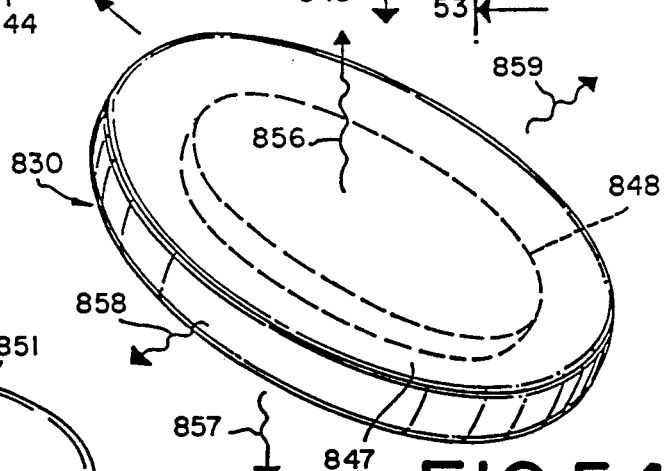
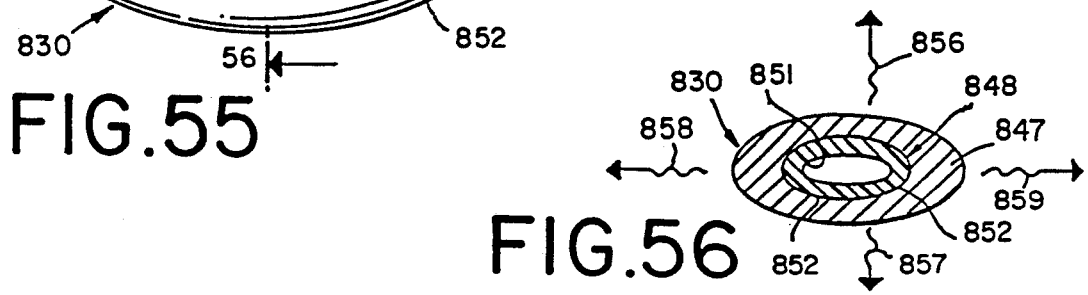

USE OF KETONES, KETOESTERS AND ALCOHOL IN REPELLING INSECTS; USE OF ALIPHATIC ESTER IN ATTRACTING INSECTS AND PROCESS AND APPARATUS FOR DETERMINATION OF INSECT REPELLENCY AND ATTRACTANCY

This is a divisional of application Ser. No. 589,016, filed 9/27/90.

BACKGROUND OF THE INVENTION

This invention relates to the use of the ketones having the structures:

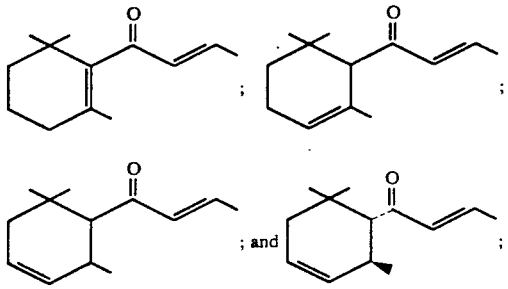

the ketoesters having structures:

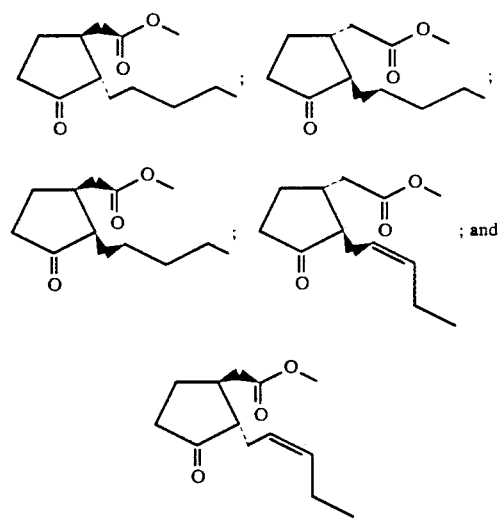

and the alcohol having the structure:

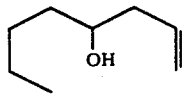

taken alone or in combination as repellents against house flies (*Musca domestica* L. (Diptera: Muscidae)) and mosquitoes (*Aedes aegyptae*). This invention also relates to the use of the ester having the structure:

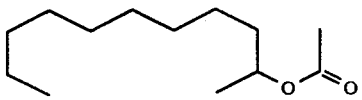

as an attractant for house flies (*Musca domestica* L. (Diptera: Muscidae)) and mosquitoes (*Aedes aegyptae*).

This invention also relates to apparatus useful in determining the attractancy for insects of such molecules including said ester having the structure:

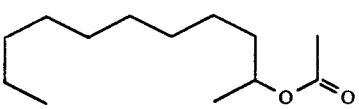

and the repellency against insects of such ketones, ketoesters and alcohol having the structures:

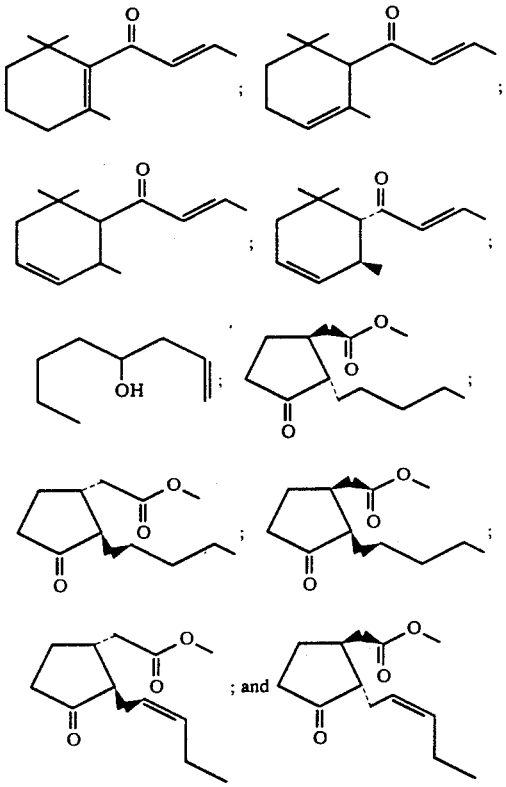

(i) which apparatus comprises active and passive insect interest electronic detecting, measuring and recording means collectively denoted as "DMR" means which is connected to an electric power supply source comprising detecting means, measuring means and recording means;

(ii) enclosed insect feeding and/or stimulating means collectively denoted as "IFS" means having controlled limited excess to the external environment surrounding said apparatus and associated with the said "DMR" means, and including said detecting means, said "IFS" means being located at a fixed "IFS" means location defined according to X, Y and Z coordinates having a defined first 3-space, said "IFS" means consisting essentially of:

(a) a substantially horizontally-positioned insect feeding and/or stimulating microporous substantially planar lamina which is a porous membrane having an upper outer surface and a lower inner surface, said lamina being located immediately above said enclosed "IFS" means;

(b) an insect attractant quantitative detecting means located immediately below said lamina and within said enclosed "IFS" means comprising at least two spaced electrically conductive elements;
  1. connected to said "DMR" means; and
  2. capable of forming a complete circuit, said elements having such dimensions and spacing from one another as to cause an attracted insect to complete a circuit of electron flow through or proximate to said elements;
(c) located on said upper outer surface of said lamina a feeding stimulant composition or stimulant compositions for insects;
(iii) steady state direct infra-red, ultra-violet or monochromatic or polychromatic visible light radiation means for supplying at least one beam of infra-red, ultra-violet or monochromatic or polychromatic visible light radiation having a given substantially constant intensity or intensities and wave length or wave lengths to said "IFS" means location, said beam(s) of radiation being directed in a direction perpendicular to the plane of said lamina along a directional vector from below said insect attractant quantitative detecting means; and
(iv) steady state air and treatment agent supply and conduction means denoted as "SAC" means for supplying and conducting air and treatment agent (e.g., one of the ketones, ketoesters, alcohol and/or ester of our invention) at a substantially constant flow rate and substantially constant linear velocity into said defined 3-space in a direction substantially parallel to the plane of said lamina at a location below said lamina simultaneously with the supplying of the beam of radiation to said "IFS" means location said insect feeding and/or stimulating lamina being constructed and said detection means being constructed so that said "DMR" means are sensitive to the completion of a circuit of electron flow through or proximate said conductive elements of said insect attractant quantitative detecting means whereby the number and frequency of the insects attracted relative to the attractancy of said radiation means to the proximity of said "IFS" means is capable of being determined using said "DMR" means.

Compositions of matter taken alone or for use in combination with other perfumes for repelling house flies as well as apparatus used in determining such repellency have been indicated to exist in U.S. Pat. No. 4,759,228 issued on July 26, 1988 (assigned jointly to International Flavors and Fragrances Inc. and The University of Florida). U.S. Pat. No. 4,759,228 discloses the use of 1-nonen-3-ol in repelling house flies. Furthermore, formulations exist in commerce which are said to provide adequate insect repellent properties, e.g., those set forth in U.S. Pat. No. 2,043,941 which indicates the repellency properties of methallyl disulfide and those set forth in U.S. Pat. No. 4,449,987 issued on May 22, 1984 which indicates the combination of methyl heptenones, coumarin and indole for use in perfumed candles.

Unsaturated alcohols other than 1-octen-4-ol and 1-nonen-3-ol and esters thereof are known with respect to controlling insects; and several have been found to attract insects and others have been found to repel such insects. Thus, U.S. Pat. No. 4,152,422 issued on May 1, 1979 sets forth 6-nonen-1-ol in a composition of matter used as an attractant for the male Mediterranean fruit fly. Chem. Abstracts Vol. 103, No. 71086p concerns the synthesis of (Z)-8-dodecen-1-ol and its acetate as pheromone components of the Oriental Fruit Moth (*Grapholita molesta*). This is an abstract of the article in Acta Chem. Scan Ser. B, 1985, B39(4), pages 267-72. U.S. Pat. No. 4,364,931 issued on Dec. 21, 1982 discloses the use of 9(Z)-tetradecen-1-ol acetate in attracting male white-line dart moths.

Chem. Abstracts Volume 80, 1974, at No. 117098f discloses the use of trans-6-nonen-1-ol acetate as an ovipositional attractant and stimulant of the melon fly. U.S. Pat. No. 2,254,665 issued on Sept. 1, 1941, on the other hand, discloses the use of aliphatic alcohols having from 10 to 14 carbon atoms to repel insects. Examples of the aliphatic alcohols of U.S. Pat. No. 2,254,665 are all saturated alcohols, to wit:
dodecyl alcohol;
octyl alcohol;
hexadecyl alcohol;
tetradecyl alcohol; and
undecyl alcohol.

U.S. Pat. No. 2,254,665 fails to disclose the use of unsaturated alcohols in insect repellent compositions.

Chem. Abstracts Volume 74, 1974 at No. 99419f discloses various nonenyl acetates as attractants for female melon flies (abstract of J. Med. Chem. 1971, 14(3), pages 236-9) including trans-2-nonen-1-yl acetate.

On the other hand, Beroza, Materials Evaluated as Insecticides, Repellents and Chemosterilants at Orlando and Gainesville, Fl., 1952-1964, Agriculture Handbook No. 340, published by The Agricultural Research Service, United States Department of Agriculture, August, 1967 discloses the following items 5443-5452 as insect repellents (on a scale of 1-10) as follows:

Item 5443—3-phenyl-2-octen-1-ol repels the yellow fever mosquito from cloth at a level of "1" on a scale of 1-10.

Item 5444—2,6-dimethyl-4-octen-3-ol repels the yellow fever mosquito from cloth at a level of "1" on a scale of 1-10.

Item 5445—3,6-dimethyl-5-octen-3-ol repels the yellow fever mosquito from cloth at a level of "1" on a scale of 1-10.

Item 5446—3-6-dimethyl-5-octen-3-ol acetate repels the yellow fever mosquito from cloth at a level of "1" on a scale of 1-10.

Item 5447—2,7-dimethyl-5-octen-4-ol acetate repels the yellow fever mosquito from cloth at a level of "1" on a scale of 1-10.

Item 5448—3,7-dimethyl-6-octen-1-ol repels the yellow fever mosquito from cloth at a level of "2" on a scale of 1-10.

Item 5449—3,7-dimethyl-6-octen-1-ol carbanilate repels the yellow fever mosquito from cloth at a level of "1" on a scale of 1-10.

Item 5450—3,7-dimethyl-6-octen-2-ol repels the yellow fever mosquito from cloth at a level of "1" on a scale of 1-10.

Item 5451—3,6-dimethyl-6-octen-3-ol repels the yellow fever mosquito from cloth at a level of "1" on a scale of 1-10.

Item 5452—3,7-dimethyl-6-octen-3-ol repels the yellow fever mosquito from cloth at a level of "2" on a scale of 1-10.

Beroza, Agriculture Handbook No. 340 at Item 7977 indicates that undecyl alcohol acetate has insect repelling properties as follows:
yellow fever mosquito: "1" on a scale of 1-10 tick at a level of "2" on a scale of 1-10.

Formulations exist in commerce which are said to provide candle body materials that are both perfuming and insect repellent but such formulations have yielded a candle body that is either insufficiently insect repellent or aesthetically displeasing from an organoleptic standpoint.

This is so, even though it was disclosed in U.S. Pat. No. 4,759,228 that 1-nonen-3-ol can be used in such candles to repel house flies (*Musca domestica* L. (Diptera: Muscidae)).

The properties of the repellent compounds of our invention have advantages which render the uses thereof unexpected, unobvious and advantageous over the use, of 1-nonen-3-ol.

When a candle burns, the heat of its flame melts a small pool of the candle body material around the base of the exposed portion of the wick, and this molten material is drawn up through the wick by capillary attraction to fuel the flame. Thus, the process that takes place in the burning of a candle imposes rather stringent functional requirements upon the candle body material.

The material of a candle body must be rigid enough to support itself and a relatively long wick filament, but it should not be excessively brittle at low temperatures. Its melting point is critical in that it should liquify at temperatures to which it can be raised by radiant heat from the candle flame. If its melting temperature is too low, the candle will drip or, in an extreme case, the entire candle body will melt, dropping the wick into a pool of molten material with the hazardous possibility that the surface of the pool will ignite when this happens. If too high a temperature is required to melt the body material, the flame will be starved because insufficient fuel will be drawn up through the wick, with the result that the flame will be too small to maintain itself. When molten, moreover, the candle body material must have a relatively low viscosity in order to insure that it will be capable of being drawn up through the wick by capillary action.

In addition to meeting these requirements the candle body material must burn with a flame that is both luminous and smokeless and such odors as are produced by its combustion should not be unpleasant and should preferably be faint.

The functional requirements outlined above have, of course, been met by various candle body materials that are well known in the art, but heretofore no known materials that meet these requirements have been in combination:

(a) perfuming to the environment surrounding the burning candle;
(b) adequately insect repellent (both to house flies and mosquitoes) in the environment surrounding the material at various environmental temperatures at atmospheric pressure, from a temperature of about 0° C. up to a temperature of about 50° C.; and
(c) substantially so substantive that the perfuming property as well as the insect repellent property will last for a period of time well beyond the removal of the burning candle from the environment which is being perfumed and exposed to the insect repellent.

The 1-nonen-3-ol of U.S. Pat. No. 4,759,228 causes the environment surrounding the burning candle to be perfumed and adequately causes house flies to be repelled but does not act in an efficacious manner with respect to the desired environmental substantivity properties as set forth supra in Section (c).

U.S. Pat. No. 3,645,705 discloses a transparent candle body composition of matter which can contain:

(a) from about 35% up to about 85% by weight of an oil which is normally liquid at room temperature which may be light mineral oil or a natural oil;
(b) from about 7% up to 40% by weight of a long chain polyamide having a molecular weight of between 6,000 and 9,000 and a softening point within the range of 185° C.-198° C.; and
(c) from about 7% up to about 30% by weight of an alcohol which may be a $C_8$-$C_{12}$ primary alcohol.

At column 3, line 56 of U.S. Pat. No. 3,645,705 it is disclosed that an odor masking agent may be incorporated into the candle composition. Generally this disclosure is set forth at lines 30-44 of U.S. Pat. No. 3,645,705 thusly:

"The inclusion in the composition of certain alcohols that produce otherwise desirable properties may result in a material that burns with an acrid or pungent odor. In such cases a small amount of an odor masking agent can be incorporated in the composition. The material sold by Fritzche, Dodge and Olcott as its 41984 has been found to have satisfactory results. If desired, a small amount of perfume can be added to the composition to complete the odor-masking effect."

Nothing in U.S. Pat. No. 3,645,705, however, discloses the applicability to the composition disclosed therein of insect repellent materials. Nothing discloses the use of a composition of matter in U.S. Pat. No. 3,645,705 which will be both a perfumant and an insect repellent.

U.S. Pat. No. 4,051,159 issued on Sept. 27, 1977 discloses a "shaped, self-supporting transparent fragrance emitting article comprising a high percentage of a thermoplastic polyamide resin having a substantially uniformly dispersed therein a $C_{14}$-$C_{22}$ alkyl alcohol and a fragrance emitting material". U.S. Pat. No. 4,051,159 however, does not indicate that the compositions of matter disclosed therein are useful for fragrance candles or insect repellent.

Indeed, much of the literature teaches away from our invention as exemplied in "Materials Tested as Insect Attractants" compiled by M. Beroza and N. Green in Agriculture Handbook No. 239 in Table 2 wherein it is stated that certain methyl substituted octenals, Items Nos. 2891, 2892, 2893, 2894 and 295 to wit:

Item 2891—2,6-dimethyl-4-octen-3-ol
Item 2892—3,6-dimethyl-5-octen-3-ol
Item 2893—3-7-dimethyl-6-octen-3-ol
Item 2894—3,7-dimethyl-6-octen-2-ol
Item 2895—3,7-dimethyl-6-octen-3-ol have attractancies for insects as follows:
Item 2891—2,6-dimethyl-4-octen-3-ol: the Oriental Fruit Fly at a level of "1" on a scale of 1-3; the Mediterranean Fruit Fly at a level of "2" on a scale of 1-3 and the Mexican Fruit Fly at a level of "1" on a scale of 1-3.
Item 2892—3,6-dimethyl-5-octen-3-ol: the Oriental Fruit Fly at a level of "1" on a scale of 1-3 and Mediterranean Fruit Fly at a level of "2" on a scale of 1-3.
Item 2893—3,7-dimethyl-6-octen-1-ol: the Oriental Fruit Fly at a level of "1" on a scale of 1-3; the Mediterranean Fruit Fly at a level of "1" on a scale of 1-3; the Mexican Fruit Fly at a level of "1" on a scale of 1-3; the Gypsy Moth on a level of "1" of on a scale of 1-3; the European Chafer at a level of "1" on a scale of 1-3 and the Pink Bull Worm at a level of "1" on a scale of 1-3.

Item 2894—3,7-dimethyl-6-octen-2-ol: the Meditteranean Fruit Fly at a level of "1" on a scale of 1-3; the Mexican Fruit Fly at a level of "1" on a scale of 1-3; the Gypsy Moth at a level of "1" on a scale of 1-3; the Pink Bull Worm at a level of "1" on a scale of 1-3 and the Bolweevil at level of "1" on a scale of 1-3.

Item 2895—3,7-dimethyl-6-octen-3-ol: the Oriental Fruit Fly at a level of "1" on a scale of 1-3; the Mediterranean Fruit Fly at a level of "3" on a scale of 1-3; the Mexican Fruit Fly at a level of "1" on a scale of 1-3; the Pink Bull Worm at a level of "1" of 1-3 and the Bolweevil at a level of "1" on a scale of 1-3.

Furthermore, in Agriculture Handbook No. 239 it is stated that 3-methyl-1-nonen-3-ol has on a scale of 1-3 an attractancy of "1" for the Oriental Fruit Fly and an attractancy of "1" for the Mediterranean Fruit Fly and 4,8-dimethyl-7-nonen-4-ol has on a scale of 1 to 3 an attractancy "2" for the Oriental Fruit Fly and an attractancy of "3" for the Mediterranean Fruit Fly and an attractancy of "1" for the Mexican Fruit Fly and an attractancy of "1" for Drosophila.

With respect to any of the octenol or nonenol derivatives set forth therein the USDA Agriculture Handbook No. 239 indicates that the octenol and nonenol derivatives are neither attractants nor repellents for house flies (that is, Musca domestica).

Furthermore the U.S.D.A. Agriculture Handbook No. 239 states no information pertaining to mosquitos (e.g. *Aedes aegyptae*).

With respect to undecyl alcohol acetate ester, Beroza, Agriculture Handbook No. 239 discloses as Item 376 the said undecyl ester of acidic acid and indicates that the Oriental Fruit Fly is attracted at a level of "1" on a scale of 1 to 3 and the Gypsy Moth is attracted at a level of "1" on a scale of 1 to 3.

Wilson, et al., U.S. Pat. No. 4,801,446 issued on Jan. 31, 1989 describes the uses of methyl-isoeugenol having the structure:

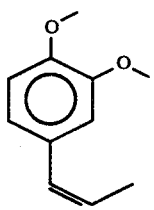

n-dodecanol having the structure:

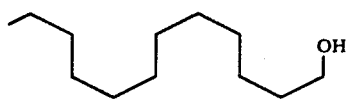

and 1-(2-butenoyl)-2,6,6-trimethyl-1,3-cyclohexadiene having the structure:

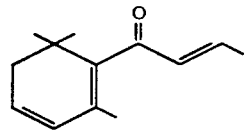

taken alone or taken in combination as attractants for house flies (*Musca domestica* L. (Diptera: Muscidae)) and stored products moths. The structure of 1-(2-butenoyl)-2,6,6-trimethyl-1, 3-cyclohexadiene is different from the structures of any of the ketones useful in the instant invention which in any event are repellents rather than attractants.

As stated supra, U.S. Pat. No. 4,759,228 discloses the process and apparatus for testing insect repellency and attractancy of molecules. The apparatus of U.S. Pat. No. 4,759,228 for testing insect repellency and attractancy of various molecules comprises:

(i) providing active and passive insect interest electronic measuring and recording means; (ii) providing enclosable insect feeding or stimulating means having controlled limited access to the external environment surrounding said apparatus and capable of being associated with said measuring and recording means, said insect feeding or stimulating means located at a fixed insect feeding or stimulating means location defined according to X, Y and Z coordinates in a first defined 3-space; said insect feeding or stimulating means consisting essentially of:

(a) an insect feeding or stimulating surface comprising at two spaced electrically conductive elements connected to said measuring and recording means, said elements having such diameters and spacing from one another as to cause an attracted insect to complete a circuit of electron flow through said conductive elements;

(b) immediately beneath said insect feeding or stimulating surface a composition of matter comprising molecules to be tested for attractancy and repellency;

(c) immediately beneath said molecules to be tested, a stimulant or feeding stimulant composition for said insects;

(iii) providing steady state direct lighting means for supplying a beam of direct light having given substantially constant intensity and wave length or wave lengths to said feeding or stimulating means location;

(iv) providing steady state air supply, air conduction and air removal means for supplying, conducting and removing air at a substantially constant mass flow rate and substantially constant linear velocity to, past and from a second 3-space immediately above said insect feeding or stimulating surface simultaneously with the supplying of said beam of direct light to said feeding or stimulating means location substantially immediately above said insect feeding or stimulating surface structure being constructed so that said measuring and recording means in sensitive to the completion of a circuit of electron flow through or proximate said conductive elements of said insect feeding or stimulating surface whereby the number and frequency of the insects attracted relative to the attractancy of said direct lighting means to the proximity of said feeding or stimulating means is capable of being determined using said measuring and recording means;

(v) anaesthetizing selected insects at a location apart from said feeding or stimulating means;
(vi) then supplying one or more anaesthetized insects to said first defined 3-space;
(vii) then enclosing said first 3-space surrounding said feeding or stimulating means whereby access thereto is limited to said air supply, air conduction and air removal means;
(viii) forming an electrical circuit connection between said feeding or stimulating means;
(ix) then supplying, conducting and removing air at a substantially constant mass flow rate and substantially constant linear velocity to, past and from second defined 3-space;
(x) simultaneously supplying said direct light to said second defined 3-space, the supplying of light in the air being carried out at such conditions and for such a period of time that the anaesthetized
(xi) insects are de-anaesthetized and recommence life activity; and observing on said measuring and recording means the number and frequency of de-anaesthetized insects attracted to the surface or proximity of said feeding or stimulating means.

The apparatus of our invention and process for using same contain features which contain radical improvements over the apparatus and process disclosed and claimed in U.S. Pat. No. 4,759,228.

Various prior art techniques for studying feeding habits of insects have been found to be useful in formulating processes and apparatus for determining relative attractancy and repellency for insects. Thus, the paper "Laboratory Blood Feed of *Culicoides mississippiensis* (Diptera: Ceratopogonidae) Through A Reinforced Silicone Membrane" by Davis, Butler, Roberts, Reinert and Kline (J. Med. Entomol. Vol 20, 2: 177-182) discloses the preparation and use of a durable silicone membrane for feeding *Culicoides mississippiensis* in the laboratory. Further, the paper entitled "IN VITRO Feeding of Ornithodoros Ticks For Rearing And Assessment of Disease Transmission", Butler, Hess, Endris and Holscher, ACAROLOGY VI, Volume 2, published 1984 by Ellis Horwood Limited, Market Cross House, Cooper Street, Chichester, West Sussex, PO 191EB, England discloses the advantages of feeding of haematophagous arthropods through artificial membranes. A number of preferred embodiments of our invention include the teachings of the aforementioned papers. Accordingly, the aforementioned papers are incorporated herein by reference.

With reference to that aspect of our invention concerning insect repellent soap compositions, U.S. Pat. No. 4,707,496 issued on Nov. 17, 1987 relates to a topical insect repellent soap composition and to a method of protection using such composition. Generally, the insect repellent soap composition of U.S. Pat. No. 4,707,496 comprises:
(1) from 63.0 to 99.5% by weight of a soap mixture containing from 4.1 to 7% by weight of a soap of caprylic acid, from 3.8 to 7% of a soap of capric acid, from 32.1 to 45% of a soap of lauric acid, from 12 to 17.5% by weight of a soap of myristic acid, from 5.0 to 10% by weight of a soap of palmitic acid, from 1.6 to 3% by weight of a soap of stearic acid, from 3.5 to 5% by weight of a soap of oleic acid and from 0.9 to 5% by weight of a soap of linoleic acid;
(2) from 0.1 to 2% by weight of one or more $C_8$-$C_{18}$ straight chain fatty acids;
(3) from 0.2 to 30% by weight of a repellent chemical; and
(4) from 0.2 to 5% by weight of an effective residual insecticide.

The aroma of the caprylic acids disclosed in U.S. Pat. No. 4,707,496 cannot be considered to be asethetically pleasing and the efficacy in repelling (*Musca domestica* L. (Diptera: Muscidae)) of these caprylic acids and the efficacy of repelling mosquitoes (*Aedes aegyptae*) of these caprylic acids is relatively low compared with the efficacy in repelling such insects of the ketones, ketoesters and alcohol of our invention.

BRIEF DESCRIPTION OF THE DRAWINGS

FIG. 1-A is a schematic diagram (blown up for illustration purposes) of an embodiment of the olfactometer apparatus of our invention useful, inter alia, in ascertaining the efficacy of the ketones, ketoesters, alcohol and ester as repellents and attractants for house flies (*Musca domestica* L. (Diptera: Muscidae)) and mosquitoes (*Aedes aegyptae*) indicating in schematic block flow diagram form the utilization of computer-assisted efficacy measuring apparatus.

FIG. 1-B is a top view of the embodiment of the apparatus of our invention shown in FIG. 1-A.

FIG. 1-C is a cut-away side elevation view of the base section of the olfactometer apparatus of our invention of FIG. 1-A showing in block flow diagram form the way in which the treatment agent (repellent or attractant being tested) is mixed with air at a mixing station and the resulting mixture is then transmitted from the mixing station into several side ports of the base section of the olfactometer of our invention.

FIG. 1-D is a cut-away side elevation view of a portion of the base section of the olfactometer apparatus of FIG. 1-C showing the directional vector of the air and treatment mixture and the relationship thereof with the detecting means and insect feeding and/or stimulating means portions of the olfactometer of our invention.

FIG. 1-E is a cut-away side elevation view of a section, in detail, of the base section of the olfactometer apparatus of FIG. 1-C showing the inter relationship of the air-treatment agent mixture flow with the active and passive insect interest electronic detecting means and the insect feeding and/or stimulating means of the olfactometer of our invention.

FIG. 1-F is a perspective view in detail of the arrangement of the active and passive insect interest electronic detecting means and the insect feeding and/or stimulating means of the olfactometer apparatus of our invention.

FIG. 1-Da is a cut-away side elevation view, in detail, of a section of the base section (shown in FIG. 1-C) of the olfactometer apparatus of our invention of FIG. 1-A in a different configuration from the configuration shown in FIGS. 1-D and 1-E; but also showing the arrangement and relationship of the air and treatment agent mixture flow vector with the active and passive insect interest electronic detecting means and with the insect feeding and/or stimulating means of the olfactometer apparatus of our invention.

FIG. 1-G is a cut-away side elevation view, in detail, of a section of the base section (shown in FIG. 1-C) of the olfactometer apparatus of our invention of FIG. 1-A thus showing another variation of the configuration of the air-treatment agent mixture flow vector with respect to the active and passive insect interest electronic detecting means and the insect feeding and/or stimulating means, whereby the entry of the air-treatment agent mixture is in a direction parallel to the plane of the insect detecting means but the flow is altered 90 degrees so that the air-treatment agent mixture vector is in a direction perpendicular to the plane of the insect detecting means and perpendicular to the plane of a horizontally-positioned insect feeding and/or stimulating microporous planar lamina.

FIG. 1-H is a schematic diagram (blown up for illustration purposes) of another embodiment of the olfactometer apparatus of our invention useful, inter alia, in ascertaining the efficacy of the ketones, ketoesters, alcohol and ester as repellents and attractants for house flies (*Musca domestica* L. (Diptera: Muscidae)) as well as mosquitoes (*Aedes aegyptae*) indicating in schematic block flow diagram form the utilization of computer-assisted efficacy measuring apparatus; and also showing in block flow diagram form the inter relationship of the air and treatment agent mixing station with the entry ports for the resulting air-treatment mixture into the olfactometer apparatus of our invention.

FIG. 1-J is an exploded perspective view of the apparatus shown in FIG. 1-H, showing in detail the inner workings of the apparatus of FIG. 1-H.

FIG. 1-L is a cut-away side elevation view of the base portion of the apparatus of FIG. 1-H, also showing in schematic block flow diagram form the utilization of computer assisted efficacy measuring apparatus together with the interrelationship of the mixing station for the air and treatment agent and the entry of the resulting air-treatment agent mixture into the entry ports of the olfactometer apparatus of our invention along a vector parallel to the plane of the active and passive insect interest electronic detecting means.

FIG. 1-L*a* is a cut-away side elevation view of the base section of the olfactometer apparatus of our invention of FIG. 1-H indicating in schematic block flow diagram form the utilization of computer assisted efficacy measuring apparatus but showing only an air supply entry into the side ports of the olfactometer apparatus with the treatment agent being contained in a control released matrix upstream from the air supply source.

FIG. 1-L*b* is a cut-away side elevation view of the base section of another embodiment of the olfactometer apparatus of FIG. 1-H, showing means for raising the temperature of the insect feeding and/or stimulating means using heating coils.

FIG. 1-L*c* is the top view of the embodiment of the olfactometer apparatus of FIG. 1-L*b*.

FIG. 1-L*d* is a cut-away cross-sectional bottom view of the embodiment of the olfactometer apparatus of our invention shown, in part, in FIG. 1-L*b*, showing in detail the location of the heating coil means in the base section of the olfactometer apparatus of our invention.

FIG. 1-M is a cut-away side elevation view of a detailed section of the base section of an embodiment of the olfactometer apparatus of FIG. 1-H indicating a partially cut-away side elevation view of the entry port for the air stream, showing control released composition-containing particles whereby the treatment agent is controllably released into the air stream which is passed on a vector from the entry port parallel to the electronic detecting means.

FIG. 1-N is a cut-away perspective view of the outside portion of the insect feeding and/or stimulating means looking down at the upper surface of the porous membrane part of said insect feeding and/or stimulating means.

FIG. 1-O is the end view in cross-section, of the wire grid section of the active and passive insect interest electronic detecting means.

FIG. 1-P is the end view, taken in cross-section, of a second embodiment of the wire grid portion of the active and passive insect interest electronic detecting means of the olfactometer apparatus of FIG. 1-H.

FIG. 2-A is a series of graphs depicted in three dimensions (in a rectangular mode for the "x" and "y" axes) showing the relative attractiveness or repellency of dimethyl sebacate, beta damascone, blood extract, diethyl sebacate, a blank, lactic acid, dibutyl sebacate and isopropyl propionate. The results are tabulated in Table I infra which list insects collected in the apparatus of FIG. 1-H, per interval.

Figure 1:
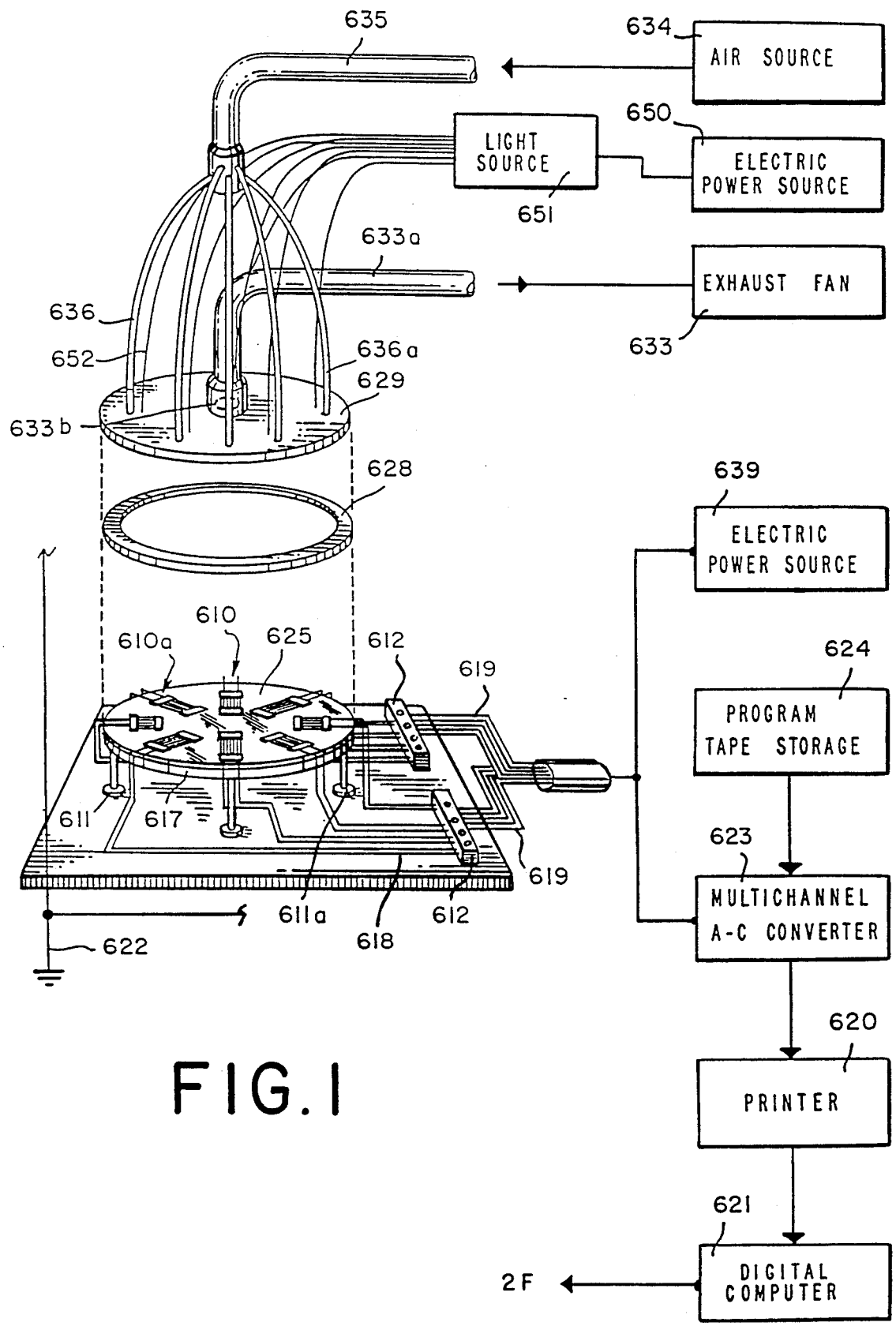
FIG. 1 is a schematic diagram (blown up for illustration purposes) of an embodiment of a prior art olfactometer apparatus useful, inter alia, in ascertaining the efficacy of the ketones, ketoesters, alcohol and ester as attractants and repellents for house flies (*Musca domestica* L. (Diptera: Muscidae)) and mosquitoes (*Aedes aegyptae*) indicating in schematic block flow diagram form the utilization of computer-assisted efficacy measuring apparatus as explained in U.S. Pat. No. 4,764,367 the specification for which is incorporated by reference herein.

In the case of FIG. 2-A the insect tested is *Musca domestica* L. (Diptera: Muscidae).

FIG. 2-B is a series of graphs depicted in three dimensions (in a circular mode for the "x" and "y" axes) showing the relative attractiveness or repellency of dimethyl sebacate, beta damascone, blood extract, diethyl sebacate, a blank, lactic acid, dibutyl sebacate and isopropyl propionate. The results are tabulated in Table I infra which lists insects (house flies) collected in the apparatus of FIG. 1-H, per interval. The graphs are based on experiments run for a total 1 hour with 6 intervals of 10 minutes each.

FIG. 2-C is a series of graphs of FIGS. 2-A and 2-B taken together and depicted in two dimensions.

FIG. 3-A is a series of graphs depicted in three dimensions (in a rectangular mode for the "x" and "y" axes) showing the relative attractiveness or repellency of eugenol, limonene, blood extract, a blank, dibutyl phthalate, Z-6-nonenol, n-dodecanol and methylisoeugenol. The graphs are based on experiments run for a total of 1 hour with 6 separate 10 minute intervals. The results are tabulated in Table II, infra.

FIG. 3-B is a series of graphs depicted in three dimensions (in a circular mode for the "x" and "y" axes) showing the relative attractiveness or repellency of eugenol, limonene, blood extract, a blank, dibutyl phthalate, Z-6-nonenol, 1-dodecanol and methylisoeugenol. The graphs are based on experiments run for a total of 1 hours with 6 intervals of 10 minutes each. The results are tabulated in Table II, infra and are the same as depicted in FIG. 3-A.

FIG. 3-C is a series of graphs depicting the data set forth in graphical form in FIGS. 3-A and 3-B depicted in two dimensions.

FIG. 4-A is a series of graphs depicted in three dimensions (in a rectangular mode for the "x" and "y" axes) showing the relative attractiveness or repellency of beta damascone, HEDIONE ® a (50:50 mixture of the compounds having the structures:

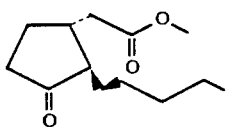

and

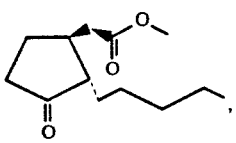

a known attractant, "extract of used fly rearing media" (a mixture of manures, alfalfa and baking soda), a blank, methyl jasmonate, a mixture of compounds having the structures:

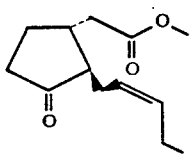

and

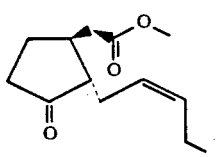

the ethyl ester of 2-methyl-3-pentenoic acid and trans, trans-delta-damascone having the structure:

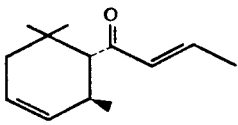

The graphs are based on experiments run for a period of 1 hour with 6 intervals of 10 minutes each. The results are tabulated in Table III, infra.

FIG. 4-B is a series of graphs depicted in three dimensions (in a circular mode for the "x" and "y" axes) showing the relative attractiveness or repellency of beta damascone, HEDIONE ® registered trademark of Firmenich, et Cie of Geneva, Switzerland), "extract of used fly rearing media" (a mixture of minerals, alfalfa and baking soda), a blank, methyl jasmonate, the ethyl ester of 2-methyl-3-pentenoic acid and trans, trans-delta-damascone. The graphs are based on experiments run for a period of 1 hour with 6 intervals of 10 minutes each. The results are tabulated in Table III, infra.

FIG. 4-C is a series of graphs depicting the data set forth in graphical form in FIGS. 4-A and 4-B depicted in two dimensions.

FIG. 5-A is a series of graphs depicting in three dimensions (in a rectangular mode for the "x" and "y" axes) showing a relative attractiveness or repellency of beta damascone, HEDIONE ® "extract of used fly rearing media", beta damascenone, a blank, methyl jasmonate, the ethyl ester of 2-methyl-3-pentenoic acid and trans, trans-delta-damascone. The graphs are based on experiments run for a total of 13 hours with five intervals of 2.6 hours each. The results are tabulated in Table IV, infra.

FIG. 5-B is a series of graphs depicting in three dimensions (in a circular mode for the "x" and "y" axes) showing the relative attractiveness or repellency of beta damascone, HEDIONE ® "extract of used fly rearing media", beta damascenone, a blank, methyl jasmonate, the ethyl ester of 2-methyl-3-pentenoic acid and trans, trans-delta-damascone. The graphs are based on experiments run for a total of 13 hours with five intervals of 2.6 hours each. The results are tabulated in Table IV, infra and are the same as depicted in FIG. 5-A.

FIG. 5-C is a series of graphs depicting the data set forth in graphical form in FIGS. 5-A and 5-B, depicted in two dimensions.

FIG. 6-A is a series of graphs depicted in three dimensions (in a rectangular mode for the "x" and the "y" axes) showing the relative attractiveness or repellency of eugenol, (−) limonene, blood extract, a blank, dibutyl phthalate, Z-6-nonenol, n-dodecanol and methylisoeugenol. The graphs are based on experiments run for a period of 1 hour with 6 intervals of 10 minutes each. The results are tabulated in Table V, infra.

FIG. 6-B is a series of graphs depicted in three dimensions (in a circular mode for the "x" and the "y" axes) showing the relative attractiveness or repellency of eugenol, (−) limonene, blood extract, a blank, dibutyl phthalate, Z-6-nonenol, n-dodecanol and methylisoeugenol. The graphs are based on experiments run for a period of 1 hour with 6 intervals of 10 minutes each. The results are tabulated in Table V, infra and are the same as depicted in FIG. 6-A.

FIG. 6-C is a series of graphs depicting the data set forth in graphical form in FIGS. 6-A and 6-B depicted in two dimensions.

FIG. 7-A is a block flow diagram showing the procedure used in conjunction with the apparatus of the prior art of FIG. 7-B in ascertaining attractancy or repellency of insects. The apparatus shown and process shown in FIGS. 7-A and 7-B is that used in determining data graphically presented in FIGS. 8-25 inclusive, infra.

FIG. 7-B is a perspective view of apparatus of the prior art used in determining attractancy or repellency of insects and was specifically used in determining the data graphically depicted in FIGS. 8-25 inclusive.

Figure 8:
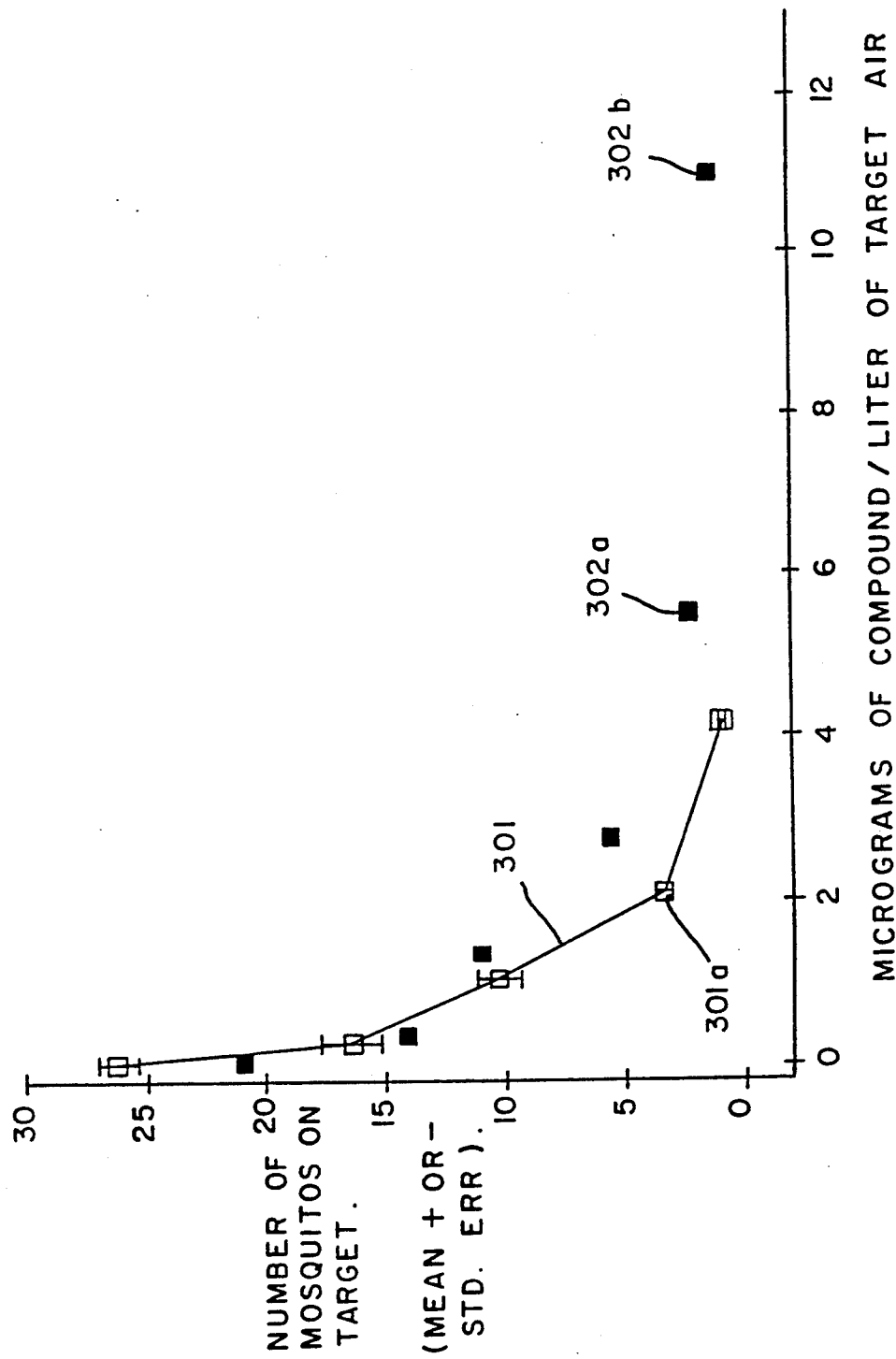

FIG. 8 is a graph in two dimensions showing a dose-response curve for each of HEDIONE ®, a 50:50 mixture of compounds having the structures:

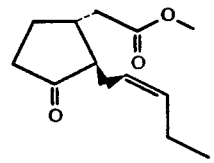

and

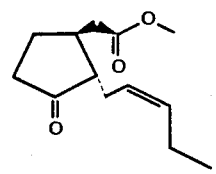

and "DEET", diethyl toluamide with the "x" axis being micrograms of compound/liter of target air and the "y" axis showing number of mosquitoes on target (carbon dioxide addition rate: 50 ml/min). The graphical data was determined using the apparatus and process shown in FIGS. 7-A and 7-B, described briefly supra.

Figure 9:
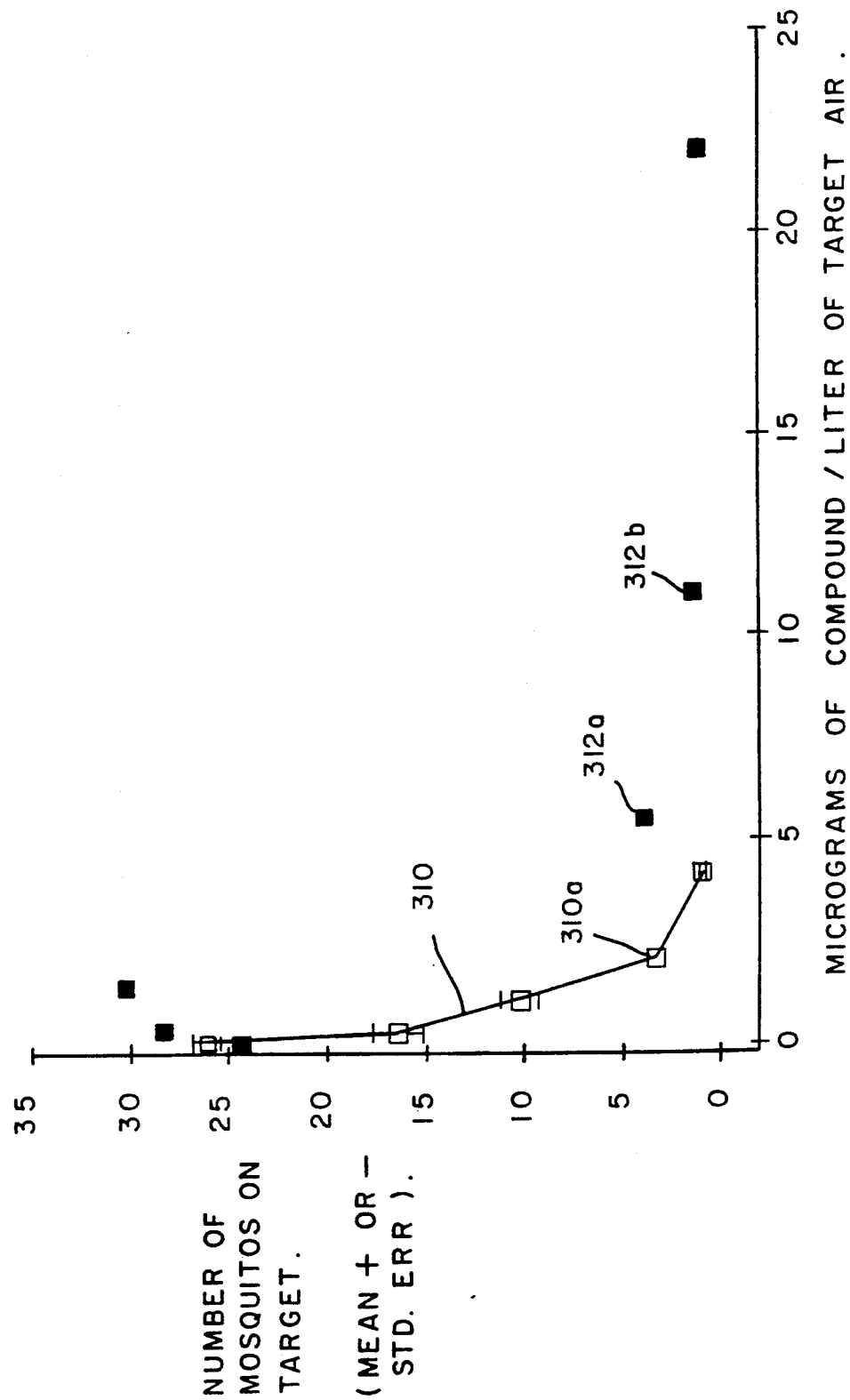

FIG. 9 is a dose-response curve for a number of mosquitoes on target (the "y" axis) versus micrograms of compound/liter of target air (the "x" axis) comparing as a mosquitoes repellent or attractant methyl jasmonate, the mixture of compounds having the structures:

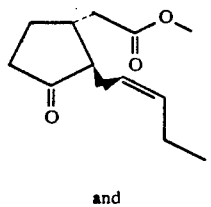

and

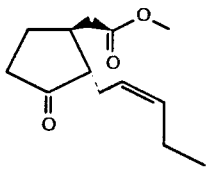

and "DEET", diethyl toluamide. The graphical data was determined using the apparatus set forth in FIG. 7-B and the process depicted in FIG. 7-A. (carbon dioxide addition rate: 50 ml/min).

Figure 10:
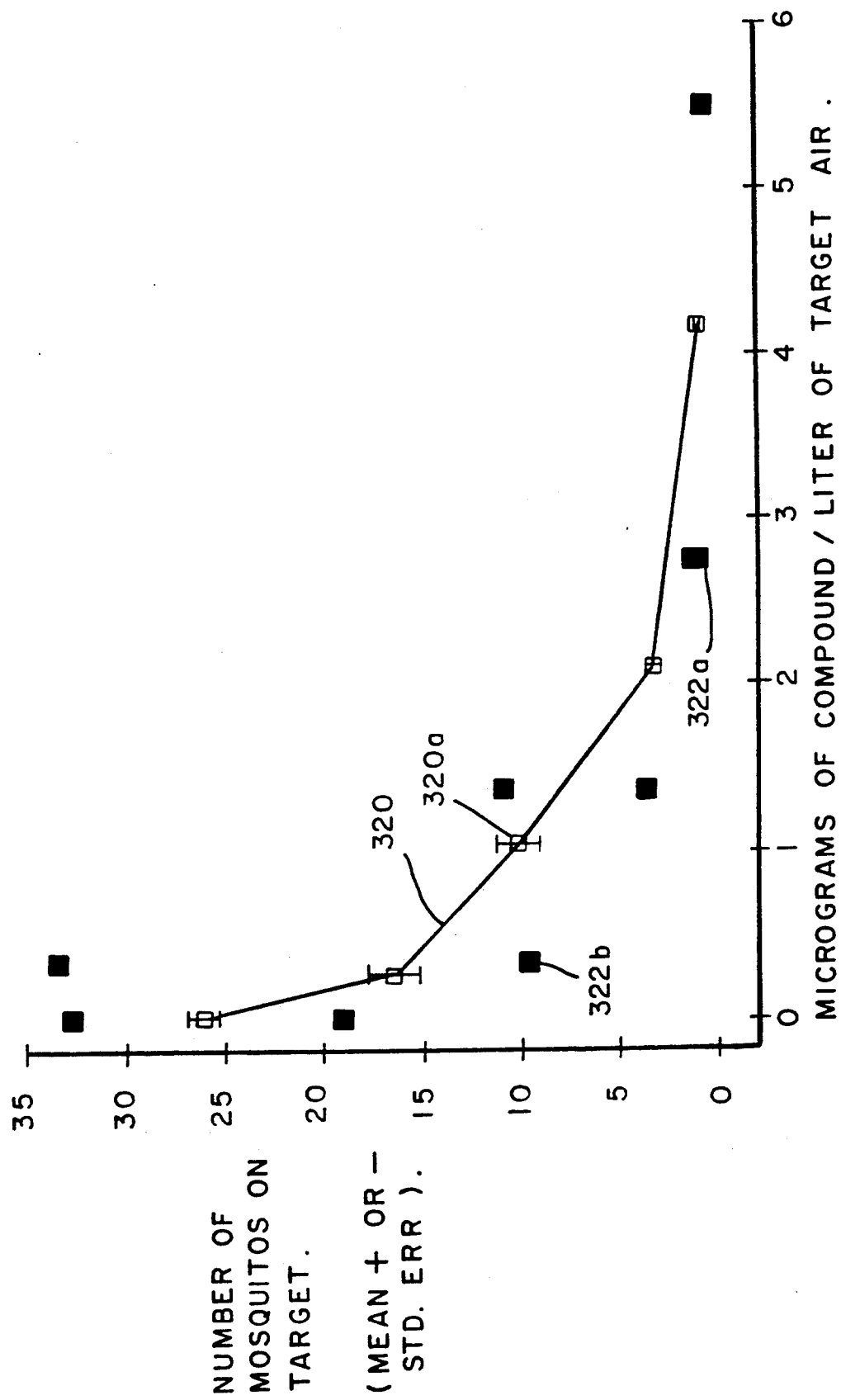

FIG. 10 is graph showing the number of mosquitoes on target (the "y" axis) versus micrograms of compound tested/liter of target air (the "x" axes, comparing the repellency or attractancy of beta damascone with DEET (diethyl toluamide). The graphs are "dose-response curves". The graphical data was determined using the apparatus shown in FIG. 7-B and the process shown in FIG. 7-A (carbon dioxide addition rate: 50 ml/min).

Figure 11:
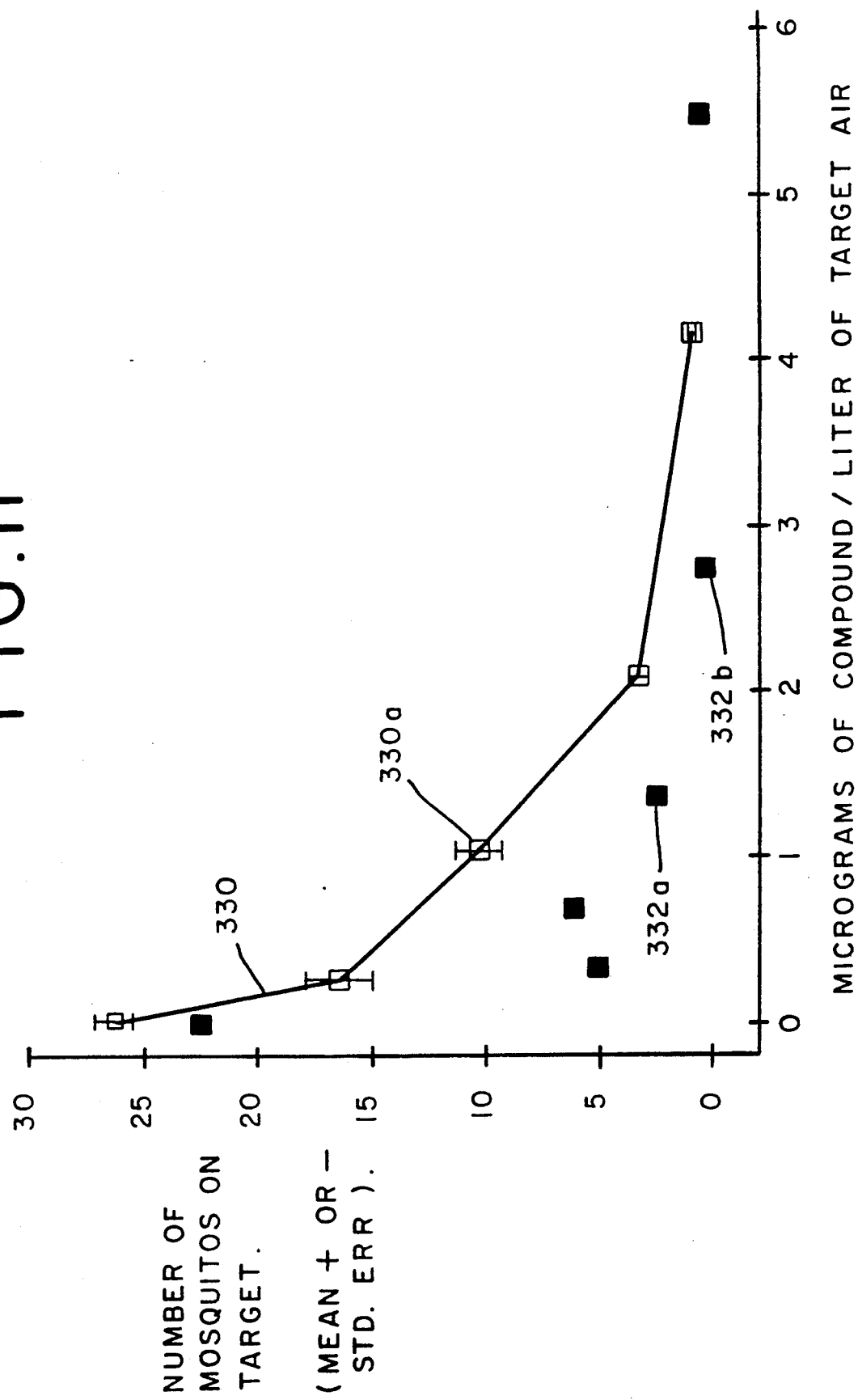

FIG. 11 sets forth two dose-response curves showing number of mosquitoes on target (the "y" axis) versus micrograms of compound to be tested/liter of target air (the "y" axis) comparing the attractancy or repellency of vanilla extract versus DEET (diethyl toluamide) (carbon dioxide addition rate: 50 ml/min). The graphical data was determined using the apparatus set forth in FIG. 7-B and the process depicted in FIG. 7-A.

Figure 12:
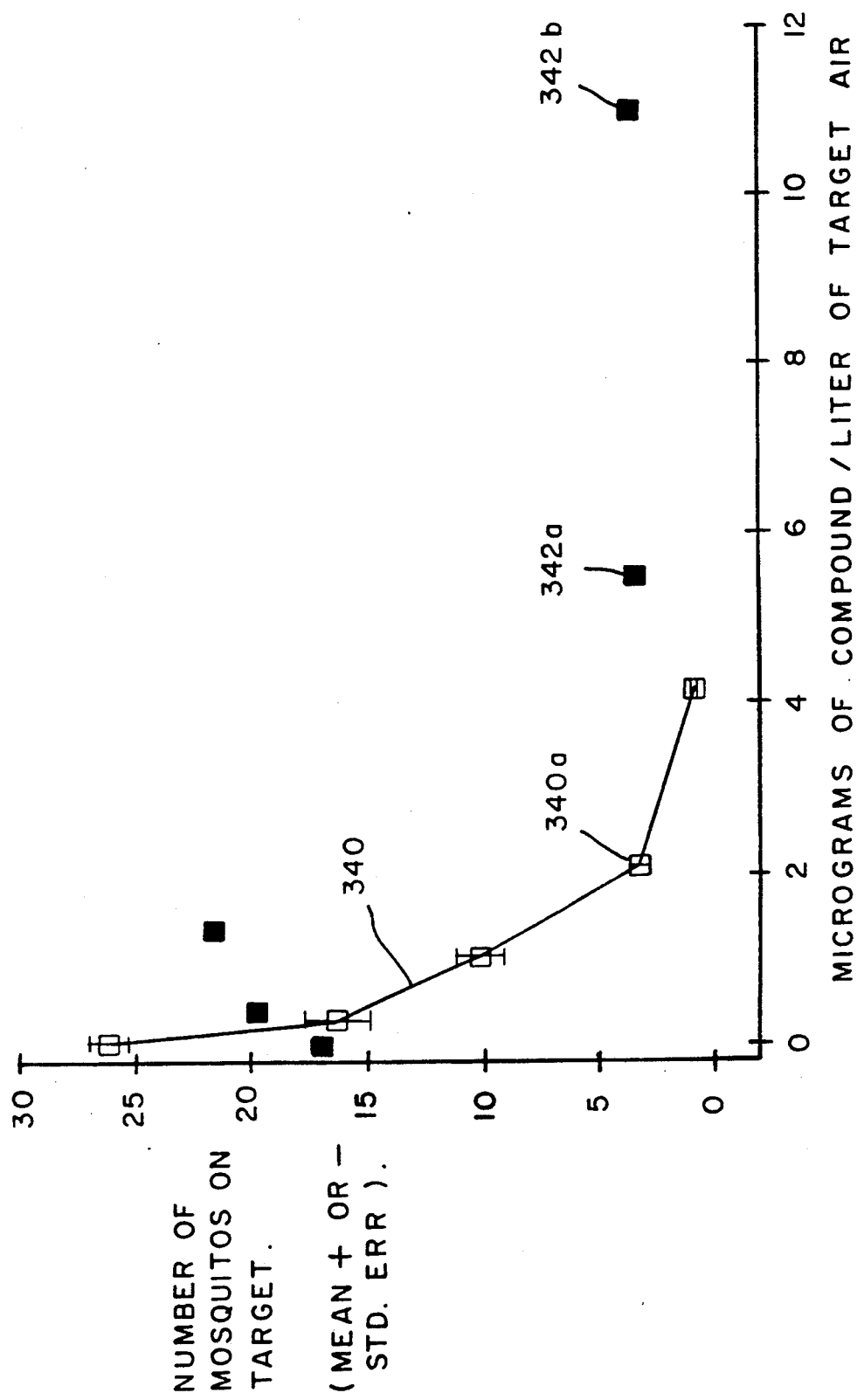

FIG. 12 sets forth dose-response curves with the number of mosquitoes on target shown on the "y" axis and the micrograms of compound to be tested/liter of target air on the "x" axis. The compounds compared are n-dodecanol and DEET (carbon dioxide addition rate: 50 ml/min). The apparatus used in determining the graphical data set forth on FIG. 12 is shown in FIG. 7-B and the process used is shown in FIG. 7-A.

Figure 13:
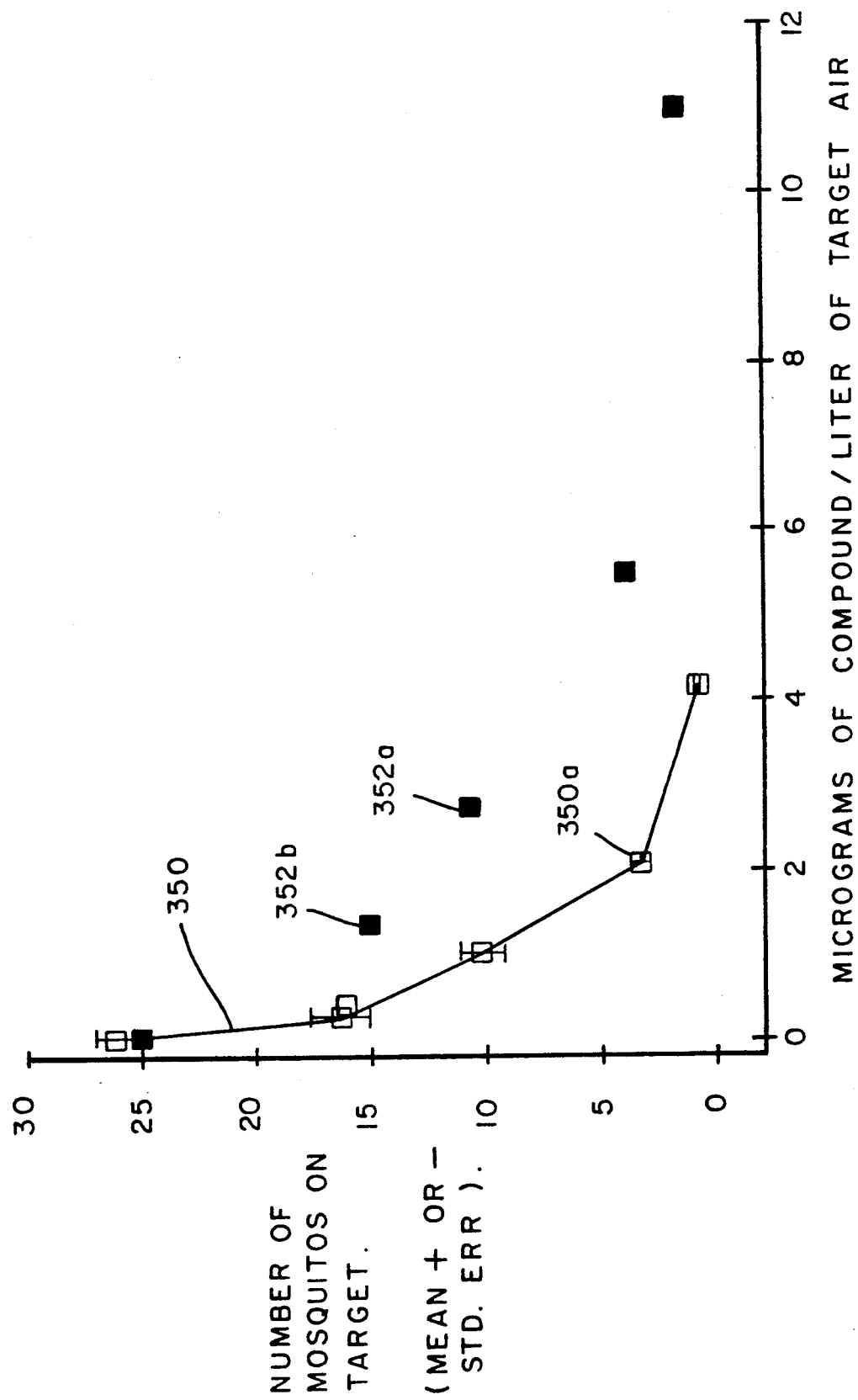

FIG. 13 sets forth dose-response curves with the number of insects on target on the "y" axis and the micrograms of compound to be tested/liter of target air on the "x" axis comparing the attractancy and repellency of Methylisoeugenol with DEET (diethyl toluamide).

Figure 14:
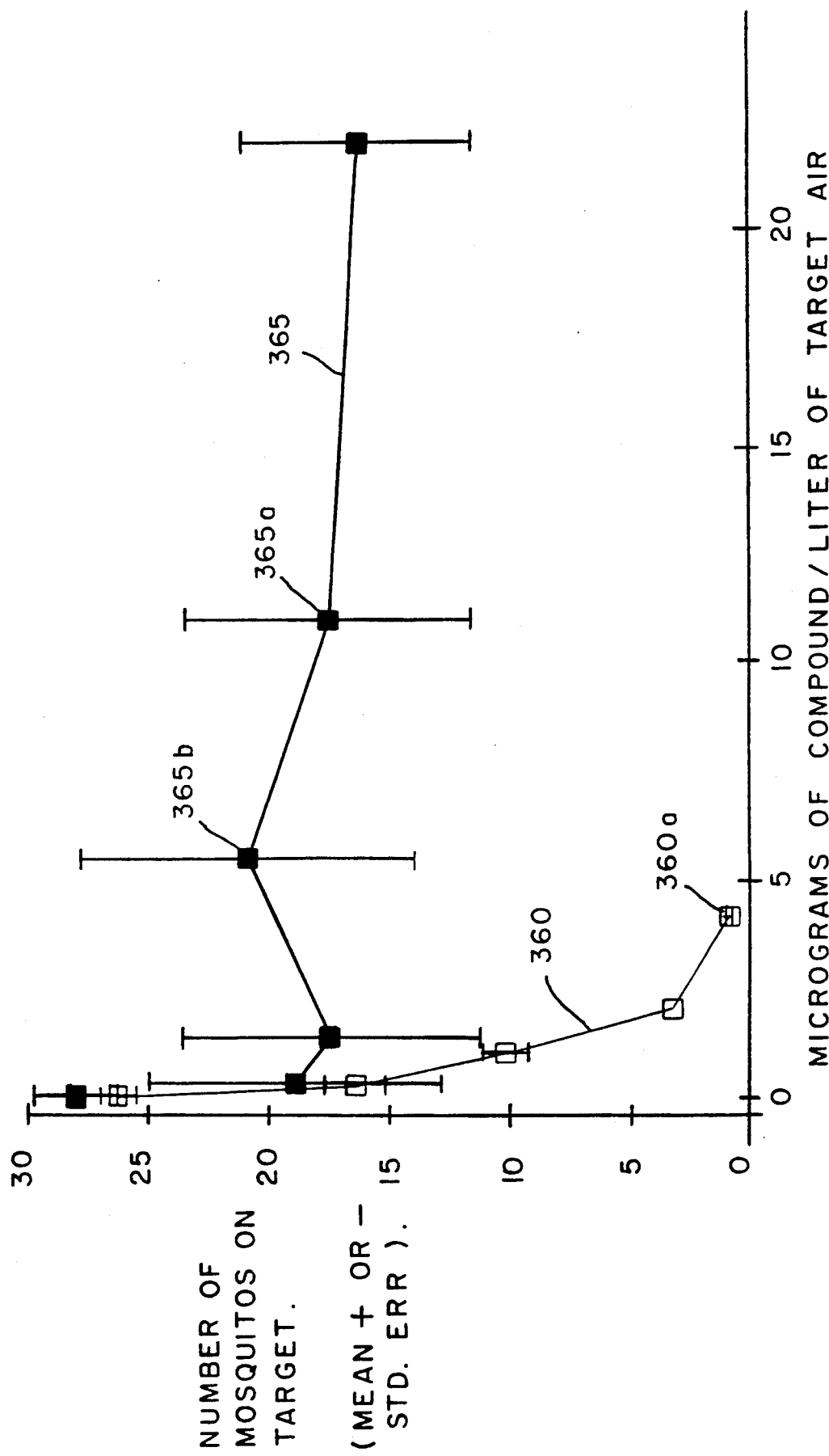

FIG. 14 sets forth dose response curves showing on the "x" axis micrograms of compound to be tested/liter of target air and on the "y" axis number of mosquitoes on target, comparing the two materials; jasmine absolute and DEET (diethyl toluamide) (carbon dioxide addition rate: 50 ml/min). The data set forth in FIG. 14 was determined using the apparatus of FIG. 7-B and the process of FIG. 7-A.

Figure 15:
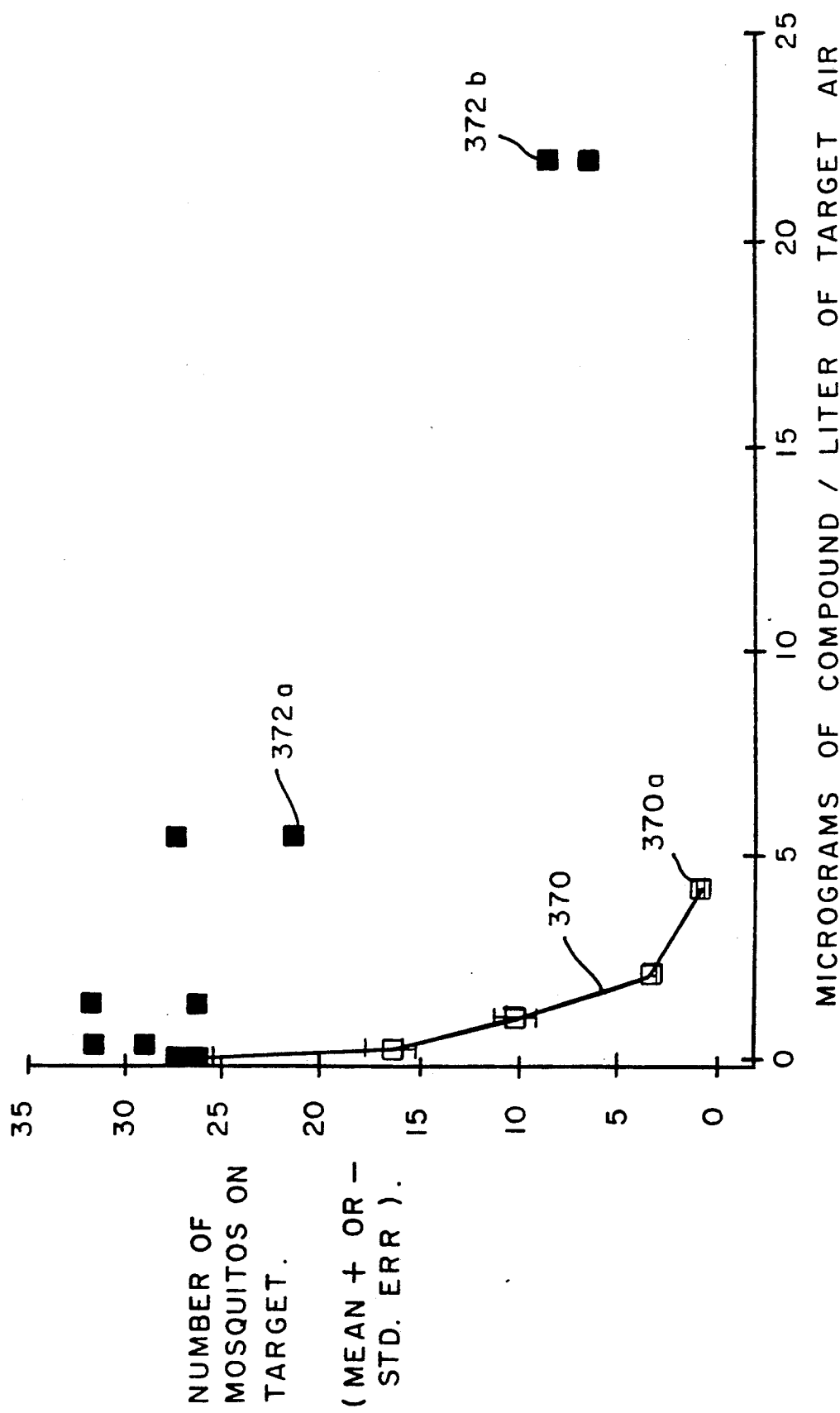

FIG. 15 are dose-response curves for a number of mosquitoes on target (the "x" axis) and micrograms of compound to be tested/liter of target air (the "x" axis) showing a comparison for the attractancy or repellency of mosquitoes for Rose Otto Bulgarian and DEET (diethyl toluamide) (carbon dioxide addition rate: 50 ml/min). The apparatus used in determining the graphical data set forth in FIG. 15 is those shown in FIG. 7-B. The process used in determining the graphical data on FIG. 15 is set forth in FIG. 7-A.

Figure 16:
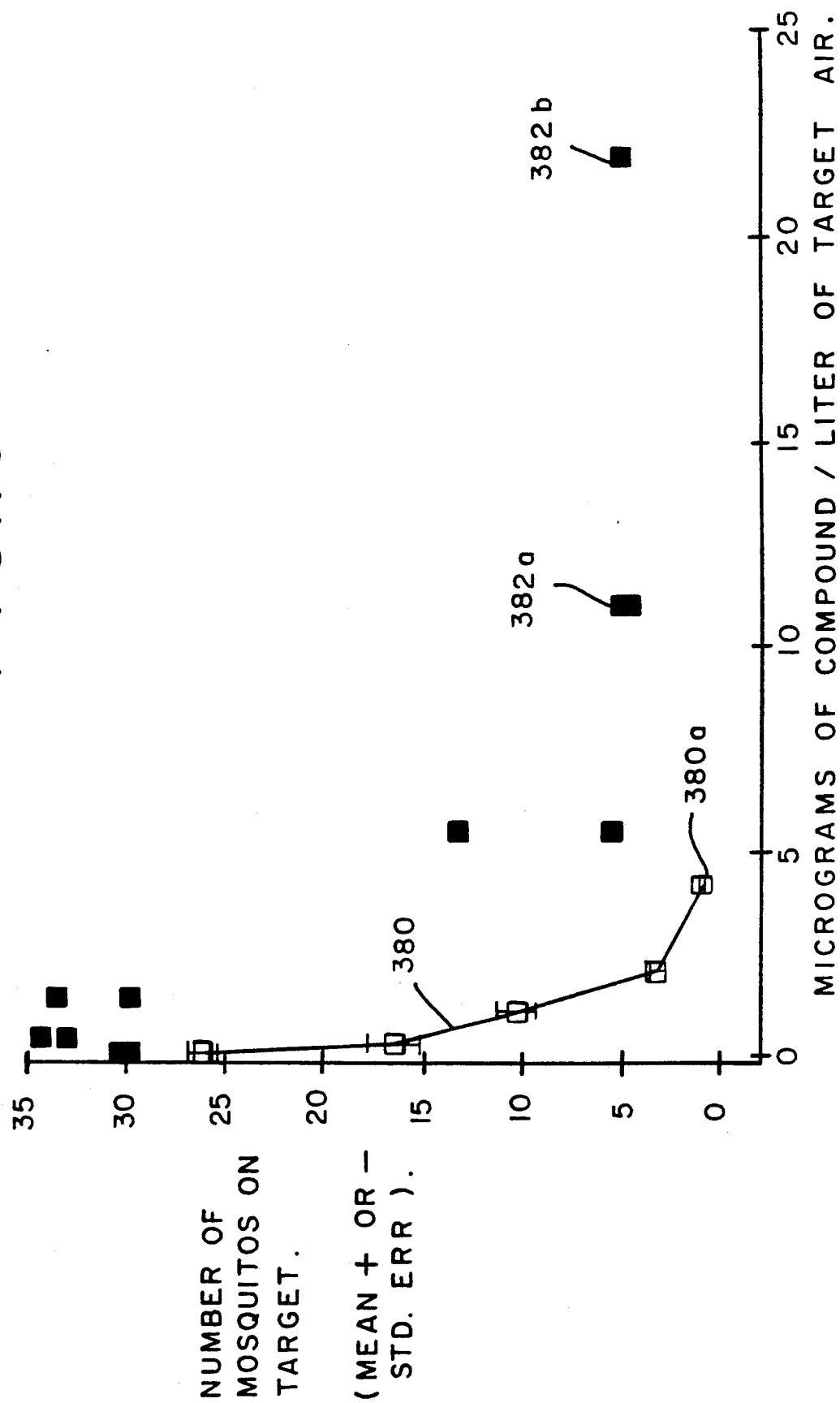

FIG. 16 sets forth dose-response curves showing number of mosquitoes on target (the "y" axis) and micrograms of compound to be tested/liter of target air) (the "x" axis) comparing the mosquito attractancy or repellency for KHARISMAL TM (a mixture of the compound having the structure:

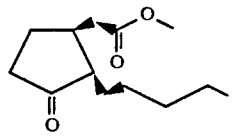

and the compounds having the structures:

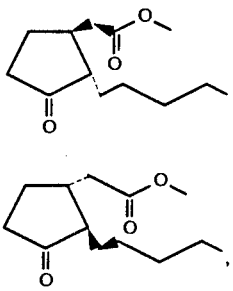

and DEET (diethyl toluamide) (carbon dioxide addition rate: 50 ml/min). The graphical data set forth on FIG. 16 was determined using the apparatus of FIG. 7-B and the process set forth in FIG. 7-A.

Figure 17:
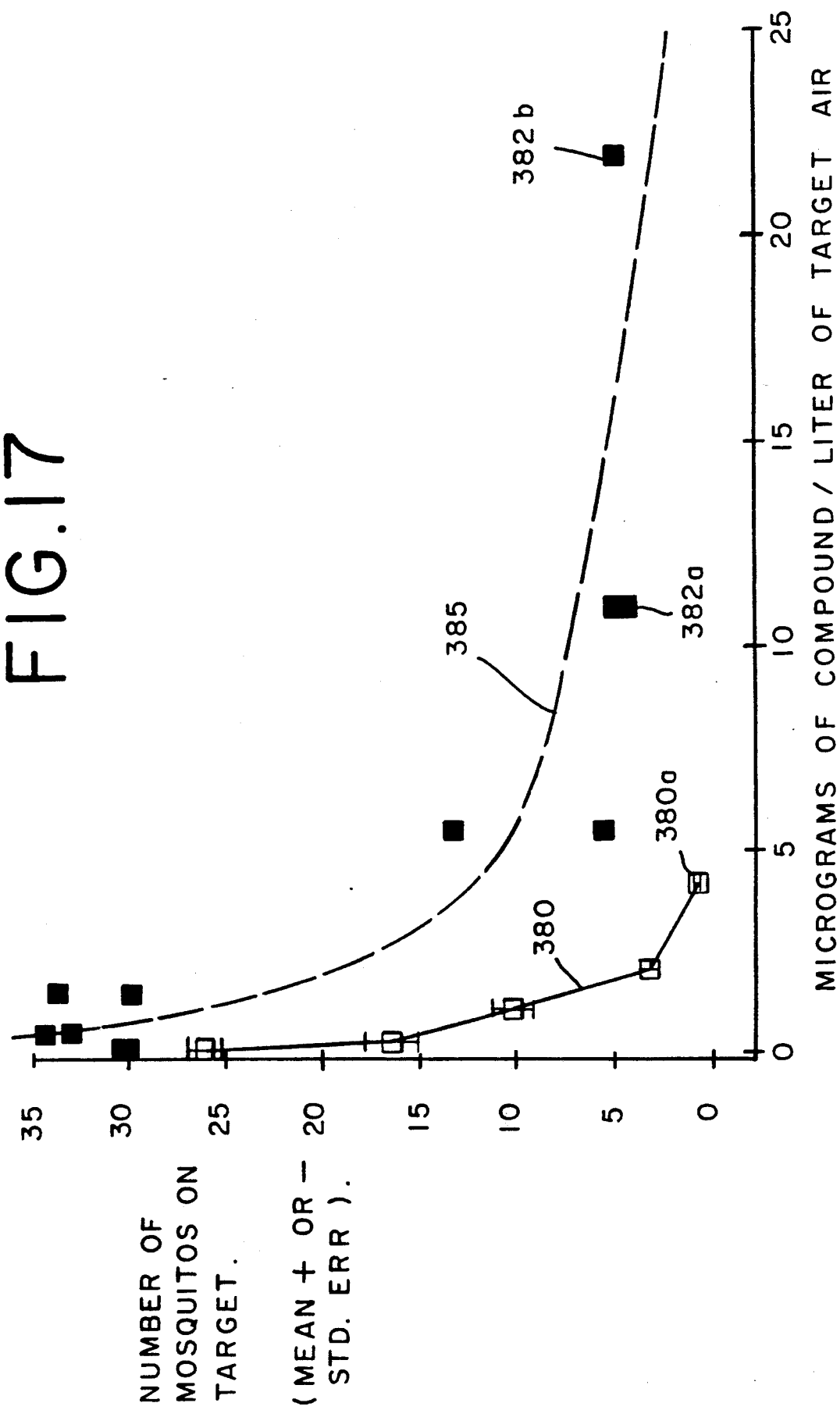

FIG. 17 is a replicate of the test results set forth in FIG. 16 depicted in graphical form in two dimensions.

Figure 18:
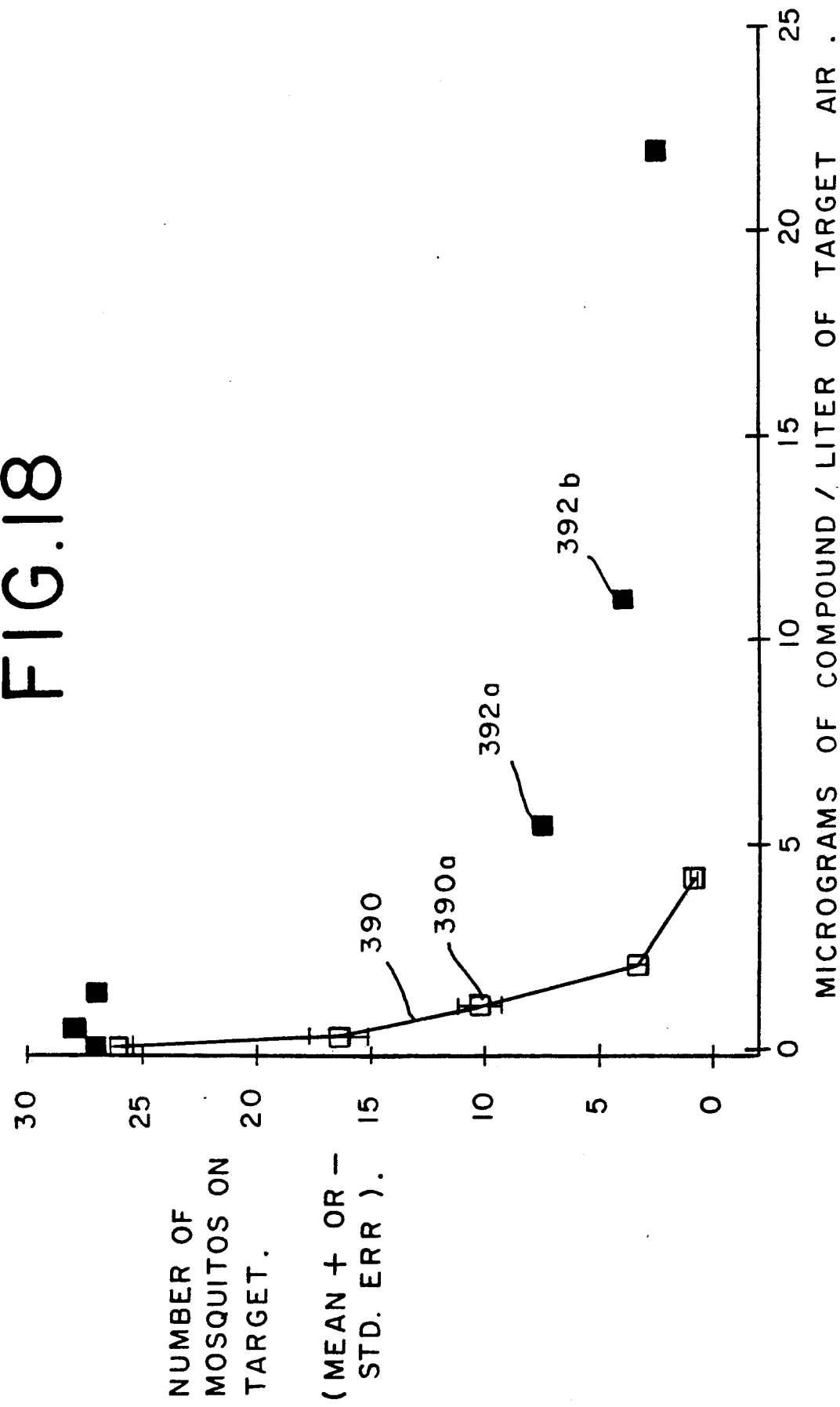

FIG. 18 sets forth dose-response curves graphically in two dimensions showing number of mosquitoes on target (the "y" axis) and micrograms of compound to be tested/liter of target air (the "x" axis) comparing alpha damascone (the compound having the structure:

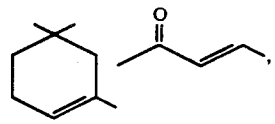

with DEET (diethyl toluamide) (carbon dioxide addition rate: 50 ml/min). The apparatus used in determining the data set forth in FIG. 18 is that shown in FIG. 7-B. The process used in determining the data of FIG. 18 is set forth in FIG. 7-A.

Figure 19:
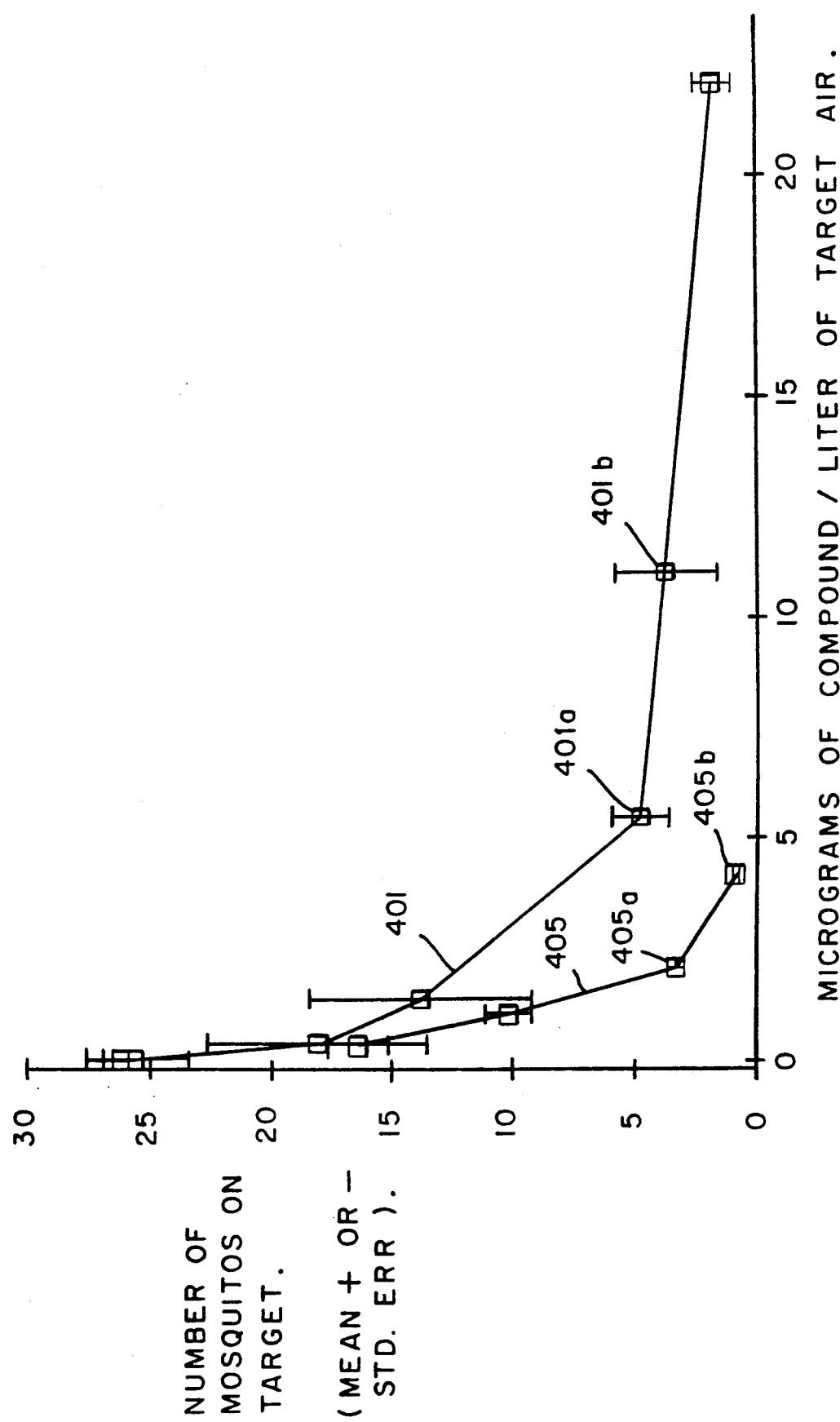

FIG. 19 sets forth dose-response curves showing number of mosquitoes on target (the "y" axis) and micrograms of compound to be tested/liter of target air (the "x" axis) comparing vanillin with DEET (diethyl toluamide) (carbon dioxide addition rate: 50 ml/min). The apparatus used in determining the data set forth in FIG. 19 is set forth in FIG. 7-B. The process used in determining the data set forth in FIG. 19 is depicted in FIG. 7-A.

Figure 20:
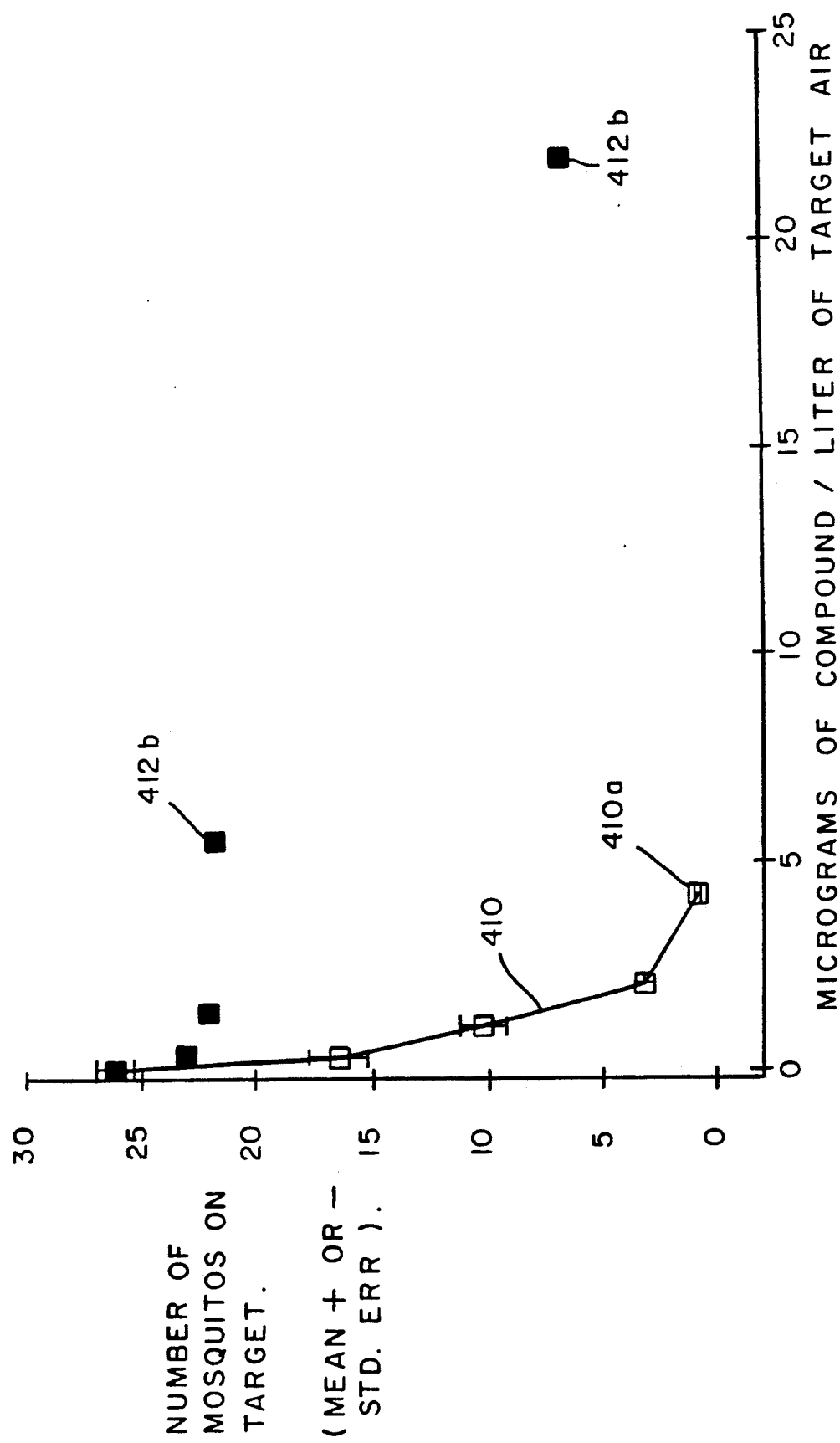

FIG. 20 sets forth dose-response curves in graphical form in two dimensions for a number of mosquitoes on target (the "y" axis) versus micrograms of compound/liter of target air (the "x" axis) comparing methyl eugenol and DEET (diethyl toluamide) for their attractancy or repellency for mosquitoes (carbon dioxide addition rate: 50 ml/min). The apparatus used in determining the data graphically depicted in FIG. 20 is set forth in FIG. 7-B. The process used in determining the graphical data set forth in FIG. 20 is set forth in FIG. 7-A.

Figure 21:
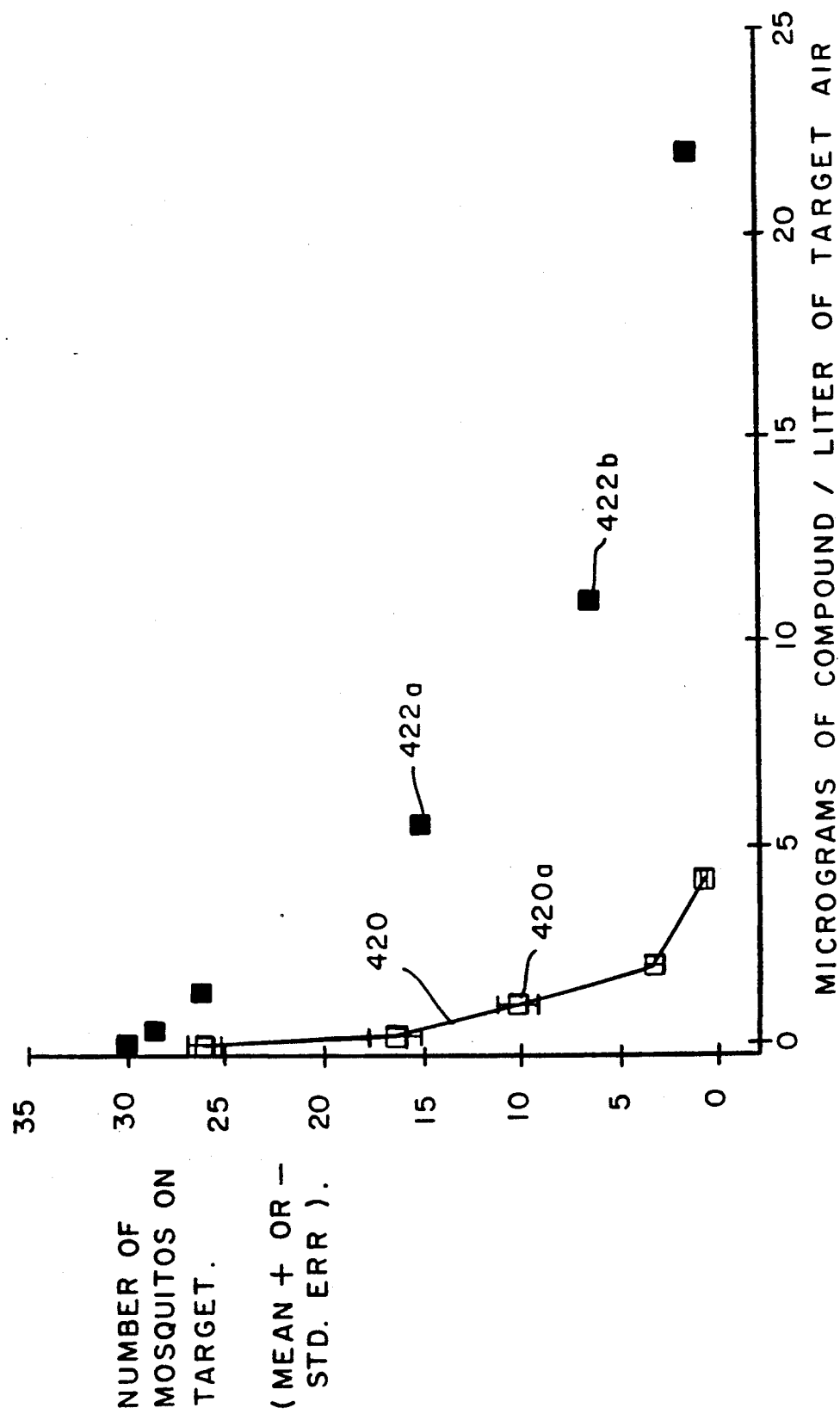

FIG. 21 sets forth dose-response curves for a number of mosquitoes on target (the "y" axis) versus micrograms of compound to be tested/liter of target air (the "x" axis) comparing for purposes of mosquito attractancy or repellency eugenol and DEET (diethyl toluamide). (carbon dioxide addition rate: 50 ml/min). The data set forth in FIG. 21 was determined using the apparatus of FIG. 7-B and the process of FIG. 7-A.

Figure 22:
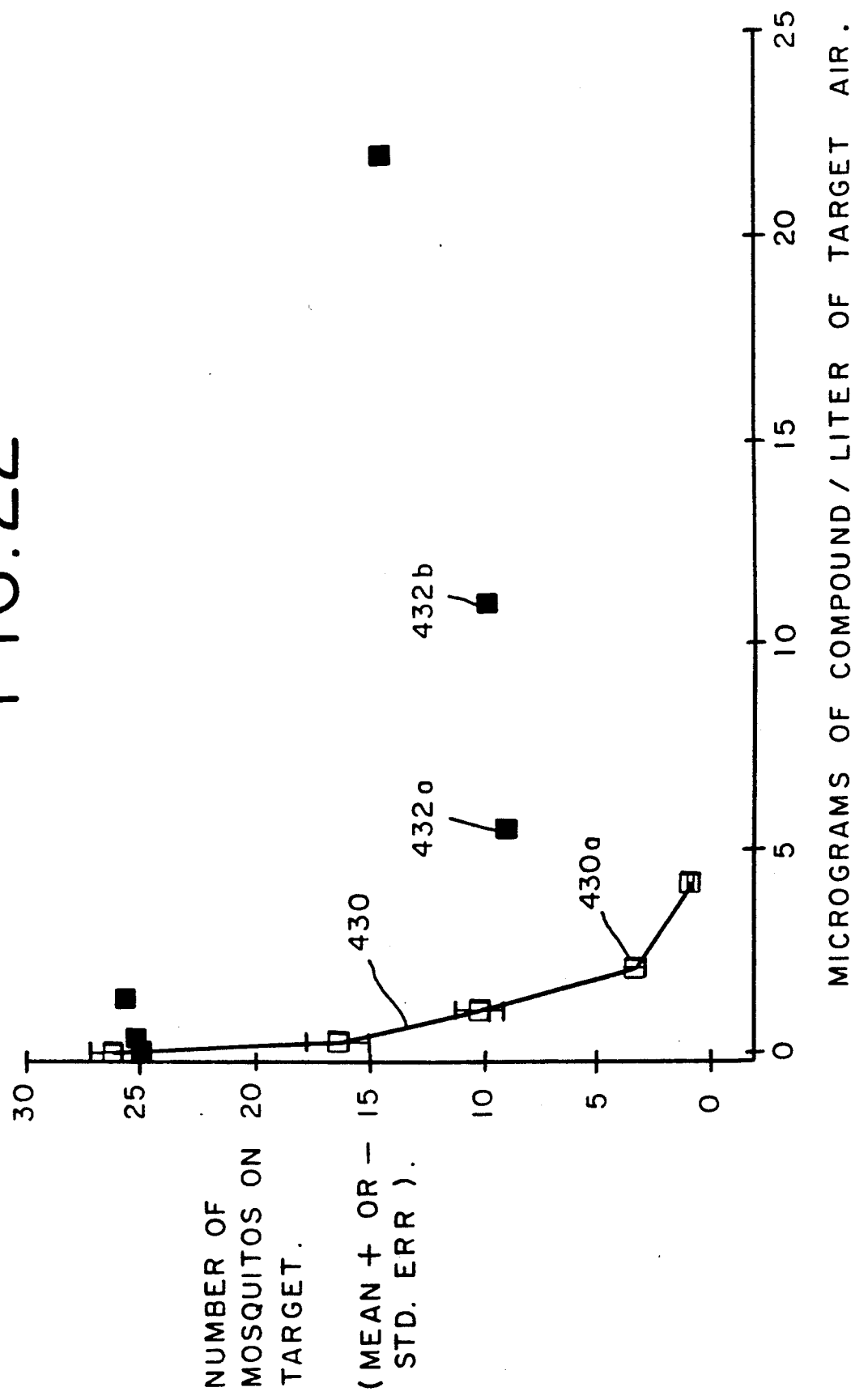

FIG. 22 sets forth dose-response curves in graphical form in two dimensions for a number of insects on target versus micrograms of compounds/liter of target air comparing n-dodecanol and DEET (diethyl toluamide) for their mosquito attractancy or repellency (carbon dioxide addition rate: 50 ml/min). The apparatus used in determining the data for FIG. 22 is shown in FIG. 7-B. The process used in determining the data for FIG. 22 is set forth in FIG. 7-A supra.

Figure 23:
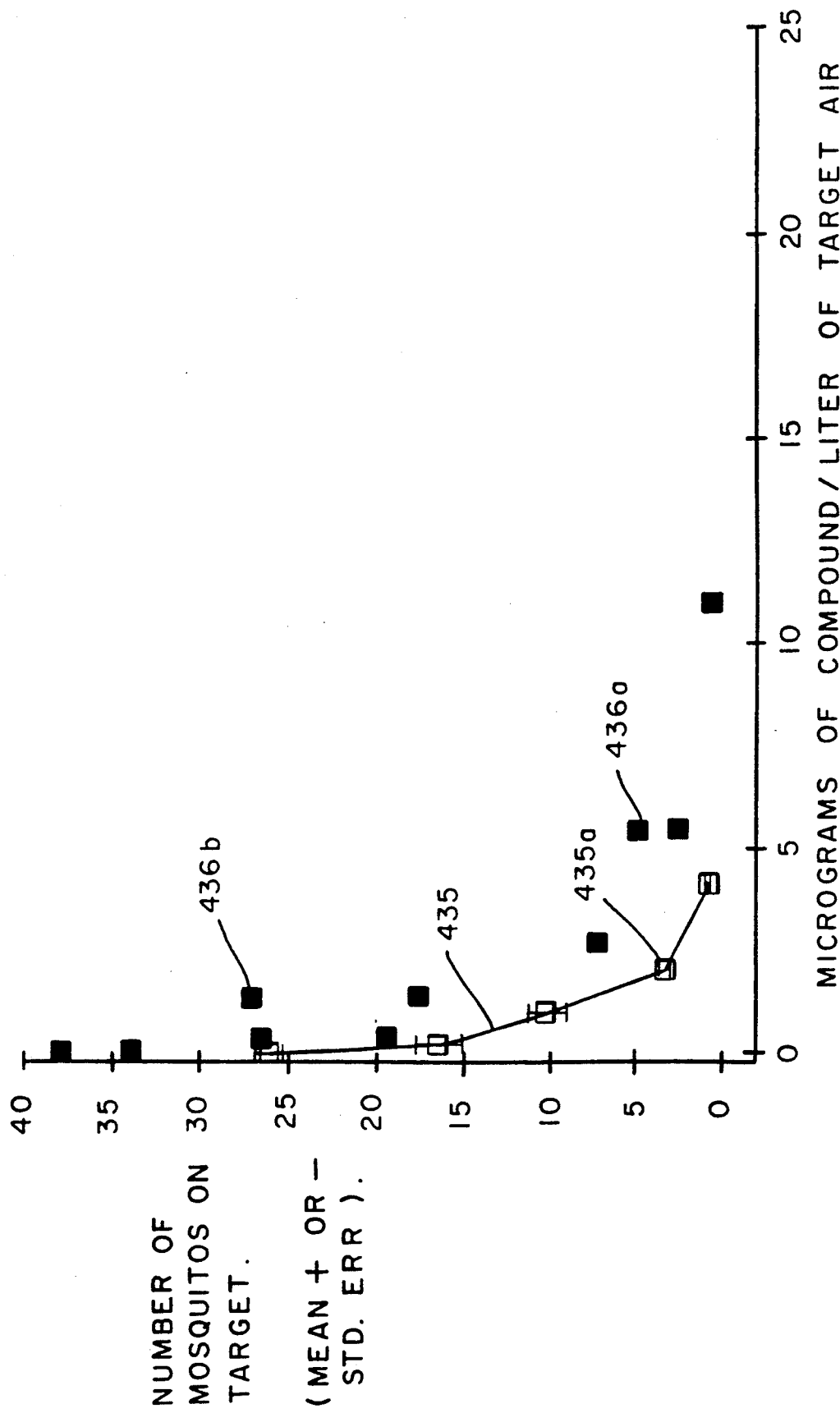

FIG. 23 sets forth dose-response curves showing number of mosquitoes on target (the "y" axis) versus micrograms of compound tested/liter of target air (the "x" axis) comparing the use as a mosquito attractant or repellent of ethyl vanillin versus DEET (diethyl toluamide). (carbon dioxide addition rate: 50 ml/min). The apparatus used in determining the data for FIG. 23 is set forth in FIG. 7-B. The process used in determining the data for FIG. 23 is set forth in FIG. 7-A.

Figure 24:
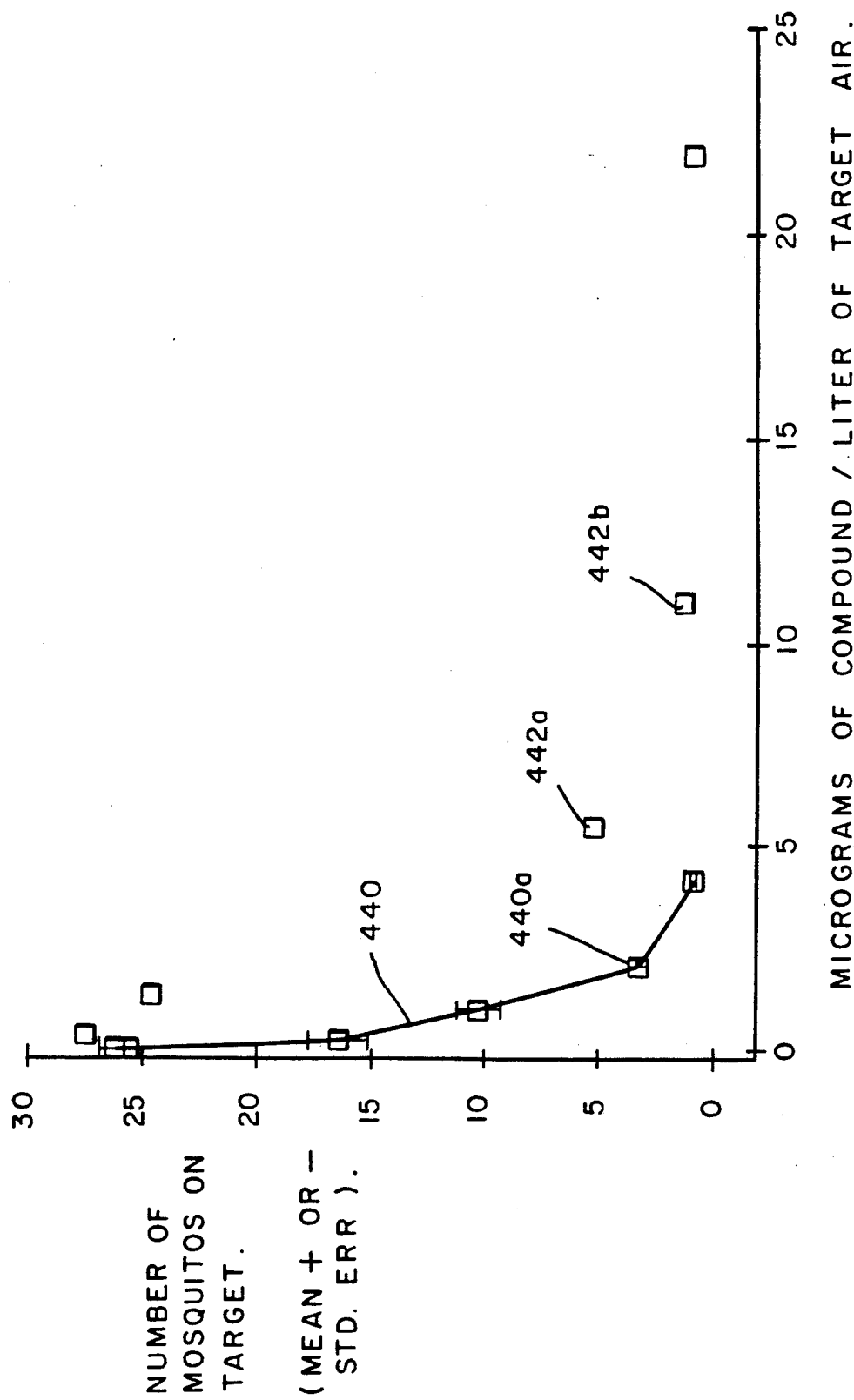

FIG. 24 sets forth dose-response curves showing number of mosquitoes on target (the "y" axis) and micrograms of compound to be tested/liter of target air (the "x" axis) comparing for their mosquito attractancy or repellency DEET (diethyl toluamide) and a formulation containing the following ingredients:

| Ingredients | Parts by Weight |
|---|---|
| HEDIONE ® | 90 |
| Trademark of Firmenich of Geneva, Switzerland) | |
| N-Dodecanol | 6 |
| Beta damascone | 1 |
| Methyl isoeugenol | 1 |
| Vanilla extract | 1 |
| Methyl jasmonate | 1 |

(carbon dioxide addition rate: 50 ml/min). The apparatus used in determining the data for FIG. 24 is set forth in FIG. 7-B. The process used in determining the data set forth in FIG. 24 is shown in FIG. 7-A.

Figure 25:
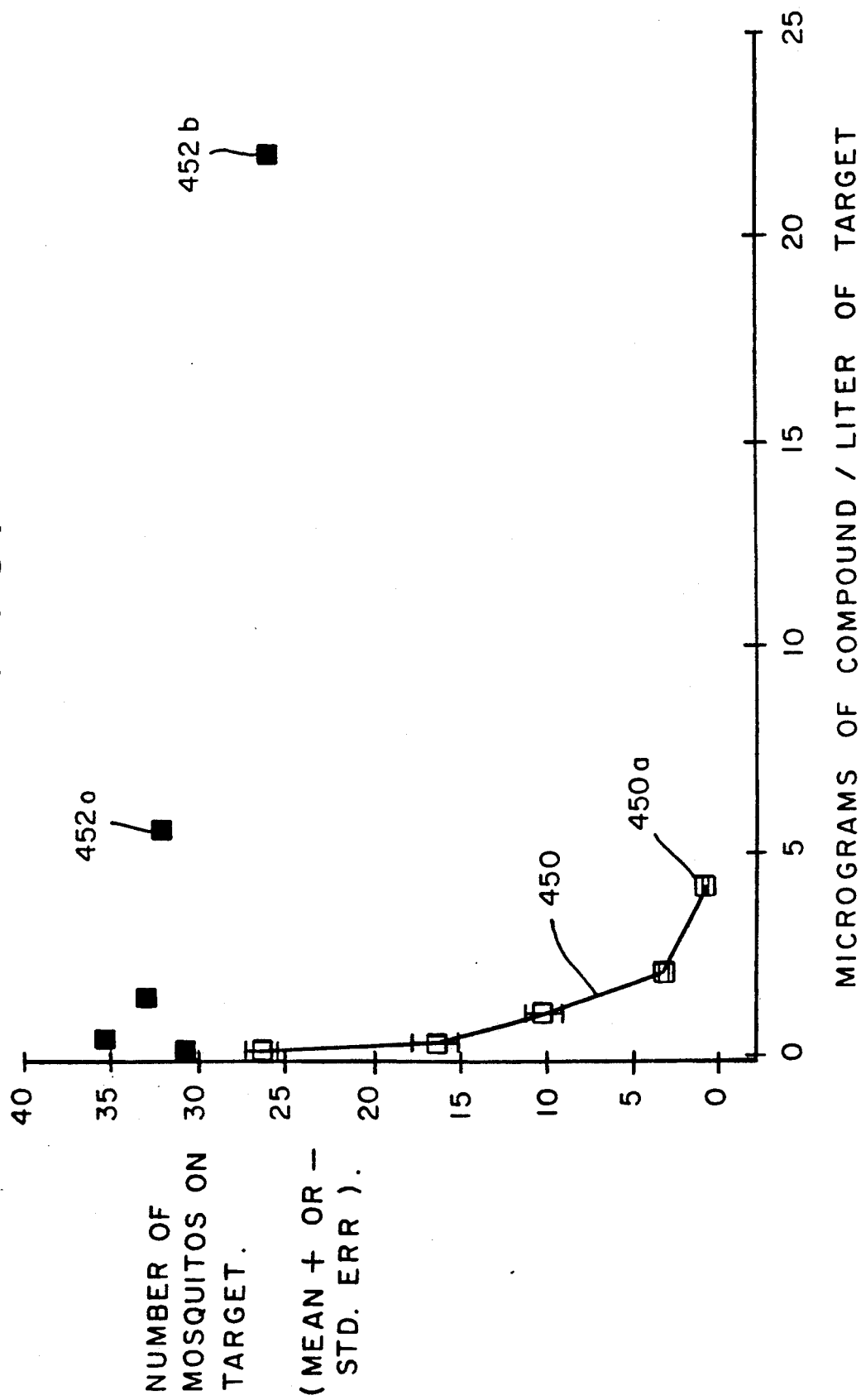

FIG. 25 sets forth dose-response curves for a number of mosquitoes on target (the "y" axis) and micrograms of compound to be tested/liter of target air (the "x" axis) comparing n-tetradecanol and DEET (diethyl toluamide) (carbon dioxide addition rate: 50 ml/min). The apparatus used in determining the graphical data for FIG. 25 is shown in FIG. 7-B. The process used in determining the data for FIG. 25 is set forth in FIG. 7-A.

Figure 26:
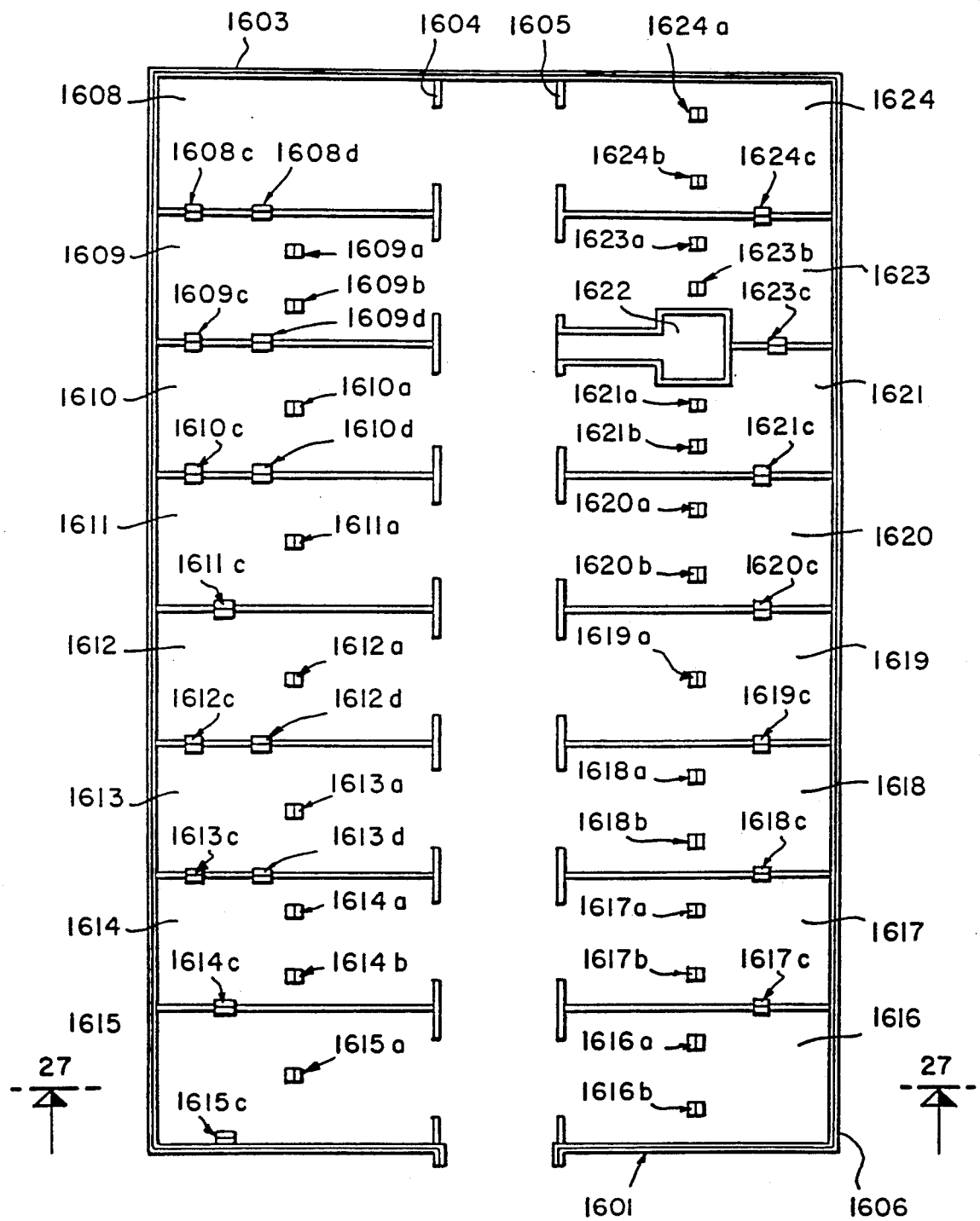

FIG. 26 is a schematic top view of the location of insect traps containing formulated slow release insect attractants and control materials (known attractant, GOLDEN MALRIN ® fly bait).

Figure 27:
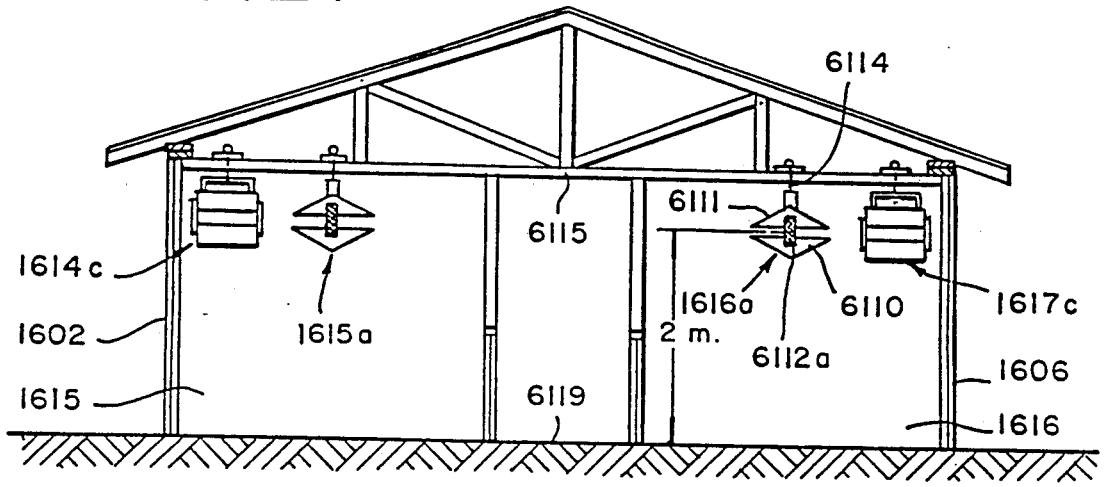

FIG. 27 is a cut-away side elevation view (schematic) indicating the positioning of sticky traps in a test barn taken along lines 27—27 of FIG. 26.

Figure 28:
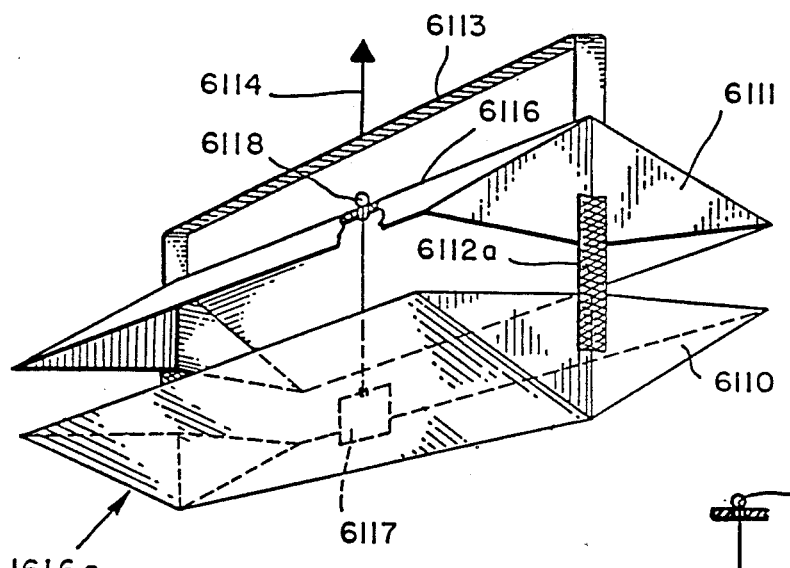

FIG. 28 is perspective schematic view of a test sticky trap showing the positioning of the slow release material suspended inside of the trap structure.

Figure 29:
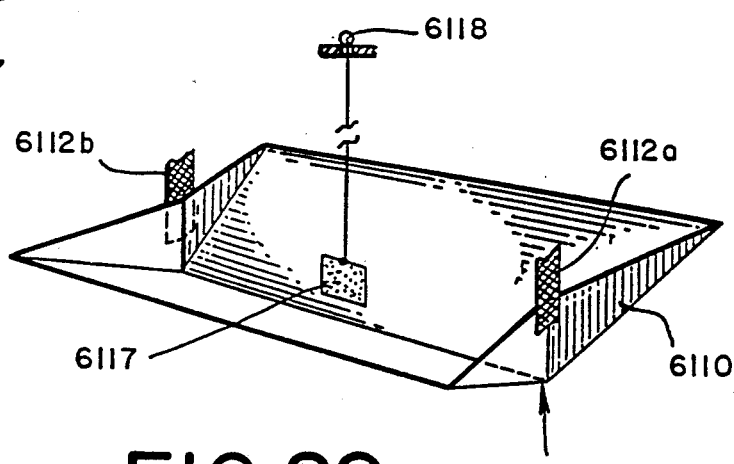

FIG. 29 is a cut-away section in perspective of the sticky trap system of FIG. 28.

Figure 30:
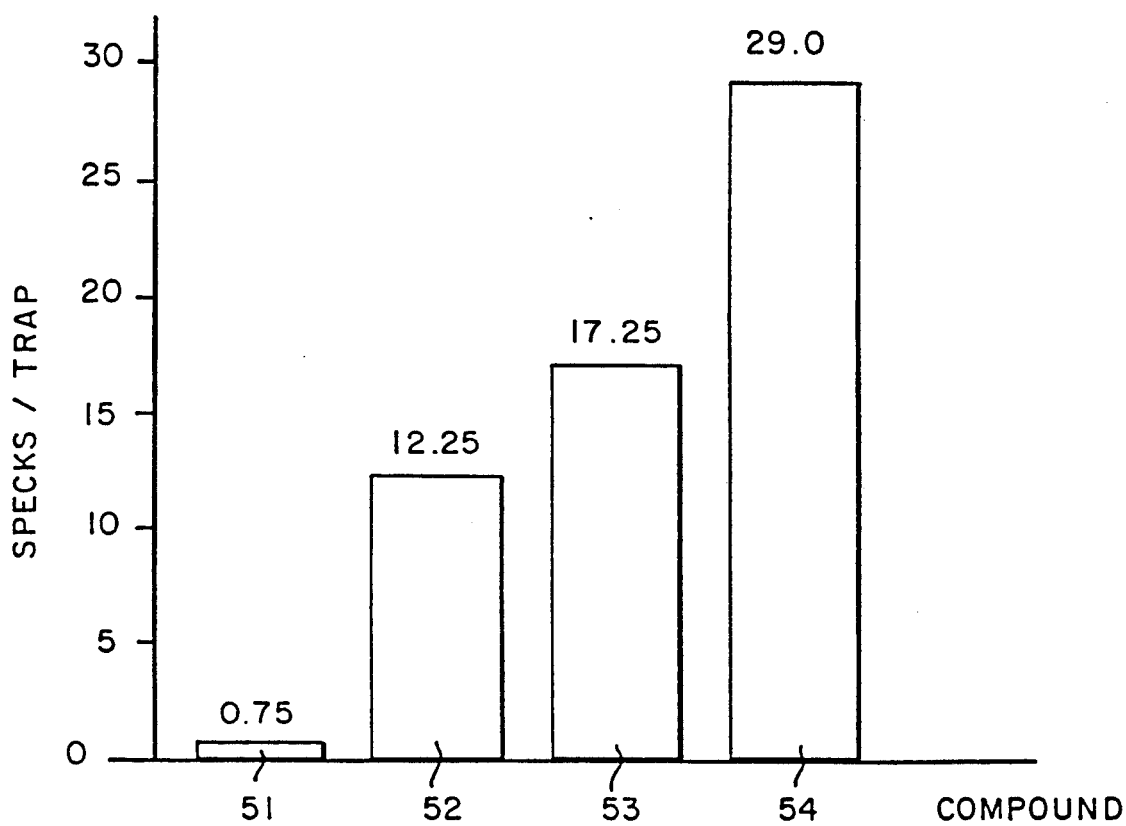

FIG. 30 is a bar graph showing a comparison of the field trial tests of attractants for house flies (Musca domestica L. (Diptera: Muscidae)) comparing methyl-isoeugenol, n-dodecanol and 1-(2-butenoyl)-2,6,6-trimethyl-1,3-cyclohexadiene (beta damascenone) and GOLDEN MALRIN ® a mixture of (Z)-9-tricosene and methomyl which is methomyl(s-methyl N-[methylcarbamoyl]oxy)thiosacetimidate the graph being compound verseus house fly specks per trap.

Figure 31:
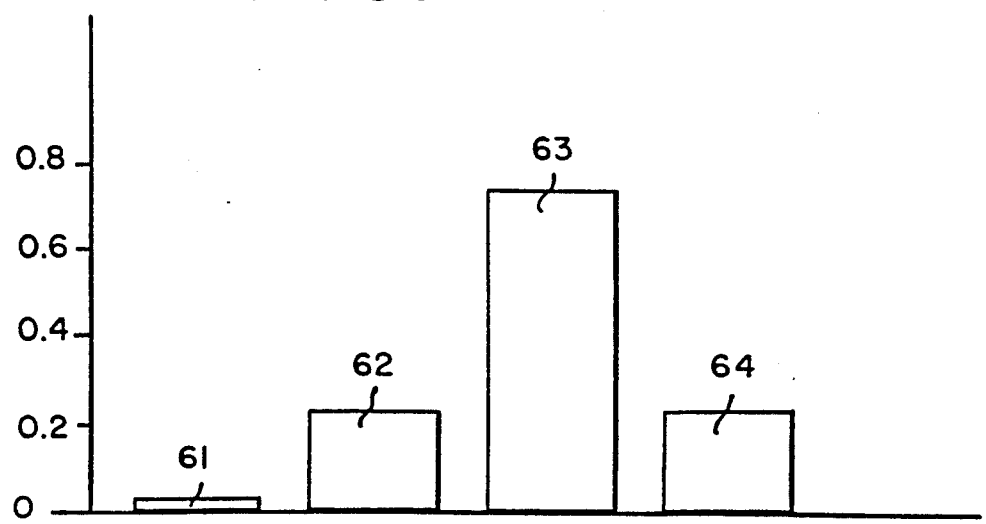

FIG. 31 is a bar graph showing field trial tests of attractants for Stored Products Moths comparing methyliseugenol, n-dodecanol and 1-(2-butenoyl)-2,6,6-trimethyl-1,3-cyclohexadiene and GOLDEN MALRIN ®, the graph being Stored Products Moth per trap versus compound.

Figure 32:
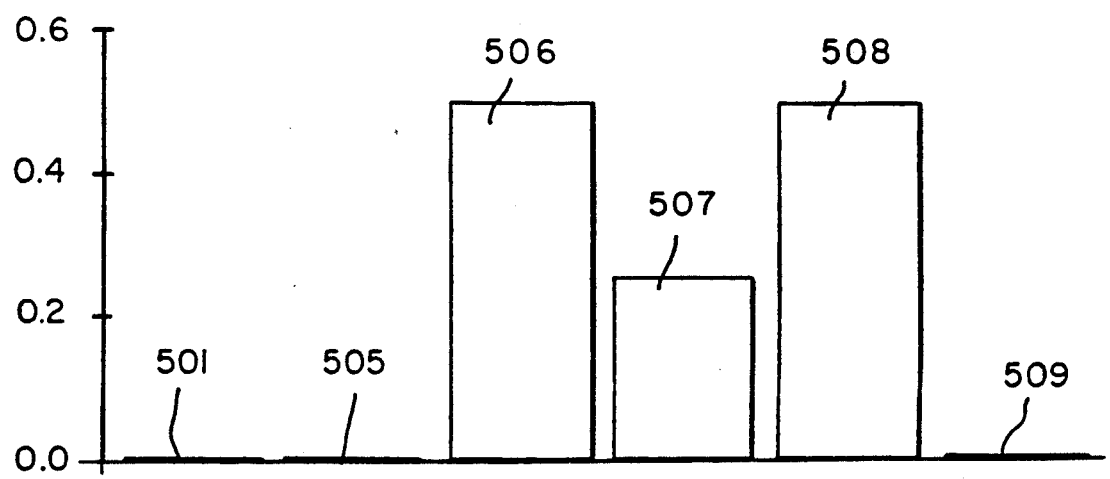

FIG. 32 is a bar graph showing a comparison of the field trial tests of attractants or repellents for mosquitoes (Aedes aegyptae) comparing 1-nonen-3-ol, beta damascenone, n-dodecanol, methyl isoeugenol, methyl-2-methylbutyrate and GOLDEN MALRIN ®, the graph being compound vs. mosquitoes per trap. The data set forth in the graph of FIG. 32 is determined using the apparatus shown in FIGS. 28 and 29 supra.

Figure 33:
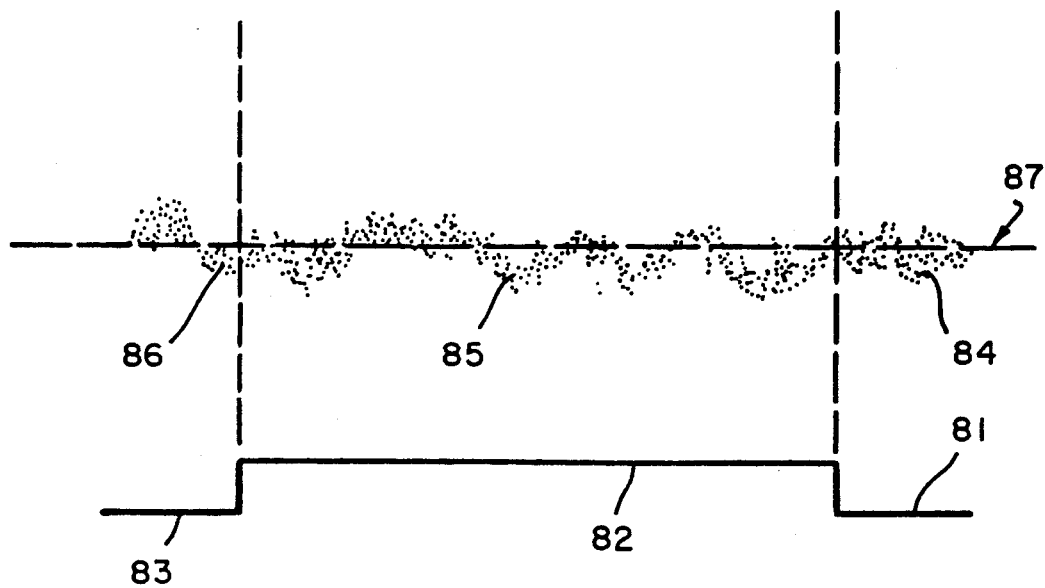

FIG. 33 is a graph of neural signal vs time recorded from the antennal lobe of the Musca domestica L. (Diptera: Muscidae) (house fly) using the prior art attractant, methyl isoeugenol as the stimulus.

Figure 34:
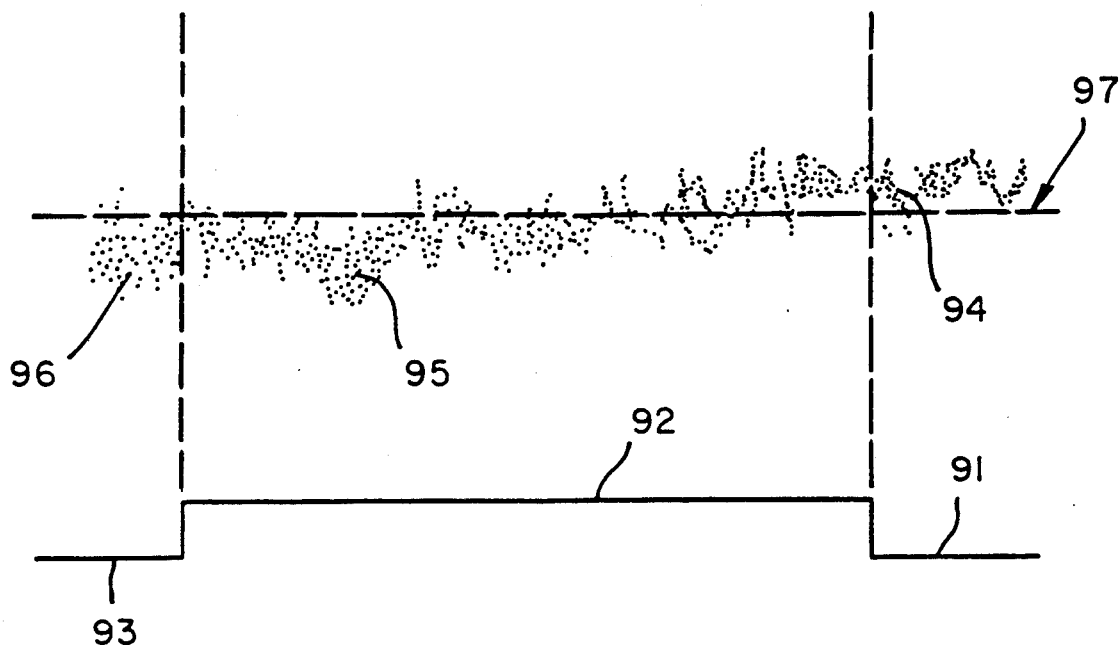

FIG. 34 is a graph of neural signal vs time recorded from the antennal lobe of the house fly (Musca domestica L. (Diptera: Muscidae)) using the known attractant called "extract of used fly rearing media" (mixture of manures, alfalfa and baking soda) as the stimulus.

Figure 35:
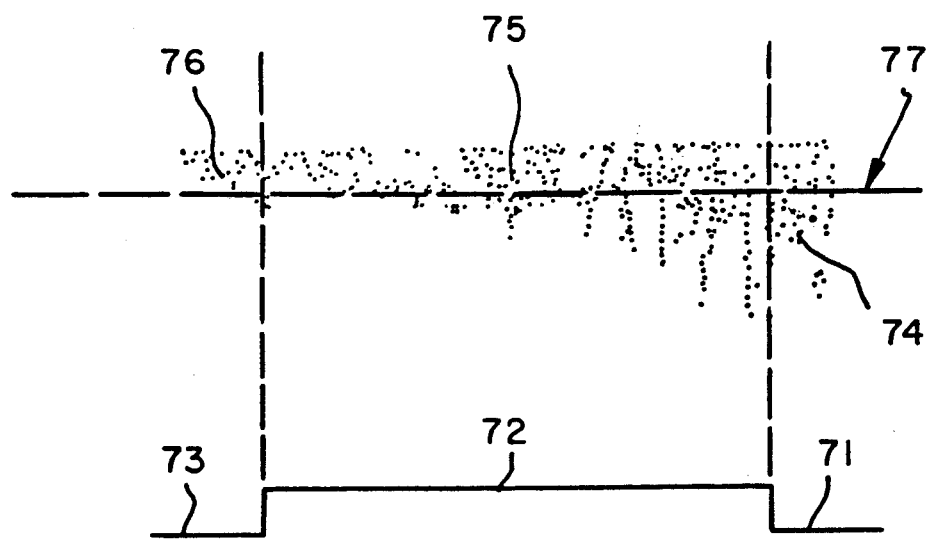

FIG. 35 is a graph of neural signal vs. time recorded from the antennal lobe of the Musca domestica L. (Deptera: Muscidae) (house fly) using the apparent repellent, n-tridecanol as the stimulas.

Figure 36:
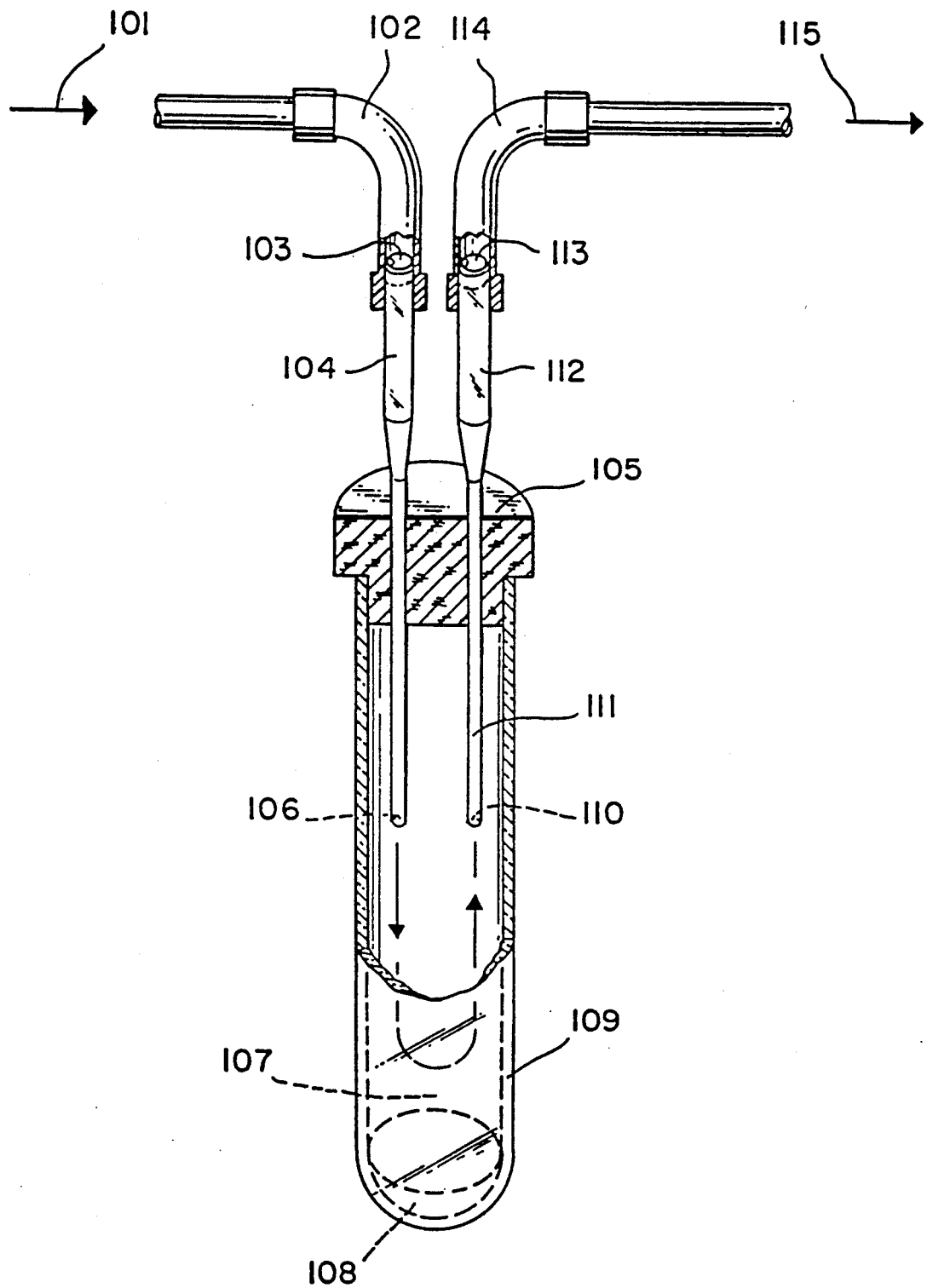

FIG. 36 is a perspective view of the odor-delivery system used to supply odor to the house fly (Musca domestica L. (Diptera: Muscidae)) when collecting data from the electrophysiological study of the neural correlates of attraction and repulsion in the house fly (Musca domestica L. (Diptera: Muscidae)).

Figure 37:
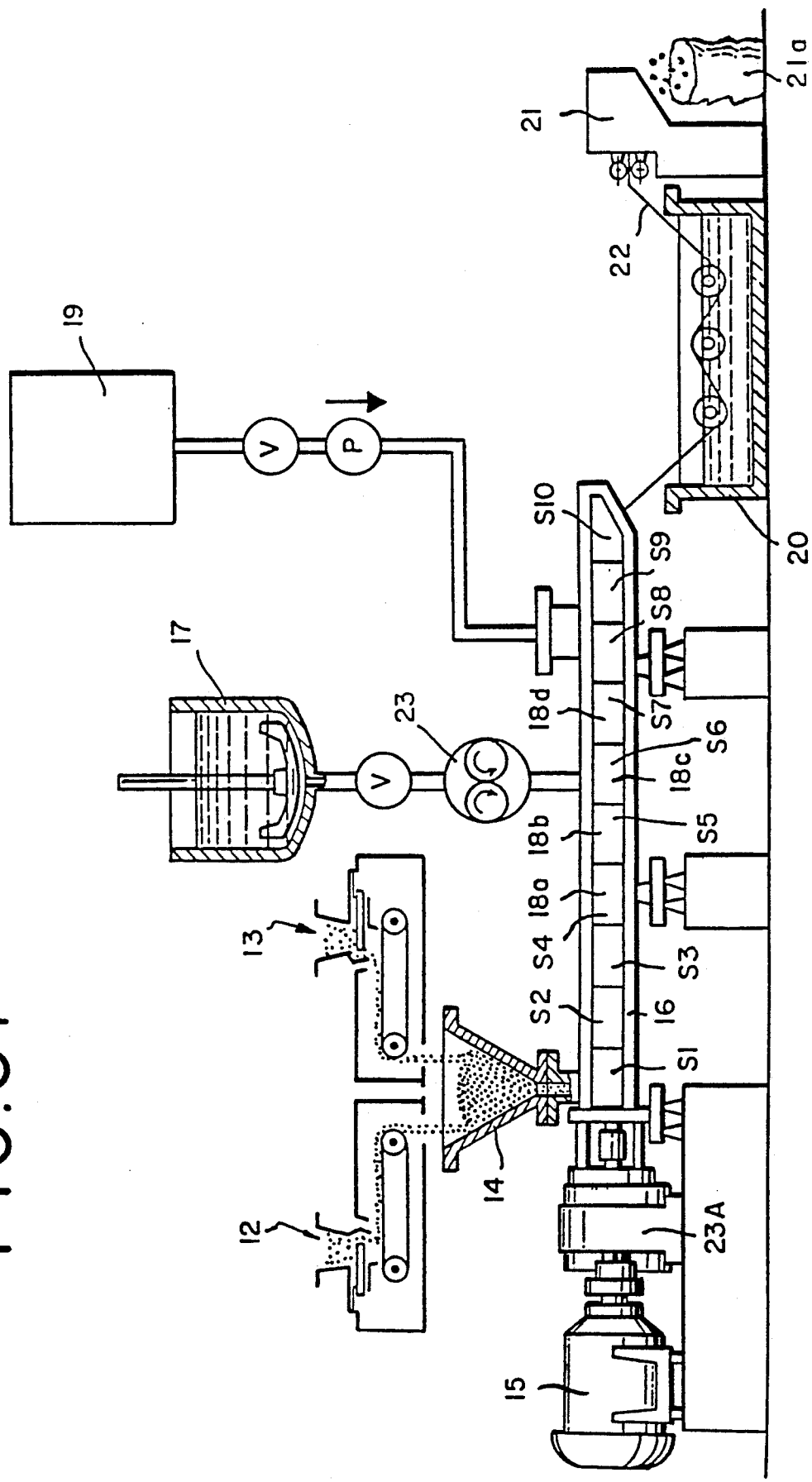

FIG. 37 is cut-away side elevation schematic diagram of a screw extruder during the compoundign of a resin with insect attractants or repellents including one or more of ketones, ketoesters, ester or alcohol of our invention while simultaneously adding forming agent into the hollow portion of the barrel of the extruder and incorporates the pelletizing apparatus used in the pelletizing of the extruded foamed tow product produced as a result of the extrusion operation.

FIG. 38-A is a series of graphs depicted in three dimensions (in a rectangular mode for the "x" and "y" axis) showing the relative attractiveness or repellency of 1-octen-4-ol, jasmine absolute, lactic acid, the "H" formulation to wit:

| Ingredients | Parts by Weight |
|---|---|
| HEDIONE ® | 90 |
| N-Dodecanol | 6 |
| Beta damascone | 1 |
| Methyl isoeugenol | 1 |
| Vanilla extract | 1 |
| Methyl jasmonate | 1 | a blank, Rose Otto Bulgarian, tobacco extract, and KHARISMAL TM, the mixture of compounds having the structures:

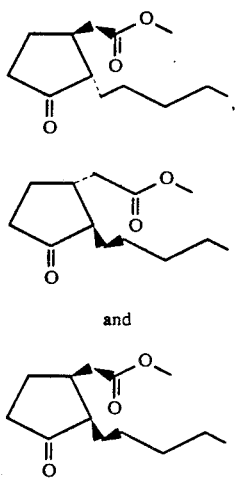

and

The graphs are based on experiments run for a period of 6 hours with 6 intervals of 1 hour each using as the insect to be tested, the mosquito (*Aedes aetyptae*). the results are tabulated in Table VI, infra.

FIG. 38-B is a series of graphs depicted in three dimensions (in a circular mode for the "x" and "y" axis) showing the relative attractiveness or repellency for mosquitoes of the materials: 1-octen-4-ol, jasmine absolute, lactic acid, the "H" formulation (described supra), a blank, Rose Otto Bulgarian, tabaccdo extract, and KHARISMAL TM, (described supra). The graphs are based on experiments run for a total of 6 hours with 6 intervals of 1 hours each. The results are tabulated in TAble VI, infra and are the same as depicted in FIG. 38-A.

FIG. 38-C is a series of graphs depicting the data set forth in graphical form in FIGS. 38-A and 38-B, depicted in two dimensions.

FIG. 39-A is series of graphs depicted in three dimensions (in a rectangular mode for the "x" and "y" axis) showing the relative attractiveness or repellency for mosquitoes of the compositions of matter: d-pulegone, secondary undecyl acetate, isobuytl formate, 1-octen-4-ol, isoamyl isobutyrate, lactic acid, a blank and anisyl acetate. The graphs are based on experiments run for a total of 1 hour with 6 intervals of 10 minutes each. The results are tabulated in Table VII, infra.

FIG. 39-B is a series of graphs depicted in three dimensions nin a circular mode for the "x" and "y" axis) showing a relative attractiveness or repellency for mosquitoes of the compositions of matter: d-pulegone, secondary undecyl acetate, isobuytl formate, 1-octen-4-ol, isoamyl or isobutyrate, lactic acid, a blank and anisyl acetate. The graphs are based on experiments run for a period of 1 hour with 6 intervals of 10 minutes. The results are tabulalted in Table VII, infra and are the same as depicted in FIG. 39-A.

FIG. 39-C is a series of graphs depicting the data set forth in graphical form in FIGS. 39-A and 39-B depicted in two dimensions.

FIG. 40-A is a series of graphs depicted in three dimensions nin a rectangular mode for the "x" and "y" axis) showing the relative attractiveness or repellency for mosquitoes of the compositions: d-pulegone, secondary undecyl acetate, isobutl formate, 1-octen-4-ol, isoamyl or isobutyrate, lacetic acid, a blank and anisyl acetate. The graphs are based on experiments run for a total of 4 hours with 6 intervals of 40 minutes each. The results are tabulated in Table VIII, infra.

FIG. 40-B is a series of graphs depicted in three dimensions (in a circular mode for the "x" and "y" axis) showing the relative attractiveness or repellency for mosquitoes of the compositions of matter: d-pulegone, secondary undecyl acetate, isobuytl formate, 1-octen-4-ol, isoamyl or isobutyrate, lactic acid, a blank and anisyl acetate. The graphs are based on experiment run for a total of 4 hours with 6 intervals of 40 minutes. The results are tabulated in Table VIII, infra and are the same as depicted in FIG. 40-A.

FIG. 40-C is a series of graphs depicting the data set forth in graphical form in FIGS. 40-A and 40-B depicted in two dimensions.

FIG. 41-A is a series of graphs depicted in three dimensions (in a rectangular mode for the "x" and "y" axis) showing the relative attractiveness or repellency for mosquitoes fo the compositions of matter: 1-octen-4-ol; the Shiff base of ethyl vanillin and methyl anthranilate; trans, trans-delta-damascone; methyl anthranilate; the Shiff base of methyl anthranilate and vanillin; lactic acid; vanillin and ethyl vanillin. the graphs are based on experiments run for a period of 1 hour with 6 intervals of 10 minutes each. The results are tabulated in Table IX, infra.

FIG. 41-B is a series of graphs depicted in three dimensions (in a circular mode for the "x" and "y" axis) showing the relative attractiveness or repellency for mosquitoes of the compositions of matter: 1-octen-4-ol, the Shiff base of ethyl vanillin and methyl anthranilate; trans, trans-delta-damascone; methyl anthranilate; the Shiff base of vanillin and methyl anthranilate; lactic acid; vanillin and ethyl vanillin. The graphs are based on experiments run for a period of 1 hour with 6 intervals of 10 minutes each. The resuts are tabulated ibn Table IX, infra and are the same as depicted in FIG. 41-A.

FIG. 41-C is a series of graphs depicting the data set forth in graphical form in FIGS. 41-A and 41-B depicted in two dimensions.

FIG. 42-A is a series of graphs depicted in three dimensions nin a rectangular mode for the "x" and "y" axis) showing the relative attractiveness or repellency for mosquitoes of the compositions: 1-octen-4-ol, the Shiff base of ethyl vanillin and methyl anthranilate; trans, trans-delts-damascone; methyl anthranilate; the Shiff base of vanillin and methyl anthranilate; lactic acid; vanillin and ethyl vanillin. The graphs are based on experiments run for a period of 1 hour with 6 intervals of 10 minutes each. The results are tabulated in Table X, infra.

FIG. 42-B is a series of graphs depicted in three dimensions (in a circular mode for the "x" and "y" axis) showing the relative attractiveness or repellency for mosquitoes of the compositions of matter: 1-octen-4-ol, the Shiff base of ethyl vanillin and methyl anthranilate; trans, trans-delta-damascone; methyl anthranilate; the Shiff base of vanillin and methyl anthranilate; lactic acid; vanillin and ethyl vanillin. The graphs are based on experiments run for a period of 1 hour with 6 intervals of 10 minutes each. The results are tabulated in Table X, infra and are the same as depicted in FIG. 42-A.

FIG. 42-C is series of graphs depicting the data set forth in graphical form in FIGS. 42-A and 42B depicted in two dimensions.

FIG. 43-A is a series of graphs depicted in three dimensions (in a rectangular mode for the "x" and "y" axis) showing the relative attractiveness or repellency for mosquitoes of the compositions as set forth in the brief description for FIG. 42-A. The data of FIG. 43-A is a replicate of the data for FIG. 42-A.

FIG. 43-B is a series of graphs depicted in three dimensions (in a circular mode for the "x" and "y" axis) showing the relative attractiveness or repellency for mosquitoes of the compositions shown in the brief description for FIG. 42-B. The data of FIG. 43-B is a replicate of the data of FIG. 42-B.

FIG. 43-C is a series of graphs depicting the data set forth in graphical form in FIGS. 43-A and 43-B depicted in two dimensions. The results are tabulated in Table XI, infra.

FIGS. 44-A, 44-B and 44-C are graphical representations of data which are replicates of the data set forth in FIGS. 43-A, 43-B and 43-C, respectively. The results are tabulated in Table XII, infra. The graphs are based on experiments run for a total of 1 hour with 6 intervals of 1 hour each.

FIGS. 45-A, 45-B and 45-C are also graphical representations of data which are replicates of the data presented in FIGS. 43-A, 43-B and 43-C, respectively. The graphs are based on experiments run for a period of 1 hour with 6 intervals of 10 minutes each. The results are tabulated in Table XIII, infra.

FIGS. 46-A, 46-B and 46-C set forth series of graphs containing data which are replicates of the data set forth in the graphs in FIGS. 43-A, 43-B and 43-C. The graphs are based on experiments run for a period of 1 hour with 6 intervals of 10 minutes each. The results are tabulated in Table XIV, infra.

FIG. 47 is a perspective view of an ellipsoidally-shaped detergent tablet containing a solid core which includes fused foamed polymeric particles which contain insect repellents which can be one or more of the ketones, ketoester or alcohol of our invention and if desired also containing an additional polymer, e.g., polyethylene. The polymer particles may, if desired, also contain additional aromatizing agents.

FIG. 48 is the top view of the ellipsoidally-shaped detergent tablet of FIG. 47.

FIG. 49 is a cut-away front view of the ellipsoidally-shaped detergent tablet of FIG. 47 in the direction of the arrows in FIG. 48.

FIG. 50 is a side-view of the ellipsoidally-shaped detergent tablet of FIG. 47.

FIG. 51 is a perspective view of a rectangular parallelepiped-shaped detergent tablet containing a rectangular parallelepiped-shaped core comprising a major proportion of fused foamed polymeric particles which contain insect repellent (e.g., one or more of the ketoesters, ketones or alcohol of our invention) and may or may not be aromatized and, if desired, an additional polymer which may or may not contain insect repellent compositions and which may or may not be aromatized.

FIG. 52 is a top view of the rectangular parallelepiped-shaped detergent tablet of FIG. 51.

FIG. 53 is cut-away front view of the rectangular parallelepiped-shaped tablet of FIG. 51 looking in the direction of the arrows in FIG. 52.

FIG. 54 is a perspective view of an ellipsoidally-shaped detergent tablet containing a hollow insect repellent agent (and if desired an aromatizing agent) containing core which includes fused foamed polymeric particles containing insect repellent and if desired aromatizing agent or in the alternative a hollow core of fused foamed polymer produced according to the process of our invention wherein the insect repellent (and if desired the aroma imparting agent) is in the solid polymer and not in the void of the plastic core.

FIG. 55 is a top view of the ellipsoidally-shaped detergent tablet of FIG. 54.

FIG. 56 is a front cut-away view of the ellipsoidally-shaped detergent tablet of FIG. 54 looking in the direction of the arrows in FIG. 55, the core thereof being hollow and either containing an insect repellent material (and if desired an aroma imparting liquid) or in the alternative being a hollow core wherein the insect repellent material (and if desired the aroma imparting material) is in the solid fused foamed polymeric particles which make up the core and wherein the void does not contain anything.

SUMMARY OF THE INVENTION

This invention relates to the uses of ketones having the structures:

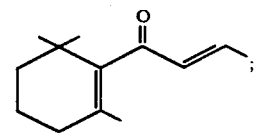

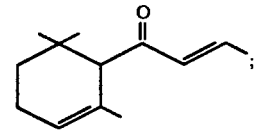

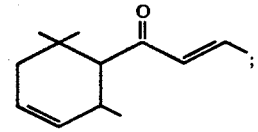

and

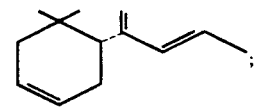

the ketoesters having the structures:

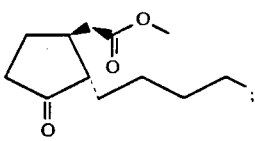

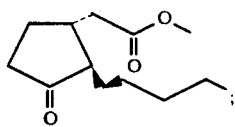

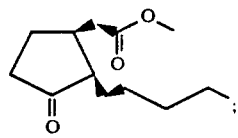

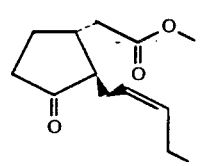

and

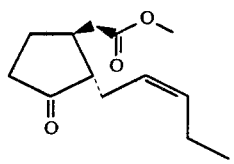

and the alcohol having the structure:

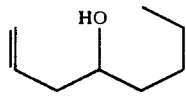

taken alone or in combination as insect repellents against house flies (*Musca domestica* L. (Diptera:Muscidae)) and mosquitoes (*Aedes aegyptae*) and the aliphatic alcohol having the structure:

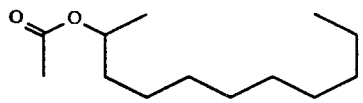

as an attractant for house flies (*Musca domestica* L. (Diptera:Muscidae)) and mosquitoes (*Aedes aegyptae*).

In the context of the various embodiments of our invention, the following terms and definitions are used:

| COMMON NAME | DEFINITION |
|---|---|
| Beta damascone | The compound having the structure: <br> 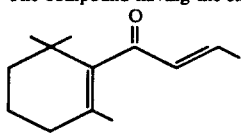 |
| Alpha damascone | The compound having the structure: |

| COMMON NAME | DEFINITION |
|---|---|
| | (structure shown) |
| HEDIONE ® | A 50:50 mixture of the compounds having the structures: <br> (structure) ; and <br> (structure) |
| Methyl jasmonate | The mixture of compounds having the structures: <br> (structure) ; and <br> (structure) |
| KHARISMAL ™ | A mixture of compounds having the structures: <br> (structure) (55-75%) <br> (structure) and <br> (structure) ) |
| FORMULATION "H" | A mixture of 90 parts by weight of HEDIONE ®, 6 parts by weight n-dodecanol; 1 part by weight beta damascone; 1 part by weight methyl isoeugenol having the structure: |

| COMMON NAME | DEFINITION |
|---|---|
| 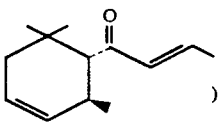 | 1 part by weight of vanilla extract and 1 part by weight methyl jasmonate. |

Thus, the instant invention applies to uses of HEDIONE ® (trademark of Firmenich, et Cie of Geneva, Switzerland) and/or KHARISMAL ™ and/or methyl jasmonate and/or alpha damascone and/or beta damascone and/or trans, trans-delta-damascone (having the structure:

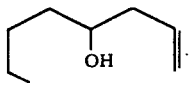

)

and/or 1-octen-4-ol having the structure:

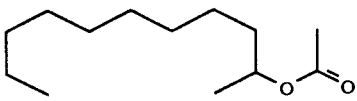

as repellents against *Musca domestica* L. (Diptera:Muscidae) and/or mosquitoes (*Aedes aegyptae*).

Our invention also relates to the use of secondary undecyl acetate having the structure:

[structure]

as an attractant for *Aedes aegyptae* or *Musca domestica* L. (Diptera:Muscidae) for the purposes of utilization in insect traps and the like.

Our invention is also related to the use of the foregoing insect repellent compositions in personal soap compositions, for example, the insect repellent soap composition described in U.S. Pat. No. 4,707,496 issued on Nov. 17, 1987, the specification for which is incorporated by reference herein. Thus, in applying the teachings of U.S. Pat. No. 4,707,496 to our invention, a topical insect repellent soap composition and a method of protection using such a composition is described where the insect repellent soap composition comprises:

(i) from 63.0 up to 99.5% by weight of a soap mixture containing from 4.1 to 7% by weight of a soap of caprylic acid, from 3.8 to 7% of a soap of capric acid, from 32.1 to 45% of a soap of lauric acid, from 12 to 17.5% by weight of a soap of myristic acid, from 5.0 up to 10% by weight of a soap of palmitic acid, from 1.6 to 3% by weight of a soap of stearic acid, from 3.5 to 5% by weight of a soap of oleic acid and from 0.9 to 5% by weight of a soap of linoleic acid;

(ii) from 0.1 up to 2% by weight of $C_8$–$C_{18}$ straight chain fatty acids;

(iii) from 10 up to 30% by weight of at least one of the repellent chemicals of our invention, e.g., one of ketoesters, ketones or alcohol set forth supra, and (iv) from 0.2 up to 5% by weight of an effective residual insecticide as described in U.S. Pat. No. 4,707,496.

Other insect repellent soaps can be produced by adding one or more of the ketoesters, ketones and/or alcohol of our invention to one or more of the compositions described and claimed in U.S. Pat. No. 4,453,909 issued on June 12, 1984 and U.S. Pat. No. 4,438,010 the specifications for which are incorporated by reference herein. Described in said U.S. Pat. No. 4,453,909 and U.S. Pat. No. 4,438,010 is a process for making a tablet of soap containing a perfume containing core, hollow, or solid fabricated from a hard plastic material either thermo setting or thermo plastic. The soap from the resulting composite tablet is useable until the core is washed clean and contains functional ingredients, e.g., the repellents described supra and optionally aromatizing agent until the core is washed clean. This obviates the wastage of soap which normally occurs as a conventional soap tablet becomes very thin on use and at the same time gives rise to a continuously functional ingredient-containing soap, (e.g., repellent and optionally aromatizing agent) tablet. Thus, this invention also relates to detergent bars having a plastic core containing one or more of the above described ketones, ketoesters and/or alcohol and optionally a perfume. More particularly, this invention relates to detergent bars intended for conventional toilet soap uses either as hand soaps or bath or shower soaps which are elastic or inelastic in nature but which contain a solid plastic core containing insect repellent and optionally perfume giving them unique properties which alleviate wastage thereof and causes the environment surrounding the soap on use thereof to be both insect repellent and optionally aromatized in an aesthetically pleasing manner.

Yet another aspect of our invention relates to the use of the aforementioned repellents, the ketoesters, ketones and alcohol of our invention taken further in combination with N-(metal toluyl)-methyl piperidines defined according to the structure:

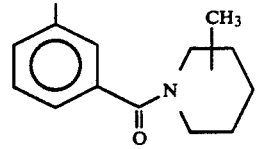

as described in U.S. Pat. No. 3,463,855 issued on Aug. 26, 1969, the specification for which is incorporated by reference herein. The compounds defined according to the structure:

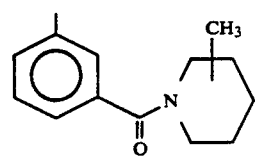

include:
N-(meta-toluyl)-2-methylpiperidine,

N-(meta-toluyl)-3-methylpiperidine, and
N-(meta-toluyl)-4-methylpiperidine.

The proportions of compounds defined according to the structure:

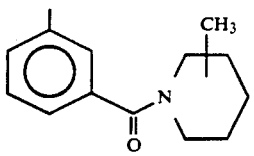

to one or a combination of any of the ketones, ketoesters or alcohol described supra are between about 1 part N-(meta-toluyl) methylpiperidine:99 parts ketone, ketoester or alcohol of our invention down to 99 parts ketone, ketoester or alcohol of our invention:1 part N-(metatoluyl)-methyl piperidines.

In addition, the compositions useful in repelling insects of our invention can also contain 1-nonen-3-ol described and claimed in U.S. Pat. No. 4,693,890 and 4,759,228 issued on July 26, 1988, the specifications for which are incorporated by reference herein. The ratio of 1-nonen-3-ol:ketone, ketoester or alcohol of our invention useful in repellent compositions may vary from about 1 part 1-nonen-3-ol:99 parts ketone, ketoester or alcohol of our invention down to 99 parts 1-nonen-3-ol:1 part ketone, ketoester or alcohol of our invention.

Our invention also relates to apparatus useful in determining the attractancy of such molecules, including, but not limited to said ester having the structure:

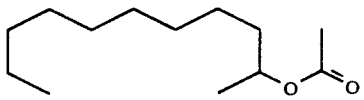

and the repellency against insects of the ketones, ketoesters and alcohol described supra against insects to wit *Musca domestica* L. (Diptera:Muscidae) and mosquitoes (*Aedes aegyptae*) and processes for using such apparatus which apparatus comprises:

(i) active and passive insect interest electronic, detecting, measuring and recording means collectively denoted as "DMR" means which is connected to an electronic power source, comprising detecting means, measuring means and recording means;

(ii) enclosed insect feeding and/or stimulating means, collectively denoted as "IFS" means, having control limited access to the external environment surrounding said apparatus and associated with the said "DMR" means and including said detecting means, said "IFS" means being located at a fixed "IFS" means location defined according to "X", "Y" and "Z" coordinates having a defined first 3-space, said "IFS" means consisting essentially of:

(a) a substantially, horizontally-positioned insect feeding and/or stimulating microporous substantially planar lamina which is a porous membrane having an upper outer surface and a lower inner surface, said lamina being located immediately above said enclosed "IFS" means;

(b) an insect attractant quantitative detecting means located immediately below said lamina and within said enclosed "IFS" means comprising at least 2-spaced electrically conductive elements;

(1) connected to said "DMR" means; and (2) capable of forming a complete circuit, said elements having such dimensions and spacing from one another as to cause an attracted insect to complete a circuit of electron flow through or proximate to said elements;

(c) located on said upper outer surface of said lamina a feeding stimulate composition or stimulate composition for insects (for example, agar);

(iii) steady state infra-red, ultra-voilet and/or visible monochromatic or polychromatic radiation means for supplying at least one beam of radiation (ultra-violet, infra-red and/or visible light) having a given substantially constant intensity or intensities and wave length or wave lengths to said "IFS" means location said beam(s) of radiation being directed in a direction perpendicular to the plane of said lamina along a directional vector from above or below said insect attractant quantitative detecting means; and (iv) steady state air and treatment (experimental or actual) supply and conduction means denoted as "SAC" means for supplying and conducting air and treatment agent (experimental or actual) at a substantially constant flow rate and substantially constant linear velocity into said defined 3-space at least initially along a vector in a direction substantially parallel to the plane of said lamina at a location below said lamina simultaneously with the supplying of the beam(s) of radiation to said "IFS" means location.

said insect feeding and/or stimulating lamina being constructed and said detecting means being constructed so that said "DMR" means are sensitive to the completion of a circuit of electron flow through or proximate said conductive elements of said insect attractant quantitative detecting means whereby the number and frequency of the insects attracted relative to the attractancy of said radiation means to the proximity of said "IFS" means is capable of being determined using said "DMR" means.

Thus, the air and treatment agent enters the apparatus at one or a plurality of side portals (e.g., as many as ten portals) substantially perpendicular to the vertical side wall of the apparatus. The treatment agent may either (i) be premixed in the gas phase (using appropriate temperature and pressure conditions) with the air at a designated premixed location or (ii) be located in a control release system (CRS TM) mode in, for example, a solid (e.g. organic polymeric or inorganic (e.g. silica)) matrix partially obstructing the air flow whereby the air screen inpinges upon a treatment agent-containing solid state matrix and the air stream extracts treatment agent molecules from the matrix into the air stream. Such solid polymers containing functional ingredients may be prepared, for example, according to the disclosure of U.S. Pat. No. 4,543,367 issued on Sept. 24, 1985 or U.S. Pat. No. 4,521,541, the specification for which is incorporated by reference herein. Thus, a process can be used for preparing extruded repellent-containing thermoplastic foamed particles using chemical blowing agents or direct gas extrusion processes. The process described in U.S. Pat. Nos. 4,543,367 and 4,521,541 involves the use of a single screw or double screw extruder wherein the resin particles are added upstream from the repellent fluid or solid which is in turn added to the extruder upstream from the point of addition of the liquid or gaseous blowing agent.

The resulting air-treatment agent gaseous stream then feeds into the enclosed "IFS" means either (i) parallel to the microporous planar lamina or (ii) is rotated (using appropriately designed fluid flow apparatus sections such as a tube elbow) about 90° and this flows substantially perpendicular to the microporous planar lamina.

Thus, in testing the insect repellency or attractancy of such molecules as the ketones, ketoesters, alcohol or ester of our invention, the apparatus set forth supra may be used or a second testing technique may be used which concerns the electrophysiological study of the neural corrolates of attraction and repulsion in *Musca domestica L.* (Diptera: Muscidae) (house flies). Different points in the house fly olfactory neuroarchitecture were studied using electrophysiology in an effort to identify the neural corrolates of attractant and repellent signals resulting from potentially attractant and repellent substances.

Recordings from the antennal lobe of the deuterocerebrum of the *Musca domestica L.* (Diptera: Muscidae) showed that the repellent signals were highly distinguishable from the attractant signals. Signals from repellents (e.g., alpha damascone, beta damascone, trans, trans-delta-damascone and the like) showed a shift in base line potential of approximately 25 m volts whereas attractant signals showed no shift.

Thus, neural signals of the antennal lobe are used herein as an assay for olfactory canvassing to predict behavioral activity of the *Musca domestica L.* (Diptera: Muscidae) (house flies).

By the same token, neural signals of the antennal base, the funiculus and the antennal nerve can be used herein as an assay for olfactory canvassing to predict behavioral activity of the *Musca domestica L.* (Diptera: Muscidae) (house flies). In addition to the soap fabrication, another aspect of our invention relates to the formation of repelling articles containing one or more of the ketones, ketoesters or alcohol, that is, articles useful for the repelling of house flies (*Musca domestica L.* (Diptera: Muscidae)) or mosquitoes (*Aedes agyptae*) in combination with compatible polymers (e.g., high density polyethylene or low density polyethylene). Thus, another aspect of our invention provides a process for forming ketones, ketoester or alcohol-containing polymeric particles such as foamed polymeric pellets which include a relatively high concentration of ketone, ketoester or alcohol of our invention as defined supra.

Thus, another aspect of our invention relates to the formation of ketone, ketoester or alcohol polymeric pellets by means of introduction into a single screw or twin screw extruder of in series from a plastic polymer followed by ketone, ketoester or alcohol of our invention which is compatible with the thermoplastic polymer, in turn, (optionally) followed by introduction of gaseous blowing agent or blowing agent which will produce a gas which is inert to the polymer and to the ketone, ketoester or alcohol previously introduced into the extruder.

The advantages of using a foamed polymeric particle are multiple to wit:
improved handling, greater retention of the ketone, ketoester or alcohol when not in use;
greater length of time during which the release of the ketone, ketoester or alcohol of our invention from the polymer is at "steady state" or "0 order".

The nature of the extruder utilized in the process of our invention to form the polymeric ketones, ketoesters or alcohol-containing polymer particles for our invention may be either single screw or double screw. Thus, the types of extruder that can be used are disclosed at pages 246–267 and 332–349 of the Modern Plastic Encyclopedia, 1982–1983, published by McGraw-Hill Publishing Company, the disclosure of which is incorporated by reference herein. More specifically, examples of extruders which are usable in carrying out one of the processes of our invention (with modification for introduction of at least one of the ketones, ketoesters or alcohol of our invention) downstream from the introduction of the polymer and with further modification that the gaseous blowing agent is introduced still further downstream from the point of introduction of the ketone, ketoester or alcohol of our invention are as follows:

1. The Welex "Super Twinch" 3.5" extruder manufactured by Welex Incorporated, 850 Jolly Road, Blue Bell, Pa. 19422;
2. Krauss-Maffei twin screw extruder manufactured by the Krauss-Maffei Corporation/Extruder Division, 3629 West 30th Street South, Wichita, Kans. 67277;
3. Modified Sterling model 4000 and 5000 series extruder manufactured by Sterling Extruder Corporation of 901 Durham Avenue, South Plainfield, N.J.;
4. CRT ("Counter-Rotating Tangential") Twin Screw Extruder manufactured by Welding Engineers, Inc. of King of Prussia, Pa. 19406;
5. The Leistritz Twin Screw Dispersion Compounder manufactured by the American Leistritz Extruder Corporation of 198 U.S. Route 206 South, Somerville, N.J. 08876;
6. The ZSK Twin Screw Co-Rotating Extruder manufactured by the Werner & Pfleiderer Corporation of 663 East Crescent Avenue, Ramsey, N.J. 07446;
7. The Farrel Extruder manufactured by Farrel Connecticut Division, Emhart Machinery Group, Ansonia, Conn. 06401;
8. The MPC/V Baker Perkins Twin Screw Extruder manufactured by the Baker Perkins Inc. Chemical Machinery Division of Saginaw, Mich. 48601; and
9. The Berstorff single screw, twin screw, or foam extrusion equipment manufactured by Berstorff Corporation, P.O. Box 240357, 8200-A Arrowridge Blvd., Charlotte, N.C. 28224.

In producting the ketone, ketoester or alcohol-containing polymer particles of our invention various polymers may be utilized, for example, low density polyethylene high density polyethylene, polypropylene, the co-polymer of ethylene and vinyl acetate, and polyvinyl chloride. More specifically, the polymers used in the practice of our invention may be co-polymers of ethylene and a polar vinyl monomer selected from (a) vinyl acetate; (b) ethyl acrylate; (c) methyl acrylate; (d) butyl acrylate and (e) acrylic acid including the hydrolyzed co-polymer of ehtylene and vinyl acetate. Preferred co-polymers are ehtylene vinyl acetate with about 9 to 60% vinyl acetate and ethylene-ethyl acrylate with about 6 to 18% ethyl acrylate.

Resins of the type disclosed for use as co-polymers are commercially available in the molding powder form. For example, ethylene vinyl acetate co-polymers are marketed by the E. I. duPont Nemours Company under the tradename "ELVAX®" and by the Arco Polymer Division under the tradermark "DYLAND®" and by the Exxon Corporation of Linden, N.J. under the trademark "DEXXON®". Ethylene/ethyl acrylate co-polymers are marketed by Union Carbide Corporation under the trademark "EEA RESIN®".

The polymer is added to the single screw or twin screw extruder at a feed rate in the range of from about 80 up to about 300 pounds per hour while maintaining the temperature of the screw extruder between about 160° and about 240° C. If the polymer or co-polymer powder is added to the extruder at a reference "barrel segment", then the ketone, ketoester or alcohol of our invention is added to the extruder under pressure downstream from the retention point of the polymer of one or more of "barrel segments" (S-2, S-3, S-5, S-6, S-7, S-8, or S-9) (referring to FIG. 37 briefly described, supra and described in detail infra).

The proportion of ketone, ketoesters and/or alcohol (taken further together with other insect repelling material) to resin can vary from small but effective amounts on the order of about 1% of the weight of resin body up to about 45% by weight of the resin body. In general, it is preferred to use between about 5% up to about 30% based on the weight of the resin body of insect repellent composition of our invention. This is an optimum amount balancing the proportion of insect repellent composition of our invention against the time period over which the article emits the insect repellent composition and against the tendency of the components of the insect repellent composition to oil out either individually or in combination. This "oiling out" is specifically avoided as a result of the use of the foaming agent discussed infra.

Various polymers are useful in the practice of our invention. Specific examples of polymers useful in the practice of our invention are as follows:
(a) DYLAN® brand of low density polyethylene. DYLAN® is a trademark owned by the Atlantic Richfield Company of Los Angeles, Calif.;
(b) DYLITE® of expandable polystyrene compositions. DYLITE® is a trademark of Atlantic Richfield Company of Los Angeles, Calif.;
(c) SUPER DYLAN® a high density polyethylene. SUPER DYLAN® is a trademark of the Atlantic Richfield Company of Los Angeles, Calif.;
(d) Blended polyethylene and carbon black as specifically taught in U.S. Pat. No. 4,369,267 issued on Jan. 18, 1983, the specification for which is incorporated by reference herein;
(e) Polystyrene as disclosed in U.S. Pat. No. 4,369,227 issued on Jan. 18, 1983, the specification for which is incorporated by reference herein;
(f) Polyene/alpha-olefin as exemplified and disclosed in U.S. Pat. No. 4,369,291, the specification for which is incorporated by reference herein;
(g) Poly-alpha-olefins as exemplified in Canadian Letters Pat. No. 1,137,069 issued on Dec. 7, 1982, the specification for which is incorporated by reference herein;
(h) Polymeric compositions as disclosed in Canadian Letters Pat. No. 1,137,068 issued on Dec. 7, 1982, the specification for which is incorporated by reference herein;
(i) Poly-apha-olefins disclosed in Canadian Letters Pat. No. 1,137,067, the specification for which is incorporated by reference herein;
(j) Polyolefins described in Canadian Letters Pat. No. 1,137,066, the specification for which is incorporated by reference herein;
(k) Polyethylene oxides as disclosed in Canadian Letters Pat. No. 1,137,065 issued on Dec. 7, 1982, the specification for which is incorporated by reference herein;
(l) Olefin polymers and co-polymers as disclosed in Canadian Letters Pat. No. 1,139,737, the disclosure of which is incorporated by reference herein. Canadian Pat. No. 1,139,737 was issued on Jan. 18, 1983;
(m) Polyolefins disclosed in Canadian Letters Pat. No. 1,139,738, the disclosure of which is incorporated by reference herein. Canadian Pat. No. 1,139,738 was issued on Jan. 18, 1983;
(n) Chlorinated PVC as disclosed in Polymer 1982, 23 (7, Suppl.), 1051–6 abstracted at Chem. Abstracts 97: 14550y, 1982;
(o) Polyepsilon caprolactone co-polymers made by means of alcohol initiated polymerization as disclosed in J. Polym. Sci. Polym. Chem. Ed. 1982, 20(2), pages 319–26, abstracted at Chem. Abstracts, Volume 96: 123625x, 1982;
(p) Styrene acrylonitrile co-polymers as disclosed in Diss. Abstracts, Int. B, 1982, 42(8), 3346 and abstracted at Chem. Abstracts 96: 143770n (1982);
(q) Co-polymers of epsilon caprolactone with 1,4-butane diol as disclosed at Kauch. Rezine, 1982, (2), 8–9, abstracted at Chem. Abstracts, Volume 96: 182506g (1982);
(r) Polyesters as disclosed in U.S. Pat. No. 4,326,010, the specification for which is incorporated by reference herein;
(s) Chlorinated polyethylene as disclosed by Belorgey, et al., J. polym. Sci. Plym. Phys. Ed. 1982, 20(2), 191–203;
(t) Plasticized polyepsilon caprolactone co-polymers containing dimethyl phthalate plasticizers as set forth in Japanese Pat. No. J81/147844, abstracted at Chem. Abstracts, Volume 96: 69984y (1982), the specification for which is incorporated by reference herein;
(u) Maleic anhydride modified adducts of polyepsilon caprolactone polyols and ethylenically unsaturated monomer as disclosed in U.S. Pat. No. 4,137,279 issued on Jan. 30, 1979, the specification for which is incorporated by reference herein;
(v) Polyurethane polymers having lactone backbones as disclosed in U.S. Pat. No. 4,156,067 issued on May 22, 1979, the disclosure of which is incorporated by reference herein;
(w) Polyurethane polyether resins wherein the resin is obtained by reacting a polyfunctional lactone with a long chain polalkylene diol and a urethane precursor as disclosed in U.S. Pat. No. 4,355,550 issued on Mar. 10, 1981, the disclosure of which is incorporated by reference herein; and
(x) Resins having polyurethane backbones as disclosed in U.S. Pat. No. 3,975,350 issued on Aug. 17, 1976, the disclosure of which is incorporated by reference herein.

Downstream from the addition point of the ketone, ketoester or alcohol taken together with other insect repellent agents, optionally, the gaseous or liquid containing blowing agent may be added (e.g. at "barrel segments" (S-5, S-6, S-7, S-8, S-9 or S-10)) using the polymer addition "barrel segment" as a reference "barrel segment" S-1. Examples of gaseous blowing agents are carbon dioxide, nitrogen, mixtures of nitrogen and carbon dioxide in proportions of from 1 up to 99% by volume nitrogen and 99 down to 1% by volume carbon dioxide, helium, mixtures of helium and nitrogen, mixtures of helium and carbon dioxide and other gases which are inert at the temperature and pressure of the polymer at the time of the extrusion operation. Thus, gas containing oxygen or other reactive gases, e.g., hydrogen, should be avoided. The pressure of the gas blowing agent being added to the extruder at the point of addition may vary from about 80 up to about 150 psig. Higher pressures may be used without adversely affecting the usefulness of the foamed insect repellent composition-containing particle.

The feed rate range of insect repellent composition-containing but not limited to the ketones, ketoesters or alcohol of our invention, may be between about 0.5% up to about 45% by weight of the polymer.

The die of the extruder may create rod, sheet, film or ribbon. The resulting product may then, if desired, be pelletized to form insect repellent composition-containing polymer particles or the ribbon may be used "as is" as an insect repellent-containing polymeric article of manufacture itself.

In addition to the optional gaseous blowing agents (which are necessarily "inert" gases), blowing agents may be added at the same point on the extruder which will create gaseous voids in the insect repellent-containing polymer articles of our invention and these "blowing agents" are well known to one having ordinary skill in the art. Examples of such non-gaseous containing materials which yield gases on admixture with the polymer in the extruder but which are still inert to the insect repellent (or attractant as the case may be) are as follows:

(i) Under high pressure, ethylene, methane, propane, butane, propylene, methyl chloride, methyl bromide, vinyl chloride and methylene dichloride as more specifically described in U.S. Pat. No. 2,387,730, the specification for which is incorporated by reference herein;

(ii) Ordinarily liquid material such as n-pentane, isopentane, cyclopentane, hexane and petroleum ether fractions or halogen hydrocarbons such as $CFCl_3$, $CF_2Cl_2$, $CH_3Cl$, $CH_2Cl_2$ separately or in admixture with one another as set forth in U.S. Pat. No. 3,758,425, column 4, line 1-5, the specification for which is incorporated by reference herein;

(iii) Dichlorotetrafluoroethane, tetramethylmethane, monochlorodifluoromethane, dichlorodifluoromethane, and dichlorotetrafluoroethane as specifications described in U.S. Pat. Nos. 2,948,664 and 2,948,665 issued on Aug. 9, 1990, the specifications for which are incorporated herein by reference; and (iv) Azo bis(formamide); diazoaminobenzene; N,N'-dinitrosopentamethylene tetramine; N,N'-dimethyl-N,N'-dinitrosoterephthalamide; p,p'-oxy-bis(-benzene sulfonyl semicarbazide); azo bis-(isobutyronitrile); p,p'-oxy-bis(benzene sulfonyl hydrazide); p,p'-diphenyl-bis(sulfonyl hydrazide); benzene-sulfonyl hydrazide; m-benzene-bis(sulfonyl hydrazide) as more specifically described in U.S. Pat. No. 3,298,975 issued on Jan. 17, 1967, the specification for which is incorporated by reference herein.

The resulting extruded (and if desired pelletized) material may then be, for example, injection molded to form a useful article. Such injection molding can be carried out in accordance with the procedure as set forth in U.S. Pat. No. 3,268,636 issued on Aug. 23, 1966, the specification for which is incorporated by reference herein.

In addition, our invention relates to candle body materials which on use are both insect repellent and perfuming which contain one or more of the ketones, ketoesters and/or alcohol and other insect repellent materials including at least one of the compounds having the structure:

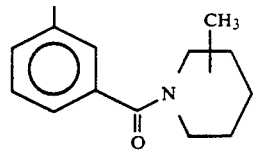

in order to repel house flies (*Musca domestica L.* (Diptera: Muscidae)) and/or mosquitoes (*Aedes agyptae*).

The house fly and mosquito-repellent-perfuming compositions which form part of the candle body materials are within the following specifications:

(I) from 5 up to 100% by weight of an efficacious perfuming/insect repellent composition containing at least one of the ketones, ketoesters and/or alcohol of our invention; and (II) from 0 up to 95% by weight of a standard perfuming substance (non-insect repellent or insect repellent) which may be one or a combination of the following materials:

the methyl ester of 2,5-dihydroxy-4,6-dimethyl benzoic acid;
dihydro myrcenol;
oakmoss absolute;
geraniol;
isobornyl acetate;
citronellyl acetate;
para-t-butyl phenyl isovaleraldehyde;
benzyl salicylate;
hexyl cinnamic aldehyde;
geranonitrile;
patchouli oil;
alpha-terpineol;
tetrahydromuguol;
phenyl ethyl alcohol;
cedrenal;
methyl ionone;
cinnamyl acetate;
benzyl benzoate;
L-Citronellal;
nerol;
geranyl formate;
geranyl acetate;
eugenol;
alpha Farnesene;
beta Farnesene;
citral;
n-Nonanal; and
n-Octanal.

The foregoing formula may require a solubilizing agent, e.g., the methyl ester of dihydroabietic acid (commercial name: HERCOLYN D ®), benzyl benzoate, isopropyl myristate and/or $C_{12}-C_{14}$ isoparaffin hydrocarbons.

The candle base composition can be standard paraffin wax, or it can be transparent or pastel shaded as more particularly described in U.S. Pat. No. 3,615,289 issued on Oct. 26, 1971 (the disclosure of which is incorporated by reference herein) and wherein the candle body comprises as the basic components a mixture of:

(i) a thermoplastic polyamide resin formed from linoleic acid polymerized with a polyamine compound;
(ii) an alkanol amide or alkanol amine; and
(iii) a stearic acid compound.

The weight ratio of candle body:insect repellent/perfumant substance of our invention may vary from about 0.8% up to about 10% with a range of from about 0.8% up to about 10% with a range of from about 0.8% up to about 2.0% being preferred when no non-insect repelling perfume oil is used in conjunction with the ketones, ketoesters and/or alcohol of our invention; and with a range of from about 1.5% up to about 10% by weight of the overall composition being preferred when a non-insect repelling perfume oil is used in conjunction with the ketones, ketoesters and/or alcohol of our invention.

Specifically, the polyamide may be a "VERSAMID" resin which is a thermoplastic condensation product of polymerized linoleic acid with various polyamine compounds such as ethylene diamine, ethylene triamine and the like. Specific "VERSAMID" compounds are "VERSAMID ® 900" "VERSAMID ® 930" "VERSAMID ® 940" "VERSAMID ® 948" "VERSAMID ® 950" and "VERSAMID ® 1635". These compounds are products of the Henkel Chemical Corporation of Minneapolis, Minn.

Another substance required in the clear candle composition consists of about 20–55% by weight of an alkanol amine or alkanol amide prepared by the reaction of a fatty acid ester and amine whereby the ester and the amine are in substantially equal proportions, for example, compounds such as BARLOL ® 12C2 (manufactured by the Barrid Chemical Company) a monoalkyl diethanolamine have 8 to 18% carbon atoms in the alkyl chain. A third component of the clear plastic candle composition comprises one or more stearic acid esters or a mixture of stearic acid esters and stearic acid. These esters include such compounds as isopropyl isostearate, butyl stearate and hexadecyl stearate. These stearic acid compounds serve as stabilizing agents which permit the ready incorporation of the insect repellent/perfumant compositions of our invention up to a level of approximately 5% (total proportion of perfume oil-insect repellent composition). They are carriers for the perfumant/insect repellent and may be used in a proportion of between 1 and 50% by weight of the composition although the preferable range is between 20 to 30%. In this connection it is possible to use up to about 10% by weight of a perfumant/insect repellent if part of the formula is replaced by the material "NEVEX ® 100", a product which is a coumarin-indene copolymer resin of very little unsaturation manufactured by the Neville Chemical Company.

Rather than being a crystalline paraffin wax the candle base of our invention may be an oil gel that has as its base a light mineral oil, an inexpensive natural oil or a combination of such oils which oil gel has a non-greasy surface and feel and sufficient rigidity to be self-supporting at room temperatures. Such a gel is disclosed in U.S. Pat. No. 3,645,705 issued on Feb. 29, 1972, the disclosure of which is incorporated by reference herein. Such compositions of matter include:

(a) from about 35% up to about 85% by weight of an oil which is normally liquid at room temperature chosen from the group consisting of light mineral oils and natural oils having iodine values substantially within the range of 40–135;

(b) from about 7% up to about 40% by weight of a long chain polyamide having a molecular weight substantially within the range of 6000–9000 and a softening point substantially within the range of 18° C.–48° C.; and (c) from about 7% up to about 30% of an alcohol selected from the group consisting of 8 to 12 carbon primary alcohols.

DETAILED DESCRIPTION OF THE DRAWINGS

FIG. 1 is an exploded view of an olfactometer apparatus of the prior art, U.S. Pat. No. 4,759,228 issued on July 26, 1988, the specification for which is incorporated by reference herein used in testing the efficacy of, for example, alpha damascone, beta damascone, delta damascone, trans, trans-delta-damascone, methyl jasmonate, HEDIONE ® and KHARISMAL ™ as house fly (*Musca domestica* L. (Diptera:Muscidae)) and mosquito (*Aedes aegyptae*) repelling materials and used in testing 2-undecyl acetate as a house fly or mosquito attracting material. Air source 634 feeds air through line 635 through air distributors 636, 636a, et seq. onto base plate 617 containing insect landing sites 610, 610a, et seq. The base plate 617 is separated from the spacer plate 629 for the air lines 636 whereby the air lines 636 are held in place at positions 631, 631a, et seq. using spacer ring 628. Air exits through line 633a using exhaust fan 633.

Such compositions may additionally include from about 1% up to about 15% of a methyl ester; up to about 5% by weight of stearic acid and up to about 5% by weight of an oxidation inhibiting agent and up to about 5% by weight of an acid selected from the group consisting of dimer and trimer acids.

Simultaneously with the supplying of air from air source 634, light is supplied through light guides 652, 652a, et seq. from light source 651 which is powered by electric power supply 650. An example of such light guide is marketed by RADIO SHACK ® Division of Tandy Corporation of Fort Worth, Tex. 76102 under the trademark ARCHER ®, Catalog No. 276-228 ("1.0 mm optical plastic fiber length 5 meters"). An example of light source 651 is KRATOS Monochromatic Illuminator GM 100 Miniture VIS-IR Grating Monochromator (Model No. GM 100-1, GM 100-2, GM 100-3 or GM 100-4) as manufactured by KRATOS Analytical Instruments Corporation, 170 Williams Drive, Ramsey, N.J. 07446. Another light supply source is the KRATOS GM 200 Double Grating Monochromator. Another example of a useful light source is the KRATOS GM 252 High Intensity Grating Monochromator.

The olfactometer of the prior art of FIG. 1 is assisted with computer apparatus shown in schematic form and block flow diagram form using reference numerals 620, 621, 623, 624 and 639. Dampers 611a, 611b, et seq. hold base plate 617 in place horizontally. When an insect lands on landing sites 610, 610a, et seq., the landing is recorded electrically through a sensor. The sensor which is, in fact, a transducer causes an electrical impulse caused by the pressure of the insects landing to proceed through wire 619 (held in position by holder 612) to a multi-channel A.C. converter 623 (using electric power supply 639). Converter 623 is associated with program tape storage 624, printer 620 and data link to digital computer 621. Thus, a recording of the data as set forth in Tables I, II, et seq., supra is effected.

FIG. 1-A is an exploded view of a first embodiment of the olfactometer apparatus of our invention used in testing, inter alia, the efficacy of, for example, trans, trans-delta-damascone as a house fly (*Musca domestica* L. (Diptera: Muscidae)) or mosquito (*Aedes aegyptae*) repelling material or 2-undecyl acetate as a house fly or mosquito attracting material. The air supply source 2634 feeds air through line 2634a to mixing station 2636. Treatment agent from source 2635 (e.g., such as the alpha-damascone, beta-damascone, trans, trans-delta damascone, methyl jasmonate or KHARISMAL ™ to be tested as a house fly or mosquito repellent agent) is fed through line 2635a to mixing station 2636. At mixing station 2636, the air is mixed with the treatment agent such as the trans, trans-delta-damascone. The resulting air-treatment agent mixture (in the gas phase) is fed through a plurality (if desired) of lines e.g., 2636a and 2636g into portals at the side of the apparatus along a directional vector parallel to the surface of base plate 2625 just above said base plate 2625 and just below insect attractant quantitative detecting means grids 2610. The base plate 2625 is separated from the spacer plate 2629 whereby the air-treatment agent lines 2636a, 2636g, et seq. are held in place using spacer ring 2628. Air and treatment agent in the gas phase exits through line 2633a using exhaust fan 2633 to the environment 2537.

The air exit is indicated by reference numeral 2537.

Simultaneously with the supplying of air and treatment agent from air supply source 2634 and treatment agent source 2635, light is supplied from above the enclosed insect feeding and/or stimulating means (collectively denoted as "IFS" means through light guides 2652 from light source 2551 which is powered by electric power supply 2550. An example of such light guide is marketed by RADIO SHACK ® division of TANDY Corporation of Fort Worth, Tex. 76102 under the trademark ARCHER ®, Catalog No. 276-228 ("1.0 mm optical plastic fiber length 5 meters"). An example of light source 2551 is KRATOS Monochromatic Illuminator GM 100 Miniture VIS-IR Grating Monochromator (Model No. GM 100-1, GM 100-2, GM 100-3 or GM 100-4) as manufactured by KRATOS Analytical Instruments Corporation, 170 Williams Drive, Ramsey, N.J. 07446. Another light supply source is the KRATOS GM 200 Double Grating Monochromator. Another example of a useful light source is the KRATOS GM 252 High Intensity Grating Monochromator.

The base plate 2625 is also separated from the spacer plate 2629 for the light guides 2652 whereby the light guides 2652 are held in place. In the first embodiment illustrated in FIG. 1-A as well as in partial views in FIGS. 1-B, 1-C, 1-D, 1-E, and 1-Da, spacer ring 2628 separates plate 2629 which holds the light guides 2652 in place from plate 2625 on which landing pads 2680 are located (shown in FIG. 1-C).

The olfactometer of FIG. 1-A is assisted with computer apparatus shown in schematic form and block flow diagram form using reference numerals 2520, 2521, 2523, 2524 and 2529. Dampers 2611 hold base plate 2625 in place horizontally. When an insect lands on landing site 2680, the landing is recorded electrically through a sensor 2610 shown in magnified form in FIG. 1-F. The sensor causes an electrical impluse caused by the pressure of the insects landing to proceed through wire 2619a, 2619b, et seq. (held in position by holder) 2512) to a multi channel A.C. converter 2523 (using electric power supply 2539). Converter 2523 is associated with program tape storage 2524, printer 2520 and data link to digital computer 2521. Thus, a recording of the data as set forth in Tables I, II, et seq., supra is effected.

FIG. 1-B is a top view looking down at spacer plate 2629 of the apparatus of FIG. 1-A showing the locations of the entry of the light guides 2652 above the sensors 2610 and showing the entry of the air and treatment agent mixture (from mixing station 2636) into portals along a directional vector parallel to the surface of plate 2629 and immediately beneath the sensors 2610.

FIG. 1-C sets forth in detail a partial cross section view of the base section of the apparatus of FIG. 1-A indicating the location of insect landing pad 2680 just below the electrical sensor 2610 and showing the electrical sensor 2610 below the light guide 2652 for provision of mono and/or polychromatic radiation in a direction along a directional vector perpendicular to the plane of the electrical sensor 2610.

FIGS. 1-D, 1-E, 1-F show detail views of (i) the active and passive insect interest electronic detecting means (collectively denoted as "DMR" means) and (ii) the enclosed insect feeding and/or stimulating means collectively denoted as "IFS" means having control limited access to the external environment surrounding the apparatus and associated with the "DMR" means.

The insect feeding and/or stimulating means consists of:

(a) a substantially, horizontally positioned insect feeding and/or stimulating microporous substantially planar lamina 2662 which is a porous membrane having an upper outer surface and a lower inner surface with the lower inner surface of element 2662 parallel to the surface of the sensor 2610 which is parallel to the plane of the insect landing pad 2680 and also parallel to the flow of the air-treatment agent stream emanating from flow line 2636g (referring to FIG. 1-D). Thus, the insect attractant quantitative detecting means which is located immediately below the lamina 262 and within the enclosed "IFS" means consists of the electrically conductive elements shown using reference numeral 2610 held by holders 2610a and 2610b and connected to the "DMR" means using wires 2619a and 2619b. Also connected to the "DMR" means is the sensing electrode 2679 (shown in FIG. 1-F) immersed in the insect feeding and/or stimulating composition 2664 (e.g., agar) contained in container 2660 with the inner void thereof, being indicated by reference numeral 2660a (shown in FIGS. 1-D, 1-E and 1-F). Each member of the grid of the sensing element 2610 is shown using reference numerals 2699. In another embodiment shown in FIG. 1-Da the sensing element 2610 rather than being held on plate 2625 is hung from spacer plate 2629 using holders 2671a and 2671b as shown in FIG. 1-Da. The sensing section 2610 is still maintained in fixed position immediately below microporous lamina 2662 and immediately above insect landing site 2680 which is located in fixed position on plate 2625.

In another embodiment, in FIG. 1-G, the treatment agent is fed through portal 2648 from line 2636g and is then rotated passed location 2646 through grid 2649 via orifices 2647 in a direction along a directional vector perpendicular to the plane of the electrical sensor 2610 and perpendicular to the plane of the sensor wires 2699 which are held in place by holders 2610a and 2610b.

FIG. 1-H sets forth in perspective an exploded view of a second embodiment of the olfactometer apparatus of our invention used in testing the efficacy of, for example, the alpha-damascone, beta-damascone, trans, trans-delta-damascone, methyl jasmonate and KHARISMAL ™ of our invention as house fly (*Musca domestica* L. (Diptera:Muscidae) and mosquito (*Aedes aegyptae*) repelling materials and of, for example, 2-undecyl acetate as house fly and mosquito attracting materials.

Air supply source 3634 provides air to mixing station 3636 wherein the air is mixed with treatment agent from treatment agent source 3635 (source of, for example, alpha-damascone). The resulting mixture passes through tube 3636g (for example) and enters the apparatus through side portals. The entry is through spacer plate 3628 and above base plate 3625. The entry of the air-treatment agent is in a direction parallel to the surface of the base plate 3625. Thus, the base plate 3625 is separated from the spacer plate 3629 for the air-treatment agent (e.g., alpha-damascone) lines 3636g (shown in FIG. 1-H) and 3636a and 3636g shown in FIG. 1-L. Air exits through line 3633a using exhaust fan 3633.

The air exit is indicated by reference numeral 3537 in FIG. 1-H.

Simultaneously, with the supplying of air and treatment agent from mixing station 3636, light is supplied from beneath the enclosed insect feeding and/or stimulating means collectively denoted as "IFS" means through light guides 3652, from light source 3551 which is powered by electric power supply 3550 marketed by RADIO SHACK ®, Division of Tandy Corporation of Fort Worth, Tex. 76102 under the trademark ARCHER ®, Catalog No. 276–228 ("1.0 mm optical plastic fiber length 5 meters"). An example of light source 3551 is KRATOS Monochromatic Illuminator GM 100 Miniture VIS-IR Grating Monochromator (Model No. GM 100-1, GM 100-2, GM 100-3 or GM 100-4) as manufactured by KRATOS Analytical Instruments Corporation, 170 Williams Drive, Ramsey, N.J. 07446. Another light supply source is the KRATOS GM 200 Double Grating Monochromator. Another example of a useful light source is the KRATOS GM 252 High Intensity Grating Monochromator. The base plate 3625 is also separated from the spacer plate 3629 for the light guides 3652 whereby the light guides 3652 are held in place in the base plate 3625 whereby the light (or other forms of radiation) is directed in a direction perpendicular to the electrical sensor element 3610. Air supply source form location 3634 and treatment agent from location 3635 is mixed at mixing station 3636 where upon treatment agent and air in admixture is passed through lines 3636a and 3636g (shown in FIG. 1-L) through portals located in the spacer element 3628 in a direction along a directional vector parallel to the electrical sensing element 3610 held in place by holders 3610a and 3610b. The electrical sensing elements are located directly below the horizontally positioned insect feeding and/or stimulating microporous substantially planar lamina 3670 which is held in place by ring 3660 located on spacer plate 3629 spaced from the base plate 3625 by spacer ring 3628. It should be noted that the spacer plate 3629, spacer ring 3628 and base plate 3625 enclosed the entire "enclose insect feeding and/or stimulating means collectively denoted as "IFS" means" which have control limited access to the external environment surrounding the apparatus and in which the insects to be tested, e.g., mosquitoes or house flies are placed.

The insect attractant quantitative detecting means made up of wires 3699 (the entire grid being denoted using reference numeral 3610) is located immediately beneath the porous membrane 3670, the outer surface of which contains a feeding stimulant composition or stimulant composition for insects (for example, agar) indicated by reference numeral 3664 in FIG. 1-M. Immersed in the feeding stimulate composition or stimulant composition for insects (e.g., agar) is electrode 3679 connected to wire 3619 which connects with either wire 3619a or 3619b which is connected to the grid wires 3699 (which make up the insect attractant quantitative detecting means located immediately below lamina 3670).

The olfactometer embodiment of FIG. 1-H (also shown in FIGS. 1-J, 1-L and 1-La is assisted with computer apparatus shown in schematic form and block flow diagram form in FIGS. 1-H and 1-L using reference numerals 3520, 3521, 3523 and 3524 as well as 3639. Dampers 3611 hold base plate 3625 in place horizontally. When an insect lands on the grid having wires 3699, the landing is recorded electrically through a sensor shown in magnified form in FIGS. 1-O and 1-P and in addition in FIG. 1-F. The sensor causes an electrical impulse caused by the pressure of the insects landing to proceed through wires 3619a and 3619b to an electrically biased differential amplifier 3639 (using electric power supply 3539 also connected to wire 3619c which is connected to the electrode 3679 which immersed in the feeding stimulant composition or stimulant for the insect 3674, and then to a multi-channel A.C. converter 3523. Converter 3523 is associated with program tape storage 3524, printer 3520 and data link to digital computer 3521. A variation is shown in FIG. 1-L wherein the differential amplifier 36 is connected in series to electrical biased for psuedo host 3669 which in turn is connected to wire 3619 which in turn is connected to the electrode 3679 immersed in the insect stimulant composition 3674 located on the surface of porous lamina 3670.

FIGS. 1-Lb, 1-Lc, and 1-Ld show the use of the optional heating elements located in base plate 3625. Thus, FIG. 1-Lb is a cut-away side elevation schematic view of a detailed section of the olfactometer of our invention and is in fact a third embodiment of the olfactometer of our invention indicating the presence of heating coils 3662a and 3662b in base plate 3625. Air and treatment agent are fed into portals located in spacing ring 3628 while radiation is transmitted through light guides 3652 held in place on base plate 3625. Base plate 3625 is spaced at a reasonable distance (e.g., 1.0") using spacer ring 3628 which is sealed in place using silicone seals for example. The sensor 3610 is held in place also as a result of being sealed in spacer ring 3628. The sensor 3610 is also suspended in a plane immediately beneath the microporous lamina 3670 on which the insect stimulating composition is located and into which electrode 3679 (connected to wire 3619c) is placed.

Thus, in this third embodiment as shown in FIGS. 1-Lb, 1-Lc and 1-Ld, a well for the heating coils 3662a and 3662b is contained in base plate 3625 and is indicated by reference numeral 3657. Base plate 3625 is located on a stand which is situated on dampers 3611. The top view of the olfactometer looking down on face plate 3629 is set forth in FIG. 1-Lc. The reference numeral 3629 refers to the face plate, per se. Hidden lines 3662a and 3662b are representations of the heating coils through which heat transfer fluid is supplied through lines 3662a and 3662b (with heated water) using pump 3663, the heat for which is controlled using controller 3664. Coils 3662a and 3662b are preferably convered at cavity 3657 with a heat transfer paste. FIG. 1-Ld is also a top view of the olfactometer with the face plate removed looking directly down on the base plate 3625.

FIG. 1-M sets forth a partial cross section of another embodiment of the apparatus of FIG. 1-H wherein the treatment agent (alpha-damascone, beta-damascone, and the like) is located in a microporous polymeric matrix and the particles of microporous polymer (e.g., polyethylene containing embedded therein alpha-damascone) is set forth using reference numeral 4635. Thus, the treatment agent is located in a control release system (CRS TM) mode shown in particles in 4635. A mixing screen 4636 is located downstream from the polymeric treatment agent-containing matrix 4635. Air flowing through tube 3636g passes through and is resisted by the particles 4635 whereupon the air becomes entrained with treatment agent, e.g., alpha-damascone. The resulting gas mixture then is further mixed in screen 4636 and then passes in a direction along a directional vector substantially parallel to grid 3699 beneath lamina 3670 on which is located insect stimulant agent 3664 (e.g., agar). Inserted into the insect stimulant agent is electrode 3679 either diagonally or vertically through portal 4619 in element 3660. Simultaneously, radiation is emitted through radiation tube 3652 in a direction perpendicular to the flow of the air-treatment stream and in a direction perpendicular to the surface of lamina 3670 on which insect stimulant agent 3664 is located. FIGS. 1-O and 1-P set forth front views of grid 3610 which is the insect sensing device. Reference numeral 3644 shows another microporous membrane. Below the microporous membrane 3644 is located the wires of the insect detecting means 3699 and on the outer surface of membrane 3644 is the insect stimulant composition (e.g., agar) indicated by reference numeral 3664. Membrane 3644 may be supported by another membrane (e.g., 3660a) or it need not be supported assuming that is thick enough to withstand the weight of the insect stimulating composition 3664. The wires 3699 have the metal core 3699x optionally coated with a very thin film of coating 3699y which prevents electrocution of the insects when they land on the wires. The thin coatings are indicated in detail in FIGS. 1-O and 1-P.

FIG. 2-A is a series of graphs depicted in three dimensions (in a rectangular mode for the "x" and "y" axes) showing the relative attractiveness or repellency of dimethyl sebacate, beta-damascone, blood extract, diethyl sebacate, a blank, lactic acid, dibutyl sebacate and isopropyl propionate. The graph indicated by reference numeral 201 is for dimethyl sebecate. The graph indicated by reference numeral 202 is for beta-damascone. The graphs indicated by reference numeral 203 is for blood extract. The graph indicated by reference numeral 204 is for diethyl sebacate. The graph indicated by reference numeral 205 is for the blank. The graph indicated by reference numeral 206 is for lactic acid. The graph indicated by reference numeral 207 is for dibutyl sebacate. The graphs indicated by reference numerals 208a and 208b are for isopropyl propionate. The graphs are based on experiments run for a total of 1 hour with 6 intervals of 10 minutes each. The results are tabulated in the following Table I:

TABLE I

| Composition Tested | Graph No. | Insects Collected per Interval | | | | | |
|---|---|---|---|---|---|---|---|
| Dimethyl sebacate | 201 | 58 | 194 | 196 | 59 | 88 | 90 |
| β-Damascone | 202 | 57 | 27 | 27 | 74 | 104 | 40 |
| Blood Extract | 203 | 327 | 153 | 274 | 147 | 143 | 135 |
| Diethyl sebacate | 204 | 76 | 242 | 265 | 70 | 13 | 41 |
| The Blank | 205 | 15 | 104 | 90 | 167 | 139 | 161 |
| Lactic acid | 206 | 76 | 114 | 89 | 184 | 121 | 321 |
| Dibutyl sebacate | 207 | 40 | 31 | 130 | 201 | 115 | 246 |

TABLE I-continued

| Composition Tested | Graph No. | Insects Collected per Interval | | | | | |
|---|---|---|---|---|---|---|---|
| Isopropyl propionate | 208 a & b | 31 | 240 | 195 | 272 | 328 | 242 | in the olfactometer apparatus set forth in FIG. 1-H.

FIG. 2-B is a series of graphs depicted in three dimensions (in a circular mode (time equals 0 at center of circle)) for the "x" and "y" axes showing the relative attractiveness or repellency of the same compositions of matter as those set forth in Table I supra and those set forth in a description of FIG. 2-A.

FIG. 2-C is the series of graphs as set forth in FIGS. 2-A and 2-B depicted in two dimensions. The graphs indicated by reference numerals 201c and 201d are graphs for dimethyl sebacate. The graphs indicated by reference numerals 202c and 202d are for beta-damascone, a repellent. The graphs indicated by reference numerals 203c and 203d are for blood extract. The graphs indicated by reference numerals 204c and 204d are for diethyl sebacate. The graphs indicated by reference numerals 205c and 205d are for a blank. The graphs indicated by reference numerals 206c and 206d are for lactic acid. The graphs indicated by reference numerals 207c and 207d are for dibutyl sebacate. The graphs indicated by reference numerals 208c and 208d are for isopropyl propionate.

FIG. 3-A is a series of graphs depicted in three dimensions (in a rectangular mode for the "x" and "y" axes) showing the relative attractancy or repellency of various compositions. The graph indicated by reference numerals 211a and 211b is for eugenol. The graph indicated by reference numeral 212 is for (−) limonene. The graph indicated by reference numeral 213 is for blood extract. The graph indicated by reference numeral 214 is for a blank. The graph indicated by reference numeral 215 is for dibutyl phthalate. The graph indicated by reference numeral 216 is for Z-6-nonenol. The graph indicated by reference numeral 217 is for 1-dodecanol.

The graph indicated by reference numeral 218 is for methyl isoeugenol. The graphs are based on experiments run for a period 1 hour with 6 intervals of 10 minutes each. The results are tabulated in Table II as follows:

TABLE II

| Composition Tested | Graph No. | Insects Collected per Interval | | | | | |
|---|---|---|---|---|---|---|---|
| Eugenol | 211 a + b | 1 | 8 | 0 | 3 | 1 | 3 |
| (−) Limonene | 212 | 0 | 3 | 0 | 0 | 1 | 0 |
| Blood Extract | 213 | 0 | 0 | 0 | 0 | 0 | 1 |
| The Blank | 214 | 0 | 451 | 289 | 77 | 0 | 0 |
| Dibutyl Phthalate | 215 | 2 | 0 | 0 | 0 | 0 | 0 |
| Z-6-nonenal | 216 | 0 | 0 | 0 | 0 | 0 | 0 |
| 1-Dodecanol | 217 | 0 | 1 | 0 | 0 | 0 | 0 |
| Methyl Isoeugenol | 218 | 0 | 0 | 0 | 0 | 0 | 0 |

The data is determined using the apparatus of FIG. 1-H.

FIG. 3-B is a series of graphs depicted in three dimensions (in a circular mode for the "x" and "y" axes) showing the relative attractiveness or repellency of the same compositions as those shown in FIG. 3-A.

FIG. 3-C is a series of graphs of FIGS. 3-A and 3-B depicted graphically in two dimensions. The graphs indicated by reference numerals 214c and 214d are for the blank.

FIG. 4-A is a series of graphs depicted in three dimensions (in a rectangular mode for the "x" and "y" axes) showing the relative attractiveness or repellency for various compositions. The graphs indicated by reference numerals 221a and 221b are for beta-damascone. The graph indicated by reference numeral 222 is for HEDIONE ®. The graph indicated by reference numeral 223 is for "spent fly media". The graph indicated by reference numeral 224 is for beta-damascenone. The graph indicated by reference numeral 225 is for the blank. The graph indicated by reference numeral 226 is for methyl jasmonate. The graph indicated by reference numeral 227 is for the ethyl ester 2-methyl-3-pentenoic acid. The graph indicated by reference numerals 228a and 228b is for trans,trans-delta-damascone. The apparatus used in determining the data is set forth in FIG. 1-H. The graphs are based on experiments run for period of 1 hour with 6 intervals of 10 minutes each. The results are tabulated in Table III, as follows:

TABLE III

| Composition Tested | Graph No. | Insects Collected per Interval | | | | | |
|---|---|---|---|---|---|---|---|
| Beta-damascone | 221 a + b | 0 | 0 | 0 | 0 | 0 | 0 |
| "HEDIONE ®" | 222 | 0 | 51 | 31 | 46 | 36 | 63 | 46 |
| Spent Fly Media | 223 | 0 | 46 | 134 | 101 | 0 | 22 | 42 |
| Beta-Damascenone | 224 | 0 | 24 | 93 | 36 | 27 | 38 | 33 |
| The Blank | 225 | 0 | 16 | 19 | 28 | 21 | 5 | 7 |
| Methyl jasmonate | 226 | 0 | 73 | 74 | 62 | 21 | 10 | 22 |
| Ethyl ester of 2-methyl-3-pentenoic acid | 227 | 0 | 48 | 70 | 60 | 51 | 28 | 18 |
| Trans, trans-delta-damascone | 228 a + b | 0 | 64 | 37 | 17 | 15 | 15 | 15 |

FIG. 4-B is a series of graphs depicted in three dimensions (in a circular mode for the "x" and "y" axes) showing the relative attractiveness or repellency of the same compositions shown in the description of FIG. 4-A.

FIG. 4-C is the series of graphs that are set forth in FIGS. 4-A and 4-B depicted in two dimensions. The graphs indicated by reference numerals 222c and 222d are for HEDIONE ®. The graphs indicated by reference numerals 223c and 223d are for "spent fly media". The graphs indicated by reference numerals 224c and 224d are for beta-damascenone. The graphs indicated by reference numerals 225c and 225d are for the blank. The graphs indicated by reference numerals 226c and 226d are for methyl jasmonate. The graphs indicated by reference numerals 227c and 227d are for the ethyl ester of 2-methyl-3-pentenoic acid. The graphs indicated by reference numerals 228c and 228d are for trans,trans-delta-damascone.

FIG. 5-A is a series of graphs depicted in three dimensions (in a rectangular mode for "x" and "y" axes) showing the relative attractiveness or repellency of the following materials. The graphs indicated by reference numerals 231a and 231b are for beta-damascone. The graph indicated by reference numeral 232 is for HEDIONE ®. The graph indicated by reference numeral 233 is for "spent fly media". The graph indicated by reference numeral 234 is for beta-damascenone. The graph indicated by reference numeral 235 is for the blank. The graph indicated by reference numeral 236 is for methyl jasmonate. The graph indicated by reference numeral 237 is for the ethyl ester of 2-methyl-3-pentenoic acid. The graphs indicated by reference numerals 238a and 238b are for trans,trans-delta-damascone. The results are tabulated in Table IV as follows:

TABLE IV

| Composition Tested | Graph No | Insects Collected per Interval | | | | | |
|---|---|---|---|---|---|---|---|
| Beta-damascone | 231 a + b | 0 | 0 | 0 | 0 | 0 | 0 |
| "HEDIONE ®" | 232 | 82 | 145 | 127 | 62 | 33 | 17 |
| Spent Fly Media | 233 | 180 | 212 | 281 | 600 | 600 | 600 |
| Beta-Damascenone | 234 | 117 | 101 | 77 | 42 | 38 | 17 |
| The Blank | 235 | 35 | 56 | 71 | 19 | 15 | 6 |
| Methyl jasmonate | 236 | 147 | 93 | 176 | 45 | 27 | 17 |
| Ethyl ester of 2-methyl-3-pentenoic acid | 237 | 118 | 139 | 99 | 52 | 35 | 13 |
| Trans, trans-delta-damascone | 238 a + b | 101 | 47 | 43 | 18 | 14 | 9 |

The tests are carried out using the apparatus of FIG. 1-H. The graphs are based on experiments run for a period of 13 hours at 6 intervals of 2.17 hours each.

FIG. 5-B is a series of graphs depicted in three dimensions (in a circular mode for the "x" and "y" axes) showing the relative attractiveness or repellency of the same compositions as those set forth in the description of FIG. 5-A.

FIG. 5-C is the series of graphs as set forth in FIGS. 5-A and 5-B depicted in two dimensions. The graphs indicated by reference numerals 232c and 232d are for HEDIONE ®. The graphs indicated by reference numerals 233c and 233d are for "spent fly media". The graphs indicated by reference numerals 234c and 234d are for beta-damascenone. The graphs indicated by reference numerals 235c and 235d are for the blank. The graphs indicated by reference numerals 236c and 236d are for methyl jasmonate. The graphs indicated by reference numerals 237c and 237d are for the ethyl ester of 2-methyl-3-pentenoic acid. The graphs indicated by reference numerals 238c and 238d are for trans,trans-delta-damascone.

FIG. 6-A is a series of graphs depicted in three dimensions (in a rectangular mode for "x" and "y" axes) showing the relative attractiveness or repellency of the various compositions. The graphs indicated by reference numerals 241a and 241b are for eugenol. The graph indicated by reference numeral 242 is for (−) limonene. The graph indicated by reference numeral 243 is for blood extract. The graph indicated by reference numeral 244 is for the blank. The graph indicated by reference numeral 245 is for dibutyl phthalate. The graph indicated by reference numeral 246 is for Z-6-nonenal. The graph indicated by reference numeral 247 is for n-dodecanol. The graphs indicated by reference numerals 248a and 248b are for methyl isoeugenol. The graphs are based on experiments run for a period of 1 hour with 6 intervals of 10 minutes. The graphs are determined using the apparatus of FIG. 1-H. The results are tabulated in Table V as follows:

TABLE V

| Composition Tested | Graph No. | Insects Collected per Interval | | | | | |
|---|---|---|---|---|---|---|---|
| Eugenol | 241 a + b | 2 | 2 | 0 | 1 | 0 | 0 |
| (−) Limonene | 242 | 0 | 0 | 0 | 0 | 3 | 0 |
| Blood Extract | 243 | 0 | 0 | 0 | 0 | 0 | 3 |

TABLE V-continued

| Composition Tested | Graph No | Insects Collected per Interval | | | | | |
|---|---|---|---|---|---|---|---|
| The Blank | 244 | 5 | 0 | 2 | 5 | 1 | 0 |
| Dibutyl Phthalate | 245 | 0 | 0 | 0 | 0 | 0 | 0 |
| Z-6-nonenal | 246 | 0 | 0 | 0 | 0 | 0 | 0 |
| 1-Dodecanol | 247 | 2 | 2 | 1 | 0 | 0 | 0 |
| Methyl Isoeugenol | 248 a + b | 0 | 5 | 7 | 4 | 3 | 3 |

FIG. 6-B is a series of graphs depicted in three dimensions (in a circular mode for the "x" and "y" axes) showing the relative attractiveness or repellency of the compositions of matter shown in the graphs for FIG. 6-A.

FIG. 6-C is a series of graphs as set forth in FIGS. 6-A and 6-B depicted in two dimensions. The graphs indicated by reference numerals 241c and 241d are for eugenol. The graphs indicated by reference numerals 242c and 242d are for (−) limonene. The graphs indicated by reference numerals 243c and 243d are for blood extract. The graphs indicated by reference numerals 244c and 244d are for the blank. The graphs indicated by reference numerals 247c and 247d are for n-dodecanol. The graphs indicated by reference numerals 248c and 248d are for methyl isoeugenol.

FIG. 7-A sets forth in block flow diagram a process for testing insects giving rise to the results set forth in graphical form in FIGS. 8, 9, 10, 11, 12, 13, 14, 15, 16, 17, 18, 19, 20, 21, 22, 23, 24 and 25. FIG. 7-A also shows in block flow diagram form the use of the apparatus shown in FIG. 7-B. Thus, fresh air from location 251 is fed into compressor 253 and then flows through pressure regulator 255 and heat exchanger 256. Simultaneously, with test material coming from ejector 259 flowing through line 261 through heat exchanger 258 the test material and air are treated in the humidifier 262. The test material flows into test cage 270 wherein insects are located. Simultaneously, the fresh air fed through blower 284 flows through heater 282 and humidifier 280 past sponge 275 and heater 273 into the test cage. Referring to FIG. 7-B, the syringe of assembly is shown using reference numeral 259. The test cage is shown using reference numeral 270 and the target is shown using reference numeral 267 upon which the camera 290 is focused. The humidifier is shown using reference numeral 262 and the carbon dioxide line is shown using reference numeral 299. The activity of the insects is measured using this apparatus in terms of number of mosquitoes on target 267 versus micrograms of compound/liter of target air with target air evolving from air source 251.

Thus, FIG. 8 sets forth a graph of dose-response for both HEDIONE ® (shown by graph points 302a and 302b and diethyl toluamide) shown by graph point 301 and graph point 301a. The "x" axis sets forth micrograms of compound/liter of target air and the "y" axis sets forth number of mosquitoes on target.

FIG. 9 is a graph using the apparatus of FIGS. 7-A and 7B showing the dose-response curves for methyl jasmonate and diethyl toluamide. The points indicated by reference numerals 312a and 312b are for methyl jasmonate. The point indicated by reference numeral 310a and the graph indicated by reference numeral 310 is for diethyl toluamide. The graph shows number of mosquitoes on target versus micrograms of compound/liter of target air.

FIG. 10 sets forth the dose-response curves for beta-damascone and diethyl toluamide. The points indicated by reference numerals 322a and 322b are for beta-damascone. The point indicated by reference numeral 320a is for diethyl toluamide. The graph indicated by reference numeral 320 for diethyl toluamide. The graph shows number of mosquitoes on target on the "y" axis and micrograms of compound to be tested/liter of target air on the "x" axis.

FIG. 11 sets forth the dose-response curves for vanilla extract versus diethyl toluamide. The points indicated by reference numerals 322a and 322b are for vanilla extract. The point indicated by reference numeral 330a is for diethyl toluamide. The graph indicated by reference numeral 330 is for diethyl toluamide. The graph shows number of mosquitoes on target on the "y" axis and micrograms of compound tested/liter of target air on the "x" axis.

FIG. 12 sets forth the dose-response graph comparing n-dodecanol with diethyl toluamide using the apparatus of FIGS. 7-A and 7-B. The points indicated by reference numerals 342a and 342b are for n-dodecanol. The point indicated by reference numeral 340a is for diethyl toluamide. The graph indicated by reference numeral 340 is for diethyl toluamide. The graph shows number of mosquitoes on target (on the "y" axis) versus micrograms of compound tested/liter of target air (on the "x" axis). The data for this graph is determined using the apparatus of FIGS. 7-A and 7-B.

FIG. 13 is the dose-response graph comparing methyl isoeugenol with diethyl toluamide. The points indicated by reference numeral 352a and 352b are for methyl isoeugenol. The point indicated by reference numeral 350a is for diethyl toluamide. The graph indicated reference numeral 350 is for diethyl toluamide. The data for this graph is determined using the apparatus of FIGS. 7A and 7B. The number of insects on target (mosquitoes) is on the "y" axis and the micrograms of compound tested/liter of target air is on the "x" axis.

FIG. 14 are the dose-response curves using the apparatus of FIGS. 7A and 7B comparing jasmine absolute and diethyl toluamide. The graph indicated by reference numeral 365 and the points indicated by reference numerals 365a and 365b are for jasmine absolute. The graph indicated by reference numeral 360 and the point indicated by reference numeral 360a is for diethyl toluamide. The number of mosquitoes on target is set forth on the "y" axis and the micrograms of compound/tested liter of target of air is set forth on the "x" axis.

FIG. 15 is the dose-reponse graph comparing Rose Otto Bulgarian and diethyl toluamide. The points indicated by reference numerals 372a and 372b (and like points) are for Rose Otto Bulgarian. The point indicated by reference numeral 370a and the graph indicated by reference numeral 370 are for diethyl toluamide. The data set forth in FIG. 15 is determined using the apparatus of FIGS. 7A and 7B. On the "x" axis is set forth the number of mosquitoes on target and on the "y" axis is set forth micrograms of compound tested/liter of target air.

FIG. 16 sets forth a graphical representation of the dose-response data for KHARISMAL TM and diethyl toluamide. The points indicated by reference numerals 382a and 382b and like points indicate the data for KHARISMAL TM. The point indicated by reference numeral 380a and the graph indicated by reference numeral 380 is for diethyl toluamide. The graph shows number of mosquitoes on target on the "y" axis and micrograms of compound tested/liter of target air on the "x" axis. The carbon dioxide addition rate is 50 ml/minute.

FIG. 17 sets forth dose-response curves for KHARISMAL ™ and for diethyl toluamide. The data is taken using the apparatus of FIGS. 7A and 7B. The graph indicated by reference numeral 385 and the points indicated by reference numerals 382a and 382b and like points are for the KHARISMAL ™. The graph indicated by reference 380 and the point indicated by reference numeral 380a is for diethyl toluamide. The graph shows number of mosquitoes on target on the "y" axis and micrograms of compound/tested liter of target air on the "x" axis. The data for FIG. 17 is determined using the apparatus of FIGS. 7A and 7B. (carbon dioxide addition rate: 50 ml/minute).

FIG. 18 is a dose-response graph showing data for alpha-damascone compared with data of diethyl toluamide. The data points are determined using the apparatus and process shown in FIGS. 7A and 7B. The points indicated by reference numerals 392a, 392b and like points are for alpha-damascone. The points indicated by reference numeral 390a and like points and the graph indicated by reference numeral 390 are for diethyl toluamide. On the "x" axis is set forth micrograms of compound tested/liter of target air and on the "y" axis is set forth number of mosquitoes on target. (carbon dioxide addition rate: 50 ml/minute).

FIG. 19 sets forth the dose-response curves for vanillin and diethyl toluamide. The curve indicated by reference numeral 401 and the points indicated by reference numerals 401a and 401b are for vanillin. The curve indicated by reference numeral 405 and the points indicated by reference numerals 405a and 405b are for diethyl toluamide. The data set forth in FIG. 19 is determined using the process and apparatus of FIGS. 7A and 7B (carbon dioxide addition rate: 50 ml/minute). The number of mosquitoes on target is set forth on the "y" axis and the micrograms of compound tested/liter of target air is set forth on the "x" axis.

FIG. 20 sets forth the dose-response data for methyl eugenol and diethyl toluamide using the apparatus and process of FIGS. 7A and 7B. The points indicated by reference numerals 412a and 412b and like points are for the methyl eugenol. The point indicated by reference numeral 410a and like points and the graph indicated by reference numeral 410 is for diethyl toluamide. On the "x" axis is the number of mosquitoes on target and on the "y" axis is set forth the micrograms of compound tested/liter of target air (carbon dioxide addition rate: 50 ml/minute).

FIG. 21 sets forth the dose-response data for eugenol and for diethyl toluamide. The points indicated by reference numerals 422a, 422b and like points are for eugenol. The points indicated by reference numerals 420a and like points and the graph indicated by reference numeral 420 is for diethyl toluamide. On the "x" axis is set forth the number of mosquitoes on target and on the "y" axis is set forth micrograms of compound tested/liter of target air. (carbon dioxide addition rate: 50 ml/minute).

FIG. 22 is the dose-response data for n-decanol versus diethyl toluamide. The points indicated by reference numerals 432a and 432b and like points are for the n-decanol. The points indicated reference numeral 430a and like points and the graph indicated by reference numeral 430 is for diethyl toluamide. The data for FIG. 22 is determined using the process and apparatus of FIGS. 7A and 7B. On the "y" axis is set forth the number of insects (mosquitoes) on target and on the "x" axis is set forth micrograms of compound tested/liter of target air. (carbon dioxide addition rate: 50 ml/minute).

FIG. 23 sets forth the dose-response data for ethyl, vanillin versus diethyl toluamide. The points indicated by reference numerals 436a, 436b and like points are for the ethyl vanillin. The points indicated by reference numerals 430a and like points and the graph indicated by reference numeral 435 are for diethyl toluamide. The data is determined using the apparatus of FIGS. 7A and 7B. On the "y" axis is set forth the number of mosquitoes on target and on the "x" axis is set forth micrograms of compound tested/liter of target air. (carbon dioxide addition rate: 50 ml/minute).

FIG. 24 sets forth the dose-response data for the "H" formulation versus diethyl toluamide (the "H" formulation components and percentages of components have been set forth supra). The points indicated by reference numerals 442a, 442b and like points are for the "H" formulation. The point indicated by reference numeral 440a and like points and the graph indicated by reference numeral 440 is for the diethyl toluamide. On the "y" axis is set forth the number of mosquitoes on target and on the "x" axis is set forth micrograms of compound tested/liter of target air. The data for FIG. 24 is determined using the apparatus and process of FIGS. 7A and 7B.

FIG. 25 sets forth the dose-response data for n-tetradecanol versus diethyl toluamide. The points indicated by reference numerals 452a and 452b and like points are for the n-tetradecanol. The point indicated by reference numeral 450a, and like points and the graph indicated by reference numeral 450 is for the diethyl toluamide. The data for FIG. 25 is determined using the apparatus and process set forth in FIG. 7A and 7B. On the "y" axis is set forth the number of mosquitoes on target and on the "x" axis is set forth micrograms of compound tested/liter of target air (carbon dioxide addition rate: 50 ml/minute).

FIGS. 26, 27, 28 and 29 show in detail the ZOECON ® sticky trap, more specifically a Zoecon Pherocon 1C Trap (e.g., in FIG. 29 indicated by reference numeral 1616a and in FIG. 26 indicated by reference numerals 1608c, 1608d, 1609a, 1609b, 1609c, 1609d, 1610a, 1610c, 1610d, 1611a, 1611c, 1612a, 1612c, 1612d, 1613c, 1613d, 1614a, 1614b, 1614c, 1615a, 1615c, 1616a, 1616b, 1617a, 1617b, 1617c, 1618a, 1618b, 1618c, 1619a, 1619c, 1620a, 1620b, 1620c, 1621a, 1621b, 1621c, 1623a, 1623b, 1623c, 1624a, 1624b, 1624c. The Zoecon Pherocon 1C Trap has suspended in it as will be seen from FIGS. 28 and 29 a 2 cm×2 cm strip of slow release polymer (polyethylene) 6117 in FIGS. 28 and 29 containing test material (e.g., insect repellent or insect attractant) e.g. the insect attractants methyl isoeugenol, n-dodecanol or beta-damascenone or mixtures thereof containing from about 0.5% up to about 99% by weight of, for example, methyl isoeugenol; from about 99% down to about 0.5% by weight of n-dodecanol and from about 0.5% up to about 99% by weight of beta-damascenone or the repellents alpha-damascone, beta-damascone, trans,trans-delta-damascone, methyl jasmonate, HEDIONE ®, or KHARISMAL ™, or the 2 cm×2 cm strip contains the GOLDEN MALRIN ® control. The 2 cm×2 cm strips 6117 is suspended in the trap 1616a from bar 6116 using holder 6118. Trap 1616a has lower tray 6110 which will catch insect droppings or dead insects which do not adhere to the 2 cm×2 cm strip 6117. The lower tray 6110 is attached via strips 6112a and 6112b to upper holder 6111 which is attached to suspension bar 6113 suspended by rod 6114 to the barn beam 6115 (in FIG. 27). The barn beam 6115 is held in a horizontal position by upright supports 1602 and 1606 (as will be seen in FIG. 27) which is firmly in place on the barn floor 6119. The 2 cm×2 cm strip 6117 is formulated in such apparatus as is in FIG. 37 set forth described in detail, infra. The traps containing the insect attractant, or insect repellent, e.g. methyl jasmonate or beta-damascone or other insect repellent composition or the attractant, 2-undecyl acetate or combinations of 2-undecyl acetate with other attractants such as methyl isoeugenol, n-dodecanol or the like or the GOLDEN MALRIN ® control are placed in the goat barn having sensing panels 1601 and 1603 and inner supports 1604 and 1605, and observation post 1622 and experimental locations 1608, 1609, 1610, 1611, 1612, 1613, 1614, 1615, 1616, 1617, 1618, 1619, 1620, 1621, 1623 and 1624 has suspended in it the several Zoecon Pherocon 1C Traps each containing 2 cm×2 cm strips of formulated slow release insect attractants or repellents. Trap placement was replicated in four quadrants of the barn. Traps 1616a, 1616b, 1615a, 1615c and other traps were placed in the barn for seven days and the insects collected were identified and counted. Evidence of various insects visiting the traps were also counted, as fly specks inside or outside the traps. All the test materials were compared with standarized check treatment consisting of 0.5 grams of GOLDEN MALRIN ® fly bait inside slow release packets hung like other compounds as in strip 6117 in FIGS. 28 and 29.

FIGS. 30 and 31 indicate the results of field trial tests using the apparatus set forth in FIGS. 26, 27, 28 and 29.

FIG. 30 is a series of bar graphs for field trial tests of the attractants methyl-isoeugenol, n-dodecanol, 1-(2-butenoyl)-2,6,6,-trimethyl-1-3-cyclohexadiene and GOLDEN MALRIN ® for house fly speck counts inside of the traps indicated by reference numeral 6117. Thus, the bar graph indicated by reference number 52 is the bar graph for methyl-isoeugenol insofar as it attracts *Musca domestica* L. (Diptera:Muscidae) inside of such traps as trap 1616a in FIGS. 28 and 29, the house fly specks being located on tray 6110 in FIGS. 28 and 29. Tray 6110 is also shown in FIG. 27. The bar graph indicated by reference numeral 53 is the bar graph for n-dodecanol insofar as it attracts *Musca domestica* L. (Diptera:Muscidae). The bar graph indicated by reference number 51 is the bar graph for GOLDEN MALRIN ® (insofar as it attracts *Musca domestica* L. (Diptera:Muscidae)). The bar graph indicated by reference numeral 54 is the bar graph for 1-(2-butenoyl)-2,6,6,-trimethyl-1-3-cyclohexadiene insofar as it attracts *Musca domestica* L. (Diptera:Muscidae) as stated supra.

FIG. 30 is a graph of fly specks/trap versus compound. Thus, the methyl isoeugenol in FIG. 30 gives rise to an attractancy of *Musca domestica* L. (Diptera:Muscidae) of 12.25 fly specks/trap; the n-dodecanol gives rise to an attractancy of 17.25 fly specks/trap; and the 1-(2-butenoyl)-2,6,6,-trimethyl-1-3-cyclohexadiene gives rise to an attractancy of 29.5 fly specks/trap; and the GOLDEN MALRIN ® gives rises to only 0.75 fly specks/trap.

FIG. 31 is a series of bar graphs of field trial tests of the attractants methyl-isoeugenol, n-dodecanol, 1-(2-butenoyl)-2,6,6,-trimethyl-1-3-cyclohexadiene and GOLDEN MALRIN ® with respect to attractancy for Stored Products Moth. The bar graph indicated by reference numeral 64 is the bar graph for the attractancy of Stored Products Moths for 1-(2-butenoyl)-2,6,6,-trimethyl-1-3-cyclohexadiene. The bar graph indicated by reference numeral 63 is the bar graph for attractancy of Stored Products Moths for n-dodecanol. The bar graph indicated by reference numeral 62 is the bar graph for attractancy of Stored Products Moths using methyl isoeugenol. The bar graph indicated by reference numeral 61 is the bar graph for attractancy of Stored Products Moths by GOLDEN MALRIN ®.

FIG. 32 is a series of bar graphs of field trial tests of attractants and repellents for mosquitoes, GOLDEN MALRIN ®, methyl-2-methyl-butyrate, methyl isoeugenol, n-dodecanol, beta-damascenone, and 1-nonen-3-ol. The absence of a bar at location 509 indicates that 1-nonen-3-ol is a mosquito repellent (repellent for *Aedes aegyptae*). The bar indicated by reference numeral 508 indicates that beta-damascenone is an attractant for mosquitoes. The bar indicated by reference numeral 507 indicates that n-dodecanol is an attractant for mosquitoes. The bar indicated by reference numeral 506 indicates that methyl isoeugenol is an attractant for mosquitoes. The absence of a bar indicated by reference numeral 505 indicates that methyl-2-methyl butyrate is a repellent against mosquitoes. The absence of a bar indicated by reference numeral 501 indicates that GOLDEN MALRIN ® is a repellent for mosquitoes.

FIG. 33 sets forth the neural signal recorded from the antennal lobes of the *Musca domestica* L. (Diptera:Muscidae) using methyl-isoeugenol. The neural signal in FIG. 33 is set forth and is shown using the reference numerals 84, 85 and 86 and the passage or treatment is shown using reference numerals 81, 82, and 83. Reference numerals 81 and 83 show no passage of test material, e.g. methyl isoeugenol. The neural signal recorded when no passage of test material takes places is set forth at reference numerals 84 and 86 (respectively for periods 81 and 83). The neural signal recorded when test material is used to treat the *Musca domestica* L. (Diptera:Muscidae) is set forth at reference numeral 85. The base line for the neural signal recorded from the antennal lobe using methyl isoeugenol is indicated by reference numeral 87. The lack of any change from the base line during treatment (82) is indicative of the fact that the methyl isoeugenol is a strong attractant for *Musca domestica* L. (Diptera:Muscidae).

Referring to the FIG. 34, FIG. 34 sets forth the neural signal recorded from the antennal lobe of *Musca domestica* L. (Diptera:Muscidae) using the attractant called "extract of used fly rearing media" as described, supra. Passage of the attractant to the *Musca domestica* L. (Diptera:Muscidae) is indicated at reference numeral 92 whereas reference numerals 91 and 93 indicate no passage of the treating material to be tested. When passage of the test material takes place, the neural signal is indicated at reference numeral 95. When there is no passage of the test material, the neural signal is indicated at reference numeral 96 and at reference numeral 94. Reference numeral 97 is the base line for the neural signal recorded from the antennal lobe using the attractant called "extract of used fly rearing media".

The house flies used for this study were supplied from a laboratory colony at the Medical and Veterinary Entomology Laboratory at the University of Florida. A female, 3-7 day old fly was restrained on a standard microscope slide using the following technique. The fly's wings were clipped off near the base in order to facilitate handling. The fly was then glued to the microscope slide, dorsal side down, using Super glue. Ski wax was melted around the head capsule to immobilize the head during electrode penetration. The slide was then placed under a dissecting microscope to enable a more accurate placement of the electrode.

Microcapillary electrodes (tip O.D. 1-5 mm) were filled with an ionic fluorescent solution which served the dual purpose of a conducting solution as well as marking the recording site. The ionic solution contained Lucifer yellow CH, a super-fluorescent lithium salt of 3,6-disulphonate 4-aminonaphlthalimide (Stewart, W. W. 1978 "Functional connections between cells as revealed by dye-coupling with a highly flourescent naphthalimide tracer" Cell 14:741-759), which is taken up by depolarizing neurons via induced endocytosis (Wilcox and Franceschini, N. 1984 "Illumination induces dye incorporation in photoreceptor cells" Science (Washington, D.C.) 225: 851-854).

The active electrode was positioned in the selected spot using Nashike micromanipulators with remote hydraulic drive. Areas for electrophysiological study were located using (Strausfeld, N.J. 1978 "Atlas of an insect brain", Springer-Verlag: Berlin) (1976) detailed anatomical study of the house fly brain, which includes a three-dimensional coordinate system. Subsequent gross dissections showed that with much practice, individual lobes on the brain could be penetrated with repeatable accuracy.

The indifferent electrode was placed either in the head capsule or thorax. The preferred position was the thorax as this places the electrode out of the way. However, care must be taken not to place the indifferent electrode in the ventral nerve cord as this results in extraneous nerve signals.

In placing the active electrode, it was necessary to prick the cuticle with a minuten pin in order to prevent deformation of the head capsule as the electrode penetrated. This method minimized damage to the underlying neural tissue.

Nerve signals were preamplified with custom neutral amplifiers at 100× and then displayed on Nicolet 3091 oscilloscope. The same signal was simultaneously sent to a Dianachart smart recorder/data logger to obtain a hard copy of the neural signal. The olfactory stimulus was initially supplied using the technique developed by (Kauer, J. S.; Shepherd, G. M. 1975 "Olfactory stimulation and monitored step pulses of odor", Brain Res. 85: 108-113) and (Getchel, T. V.; Shepherd, G. M. 1978 "Responses of olfactory receptor cells to step pulses of odor at different concentrations in the salamander", J. Physiol. 282: 521-540) which uses three concentric pipettes, one to apply the odor and the other two to exhaust the odor. However, this system proved to be too bulky for house flies due to their small size, as it was not possible to form three concentric pipettes which were small enough not to be bulky, but not so small as to restrict air flow.

Consequently, a system was developed which used pressurized air to delivery the odor and an exhaust system was built around the entire set up. The delivery system was a test tube containing 2 ml of odor extract, stoppered, and with two disposable pipettes through the rubber stopper through the rubber stopper (as is shown in FIG. 36). One pipette 104 was attached to a pressurized air tank and the other pipette 112 was attached to a tygon tube terminating in a capillary tube which could be positioned directly in front of the fly's antennae.

Odor delivery (e.g. methyl isoeugenol) was controlled with a valve 113 so that abrupt onset of the stimulus was possible. Each stimulus was approximately 4-5 seconds in duration. A minimum of 15 minutes was used between odor stimulus to allow the previous odor to be completely exhausted from the area.

FIG. 37 is a schematic cut-away elevation diagram of an extrusion and pelletizing apparatus useful in carrying out a process of our invention during the operation of said apparatus whereby the insect attractant or repellent is incorporated into a polymer such as a polyethylene. Motor 15 drives the extruder screws located at 23A in barrel 16, the extruder being operated at temperatures in the range of about 150° C. up to about 250° C. At the beginning of the barrel resin at source 12 together with additives, e.g., processing aids and densifiers at location 13 is added via addition funnel 14 into the extruder. Simultaneously (when the operation reaches "steady state"), insect attractant, 2-undecyl acetate or insect repellent, e.g., alpha-damascone, beta-damascone, methyl jasmonate or any of the other ketones, ketoesters or alcohol of our invention is added to the extruder at one or more barrel segments S-3, S-4, S-5, S-6, S-7 and S-8 of the extruder (which may be a twin screw or single screw extruder) at locations 18a, 18b, 18c and 18d (for example) by means of gear pump 23 from source 17. From source 19 into barrel segments S-5, S-6, S-7, S-8, S-9 and S-10, a gaseous or liquid blowing agent, e.g., nitrogen, carbon dioxide and the like as described, supra, are added simultaneously with the addition of insect attractant, e.g., 2-undecyl acetate or insect repellent e.g., one or more of the ketones, ketoesters or alcohol of our invention. The feed rate range of resin is about 80-300 pounds per hour. The feed rate range of insect attractant or repellent is between 1 and 35% of the feed rate range of the resin. The blowing agent range is such that the pressure of the gas or the pressure over the liquid being fed into the extruder is between about 50 and 200 psig if, indeed, blowing agent is added. If desired the extruded ribbon or cylinder may be passed through water bath 20 and pelletizer 21 into collection apparatus 21a.

FIG. 38-A is a series of graphs depicted in three dimensions (in a rectangular mode for the "x" and "y" axes) showing the relative attractiveness or repellency of several compositions of matter. The graph indicated by reference numeral 701 and 701a is for 1-octen-4-ol. The graph indicated by reference numeral 702 is the graph for jasmine absolute. The graph indicated by reference numeral 703 is the graph for lactic acid. The graph indicated by reference numeral 704 is the graph for the "H" formulation. The graph indicated by reference numeral 705 is the graph for the "blank". The graph indicated by reference numeral 706 is for the Rose Otto Bulgarian. The graph indicated by reference numeral 707 is for tobacco extract. The graph indicated by reference numeral 708 and the graph indicated by reference numeral 708a are for KHARISMAL TM. The graphs show the attractancy or repellency for mosquitoes (*Aedes aegyptae*) using the apparatus of FIG. 1-H. The graphs are based on experiments run for a total of 1 hour with 6 intervals of 10 minutes each. The results are tabulated in Table VI as follows:

TABLE VI

| Composition Tested | Graph No. | Insects Collected per Interval | | | | | |
|---|---|---|---|---|---|---|---|
| 1-octen-4-ol | 701 | 5 | 0 | 0 | 0 | 0 | 0 |
| Jasmine absolute | 702 | 0 | 0 | 0 | 0 | 1 | 1 |
| Lactic acid | 703 | 11 | 1 | 11 | 127 | 14 | 40 |
| HEDIONE ® | 704 | 1 | 51 | 4 | 0 | 0 | 1 |

TABLE VI-continued

| Composition Tested | Graph No. | Insects Collected per Interval | | | | | |
|---|---|---|---|---|---|---|---|
| The Blank | 705 | 29 | 56 | 90 | 42 | 60 | 99 |
| ROSE OTTO BULGARIAN | 706 | 0 | 0 | 0 | 0 | 0 | 0 |
| Tobacco extract | 707 | 71 | 103 | 91 | 159 | 150 | 76 |
| KHARISMAL ™ | 708 a & b | 0 | 2 | 1 | 1 | 2 | 7 |

FIG. 38-B is a series of graphs depicted in three dimensions (in a circular mode) time equals "0" at center of circle (for the "x" and "y" axes) showing the relative attractiveness or repellency for mosquitoes (*Aedes aegyptae*) of the compounds set forth in the description of FIG. 38-A.

FIG. 38-C is a series of graphs setting forth data previously set forth in FIGS. 38-A and 38-B depicted in two dimensions. The graphs indicated by reference numerals 701c and 701d are for 1-octen-4-ol. The graphs indicated by reference numerals 703c and 703d are for lactic acid. The graphs indicated by reference numerals 704c and 704d are for the "H" formulation. The graphs indicated by reference numerals 705c and 705d are for the blank. The graphs indicated by reference numerals 707c and 707d are for tobacco extract. The graphs indicated by reference numerals 708c and 708d are for KHARISMAL ™.

FIG. 39-A is a series of graphs depicted in three dimensions (in a rectangular mode for the "x" and "y" axes) showing the relative attractiveness or repellency of various compositions of matter for mosquitoes (*Aedes aegyptae*). The graphs indicated by reference numerals 710 and 710a are for d-pulegone. The graph indicated by reference numeral 712 is for secondary undecyl acetate. The graph indicated by reference numeral 713 is for isobutyl formate. The graph indicated by reference numeral 714 is for 1-octen-4-ol. The graph indicated by reference numeral 715 is for isoamyl isobutyrate. The graph indicated by reference numeral 716 is for lactic acid. The graph indicated by reference numeral 717 is for the blank. The graphs indicated by reference numerals 718 and 718a are for anisyl acetate. The data for the graphs set forth in FIG. 39-A were obtained using the apparatus of FIG. 1-H. The results are tabulated in Table VII.

TABLE VII

| Composition Tested | Graph No. | Insects Collected per Interval | | | | | |
|---|---|---|---|---|---|---|---|
| d-pulegone | 710a | 9 | 0 | 1 | 1 | 0 | 0 |
| Secondary undecyl acetate | 712 | 65 | 363 | 286 | 250 | 371 | 301 |
| Isobutyl formate | 713 | 0 | 18 | 27 | 20 | 4 | 19 |
| 1-octen-4-ol | 714 | 1 | 12 | 22 | 11 | 12 | 8 |
| Isoamyl isobutyrate | 715 | 0 | 0 | 0 | 0 | 1 | 0 |
| Lactic acid | 716 | 1 | 1 | 2 | 6 | 6 | 4 |
| The Blank | 717 | 10 | 17 | 32 | 23 | 31 | 37 |
| Anisyl Acetate | 718 a + b | 1 | 0 | 0 | 0 | 0 | 0 |

FIG. 39-B is a series of graphs of depicted in three dimensions (in a circular mode for the "x" and "y" axes) showing the relative attractiveness or repellency for mosquitoes (*Aedes aegyptae*) of the compositions of matter shown in FIG. 39-A. The graphs are based on experiments run for a period of 1 hour with 6 intervals of 10 minutes each.

FIG. 39-C is a series of graphs for data set forth in FIGS. 39-A and 39-B depicted in two dimensions. The graphs indicated by reference numerals 712c and 712d are for secondary undecyl acetate (showing mosquito attractancy). The graphs indicated by reference numerals 713c and 713d are for isobutyl formate. The graphs indicated by reference numerals 714c and 714d are for 1-octen-4-ol. The graphs indicated by reference numerals 716c and 716d are for lactic acid. The graphs indicated by reference numerals 717c and 717d are for the blank.

FIG. 40-A is a series of graphs depicted in three dimensions (in a rectangular mode for the "x" and "y" axes) showing the relative attractiveness or repellency for mosquitoes (*Aedes aegyptae*) for a series of compositions. The graph indicated by reference numerals 721 and 721a are for d-pulegone. The graph indicated by reference numeral 722 are for secondary undecyl acetate. The graph indicated by reference numeral 723 is for isobutyl formate. The graph indicated by reference numeral 724 is for 1-octen-4-ol. The graph indicated by reference numeral 725 is for isoamyl isobutyrate. The graph indicated by reference numeral 726 is for lactic acid. The graph indicated by reference numeral 727 is for the blank. The graphs indicated by reference numerals 728 and 728a are for anisyl acetate. The data for the graphs of FIG. 40-A was determined using the apparatus of FIG. 1-H. The graphs are based on experiments run for a total of 4 hours with 6 intervals of 40 minutes each. The results are tabulated in Table VIII as follows:

TABLE VIII

| Composition Tested | Graph No. | Insects Collected per Interval | | | | | |
|---|---|---|---|---|---|---|---|
| d-pulegone | 721 + a | 11 | 0 | 0 | 0 | 1 | 0 |
| Secondary undecyl acetate | 722 | 1636 | 963 | 790 | 532 | 277 | 463 |
| Isobutyl formate | 723 | 88 | 93 | 16 | 61 | 2 | 28 |
| 1-octen-4-ol | 724 | 66 | 44 | 14 | 36 | 8 | 20 |
| Isoamyl isobutyrate | 725 | 1 | 8 | 31 | 5 | 8 | 10 |
| Lactic acid | 726 | 20 | 9 | 16 | 5 | 5 | 28 |
| The Blank | 727 | 150 | 134 | 57 | 40 | 31 | 185 |
| Anisyl Acetate | 728 a + b | 1 | 1 | 0 | 1 | 202 | 340 |

FIG. 40-B is a series of graphs depicted in three dimensions (in a circular mode for the "x" and "y" axes) showing the relative attractiveness or repellency of the compositions which were tested as shown in the description of FIG. 40-A.

FIG. 40-C is a series of graphs for data set forth in FIGS. 40-A and 40-B depicted in two dimensions. The graphs indicated by reference numerals 722c and 722d are for secondary undecyl acetate (showing it as an attractant for mosquitoes). The graphs indicated by reference numerals 723c and 723d are for isobutyl formate. The graphs indicated by reference numerals 724c and 724d are for 1-octen-4-ol indicating it to be repellent for mosquitoes. The graphs indicated by reference numerals 727c and 727d are for the blank. The graphs indicated by reference numerals 728c and 728d are for anisyl acetate.

FIG. 41-A is a series of graphs depicted in three dimensions (in a rectangular mode for the "x" and "y" axes) showing the relative attractiveness or repellency of various compositions of matter for mosquitoes (*Aedes aegyptae*). The graphs indicated by reference numerals 731 and 731a are for 1-octen-4-ol. The graph indicated by reference numeral 732 is for the Schiff base of ethyl vanillin and methyl anthranilate. The graph indicated by reference numeral 733 is for trans,trans-delta-damascone. The graph indicated by reference numeral 734 is for methyl anthranilate. The graph indicated by reference numeral 735 is for the Schiff base of vanillin and methyl anthranilate. The graph indicated by reference numeral 736 is for lactic acid. The graph indicated by reference numeral 737 is for vanillin. The graphs indicated by reference numerals 738 and 738a are for ethyl vanillin. The data set forth in the graphs of FIG. 41-A were obtained using the apparatus of FIG. 1-H. The graphs are based on experiments run for a total 1 hour with 6 intervals of 10 minutes each. The results are tabulated in Table IX as follows:

TABLE IX

| Compositions of Matter Tested | Graph No. | Insects Per Interval | | | | | |
|---|---|---|---|---|---|---|---|
| 1-octen-4-ol | 731 + a | 0 | 0 | 0 | 0 | 0 | 0 |
| The Schiff base ethyl vanillin methyl anthranilate | 732 | 5 | 6 | 31 | 16 | 14 | 6 |
| trans, trans-delta-damascone | 733 | 7 | 3 | 9 | 1 | 0 | 3 |
| Methyl anthranilate | 734 | 5 | 8 | 20 | 46 | 10 | 26 |
| The Schiff base of vanillin and methyl anthranilate | 735 | 1 | 2 | 8 | 6 | 6 | 6 |
| Lactic Acid | 736 | 6 | 24 | 16 | 4 | 2 | 21 |
| Vanillin | 737 | 14 | 1 | 5 | 2 | 5 | 18 |
| Ethyl Vanillin | 738 + a | 23 | 33 | 9 | 10 | 3 | 66 |

FIG. 41-B is a series of graphs depicted in three dimensions (in a circular mode for the "x" and "y" axes) showing the relative attractiveness or repellency of the same compositions of matter as those set forth in the description of FIG. 41-A.

FIG. 41-C is a series of graphs setting forth the data shown in FIGS. 41-A and 41-B depicted in two dimensions. The graphs indicated by reference numerals 732c and 732d are for the Schiff base of ethyl vanillin and methyl anthranilate. The graphs indicated by reference numerals 733c and 733d are for trans,trans-delta-damascone. The graphs indicated by reference numerals 734c and 734d are for methyl anthranilate. The graphs indicated by reference numerals 735c and 735d are for the Schiff base of methyl anthranilate and vanillin. The graphs indicated by reference numerals 736c and 736d are for lactic acid. The graphs indicated by reference numerals 737c and 737d are for vanillin. The graphs indicated by reference numerals 738c and 738d are for ethyl vanillin.

FIG. 42-A is a series of graphs depicted in three dimensions (in a rectangular mode for the "x" and "y" axes) showing the relative attractiveness or repellency for mosquitoes (Aedes aegyptae). The data shown in FIG. 42-A is a replicate of data set forth in FIG. 41-A. The graphs indicated by reference numerals 741 and 741a are for 1-octen-4-ol. The graph indicated by reference numeral 742 is the graph for the Schiff base of ethyl vanillin and methyl anthranilate. The graph indicated by reference numeral 743 is the graph for trans,-trans-delta-damascone. The graph indicated by reference numeral 744 is for methyl anthranilate. The graph indicated by reference numeral 745 is for the Schiff base of vanillin and methyl anthranilate. The graph indicated by reference numeral 746 is for lactic acid. The graph indicated by reference numeral 747 is for vanillin. The graphs indicated by reference numerals 748 and 748a are for ethyl vanillin. The data set forth in the graphs of FIG. 42-A were determined using the apparatus of FIG. 1-H. The graphs are based on experiments run for a period of 1 hour with 6 intervals of 10 minutes each. The results are tabulated in Table X as follows:

TABLE X

| Compositions of Matter Tested | Graph No. | Insects Per Interval | | | | | |
|---|---|---|---|---|---|---|---|
| 1-octen-4-ol | 741 + a | 0 | 0 | 0 | 0 | 0 | 0 |
| The Schiff base of Ethyl vanillin and methyl anthranilate | 742 | 0 | 34 | 9 | 17 | 0 | 0 |
| trans, trans-delta-damascone | 743 | 0 | 0 | 0 | 1 | 2 | 1 |
| Methyl anthranilate | 744 | 14 | 10 | 2 | 8 | 8 | 4 |
| Schiff base of vanillin and methyl anthranilate | 745 | 19 | 13 | 1 | 7 | 6 | 15 |
| Lactic Acid | 746 | 3 | 3 | 0 | 2 | 12 | 0 |
| Vanillin | 747 | 1 | 0 | 0 | 1 | 0 | 1 |
| Ethyl Vanillin | 748 + a | 0 | 0 | 0 | 2 | 0 | 0 |

FIG. 42-B is a series of graphs depicted in three dimensions (in a circular mode for the "x" and "y" axes) showing the relative attractiveness or repellency of the same compositions of matter of those set forth in FIG. 42-A.

FIG. 42-C is a series of graphs showing data set forth in FIGS. 42-A and 42-B depicted in two dimensions. The graphs indicated by reference numerals 742c and 742d are for the Schiff base of ethyl vanillin and methyl anthranilate. The graphs indicated by reference numerals 743c and 743d are for trans,trans-delta-damascone. The graphs indicated by reference numerals 744c and 744d are for methyl anthranilate. The graphs indicated by reference numerals 745c and 745d are for the Schiff base of vanillin and methyl anthranilate. The graphs indicated by reference numerals 746c and 746d are for lactic acid. The graphs indicated by reference numerals 747c and 747d are for vanillin. The graphs indicated by reference numerals 748c and 748d are for ethyl vanillin.

FIG. 43-A is a series of graphs depicted in three dimensions (in a rectangular mode for the "x" and "y" axes) showing the relative attractiveness or repellency of the same compositions of matter as those set forth in FIG. 42-A with the attractiveness or repellency being for mosquitoes (Aedes aegyptae). The graphs indicated by reference numerals 751 and 751a are for 1-octen-4-ol. The graph indicated by reference numeral 752 is for the Schiff base of ethyl vanillin and methyl anthranilate. The graph indicated by reference numeral 753 is for trans,trans-delta-damascone. The graph indicated by reference numeral 754 is for methyl anthranilate. The graph indicated by reference numeral 755 is for the Schiff base of vanillin and methyl anthranilate. The graph indicated by reference numeral 756 is for lactic acid. The graph indicated by reference numeral 757 is for vanillin. The graph indicated by reference numeral 758 is for ethyl vanillin. The data used in setting forth the graphs for FIG. 43-A was determined using the apparatus of FIG. 1-H. The graphs are based on experiments run for a period of 1 hour with 6 intervals of 10 minutes each. The results are tabulated in Table XI as follows:

TABLE XI

| Compositions of Matter Tested | Graph No. | Insects Per Interval | | | | | |
|---|---|---|---|---|---|---|---|
| 1-octen-4-ol | 741 + a | 0 | 0 | 0 | 0 | 0 | 0 |
| The Schiff base of Ethyl vanillin and methyl anthranilate | 752 | 6 | 58 | 30 | 48 | 10 | 29 |
| trans, trans-delta-damascone | 753 | 3 | 52 | 17 | 37 | 5 | 17 |
| Methyl anthranilate | 754 | 17 | 13 | 50 | 12 | 5 | 6 |
| The Schiff base of vanillin | 755 | 1 | 3 | 12 | 36 | 2 | 11 |

TABLE XI-continued

| Compositions of Matter Tested | Graph No. | Insects Per Interval | | | | | |
|---|---|---|---|---|---|---|---|
| and methyl anthranilate | | | | | | | |
| Lactic Acid | 756 | 1 | 23 | 2 | 7 | 16 | 42 |
| Vanillin | 757 | 0 | 19 | 6 | 8 | 5 | 0 |
| Ethyl Vanillin | 758 + a | 3 | 9 | 10 | 15 | 18 | 4 |

FIG. 43-B is a series of graphs depicted in three dimensions (in a circular mode for the "x" and "y" axes) showing the relative attractiveness or repellency for mosquitoes (Aedes aegyptae) for the same compounds as those set forth in the description of FIG. 43-A.

FIG. 43-C is the series of graphs for data set forth in FIGS. 43-A and 43-B depicted in two dimensions. The graphs indicated by reference numerals 752d and 752c are for the Schiff base of ethyl vanillin and methyl anthranilate. The graphs indicated by reference numerals 753c and 753d are for trans,trans-delta-damascone. The graphs indicated by reference numerals 754c and 754d are for methyl anthranilate. The graphs indicated by reference numerals 755c and 755d are for the Schiff base of vanillin and methyl anthranilate. The graphs indicated by reference numerals 756c and 756d are for lactic acid. The graphs indicated by reference numerals 757c and 757d are for vanillin. The graphs indicated by reference numerals 758c and 758d are for ethyl vanillin.

FIG. 44-A is a series of graphs depicted in three dimensions (in a rectangular mode for the "x" and "y" axes) showing the relative attractiveness or repellency for mosquitoes (Aedes aegyptae) for the same compositions of matter of those set forth in FIG. 43-A. The graphs indicated by reference numerals 761 and 761a are for 1-octen-4-ol. The graph indicated by reference numeral 762 is for the Schiff base of ethyl vanillin and methyl anthranilate. The graph indicated by reference numeral 763 is for trans,trans-delta-damascone. The graph indicated by reference numeral 764 is for methyl anthranilate. The graph indicated by reference numeral 765 is for the Schiff base of vanillin and methyl anthranilate. The graph indicate by reference numeral 766 is for lactic acid. The graph indicated by reference numeral 767 is for vanillin. The graphs indicated by reference numerals 768 and 768a are for ethyl vanillin. The graphs are based on experiments run for a period of 1 hour with 6 intervals of 10 minutes each. The data used for the graphs of FIG. 44-A were obtained using apparatus of FIG. 1-H. The results are tabulated in Table XII as follows:

TABLE XII

| Compositions of Matter Tested | Graph No. | Insects Per Interval | | | | | |
|---|---|---|---|---|---|---|---|
| 1-octen-4-ol | 761 + a | 0 | 2 | 0 | 0 | 0 | 0 |
| The Schiff base of Ethyl vanillin and methyl anthranilate | 762 | 37 | 13 | 4 | 2 | 4 | 13 |
| trans, trans-delta-damascone | 763 | 5 | 0 | 0 | 1 | 0 | 5 |
| Methyl anthranilate | 764 | 0 | 16 | 7 | 9 | 11 | 7 |
| The Schiff base of vanillin and methyl anthranilate | 765 | 5 | 12 | 8 | 2 | 4 | 13 |
| Lactic Acid | 766 | 2 | 2 | 0 | 13 | 0 | 9 |
| Vanillin | 767 | 0 | 2 | 0 | 0 | 0 | 0 |
| Ethyl Vanillin | 768 + a | 3 | 2 | 0 | 0 | 0 | 0 |

FIG. 44-B is a series of graphs depicted in three dimensions (in a circular mode for the "x" and "y" axes) showing the relative attractiveness or repellency for mosquitoes (Aedes aegyptae) of the same compositions as those set forth in the description of FIG. 44-A.

FIG. 44-C is a series of graphs showing data set forth in FIGS. 44-A and 44-B depicted in two dimensions. The graphs indicated by reference numerals 761c and 761d are for 1-octen-4-ol showing that 1-octen-4-ol is a repellent. The graphs indicated by reference numerals 762c and 762d are for the Schiff base of ethyl vanillin and methyl anthranilate. The graphs indicated by reference numerals 763d and 763c are for trans,trans-delta-damascone showing that trans,trans-delta-damascone is a repellent for mosquitoes. The graphs indicated by reference numerals 764c and 764d are for methyl anthranilate. The graphs indicated by reference numerals 765c and 765d are for Schiff base of methyl anthranilate and vanillin. The graphs indicated by reference numerals 766d and 766c are for lactic acid. The graphs indicated by reference numerals 767c and 767d are for vanillin. The graphs indicated by reference numerals 768c and 768d are for ethyl vanillin.

FIG. 45-A is a series of graphs depicted in three dimensions (in a rectangular mode for the "x" and "y" axes) showing the relative attractiveness or repellency for mosquitoes (Aedes aegyptae) for the same compounds for those set forth in the description of FIG. 44-A. The graphs indicated by reference numerals 771 and 771a are for 1-octen-4-ol. The graph indicated by reference numeral 772 is for the Schiff base of ethyl vanillin and methyl anthranilate. The graph indicated by reference numeral 773 is for trans,trans-delta-damascone. The graph indicated by reference numeral 774 is for methyl anthranilate. The graph indicated by reference numeral 775 is for the Schiff base of methyl anthranilate and vanillin. The graph indicated by reference 776 is for lactic acid. The graph indicated by reference numeral 777 is for vanillin. The graphs indicated by reference numerals 778 and 778a are for ethyl vanillin. The data used for the graphs of FIG. 45-A were obtained by use of the apparatus set forth in FIG. 1-H. The graphs are based on experiments run for period of 1 hour with 6 intervals of 10 minutes each. The results are tabulated in Table XIII as follows:

TABLE XIII

| Compositions of Matter Tested | Graph No. | Insects Per Interval | | | | | |
|---|---|---|---|---|---|---|---|
| 1-octen-4-ol | 771 + a | 0 | 0 | 0 | 2 | 2 | 1 |
| The Schiff base of Ethyl vanillin and methyl anthranilate | 772 | 1 | 2 | 2 | 25 | 12 | 61 |
| trans, trans-delta-damascone | 773 | 0 | 0 | 0 | 3 | 17 | 16 |
| Methyl anthranilate | 774 | 1 | 1 | 18 | 20 | 11 | 49 |
| The Schiff base of vanillin and methyl anthranilate | 775 | 1 | 1 | 1 | 4 | 3 | 6 |
| Lactic Acid | 776 | 6 | 2 | 9 | 9 | 4 | 15 |
| Vanillin | 777 | 0 | 2 | 1 | 3 | 5 | 8 |
| Ethyl Vanillin | 778 + a | 7 | 2 | 1 | 33 | 15 | 29 |

FIG. 45-B is a series of graph depicted in three dimensions (in a circular mode for the "x" and "y" axes) showing the relative attractiveness or repellency for mosquitoes (Aedes aegyptae) for the same compositions of matter as those set forth in the description of FIG. 45-A.

FIG. 45-C is a series of graphs for data set forth in FIGS. 45-A and 45-B depicted in two dimensions. The graphs indicated by reference numerals 771c and 771d are for 1-octen-4-ol indicating that 1-octen-4-ol is a repellent for mosquitoes (Aedes aegyptae). The graphs indicated by reference numerals 772c and 772d are for the Schiff base of ethyl vanillin and methyl anthranilate. The graphs indicated by reference numerals 773c and 773d is for trans,trans-delta-damascone. The graphs indicated by reference numerals 774c and 774d are for methyl anthranilate. The graphs indicated by reference numeral 775c and 775d are for the Schiff base of methyl anthranilate and vanillin. The graphs indicated by reference numerals 776c and 776d are for lactic acid. The graphs indicated by reference numerals 777c and 777d are for vanillin. The graphs indicated by reference numerals 778c and 778d are for ethyl vanillin.

FIG. 46-A is a series of graphs depicted in three dimensions (in a rectangular mode for the "x" and "y" axes) showing the relative attractiveness or repellency for mosquitoes (Aedes aegyptae) for the same compositions of matter as those set forth in the description of FIG. 45-A. The graphs indicated by reference numerals 781 and 781a are for 1-octen-4-ol. The graph indicated by reference numeral 782 is for the Schiff base of methyl anthranilate and ethyl vanillin. The graph indicated by reference numeral 783 is for trans,trans-delta-damascone. The graph indicated by reference numeral 784 is for methyl anthranilate. The graph indicated by reference numeral 785 is for the Schiff base of vanillin and methyl anthranilate. The graph indicated by reference numeral 786 is for lactic acid. The graph indicated by reference numeral 787 is for vanillin. The graphs indicated by reference numerals 788 and 788a are for ethyl vanillin. The graphs are based on experiments run for a period of 1 hour with 6 intervals of 10 minutes each. The results are tabulated in Table XIV as follows:

TABLE XIV

| Compositions of Matter Tested | Graph No. | Insects Per Interval | | | | | |
|---|---|---|---|---|---|---|---|
| 1-octen-4-ol | 781 + a | 0 | 0 | 0 | 0 | 0 | 0 |
| The Schiff base of Ethyl vanillin and methyl anthranilate | 782 | 116 | 70 | 11 | 4 | 12 | 3 |
| trans, trans-delta-damascone | 783 | 2 | 15 | 0 | 2 | 1 | 0 |
| Methyl anthranilate | 784 | 7 | 9 | 18 | 7 | 0 | 6 |
| The Schiff base of vanillin and methyl anthranilate | 785 | 21 | 6 | 1 | 4 | 5 | 0 |
| Lactic Acid | 786 | 6 | 27 | 9 | 32 | 23 | 18 |
| Vanillin | 787 | 5 | 6 | 1 | 3 | 10 | 0 |
| Ethyl Vanillin | 788 + a | 0 | 0 | 1 | 0 | 0 | 0 |

The data set forth in FIG. 46-A was obtained using the apparatus of FIG. 1-H.

FIG. 46-B is a series of graphs depicted in three dimensions (in a circular mode for the "x" and "y" axes) showing the relative attractiveness or repellency for mosquitoes (Aedes aegyptae) of the compositions of matter set forth in the description of FIG. 46-A.

FIG. 46-C is a series of graphs showing data previously set forth in FIGS. 46-A and 46-B depicted in two dimensions. The graphs indicated by reference numerals 782c and 782d are for the Schiff base of methyl anthranilate and ethyl vanillin. The graphs indicated by reference numerals 783c and 783d are for trans,trans-delta damascone. The graphs indicated by reference numerals 784c and 784d are for methyl anthranilate. The graphs indicated by reference numerals 785c and 785d are for Schiff base of vanillin and methyl anthranilate. The graphs indicated by reference numerals 786c and 786d are for lactic acid. The graphs indicated by reference numerals 787c and 787d are for vanillin.

A preferred embodiment of our invention comprises an ellipsoidally-shaped detergent table 830 containing a solid plastic core 832 which can be fabricated from, for example, polyethylene, polypropylene, nylon or any polymer capable of having therein microvoids from which an insect repelling substance, e.g. trans,trans-delta-damascone will be controllably transported from the plastic core into and through the soap cake over a reasonable period of time during the use of the soap cake. Such polymers can be microporous polymers such as those described in U.S. Pat. No. 4,247,498 issued on Jan. 27, 1981, the specification for which is incorporated herein by reference. Surrounding the central plastic core containing insect repellent 832, is detergent 830' which is in the solid phase at ambient conditions, e.g., room temperature and atmospheric pressure. Examples of workable detergents 830' are "elastic" detergents such as those described in U.S. Pat. No. 4,181,632 issued on Jan. 1, 1980, the disclosure of which is incorporated herein by reference, or "transparent" soaps such as those set forth in U.S. Pat. No. 4,165,293 issued on Aug. 21, 1979, the disclosure of which is incorporated herein by reference. Other examples of the detergent 830' useful in our invention are those set forth as "variegated soaps" in Canadian Letters Patent No. 1,101,165 issued on May 19, 1981, the disclosure of which is incorporated by reference herein.

On use of the soap tablet 830 or detergent bar, the insect repellent agent originally located in plastic core 832 is transported at a steady state from core 832 through core surface 831 through the detergent 830' and finally through the surface of the detergent bar at, for example, 833, 834, 835 and 836.

The detergent bar or tablet 830 of our invention may be of any geometric shape, for example, a rectangular parallelpiped tablet is shown in FIGS. 51, 52 and 53 containing solid plastic core 839. The insect repellent located in solid plastic core 839 on use of the detergent bar passes through at steady state surface 837 of FIG. 52, detergent 838 and finally surface 839 at, for example, locations 840, 841, 842 and 843. The environment surrounding the detergent bar on use thereof is then treated with the insect repellent at 843, 844 and 845, for example. Optionally, aromatizing agent can also be contained in the detergent bar and so the environment surrounding the detergent bar on use thereof would also be aesthetically aromatized at 843, 844 and 845, for example.

As is shown in FIGS. 54, 55 and 56 the plastic core of the detergent tablet 830 may have a single finite void at its center 851 (of FIGS. 55 and 56) in which the insect repellent agent and optionally the aromatizing agent is contained. The plastic core then is a shell 848 having outer surface 852 (shown in FIGS. 55 and 56). The insect repellent agent (and optionally the aromatizing agent) contained in the void in the plastic core permeates through shell 848, past surface 852 at a steady state, through the detergent 847 and to the environment at, for example, 856, 857, 858 and 859.

In addition to the insect repellent contained in the core, e.g. core 839 or core void the core can also contain other materials for therapeutic use, for example, bacteriastats, deodorizing agents and the like which are compatible with insect repellents such as the ketones, ketoesters and alcohol of our invention. In the alternative, the plastic core of the detergent tablet of FIGS. 54, 55 and 56 may have an empty single finite void at its center 851 with the insect repellent contained in the shell 848.

At the end of the use of the detergent tablet, the hollow core or the solid core can be used as an insect imparting and aroma imparting or air freshener household article. In addition, depending on the ratio of the volume of the void 851, to the solid part of the detergent tablet of FIGS. 54, 55 and 56, the detergent tablet of FIGS. 54, 55 and 56 can be so fabricated that it will float on the surface of the liquid in which it is being used and this physical attribute has certain obvious advantages.

EXAMPLE I

PARAFFIN WAX CANDLE BODY

The following composition is prepared:

| INGREDIENTS | PARTS BY WEIGHT |
|---|---|
| Paraffin Wax | 95.0 |
| 50:50 mixture of trans, trans-delta-damascone and 1-octen-4-ol | 5.0 |

Paraffin wax is intimately admixed at 150° C. and 10 atmospheric pressure with the mixture of trans,trans-delta-damascone and 1-octen-4-ol in an autoclave with intensive shaking. The autoclave pressure is maintained with a nitrogen atmosphere. At the end of the period of 1 hour the autoclave is depressurized, the autoclave is opened and the resulting mixture is poured into cylindrical candle molds containing wicks.

The resulting candles on use evolve an aesthetically pleasing aroma and, in addition, give rise to efficacious house fly and mosquito repellency. The candles are effective in preventing house flies and mosquitoes from entering a room in which one candle is burning for a period of 10 minutes, the said room having the dimensions 6'×15'×15' having a 3'×3' open portal adjacent to a house fly and mosquito-infested region in the month of August in the temperate zone (location: Highlands, N.J. next to Raritan Bay).

EXAMPLE II

The transparent candle base mixture is produced by intimately admixing the following ingredients:

| INGREDIENTS | PARTS BY WEIGHT |
|---|---|
| VERSAMID ® 1635 | 34.0 |
| Barlol 12C2 | 51.0 |
| Butyl Stearate | 3.5 |
| NEVEX ® 100 | 5.0 |
| SPAN ® | 1.5 |
| Isopropyl Isostearate | 4.0 |
| Isopropyl Myristate | 4.0 |

The foregoing mixture is placed in an autoclave and intimately admixed with a perfuming-insect repellent composition containing 3 parts by weight alpha-damascone, 3 parts by weight beta-damascone and 4 parts by weight methyl jasmonate at the rate of 8% by weight of the total candle base composition.

The autoclave is sealed and heated to 180° C. under 15 atmospheres pressure and maintained with vigorous shaking for a period of 5 hours. At the end of the 5 hour period the autoclave is depressurized (being under a nitrogen pressure atmosphere) and the autoclave is opened and the contents are then poured into cylindrical candle molds four inches in height and two inches in diameter containing 0.125" wicks. The resulting candles have efficacious mosquito and house fly repellencies and have aesthetically pleasing aromas on use.

The candles are effective in preventing house flies and mosquitoes from entering a room in which two candles have been burning for 15 minutes, the said room having dimensions of 6'×15'×15' and having a 3'×3' open portal adjacent a house fly and mosquito-infested region in the month of August, in the temperate zone of Highlands, N.J. adjacent Raritan Bay.

EXAMPLE III

The following candle base composition of matter is prepared:

| INGREDIENTS | PARTS BY WEIGHT |
|---|---|
| Polyamide (VERSAMID ® 940 manufactured by the Henkel Chemical Corporation of Minneapolis, Minnesota) | 30.0 |
| Stearic acid | 5.0 |
| Methyl-12-hydroxy stearate | 5.0 |
| 10 Carbon primary alcohol (Continental Oil Company ALFOL ® 10) (ALFOL ® is a trademark of Conoco Division of E. I. DuPont of Wilmington, Delaware) | 5.0 |
| Myristyl Myristate | 10.0 |
| Stearic hydrazide | 0.1 |
| "H" Formulation | 4.0 |
| Light white mineral oil q.s. to | 100% |

All of the materials except the polyamide are mixed at room temperature. The mixture is then heated gradually with gradual addition of the polyamide and with agitation beginning with the commencement of addition of the polyamide. In the proportion required, the polyamide does not become fully soluble until the mixture reaches the temperature of about 220° F. The temperature on the order of 220° F. to 230° F. is maintained at atmospheric pressure with continued agitation until the polyamide is fully dissolved. Since higher temperatures promote solution of the polyamide this temperature range can be slightly exceeded with some advantages.

As soon as the polyamide has dissolved completely, the mixture is poured into molds following the conventional practice in the manufacture of molded candles. As the candles cool they harden. The candles are then freed from the molds and tested for insect (house flies and mosquitoes) repellency.

The candles are effective in preventing house flies and mosquitoes from entering a room in which two candles have been burning for 15 minutes, and said room having dimensions of 6'×15'×15' and having a 3'×3' open portal adjacent a house fly and mosquito-infested region in the month of August in the temperate zone of Highlands, N.J. adjacent Raritan Bay.

EXAMPLE IV

A study was conducted to evaluate the efficacy of candles which are designated as "A", "B", and "C" in repelling house flies (*Musca domestica*).

Candle "A" contained 95% Paraffin Wax and 5% of the following composition:
100 parts by weight of KHARISMAL ™; and
700 parts by weight of a perfume composition containing the following ingredients:

| INGREDIENTS | PARTS BY WEIGHT |
|---|---|
| (i) Perfume mixture of essential oils and chemicals, to wit: | 83.8 grams |

| INGREDIENTS | PARTS BY WEIGHT |
|---|---|
| the methyl ester of 2.5-dihydroxy-4-6-dimethyl benzoic acid; dihydro myrcenol; oakmoss absolute; benzyl acetate; geraniol; isobornyl acetate; citronellyl acetate; para-t-butyl phenyl isovaleraldehyde; benzyl salicylate; hexyl cinnamic aldehyde; geranonitrile; patchouli oil; alpha-terpineol; tetrahydromuguol; phenyl ethyl alcohol; cedrenal; methyl ionone; cinnamyl acetate; benzyl benzoate; | |
| (ii) Solvent:<br>the methyl ester of dihydroabietic acid | 4.0 grams |

Candle "B" contained 90% Paraffin Wax and 10% citronella oil.

Candle "C" contained only Paraffin Wax.

The candles are allowed to burn for 20 minutes and the number of house flies and mosquitoes repelled is recorded for the next 60 minutes with the following equipment and procedure:

Materials

Test Chamber

The evaluation was conducted in a 28.3 cubic meter chamber with airing ports. A screened cage measuring 15 cm×15 cm×47.5 cm was attached inside an upper airing port, and a screened repellency observation cage measuring 15 cm×15 cm×32.5 cm was attached outside the upper airing port. The two cages were held together by a Masonite plate which fit firmly in the airing port. A 4-cm hole located in the center of each Masonite plate provided an escape for the test insects. A barrier was used to close the hole.

Attractant

A caged mouse was used as an attractant and was placed inside the chamber in the larger section of the repellency cage.

Test Insect

Adult house flies (*Musca domestica*) are test insects.

Procedure

For each replicate, 75 to 100 adult house flies were removed from the rearing cage by means of a vacuum aspirator, and transferred by carbon dioxide anesthesia to the inner cage containing the mouse. The assembled cage was placed in one of the upper ventilation ports of the chamber. For each experimental situation the test insects were transferred to a clean cage containing the mouse. A house fly candle was placed centrally on the chamber floor and burned for 20 minutes before initiating the repellency counts. The maximum period for the repellency counts was 60 minutes. The first repellency count was made at 10 minutes after the burning ended, and subsequent counts were taken at 5-minute intervals thereafter. The number of house flies repelled were those escaping to the outside cage. For the control, counts were made in a similar manner, but no candle was burned.

The same three candles were used for all four replicates. Between replicates the chamber was exhausted, the Kraft paper flooring for the chamber was replaced, and the two screened repellency cages were submerged in hot detergent water, rinsed and dried.

Results

The overall average percent of house flies repelled for each candle for 60 minutes was as follows:
Candle A: 83%
Candle B: 52%
Candle C: 17%.

What is claimed is:

1. A method of repelling *Musca domestica* L. (Diptera Muscidae) or *Aedes aegyptae* for a finite period of time from a three-dimensional space inhabitable by said *Musca domestica* L. (Diptera Muscidae) or said *Aedes aegyptae* consisting essentially of the step of exposing said three-dimensional space to an effective *Musca domestica* L. (Diptera Muscidae) or *Aedes aegyptae* repelling concentration and quantity of a compound selected from the group consisting of a compound defined according to the structure:

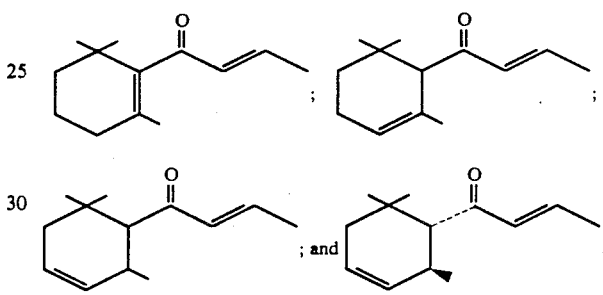

2. The method of claim 1 wherein the three dimensional space is exposed to alpha-damascone having the structure:

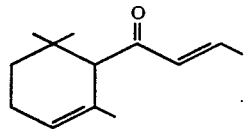

3. The method of claim 1 wherein the three dimensional space is exposed to beta-damascone having the structure:

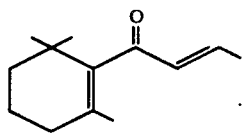

4. The method of claim 1 wherein the three dimensional space is exposed to trans,trans-delta-damascone having the structure:

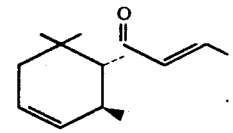

* * * * *